US012679827B2

(12) United States Patent
Chang et al.

(10) Patent No.: US 12,679,827 B2
(45) Date of Patent: Jul. 14, 2026

(54) PYRIMIDINE COMPOUNDS AND THEIR PHARMACEUTICAL USES

(71) Applicant: National Health Research Institutes, Miaoli County (TW)

(72) Inventors: Chun-Ping Chang, Miaoli County (TW); Ya-Hui Chi, Miaoli County (TW); Chiung-Tong Chen, Miaoli County (TW); Chuan Shih, Carmel, IN (US); Yi-Yu Ke, Miaoli County (TW)

(73) Assignee: National Health Research Institutes, Miaoli County (TW)

( * ) Notice: Subject to any disclaimer, the term of this patent is extended or adjusted under 35 U.S.C. 154(b) by 877 days.

(21) Appl. No.: 17/802,307

(22) PCT Filed: Mar. 3, 2021

(86) PCT No.: PCT/US2021/020594

§ 371 (c)(1), (2) Date: Aug. 25, 2022

(87) PCT Pub. No.: WO2021/178485

PCT Pub. Date: Sep. 10, 2021

(65) Prior Publication Data

US 2023/0131830 A1 Apr. 27, 2023

Related U.S. Application Data

(60) Provisional application No. 62/986,024, filed on Mar. 6, 2020.

(51) Int. Cl.

| | |
|---|---|
| ***C07D 403/14*** | (2006.01) |
| ***A61P 11/00*** | (2006.01) |
| ***A61P 35/00*** | (2006.01) |
| ***C07D 401/14*** | (2006.01) |
| ***C07D 403/12*** | (2006.01) |
| ***C07D 405/14*** | (2006.01) |
| ***C07D 413/14*** | (2006.01) |
| ***C07D 417/14*** | (2006.01) |
| ***C07D 487/08*** | (2006.01) |

(52) U.S. Cl.

CPC ............ *C07D 403/14* (2013.01); *A61P 11/00* (2018.01); *A61P 35/00* (2018.01); *C07D 401/14* (2013.01); *C07D 403/12* (2013.01); *C07D 405/14* (2013.01); *C07D 413/14* (2013.01); *C07D 417/14* (2013.01); *C07D 487/08* (2013.01)

(58) Field of Classification Search

None

See application file for complete search history.

(56) References Cited

U.S. PATENT DOCUMENTS

| | | | |
|---|---|---|---|
| 8,815,882 | B2 | 8/2014 | Baker-Glenn et al. |
| 2009/0192174 | A1 | 7/2009 | Kato et al. |
| 2010/0310675 | A1 | 12/2010 | Binch et al. |
| 2018/0305322 | A1 | 10/2018 | Bennett et al. |

FOREIGN PATENT DOCUMENTS

| | | | | |
|---|---|---|---|---|
| CN | 110218191 | A * | 9/2019 | .......... C07D 239/88 |
| JP | 2000512623 | A | 9/2000 | |
| KR | 20000005228 | A | 1/2000 | |
| WO | 97/43279 | A1 | 11/1997 | |
| WO | 2001/047921 | A1 | 7/2001 | |
| WO | 2004/052862 | A1 | 6/2004 | |
| WO | 2005/040159 | A1 | 5/2005 | |
| WO | 2006/046734 | A2 | 5/2006 | |
| WO | 2006/074057 | A2 | 7/2006 | |
| WO | 2006/129842 | A1 | 12/2006 | |
| WO | 2008/005538 | A2 | 1/2008 | |
| WO | 2008/071587 | A2 | 6/2008 | |
| WO | 2009/104802 | A1 | 8/2009 | |
| WO | 2010/106016 | A1 | 9/2010 | |
| WO | 2013/017461 | A1 | 2/2013 | |
| WO | WO-2016065138 | A1 * | 4/2016 | .......... C07D 417/12 |

OTHER PUBLICATIONS

CN110218191A—Machine Translation (Year: 2019).*

"Pubchem CID 132424281" Create Date: Mar. 2, 2018 (Mar. 2, 2018) Date Accessed: Jun. 15, 2021 (Jun. 15, 2021); p. 2, compound listed.

Long, et al., "Synthesis and biological evaluation of aurora kinases inhibitors based on N-trisubstituted pyrimidine scaffold," Eur J Med Chem; 145:805-812, 2018.

International Search Report for International Application No. PCT/US21/20594 mailed Jul. 21, 2021.

Kollareddy, et al., "Aurora kinase inhibitors: Progress towards the clinic," Invest. New Drugs, 30:2411-2432, 2012.

Chi, et al., "Discovery and Synthesis of a Pyrimidine-Based Aurora Kinase Inhibitor to Reduce Levels of MYC Oncoproteins," J. Med. Chem., 64, 7312-7330, 2021.

Pubchem CID 132424281, Create Date: Mar. 2, 2018, Date Accessed: Jun. 15, 2021; p. 2, compound listed.

(Continued)

*Primary Examiner* — Adam C Milligan

*Assistant Examiner* — Jed A Kucharczk

(74) *Attorney, Agent, or Firm* — Morse, Barnes-Brown & Pendleton, P.C.; Lisa M. Warren, Esq.; Russell L. Widom

(57) ABSTRACT

Pyrimidine compounds of Formula (I). Assignments to the variables in the formula are set forth herein. Also disclosed is a method of treating cancer with one of the pyrimidine compounds.

(I)

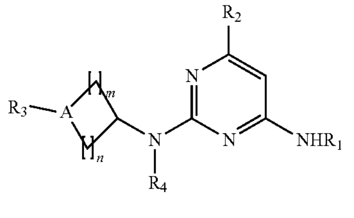

10 Claims, 3 Drawing Sheets

(56) References Cited

OTHER PUBLICATIONS

Vasilevich, et al., "Search for Potent and Selective Aurora A Inhibitors Based on General Ser/Thr Kinase Pharmacophore Model," Pharmaceuticals (Basel);9(2):19, 2016.
Martyn et al., "Synthesis and antiplasmodial acitvity of novel 2,4-diaminopyrimidines", Bioorganic & Medicinal Chemistry Letters, 20: 228-231 (2010).
Mohamed et al., "Development and evaluation of mutlifunctional agents for potential treatment of Alzheimer's disease: Application to a pyramidine-2,4-diamine template", Bioorganic & Medicinal Chemistry Letters, 20: 4707-4712 (2012).
Mohamed et al., "Design, Synthesis and Structure-Activity Relationship (SAR) Studies of 2,4-Disubstituted Pyrimidine Derivatives: Dual Activity as Cholinesterase and AB-Aggregation Inhibitors", Bioorg. Med. Chem., 19(7): 2269-2281 (2011).
CAS Registry compound list (e.g., RN 1269228-22-9, RN 1269186-29-9, RN 1269117-25-0, RN 2307287-66-5, RN 2307041-13-8, RN 2296473-51-1) retrieved on May 11, 2024 by Japanese Patent Office in corresponding Japanese Application No. 2022-553672.
Examination Report No. 2 issued in Australian application No. 2021230288 dated Oct. 17, 2025.
First examination report issued in NZ application No. 791121 dated Oct. 23, 2025.
Shen, M. et al., 'Discovery and optimization of triazine derivatives as ROCK1 inhibitors: molecular docking, molecular dynamics simulations and free energy calculations', Mol. BioSyst., 9: 361-374 (2013).
Singla, P. et al. , 'Synthesis and in vitro evaluation of novel triazine analogues as anticancer agents and their interaction studies with bovine serum albumin', Eur J Med Chem, 117: 59-69 (2016).

* cited by examiner

Figure 1. Reducing the Expression Levels of cMYC and MYCN by Compounds 41 and 86 in NCI-H82 and SK-N-BE(2) cells
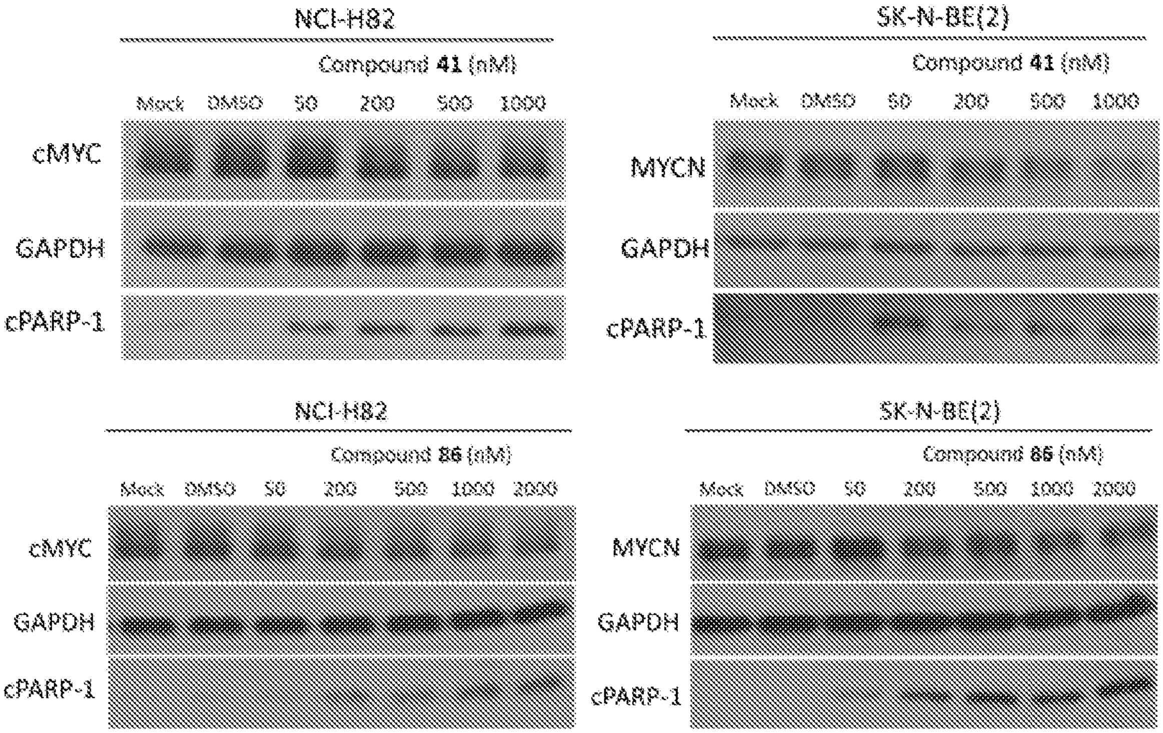

Figure 2. Inhibition of Tumor Growth by Compound 71, Compound 122, MLN8237, and LY3295668 in NCI-H446-Xenografted Tumorigenicity Mice

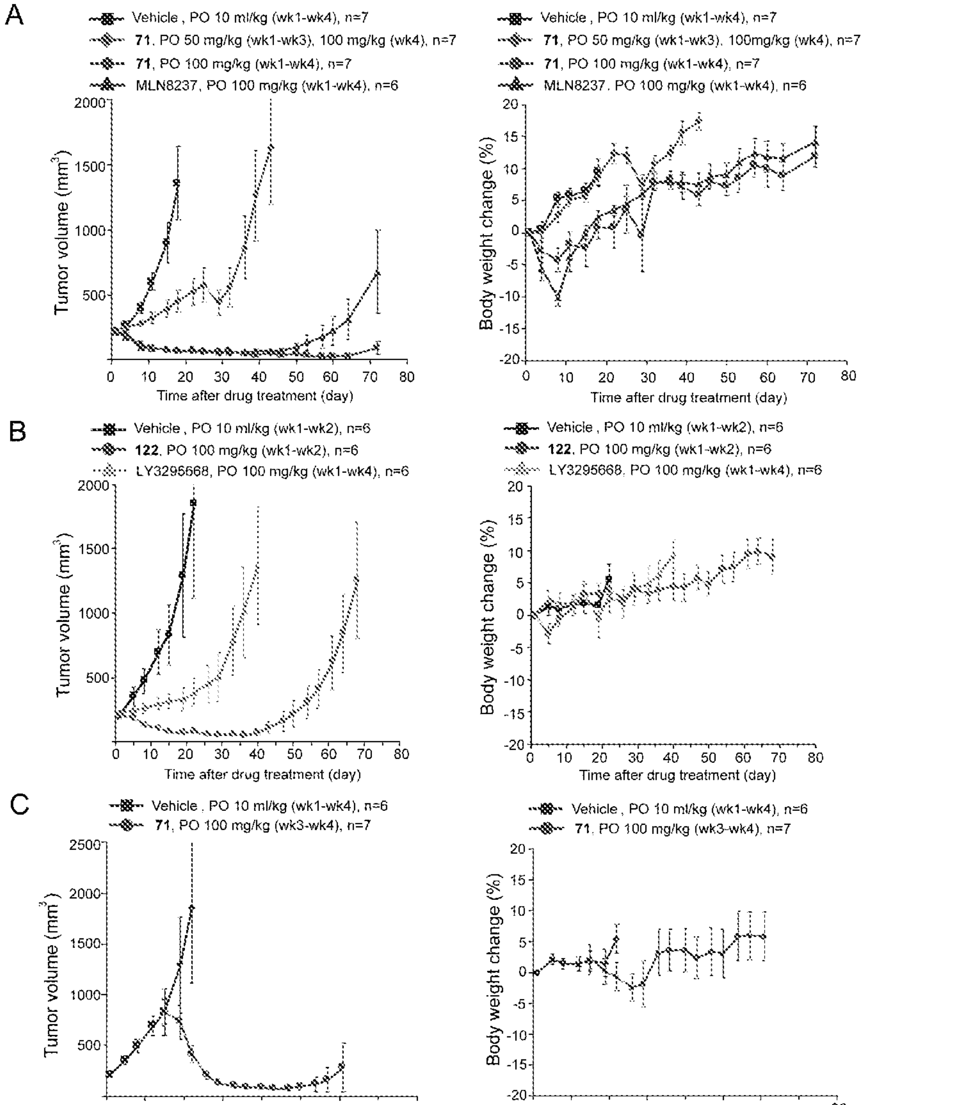

(A) Antitumor efficacy of compound 71 at 50 mg/kg and 100 mg/kg in tumor-bearing mice each having a tumor size of 250 $mm^3$, compared to that of the vehicle at 10 ml/kg and reference compound MLN8237 at 100 mg/kg.

(B) Antitumor efficacy of compound 122 at 100 mg/kg in tumor-bearing mice each having a tumor size of 250 $mm^3$, compared to that of the vehicle at 10 ml/kg and reference compound LY3295668 at 100 mg/kg.

(C) Antitumor efficacy of compound 71 at 100 mg/kg in tumor-bearing mice each having a tumor size larger than 750 $mm^3$, compared to that of the vehicle.

Figure 3. *In vivo* Efficacy of Compound 71 in Reducing cMYC Protein Level and Inducing Cell Apoptosis

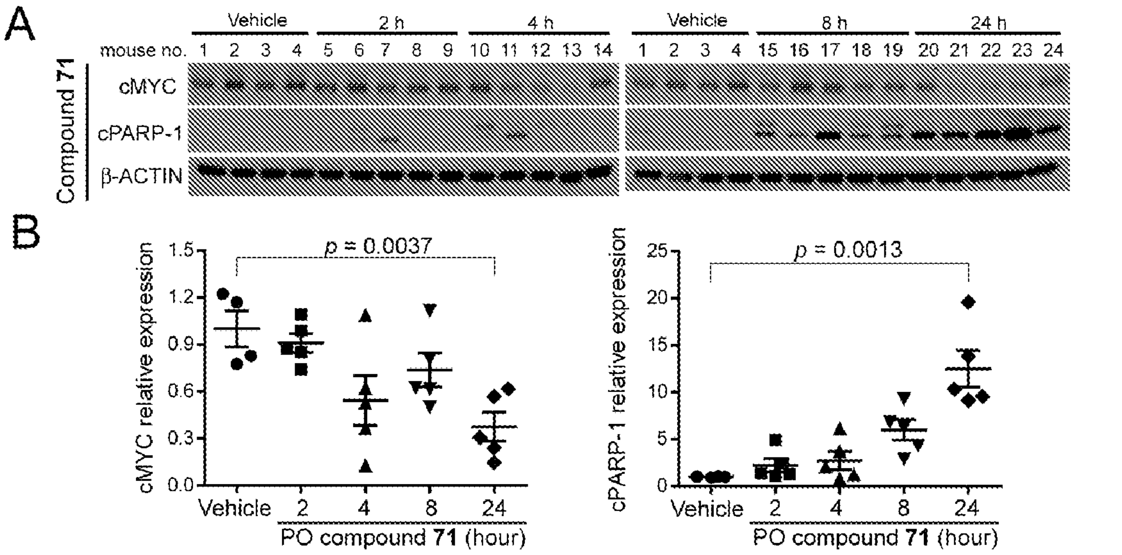

(A) Western analysis for the expression of cMYC, cleaved PARP-1 (cPARP-1) in xenografted NCI-H446 tumors in mice oral administered with vehicle or compound 71 at 100 mg/kg. Expression of β-ACTIN was used as a loading control.

(B) Quantification of the relative protein expression levels of cMYC and cPARP-1 as shown in (A).

*P* values: t-test.

PYRIMIDINE COMPOUNDS AND THEIR PHARMACEUTICAL USES

CROSS REFERENCE TO RELATED APPLICATIONS

This patent application is the national stage of International Patent Application No. PCT/US2021/020594, filed on Mar. 3, 2021, which claims the benefit and priority of U.S. Provisional Patent Application No. 62/986,024, filed on Mar. 6, 2020. The disclosures of both applications are incorporated by reference in their entirety.

BACKGROUND

Aurora A kinase is a serine/threonine kinase that regulates mitotic progression, centrosome maturation, and spindle assembly. This kinase plays an important role in stabilizing MYC-family oncoproteins, gene amplifications of which have been observed in 28% of cancers according to The Cancer Genome Atlas (TCGA). Small molecule inhibitors that induce a conformational change of the DFG-loop of Aurora A kinase leads to degradation of MYC-family oncoproteins, thus offering potential for cancer treatment.

Aurora A kinase inhibitors, including compound CD532, have been identified. See WO 2014/190207A1. However, CD532 has weak in vivo efficacy.

There is a need to develop new compounds that effectively inhibit Aurora A kinase activity.

SUMMARY

The present invention is based on a discovery that certain pyrimidine compounds are effective in inhibiting Aurora A kinase activity both in vitro and in vivo.

In one aspect, this invention relates to the compounds of Formula (I) shown below:

(I)

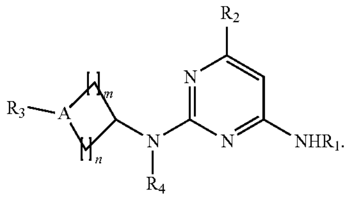

In this formula, A is CH or N; $R_1$ is $C_{1-6}$ alkyl, $C_{1-6}$ alkoxyl, $C_{3-10}$ cycloalkyl, aryl, or heteroaryl; $R_2$ is H, $C_{1-6}$ alkyl, $R_5NDNR_6R_7$, or $C_{1-10}$ heterocycloalkyl, each of $R_5$, $R_6$, and $R_7$, independently, being H or $C_{1-6}$ alkyl, D being a $C_{1-6}$ bivalent aliphatic radical; $R_3$ is $C_{1-6}$ alkyl, $C_{1-6}$ alkoxyl, $C_{3-10}$ cycloalkyl, $C_{7-12}$ aralkyl, $C_{1-12}$ heteroaralkyl, —C(O) $R_8$, or —$S(O)_2R_8$, in which $R_8$ is aryl or heteroaryl; $R_4$ is $C_{1-6}$ alkyl or, preferably, H; and each of m and n, independently, is 1 or 2.

Each of $C_{1-6}$ alkyl, $C_{1-6}$ alkoxyl, $C_{3-10}$ cycloalkyl, $C_{1-10}$ heterocycloalkyl, $C_{7-12}$ aralkyl, $C_{1-12}$ heteroaralkyl, aryl, and heteroaryl, independently, is mono-, di-, or tri-substituted with halo, OH, CN, $NH_2$, $NO_2$, $SO_2$, $C_{1-6}$ alkyl, $C_{1-6}$ haloalkyl, $C_{3-13}$ cycloalkyl, $C_{2-8}$ heterocycloalkyl, $C_{1-6}$ alkoxyl, $C_{1-6}$ haloalkoxyl, $C_{1-6}$ alkylamino, $C_{2-6}$ dialkylamino, $C_{7-12}$ aralkyl, $C_{1-12}$ heteroaralkyl, aryl, heteroaryl, —C(O)$R_9$, —C(O)O$R_9$, or —C(O)N$R_9R_{10}$, each of $R_9$ and $R_{10}$, independently, being H, halo, OH, CN, COOH, acetyl, acetamide, dialkylamino, alkylamino, $C_{1-6}$ alkyl, $C_{1-6}$ multihaloalkyl, $C_{1-6}$ alkoxyl, $C_{1-6}$ multihaloalkoxyl, $C_{3-8}$ cycloalkyl, $C_{1-10}$ heterocycloalkyl, aryl, or heteroaryl.

The term "alkyl" herein refers to a straight or branched hydrocarbon group, containing 1-20 (e.g., 1-10 and 1-6) carbon atoms. Examples include methyl, ethyl, n-propyl, i-propyl, n-butyl, i-butyl, and t-butyl. The term "haloalkyl" refers to alkyl substituted with one or more halogen (chloro, fluoro, bromo, or iodo) atoms. Examples include trifluoromethyl, bromomethyl, and 4,4,4-trifluorobutyl. The term "alkoxyl" refers to an —O— alkyl group. Examples include methoxy, ethoxy, propoxy, and isopropoxy. The term "haloalkoxy" refers to alkoxy substituted with one or more halogen atoms. Examples include —O—$CH_2Cl$ and —O—$CHClCH_2Cl$.

The term "cycloalkyl" refers to a saturated and partially unsaturated monocyclic, bicyclic, tricyclic, or tetracyclic hydrocarbon group having 3 to 12 carbons. Examples of cycloalkyl groups include, but are not limited to, cyclopropyl, cyclobutyl, cyclopentyl, cyclopentenyl, cyclohexyl, cyclohexenyl, cycloheptyl, and cyclooctyl.

The term "heterocycloalkyl" refers to a nonaromatic 5-8 membered monocyclic, 8-12 membered bicyclic, or 11-14 membered tricyclic ring system having one or more heteroatoms (e.g., O, N, P, and S). Examples of heterocycloalkyl groups include, but are not limited to, piperazinyl, imidazolidinyl, azepanyl, pyrrolidinyl, dihydrothiadiazolyl, dioxanyl, morpholinyl, tetrahydropuranyl, and tetrahydrofuranyl.

The term "aryl" refers to a 6-carbon monocyclic, 10-carbon bicyclic, 14-carbon tricyclic aromatic ring system wherein each ring may have 1 to 5 substituents. Examples of aryl groups include phenyl, naphthyl, and anthracenyl. The term "arylene" refers to bivalent aryl. The term "aralkyl" refers to alkyl substituted with an aryl group.

The term "heteroaryl" refers to an aromatic 5-8 membered monocyclic, 8-12 membered bicyclic, or 11-14 membered tricyclic ring system having one or more heteroatoms (e.g., O, N, P, and S). Examples include triazolyl, oxazolyl, thiadiazolyl, tetrazolyl, pyrazolyl, pyridyl, furyl, imidazolyl, benzimidazolyl, pyrimidinyl, thienyl, quinolinyl, indolyl, thiazolyl, and benzothiazolyl. The term "heteroaralkyl" refers to an alkyl group substituted with a heteroaryl group.

The term "halo" refers to a fluoro, chloro, bromo, or iodo radical. The term "amino" refers to a radical derived from amine, which is unsubstituted or mono-/di-substituted with alkyl, aryl, cycloalkyl, heterocycloalkyl, or heteroaryl. The term "alkylamino" refers to alkyl-NH—. The term "dialkylamino" refers to alkyl-N(alkyl)-.

The term "acyl" refers to —C(O)-alkyl, —C(O)-aryl, —C(O)-cycloalkyl, —C(O)-heterocycloalkyl, or —C(O)-heteroaryl.

Alkyl, cycloalkyl, heterocycloalkyl, aryl, heteroaryl, aralkyl, heteroaralkyl, alkoxy, and aryloxy mentioned herein include both substituted and unsubstituted moieties. Examples of substituents include, but are not limited to, halo, hydroxyl, amino, cyano, nitro, mercapto, alkoxycarbonyl, amido, carboxy, alkanesulfonyl, alkylcarbonyl, carbamido, carbamyl, carboxyl, thioureido, thiocyanato, sulfonamido, alkyl, alkenyl, alkynyl, alkyloxy, aryl, heteroaryl, cycloalkyl, and heterocycloalkyl, in which alkyl, alkenyl, alkynyl, alkyloxy, aryl, heteroaryl cycloalkyl, and heterocycloalkyl may further substituted.

In another aspect, this invention relates to a method for treating cancer. The method includes administering to a subject in need of an effective amount of a compound of Formula (I) described above.

The term "compound", when referring to a compound of Formula (I), also covers its salts, solvates, and prodrugs. A salt can be formed between an anion and a positively charged group (e.g., amino) on a compound; examples of a suitable anion include chloride, bromide, iodide, sulfate, nitrate, phosphate, citrate, methanesulfonate, trifluoroacetate, acetate, malate, tosylate, tartrate, fumurate, glutamate, glucuronate, lactate, glutarate, and maleate. A salt can also be formed between a cation and a negatively charged group; examples of a suitable cation include sodium ion, potassium ion, magnesium ion, calcium ion, and an ammonium cation such as tetramethylammonium ion. A salt further includes those containing quaternary nitrogen atoms. A solvate refers to a complex formed between an active compound and a pharmaceutically acceptable solvent. Examples of a pharmaceutically acceptable solvent include water, ethanol, isopropanol, ethyl acetate, acetic acid, and ethanolamine A prodrug refers to a medication or compound that, after administration, is metabolized into a pharmaceutically active drug. Examples of prodrugs include esters and other pharmaceutically acceptable derivatives, which, upon administering to a subject, are capable of providing active pyrimidine compounds.

The details of one or more embodiments of the invention are set forth in the description below. Other features, objects, and advantages of the invention will be apparent from the description and from the claims.

BRIEF DESCRIPTION OF THE DRAWINGS

FIG. 1 illustrates in vitro efficacy of two representative compounds, i.e., compounds 41 and 86, in reducing expression levels of cMYC and MYCN in NCI-H82 and SK-N-BE(2) cells.

FIG. 2 illustrates in vivo antitumor efficacy of two represention compounds, i.e., compounds 71 and 122, and two reference compounds, i.e., MLN8237 and LY3295668, in NCI-H446 xenografted tumorigenicity mice.

FIG. 3 illustrates in vivo efficacy of compound 71 in reducing cMYC protein levels and inducing cell apoptosis.

DETAILED DESCRIPTION

Described in detail below are the pyrimidine compounds of Formula (I) reproduced below, as well as their syntheses and their anticancer efficacy.

(I)

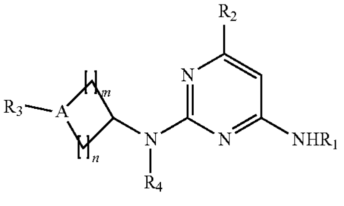

$R_1$-$R_4$, m, n, and A are defined in the SUMMARY section above.

In a preferred set of compounds of Formula (I), the sum of m and n is 3; A is N; $R_1$ is $C_{3-10}$ cycloalkyl or 5-membered heteroaryl; $R_2$ is

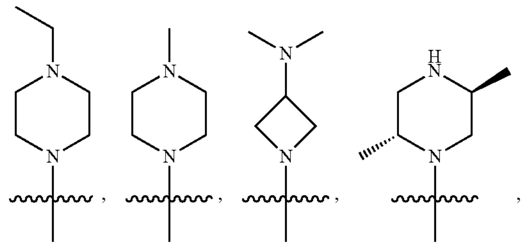

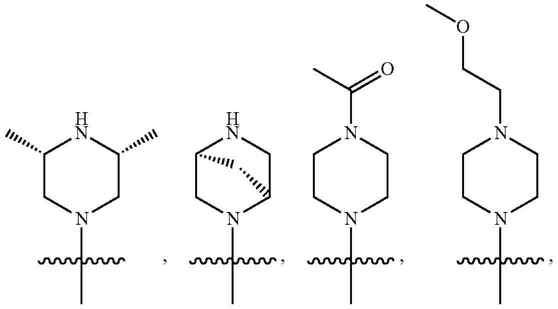

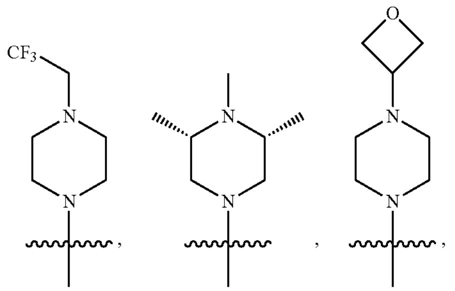

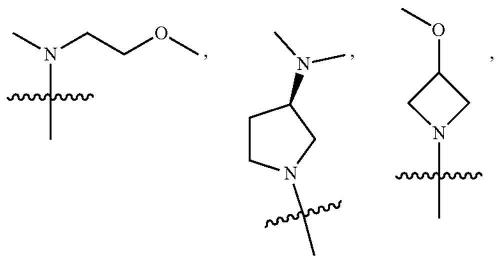

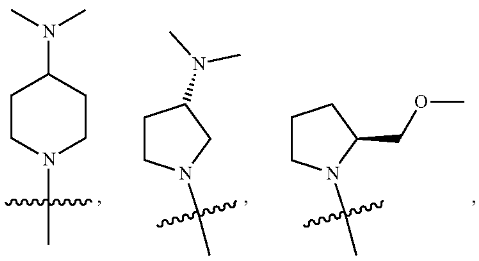

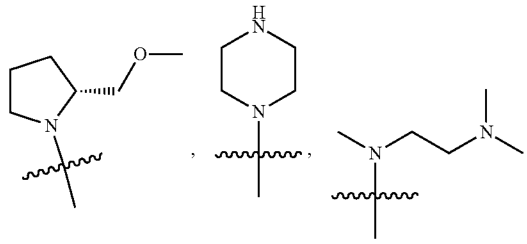

or

-continued

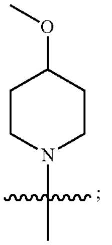;

and $R_3$ is $C_{7-12}$ aralkyl, —C(O)$R_8$, or —S(O)$_2R_8$.

In another preferred set of compounds covered by Formula (I), each of m and n is 2; A is N; $R_1$ is $C_{3-10}$ cycloalkyl or 5-membered heteroaryl; $R_2$ is H, $C_{1-6}$ alkyl,

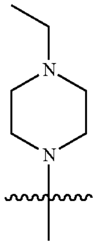, 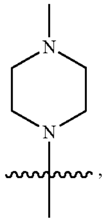, 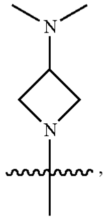, 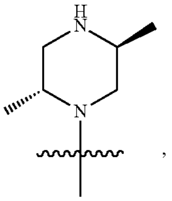,

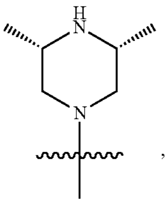, 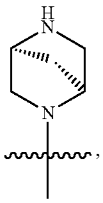, 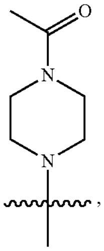, 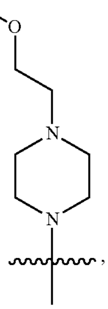,

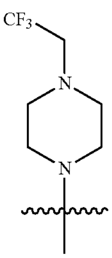, 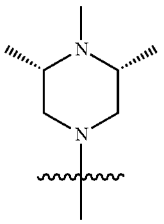, 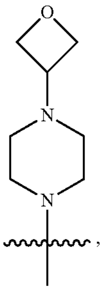,

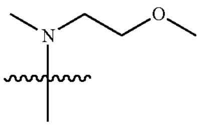, 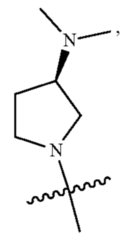, 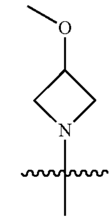,

-continued

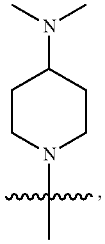, 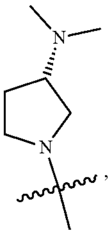, 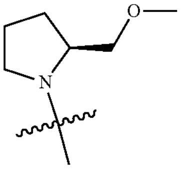,

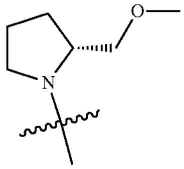, 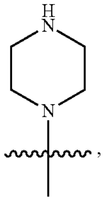, 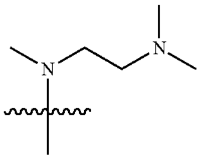, or

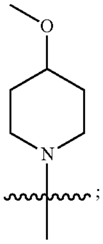;

$R_3$ is $C_{7-12}$ aralkyl, —C(O)$R_8$, or —S(O)$_2R_8$.

The compounds of this invention can be prepared by synthetic methods well known in the art. See, e.g., R. Larock, Comprehensive Organic Transformations (2$^{nd}$ Ed., VCH Publishers 1999); P. G. M. Wuts and T. W. Greene, Greene's Protective Groups in Organic Synthesis (4$^{th}$ Ed., John Wiley and Sons 2007); L. Fieser and M. Fieser, Fieser and Fieser's Reagents for Organic Synthesis (John Wiley and Sons 1994); and L. Paquette, ed., Encyclopedia of Reagents for Organic Synthesis (2$^{nd}$ ed., John Wiley and Sons 2009) and subsequent editions thereof.

The compounds mentioned herein may contain a non-aromatic double bond and one or more asymmetric centers. Thus, each compound occurs as a racemate or a racemic mixture, a single R enantiomere, a single S enantiomer, an individual disasteromer, a diastereometric mixture, or a cis- or trans-isomer. Compounds of all such isomeric forms are within the scope of this invention.

The compounds of Formula (I) thus prepared can be initially screened using the enzymatic Aurora A kinase activity inhibition assay described in Example 2 below for their potency in inhibiting Aurora A kinase activity. They can be subsequently evaluated using in vitro assays, e.g., the MYC- or MYCN-amplified cancer cell line assays described in Example 3 and the cell proliferation inhibition assays described in Examples 4 and 5, for their efficacies in inhibiting cancer cell proliferation. The selected compounds can be further tested to verify their efficacy in treating cancer. For example, as described in Examples 6 and 7, a compound can be adminstered to an animal (e.g., a mouse) having a xenografted tumor and its therapertic effects are then assessed.

Also within this invention is a method for treating cancer. The method includes administering to a subject in need thereof an effective amount of a compound of Formula (I). Examples of cancer include leukemia, lung cancer, neuroblastoma, pancreatic cancer, colon cancer, prostate cancer, breast cancer, liver cancer, brain cancer, and cholangiocarcinoma.

This invention also covers a pharmaceutical composition containing a compound of Formula (I) and a pharmaceutical carrier. The pharmaceutical composition can be used for treating cancer.

To practice the method of the present invention, a composition having one or more of the above-described pyrimidine compounds can be administered parenterally, orally, nasally, rectally, topically, or buccally. The term "parenteral" as used herein refers to subcutaneous, intracutaneous, intravenous, intraperitoneal, intramuscular, intraarticular, intraarterial, intrasynovial, intrasternal, intrathecal, intralesional, or intracranial injection, as well as any suitable infusion technique.

A sterile injectable composition can be a solution or suspension in a non-toxic parenterally acceptable diluent or solvent, such as a solution in 1,3-butanediol. Among the acceptable vehicles and solvents that can be employed are mannitol, water, Ringer's solution, and isotonic sodium chloride solution. In addition, fixed oils are conventionally employed as a solvent or suspending medium (e.g., synthetic mono- or di-glycerides). Fatty acid, such as oleic acid and its glyceride derivatives are useful in the preparation of injectables, as are natural pharmaceutically acceptable oils, such as olive oil and castor oil, especially in their polyoxyethylated versions. These oil solutions or suspensions can also contain a long chain alcohol diluent or dispersant, carboxymethyl cellulose, or similar dispersing agents. Other commonly used surfactants such as Tweens and Spans or other similar emulsifying agents or bioavailability enhancers which are commonly used in the manufacture of pharmaceutically acceptable solid, liquid, or other dosage forms can also be used for the purpose of formulation.

A composition for oral administration can be any orally acceptable dosage form including capsules, tablets, emulsions and aqueous suspensions, dispersions, and solutions. In the case of tablets, commonly used carriers include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added. Oral solid dosage forms can be prepared by spray dried techniques; hot melt extrusion strategy, micronization, and nano milling technologies.

A nasal aerosol or inhalation composition can be prepared according to techniques well known in the art of pharmaceutical formulation. For example, such a composition can be prepared as a solution in saline, employing benzyl alcohol or other suitable preservatives, absorption promoters to enhance bioavailability, fluorocarbons, and/or other solubilizing or dispersing agents known in the art. A composition having an active compound can also be administered in the form of suppositories for rectal administration.

The carrier in the pharmaceutical composition must be "acceptable" in the sense that it is compatible with the active ingredient of the composition (and preferably, capable of stabilizing the active ingredient) and not deleterious to the subject to be treated. One or more solubilizing agents can be utilized as pharmaceutical excipients for delivery of an active compound. Examples of other carriers include colloidal silicon oxide, magnesium stearate, cellulose, sodium lauryl sulfate, and D&C Yellow #10.

The term "treating" refers to application or administration of the compound to a subject with the purpose to cure, alleviate, relieve, alter, remedy, improve, or affect the disease, the symptom, or the predisposition. "An effective amount" refers to the amount of the compound which is required to confer the desired effect on the subject. Effective amounts vary, as recognized by those skilled in the art, depending on route of administration, excipient usage, and the possibility of co-usage with other therapeutic treatments such as use of other active agents.

Without further elaboration, it is believed that one skilled in the art can, based on the above description, utilize the present invention to its fullest extent. The following examples are to be construed as merely illustrative and not limitative of the remainder of the disclosure in any way whatsoever. All publications cited herein are hereby incorporated by reference in their entirety.

Set forth below are the structures of 127 exemplary compounds of this invention:

1

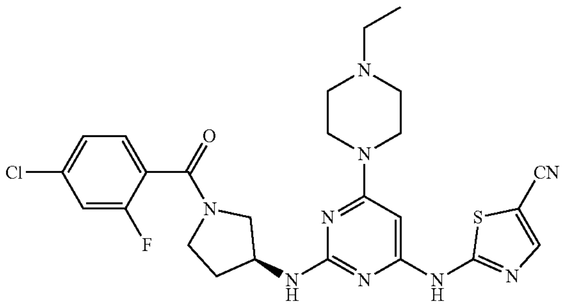

2

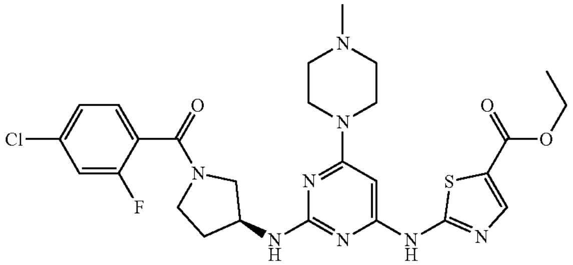

3

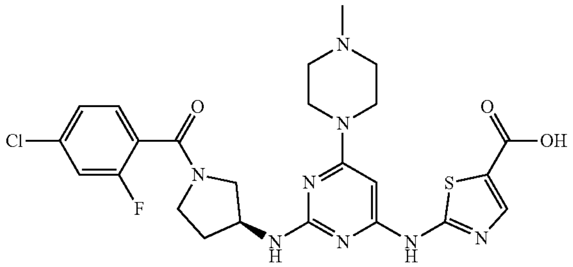

-continued
4
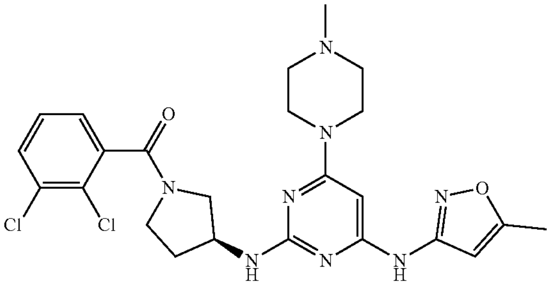
5
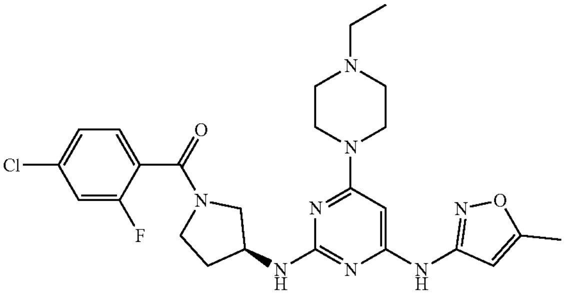
6
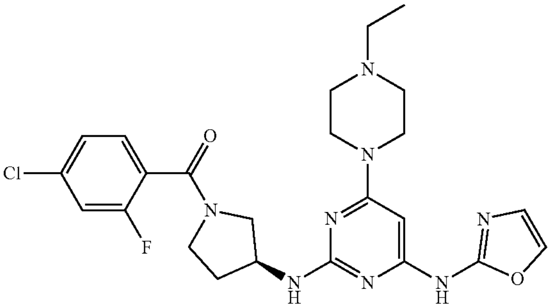
7
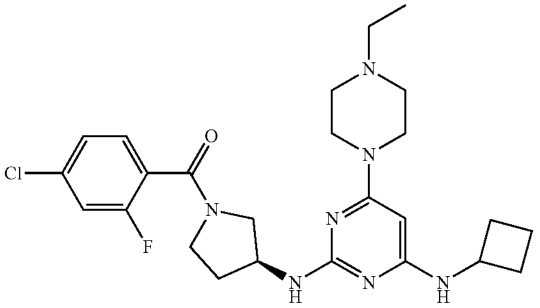
8
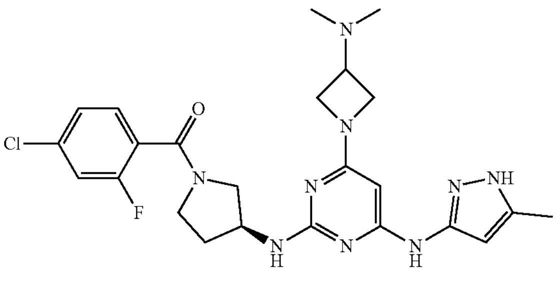
-continued
9
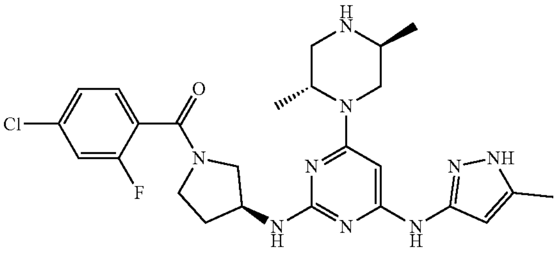
10
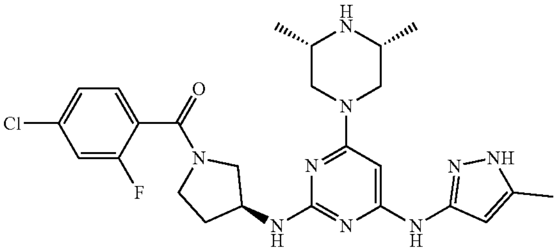
11
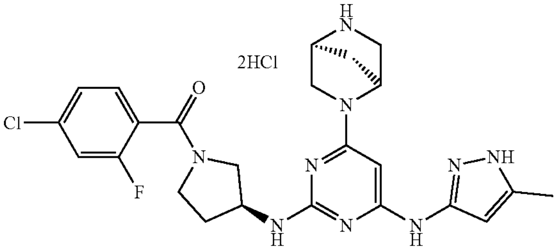
12
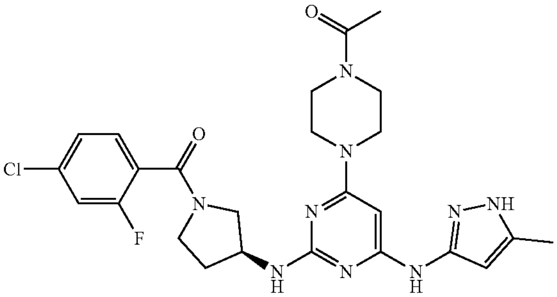
13
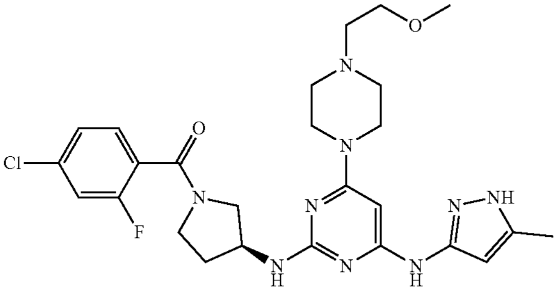

-continued
14
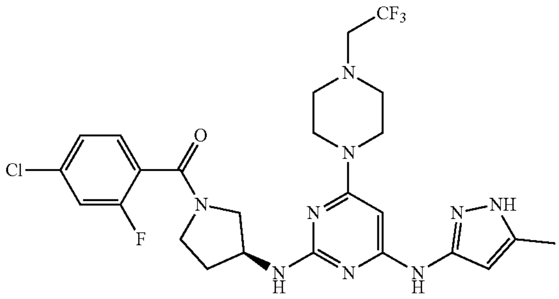
15
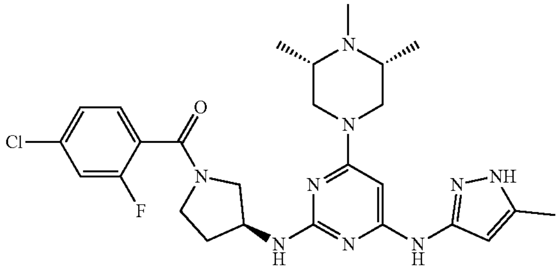
16
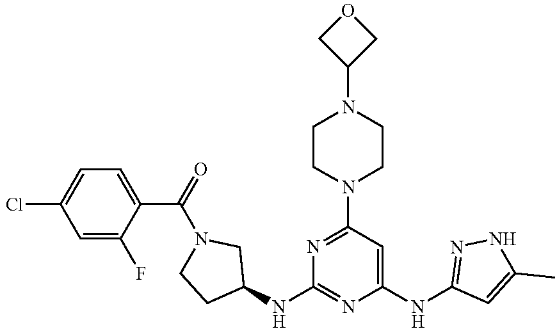
17
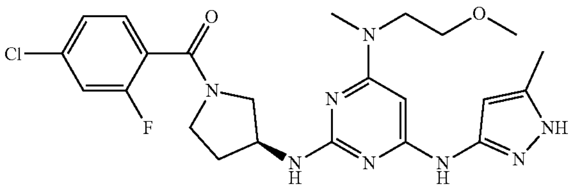
18
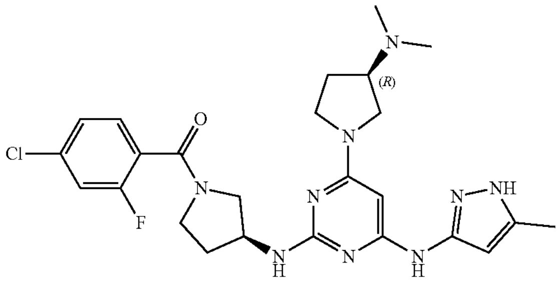
-continued
19
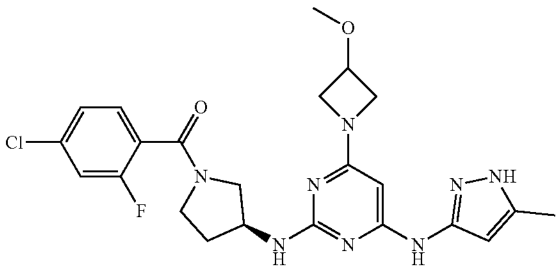
20
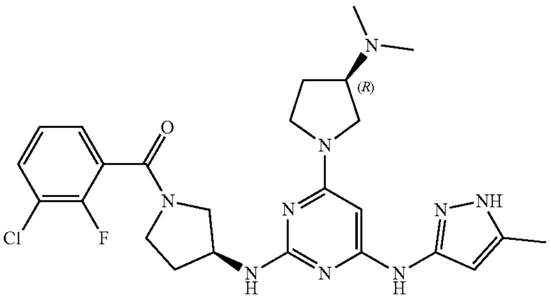
21
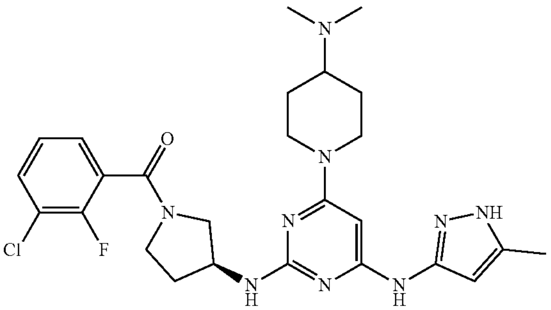
22
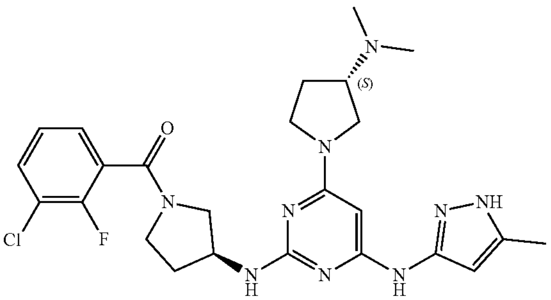
23
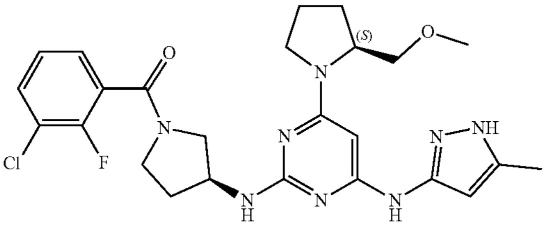

-continued
24
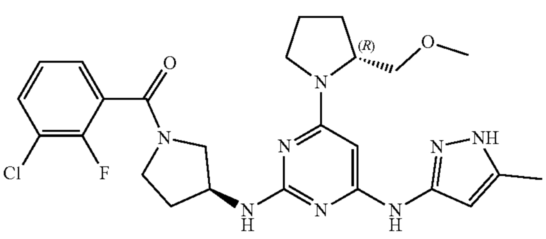
25
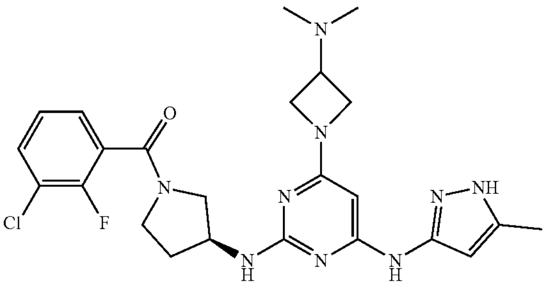
26
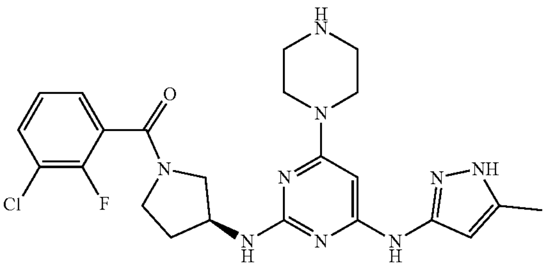
27
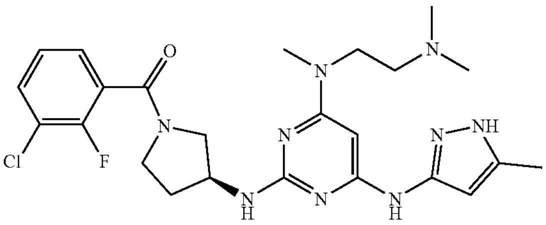
28
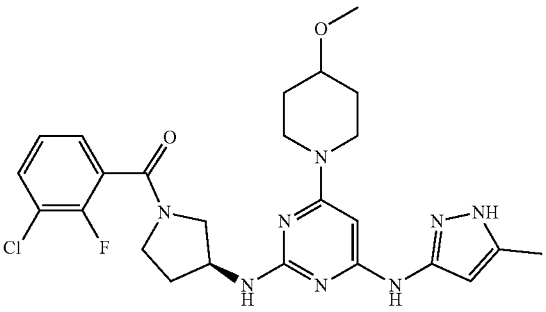
-continued
29
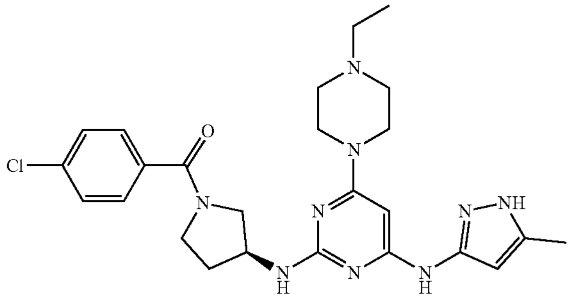
30
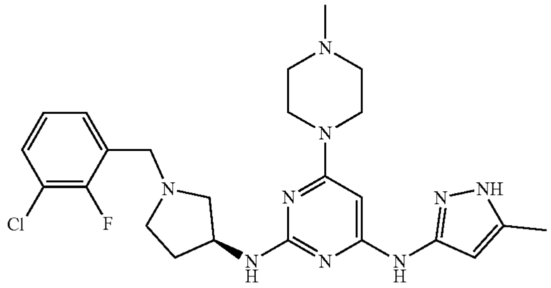
31
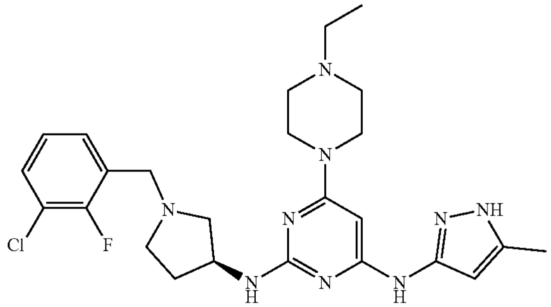
32
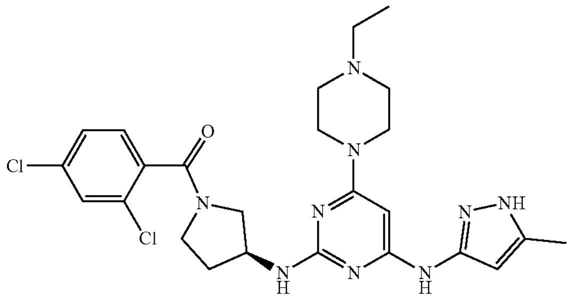
33
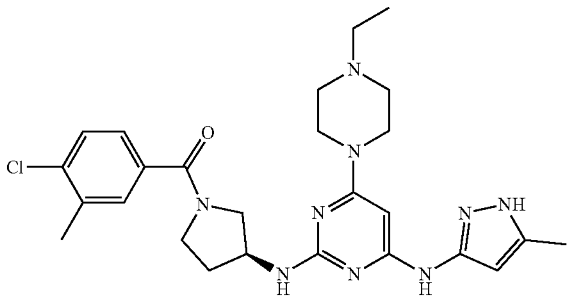

-continued
34
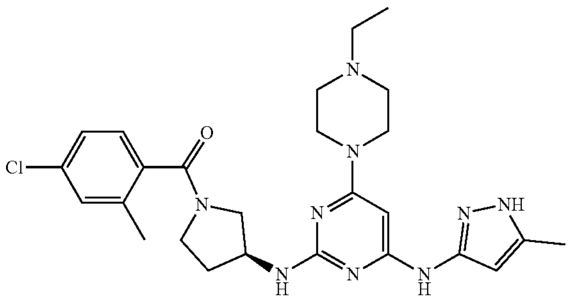
35
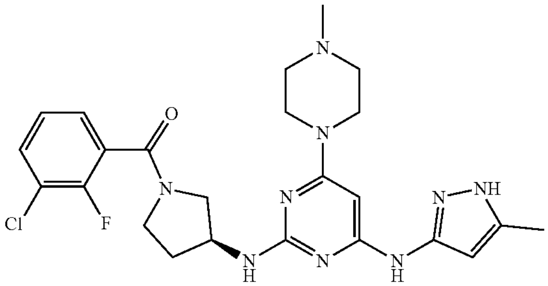
36
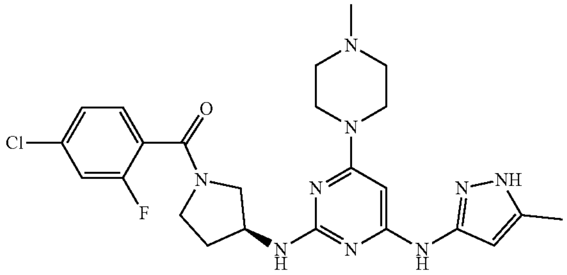
37
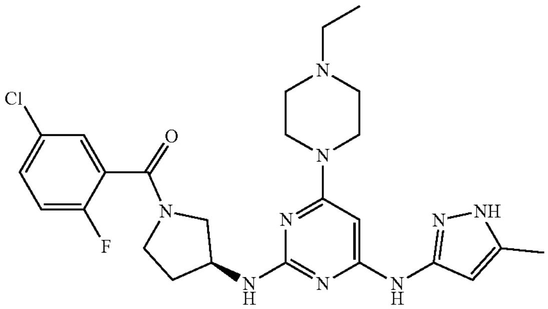
38
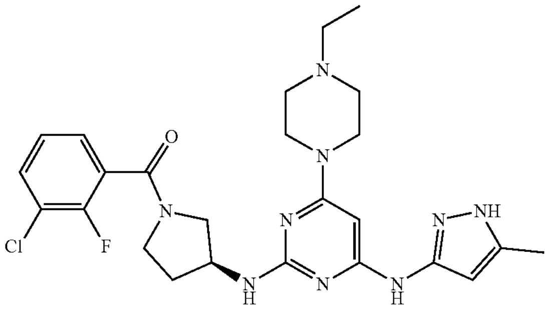
-continued
39
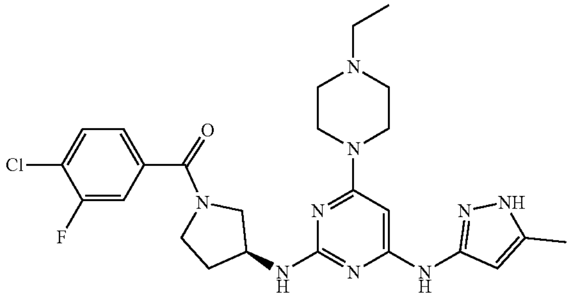
40
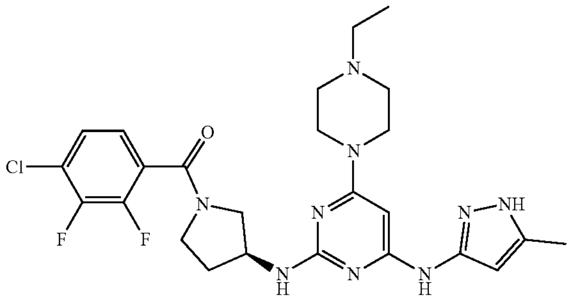
41
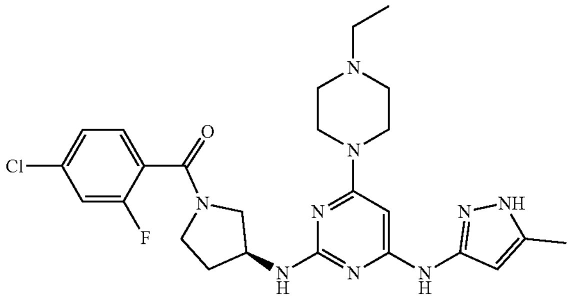
42
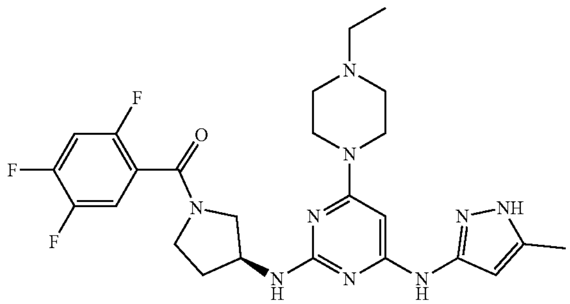
43
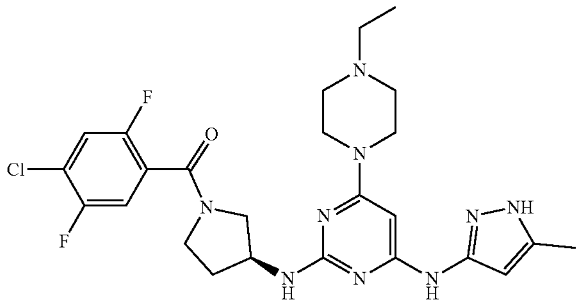

-continued
44
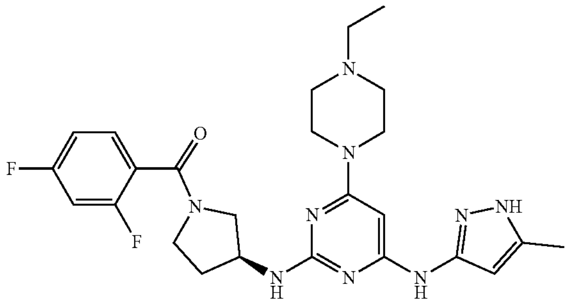
45
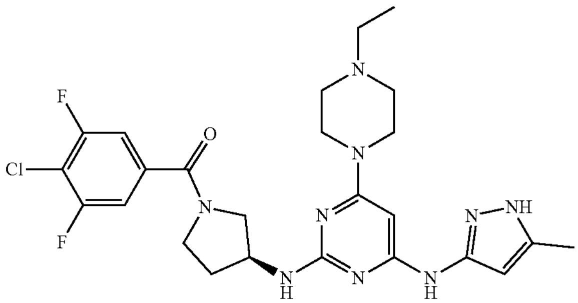
46
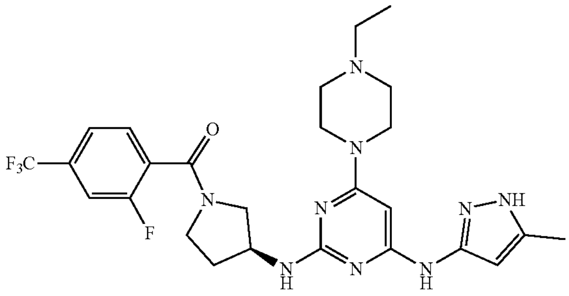
47
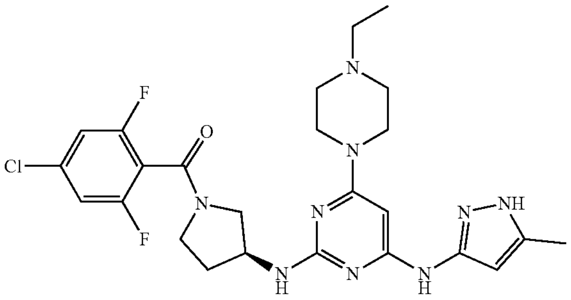
48
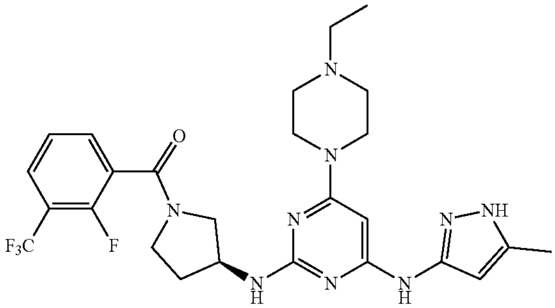
-continued
49
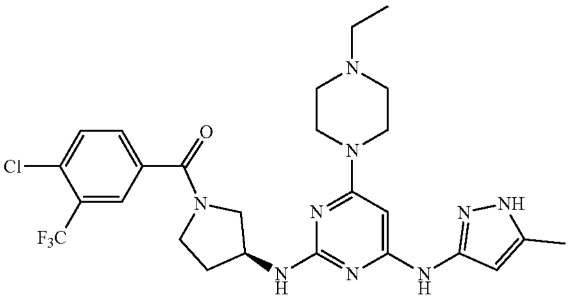
50
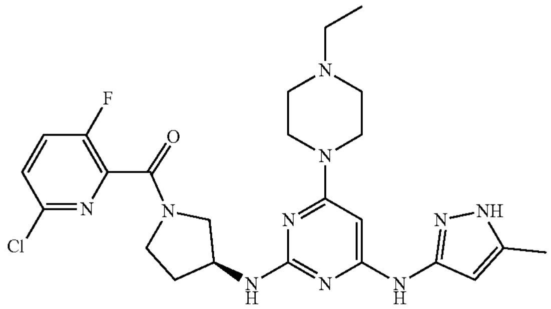
51
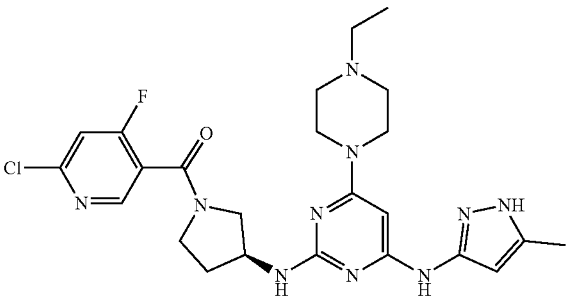
52
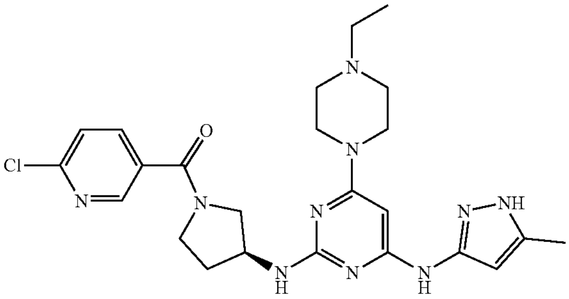
53
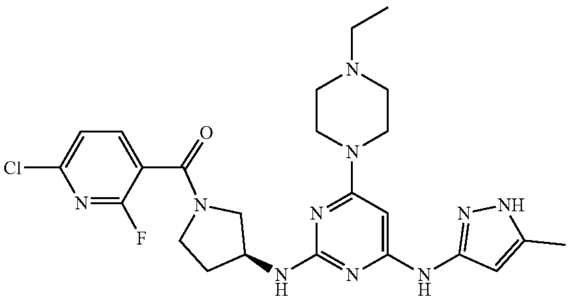

-continued
54
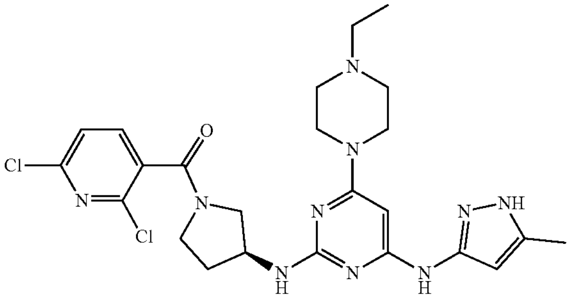
55
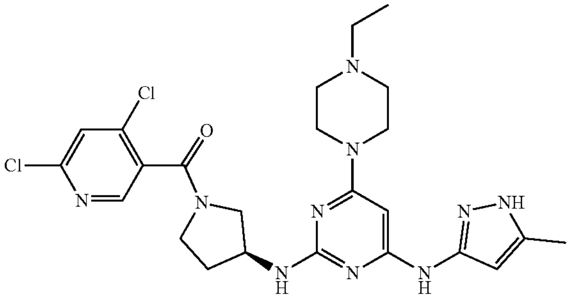
56
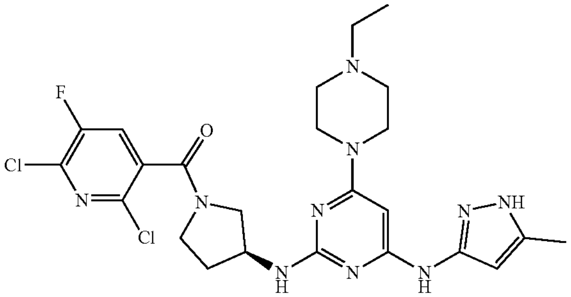
57
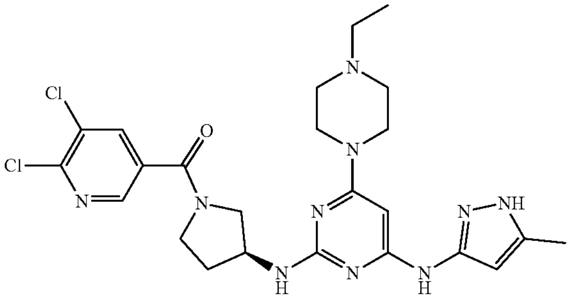
58
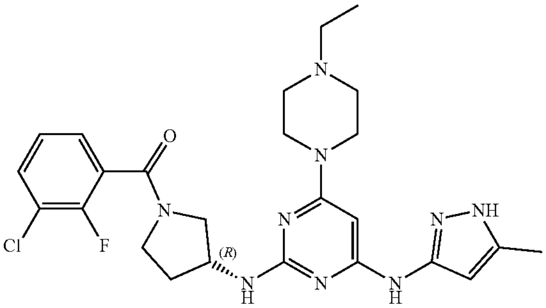
-continued
59
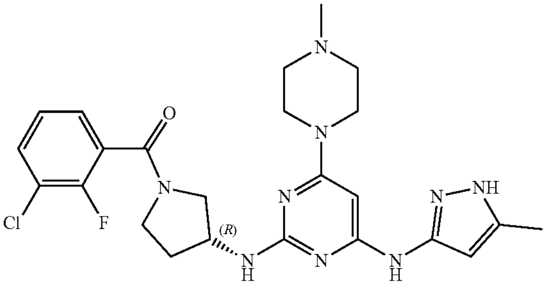
60
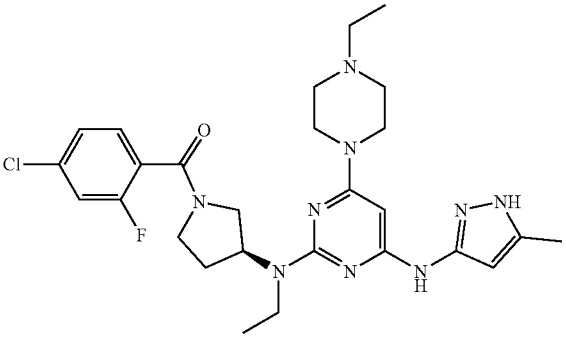
61
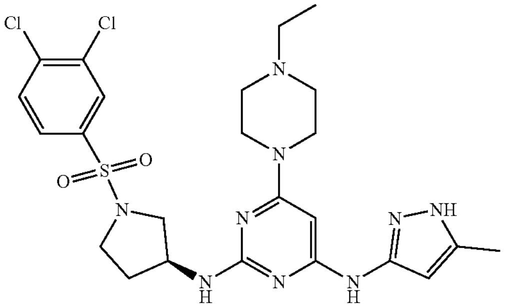
62
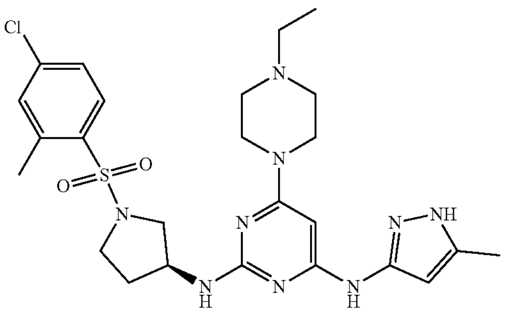

-continued
63
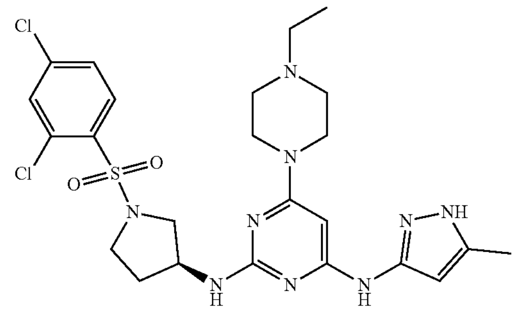
64
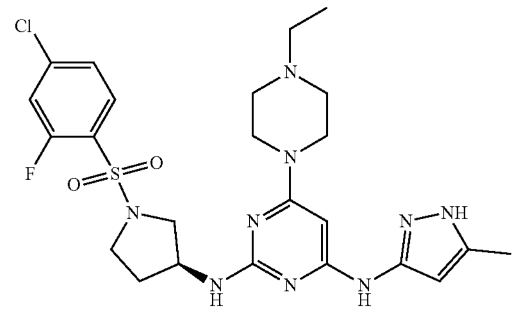
65
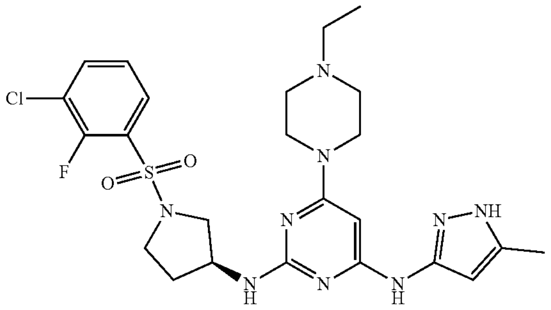
66
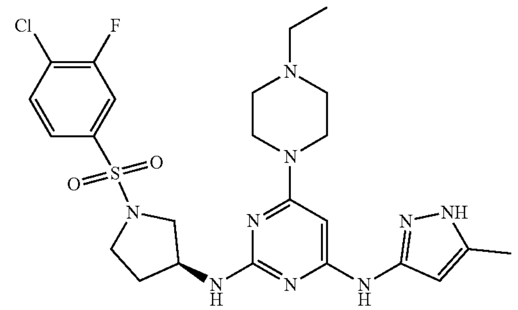
67
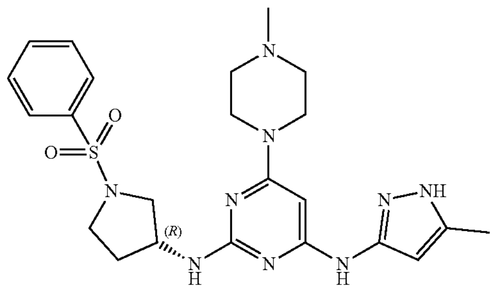
-continued
68
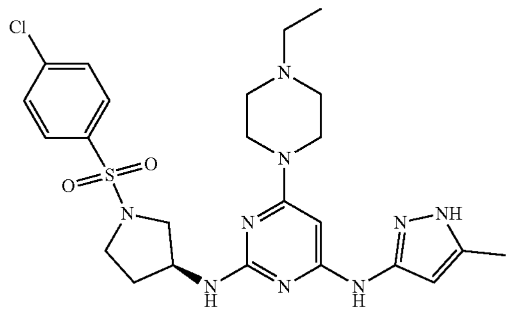
69
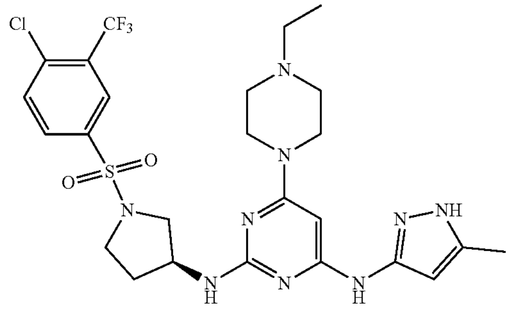
70
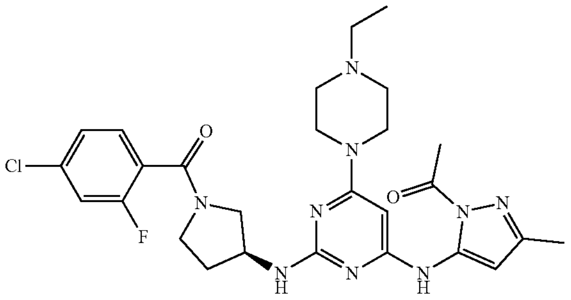
71
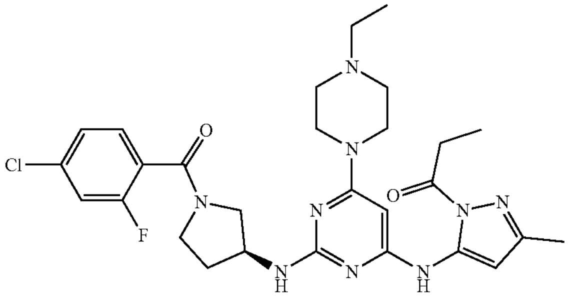
72
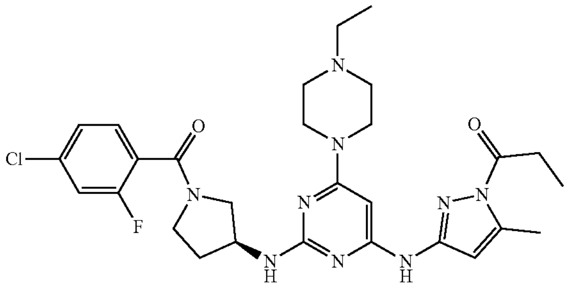

-continued
73
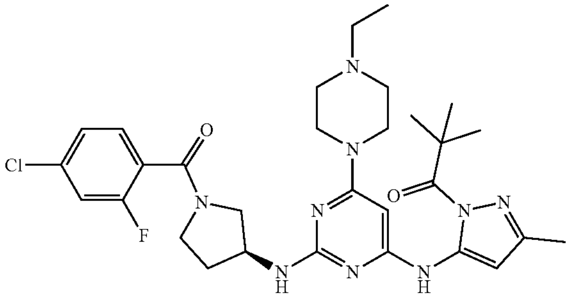
74
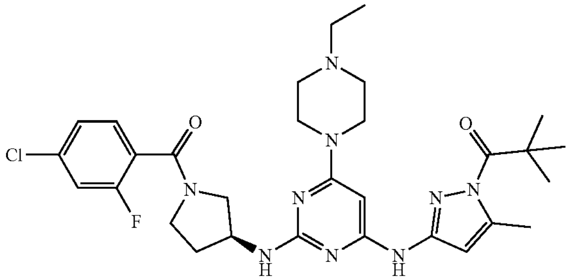
75
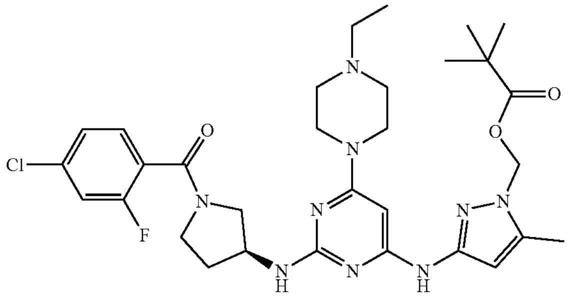
76
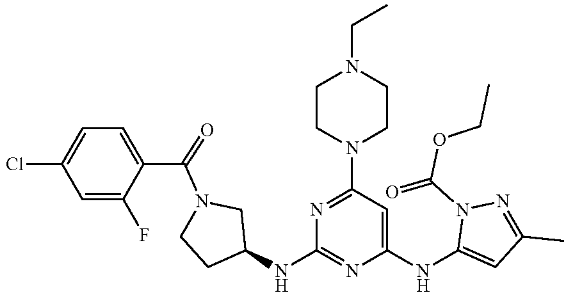
77
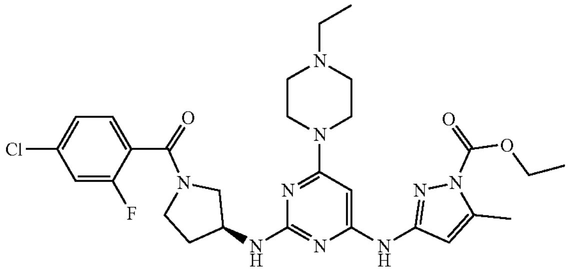
-continued
78
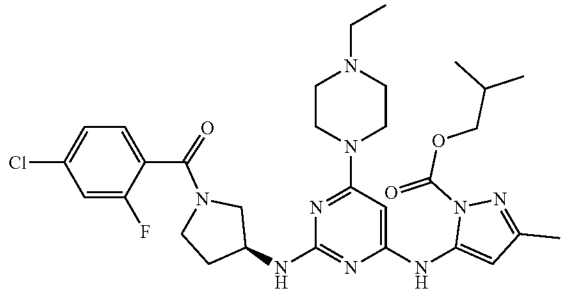
79
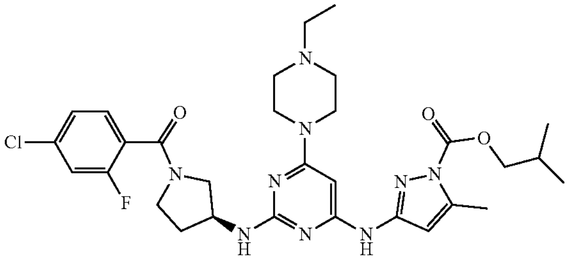
80
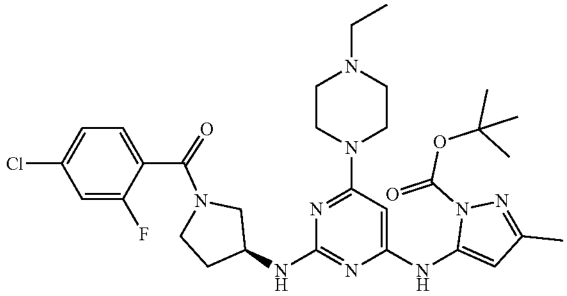
81
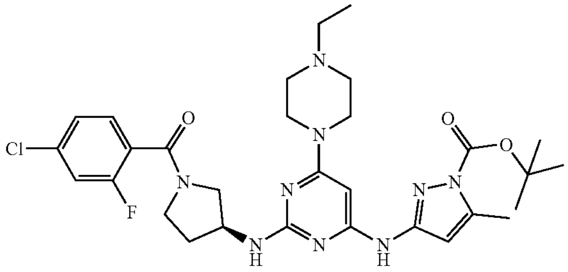
82
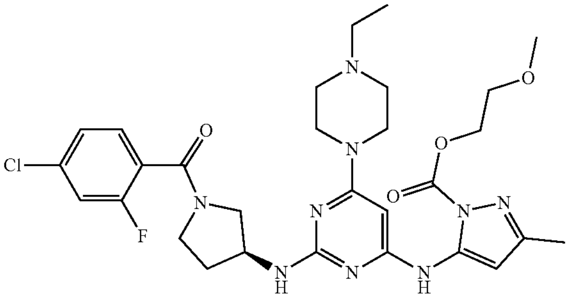

-continued
83
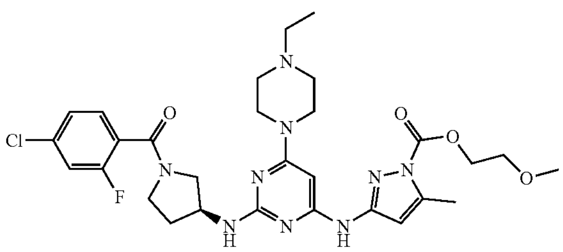
84
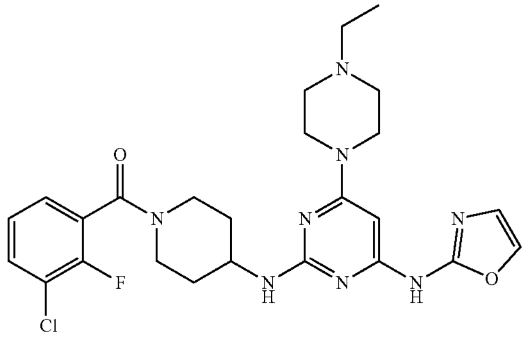
85
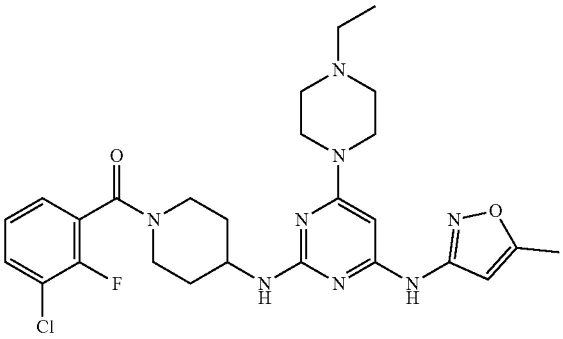
86
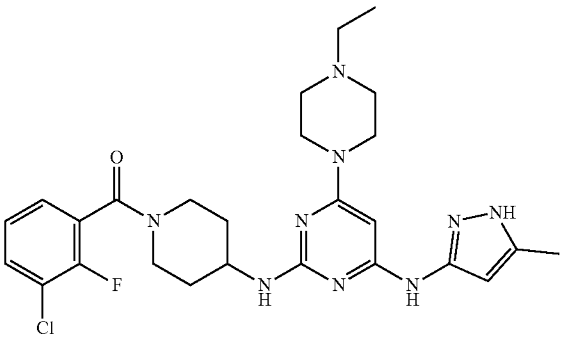
-continued
87
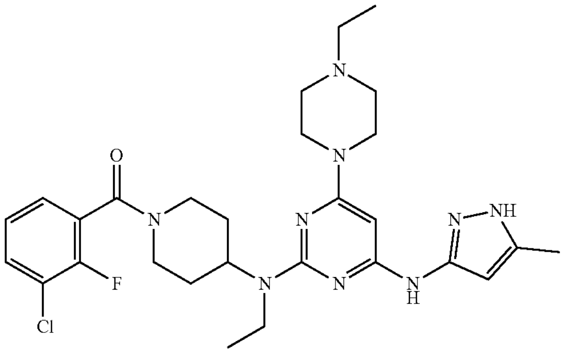
88
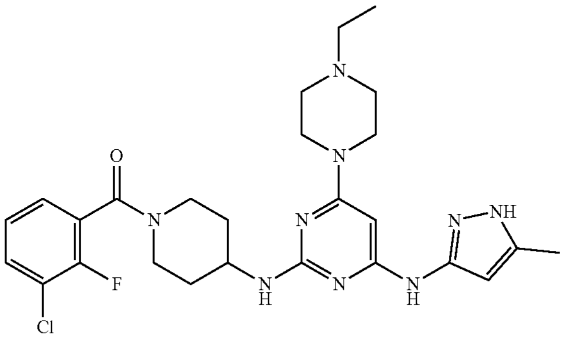
89
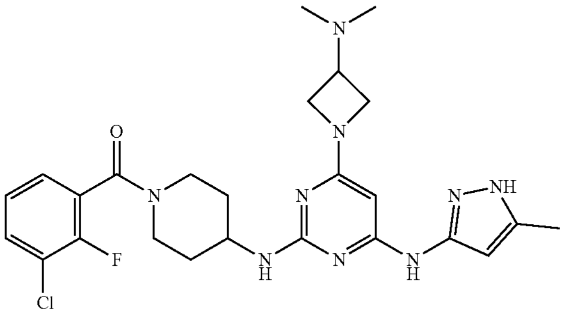
90
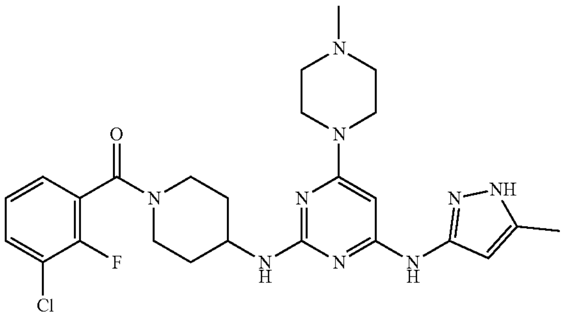

-continued
91
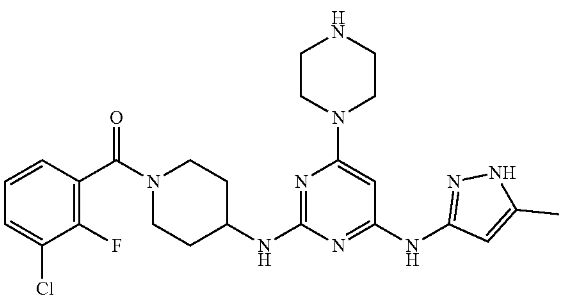
92
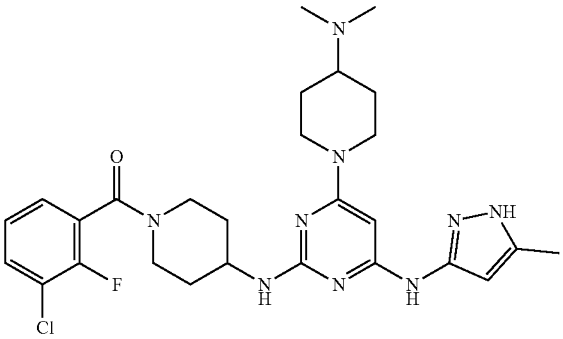
93
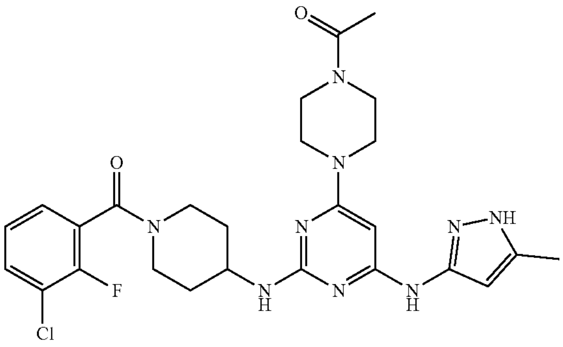
94
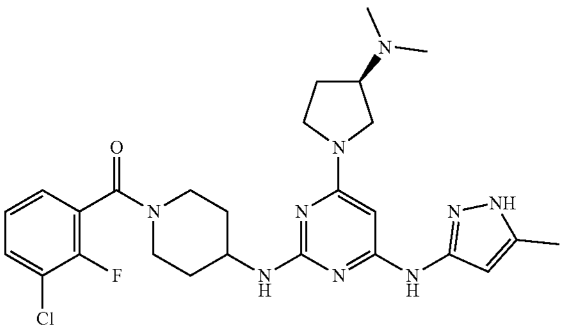
-continued
95
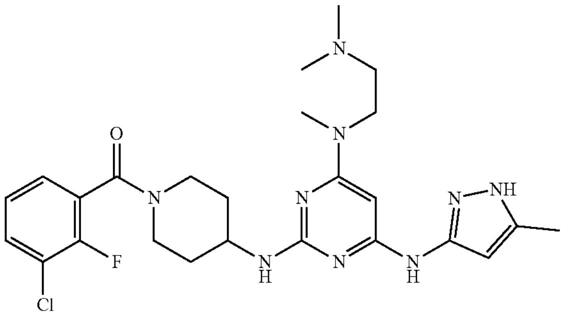
96
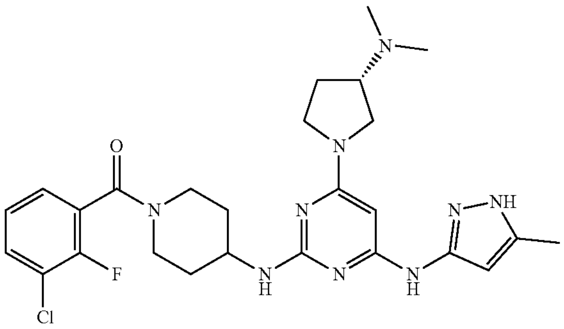
97
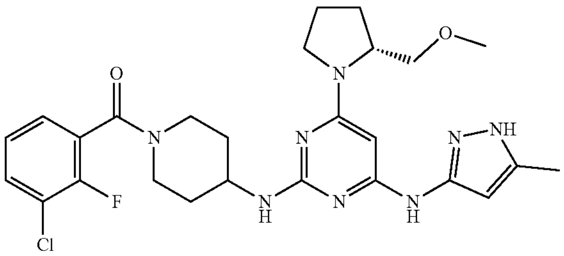
98
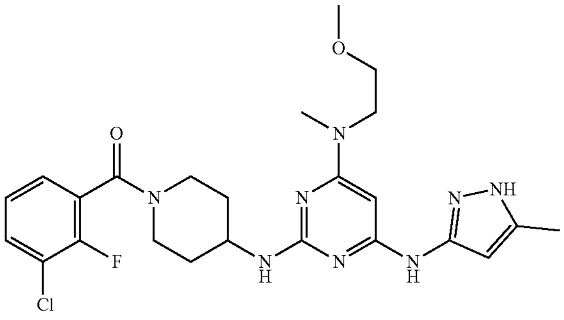
99
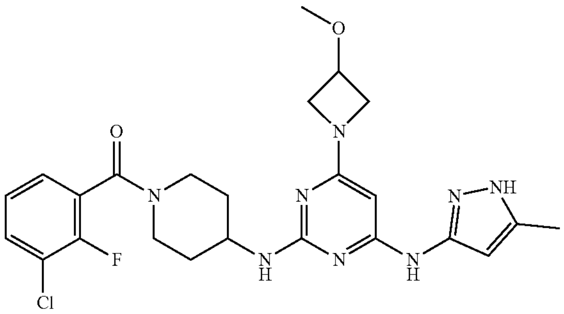

-continued
100
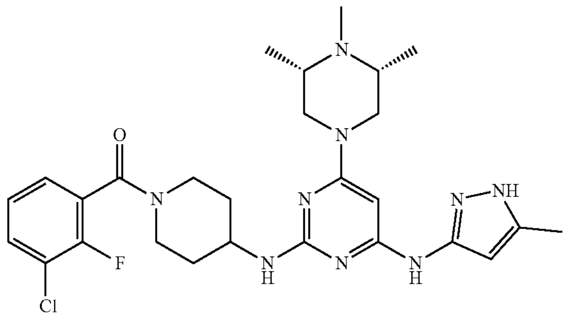
101
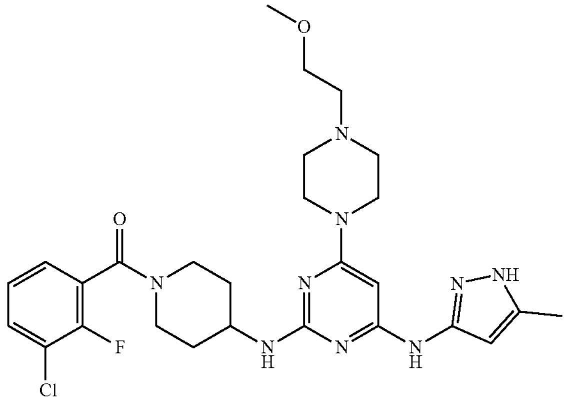
102
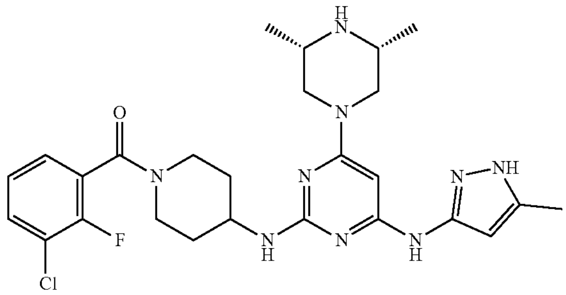
103
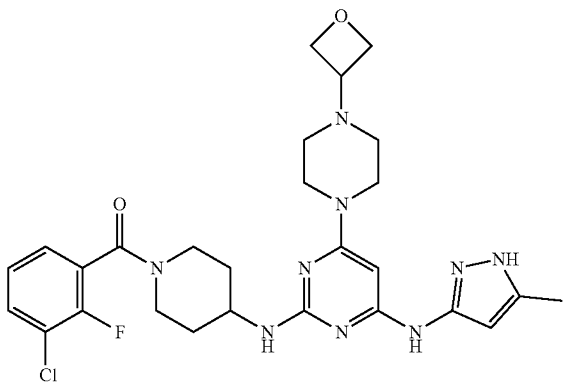
-continued
104
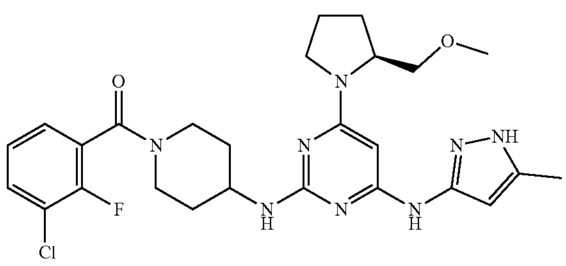
105
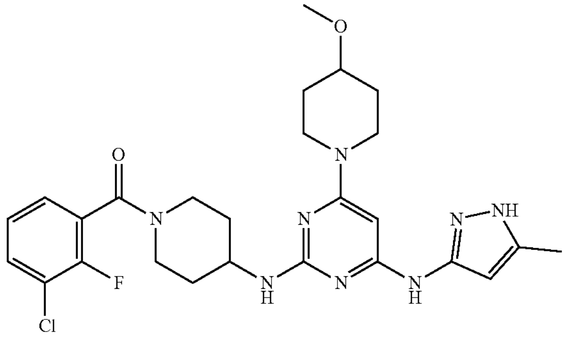
106
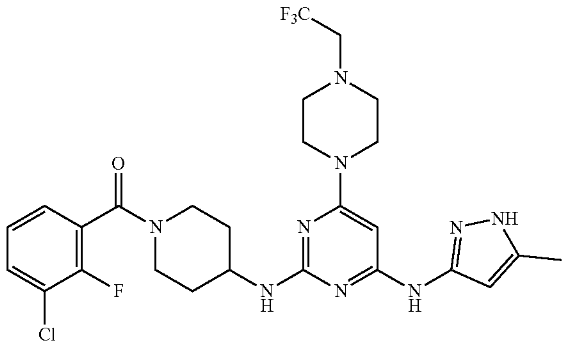
107
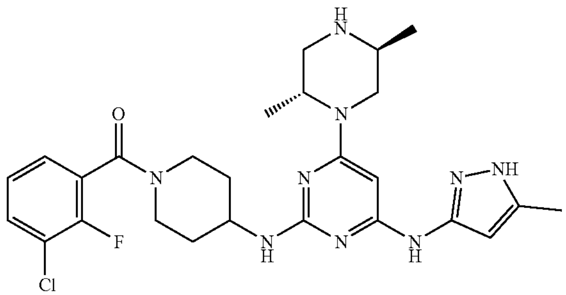
108
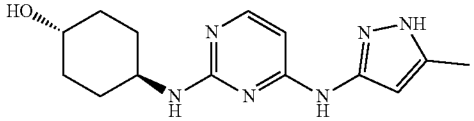

-continued
109
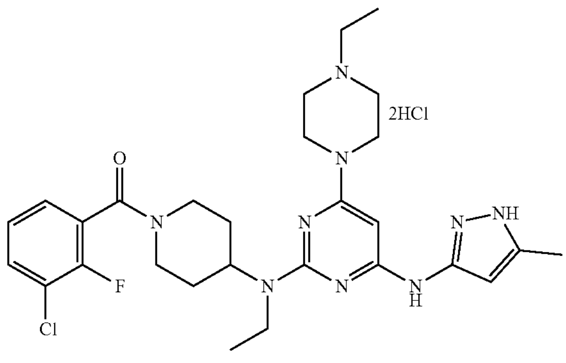
110
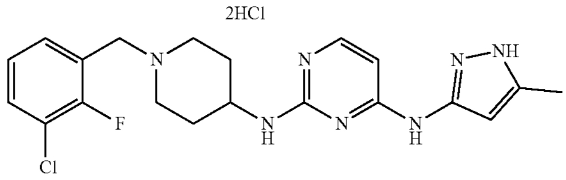
111
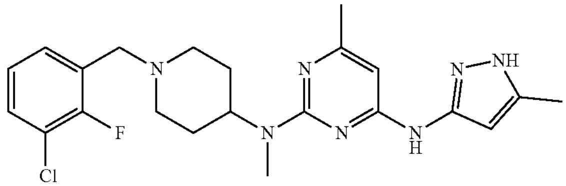
112
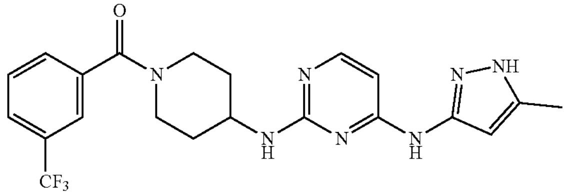
113
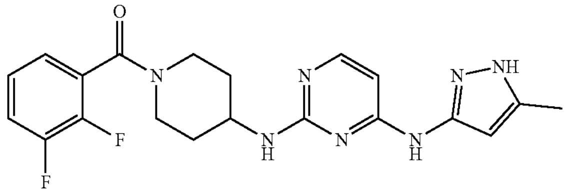
114
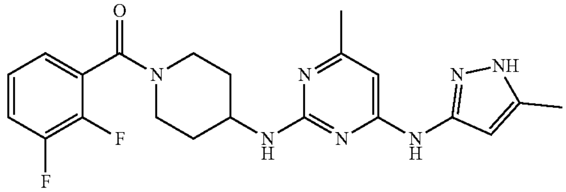
-continued
115
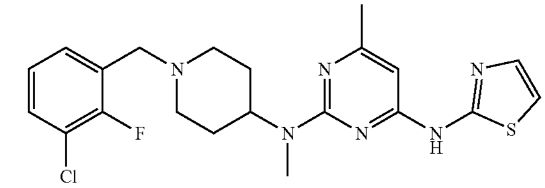
116
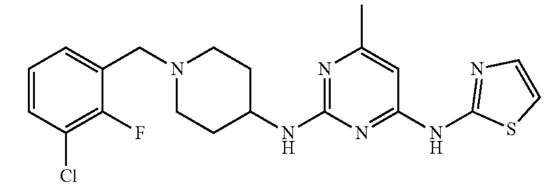
117
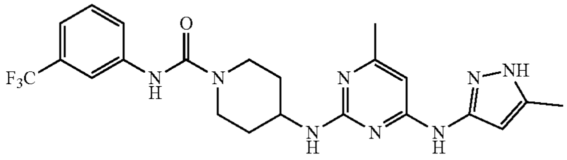
118
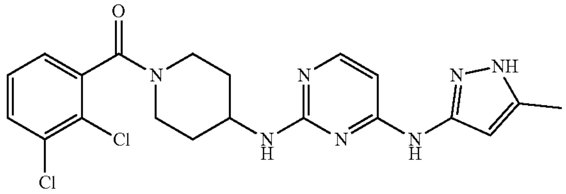
119
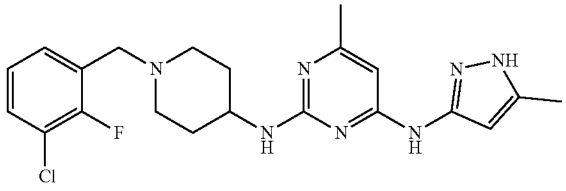
120
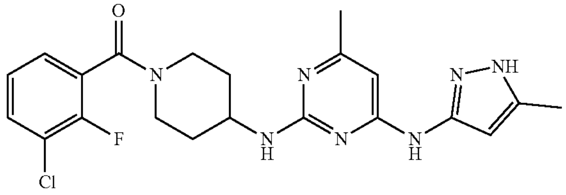
121
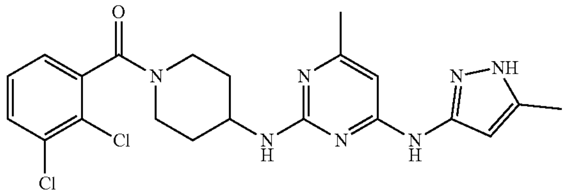

-continued
122
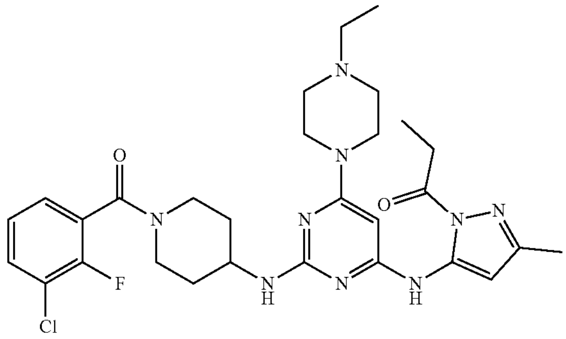
123
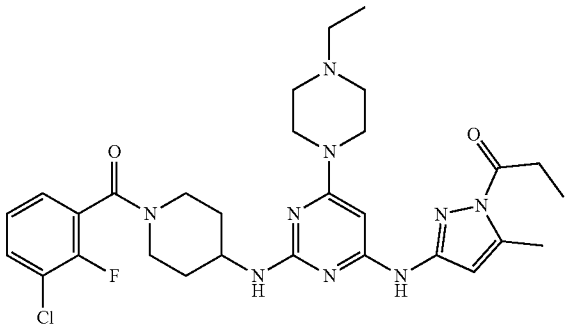
124
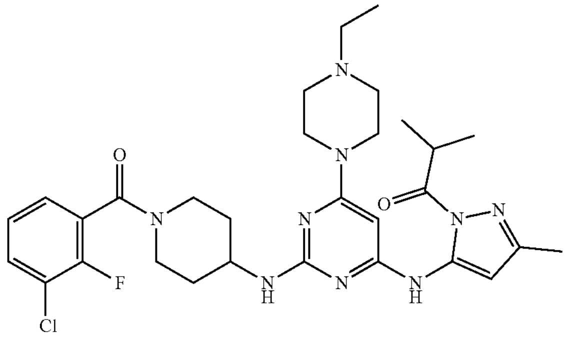
-continued
125
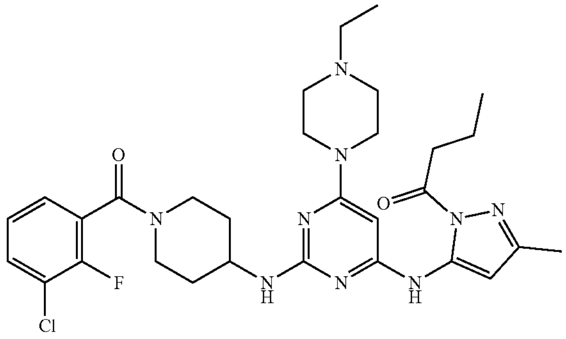
126
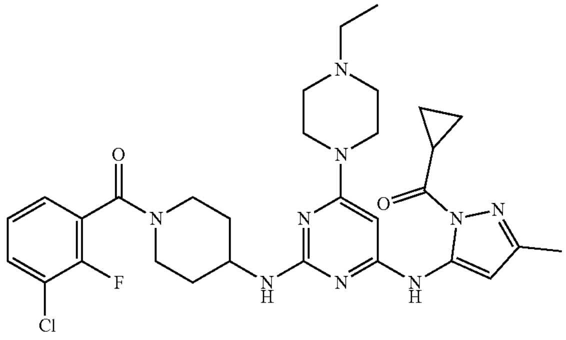
127
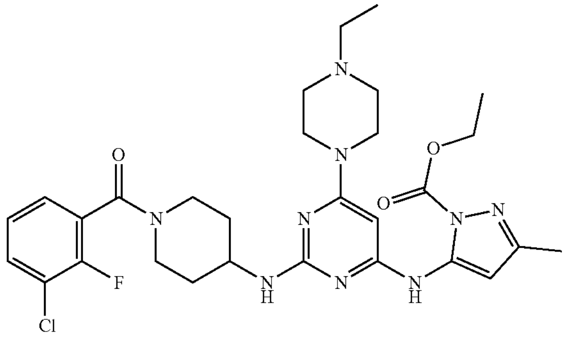
Provided below are exemplary methods for preparing the above compounds and other compounds of this invention, as well as exemplary methods for determining their anti-cancer activities.
Example 1. Preparation of Compounds 1-127
Compounds 41, 71, and 72 were prepared according to the scheme shown below, which includes 6 steps.
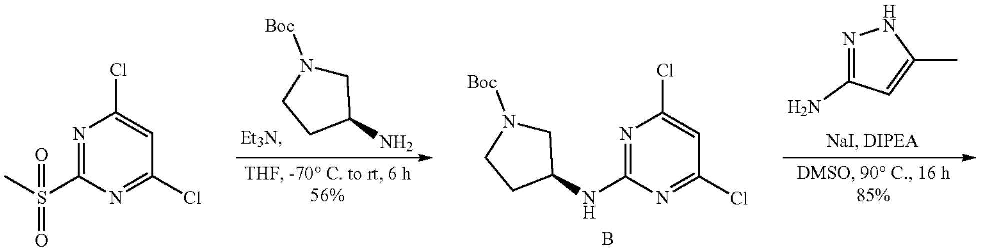
A
B -continued

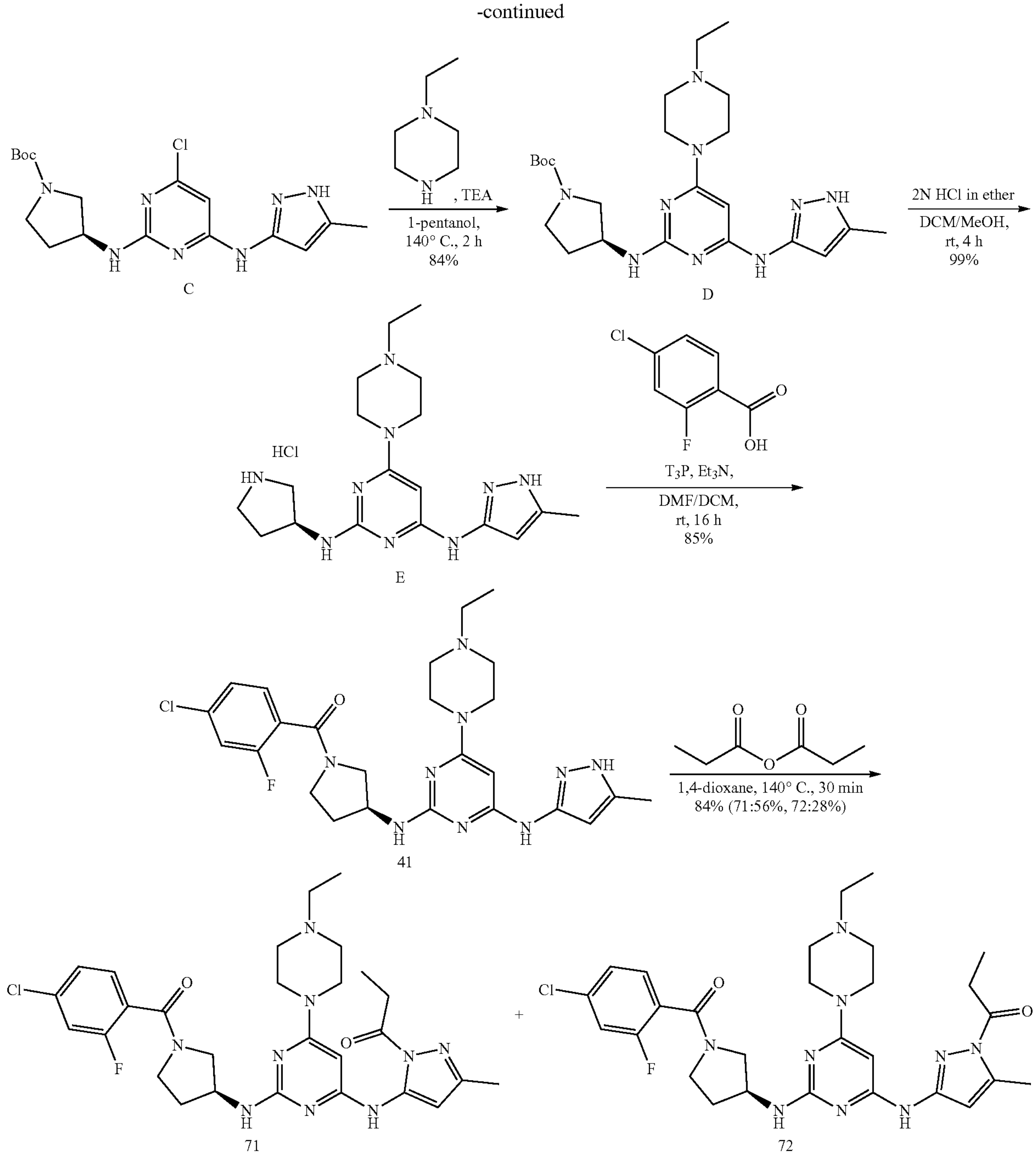

Step 1: Preparation of Compound B

Tert-butyl (S)-3-aminopyrrolidine-1-carboxylate (20 g, 105.7 mmol) was added dropwise at −70° C. over 1 h to a solution of the starting material 4,6-dichloro-2-(methylsulfonyl)pyrimidine (20 g, 88.1 mmol), triethylamine (25.5 mL, 176.2 mmol) in THF (200 mL). The reaction mixture was warmed up to room temperature, stirred for 6 h and then quenched with brine (100 mL). The aqueous phase was extracted with ethyl acetate (3×200 mL). The combined organic extracts were washed with water and brine, dried over magnesium sulfate, and filtered. The filtrate was concentrated to afford crude residue. The residue was purified by flash column chromatography over silica gel with n-hexane/ethyl acetate (4:1) to afford compound B (16.4 g, 49.3 mmol, 56% yield) as a white solid.

$^1$H NMR (400 MHz, $CDCl_3$) δ 6.65 (s, 1H), 5.42 (brs, 1H), 4.60-4.47 (m, 1H), 3.69 (dd, J=11.2, 6.0 Hz, 1H), 3.52-3.40 (m, 3H), 3.35-3.15 (m, 1H), 2.23 (m, 1H), 1.85-1.75 (m, 1H), 1.47 (s, 9H). ESMS m/z: 355.1 (M+23).

Step 2: Preparation of Compound C

A solution of compound B (7 g, 21.0 mmol), 3-amino-5-methylpyrazole (8.1 g, 84.0 mmol), triethylamine (3.5 mL, 25.2 mmol) and NaI (4.7 g, 31.5 mmol) in DMSO (70 mL) was stirred at 90° C. for 16 h. The solution was cooled down to room temperature and poured into water. A precipitate formed which was collected and purified by flash column chromatography over silica gel with n-hexane/ethyl acetate (1:1) to give compound C (7 g, 17.9 mmol, 85% yield) as a yellow solid.

$^1$H NMR (400 MHz, $CDCl_3$) δ 6.32 (s, 1H), 5.93 (s, 1H), 4.48 (brs, 1H), 3.85-3.60 (m, 1H), 3.60-3.40 (m, 4H), 2.31 (s, 3H), 1.46 (s, 9H). ESMS m/z: 394.1 (M+1).

Step 3: Preparation of Compound D

A solution of compound C (7 g, 17.8 mmol), 1-ethylpiperazine (4.1 g, 35.6 mmol) in 1-pentanol (14 mL) was heated at 140° C. for 2 h, then quenched with brine (100 mL). The aqueous phase was extracted with ethyl acetate (3×200 mL). The combined organic extracts were washed with water and brine, dried over magnesium sulfate, and filtered. The filtrate was concentrated to give the crude residue, which was purified by flash column chromatography over silica gel with ethyl acetate/methanol (90:10) to afford compound D (7 g, 14.9 mmol, 84% yield) as a yellow solid.

$^1$H NMR (400 MHz, $CDCl_3$) δ 5.87 (s, 1H), 5.62 (s, 1H), 4.70-4.39 (m, 1H), 3.80-3.30 (m, 7H), 2.52-2.40 (m, 6H), 2.27 (s, 3H), 2.24-2.04 (m, 2H), 1.46 (s, 9H), 1.11 (t, J=7.2 Hz, 3H). ESMS m/z: 472.1 (M+1).

Step 4: Preparation of Compound E

A solution of 2 N hydrochloric acid in ether (52 mL, 104 mmol) was added to a solution of compound D (9.8 g, 20.8 mmol) in dichloromethane/methanol (2:1, 75 mL) at room temperature. The resulting mixture was stirred at room temperature for 4 h and then concentrated in vacuo to get compound E (9.9 g, 2.1 mmol, 99% yield) as a yellow oil.

$^1$H NMR (400 MHz, DMSO-d6) δ 6.34 (s, 1H), 5.86 (s, 1H), 4.39 (s, 1H), 3.56-2.98 (m, 8H), 2.98-2.49 (m, 6H), 2.25 (s, 3H), 2.03-1.98 (m, 2H), 1.28 (t, J=7.6 Hz, 3H). ESMS m/z: 372.66 (M+1).

Step 5: Preparation of Compound 41

A solution of compound E (9 g, 18.7 mmol), triethylamine (15.7 mL, 112.0 mmol) and 4-chloro-2-fluorobenzoic acid (3.6 g, 20.6 mmol) and propanephosphonic acid anhydride (T3P; ≥50 wt % in ethyl acetate; 17.9 g, 28.1 mmol) were added to a solution of amine salt in DMF/dichloromethane (1:3, 50 mL) at room temperature. The resulting mixture was stirred at room temperature for 16 h and then quenched with brine (100 mL). The aqueous phase was extracted with ethyl acetate (3×200 mL). The combined organic extracts were washed with water and brine, dried over magnesium sulfate, and filtered. The filtrate was concentrated to afford the crude residue which was purified by flash column chromatography over silica gel with ethyl acetate/methanol (85:15) to give compound 41 (8.4 g, 15.9 mmol, 85% yield) as a white solid.

$^1$H NMR (400 MHz, $CD_3OD$) δ 7.46-7.25 (m, 3H), 5.95-5.75 (m, 1H), 5.62-5.45 (m, 1H), 4.53 and 4.36 (brs, 1H), 3.98-3.64 (m, 3H), 3.63-3.56 (m, 2H), 3.54-3.40 (m, 4H), 2.60-2.40 (m, 6H), 2.36-2.29 (m, 1H), 2.23 and 2.22 (s, 3H), 2.10-1.90 (m, 1H), 1.15 and 1.14 (t, J=7.2 Hz, 3H). ESMS m/z: 528.2 (M+1).

Step 6: Preparation of Compounds 71 and 72

A solution of propionic anhydride (1.7 mL, 13.29 mmol) in 1,4-dioxane (10 mL) was added to a solution of compound 41 (5.4 g, 10.23 mmol) in 1,4-dioxane (100 mL) at 140° C. The resulting mixture was stirred at 140° C. for 30 min, cooled to room temperature, and then concentrated in vacuo. The residue was purified by flash column chromatography over silica gel with n-hexane/ethyl acetate/triethylamine (60:35:5) to afford compound 71 (3.34 g, 5.73 mmol, 56% yield) and compound 72 (1.67 g, 2.86 mmol, 28% yield) as pale yellow solids.

Compound 71: $^1$H NMR (300 MHz, $CDCl_3$) δ 9.88 and 9.84 (brs, 1H), 7.34 and 7.32 (t, J=7.7 Hz, 1H), 7.12 (q, J=8.3 Hz, 1H), 7.05 (d, J=9.3 Hz, 1H), 6.51 and 6.42 (s, 1H), 5.30 and 5.25 (s, 1H), 4.72 (brs, 1H), 4.60-4.40 (m, 1H), 4.00-3.60 (m, 3H), 3.60-3.15 (m, 5H), 3.06 and 3.05 (q, J=8.3 Hz, 2H), 2.65-2.37 (m, 6H), 2.35-2.23 (m, 1H), 2.19 and 2.17 (s, 3H), 2.03-1.92 (m, 1H), 1.23-1.07 (m, 6H). ESMS m/z: 584.3 (M+1).

Compound 72: $^1$H NMR (400 MHz, $CDCl_3$) δ 7.35 (q, J=6.8 Hz, 1H), 7.15 (q, J=9.7 Hz, 1H), 7.09 (d, J=9.6 Hz, 1H), 6.35 and 6.30 (s, 1H), 6.04 and 6.00 (s, 1H), 5.03 and 4.93 (brs, 1H), 4.55 and 4.44 (d, J=5.7 Hz, 1H), 4.03-3.34 (m, 7H), 3.30-3.16 (m, 1H), 3.04 (t, J=7.8 Hz, 2H), 2.60-2.36 (m, 5H), 2.47-2.36 (m, 4H), 2.35-2.18 (m, 2H), 1.29-1.19 (m, 3H), 1.11 (t, J=7.0 Hz, 3H). ESMS m/z: 584.3 (M+1).

Compounds 86, 122, and 123 were prepared according to the scheme shown below, which includes 5 steps.

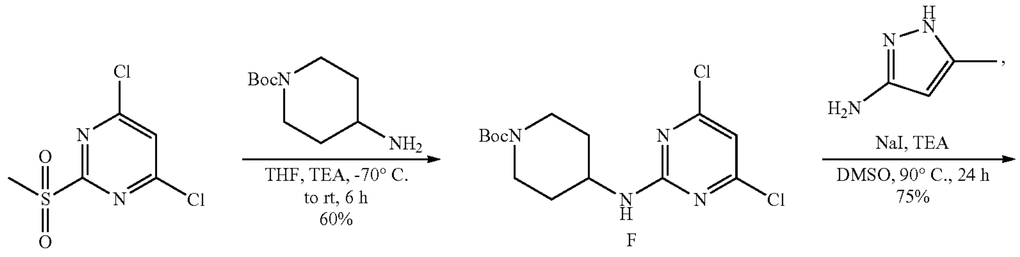

A F

-continued

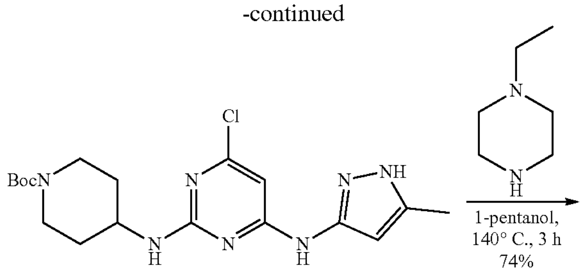

G

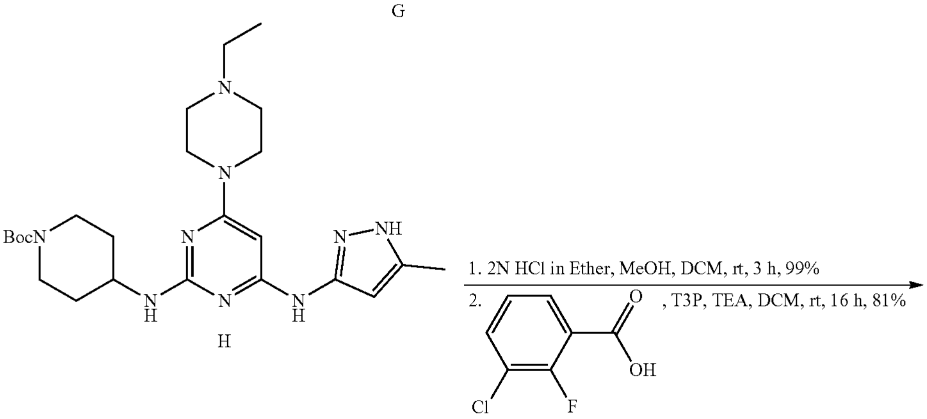

H

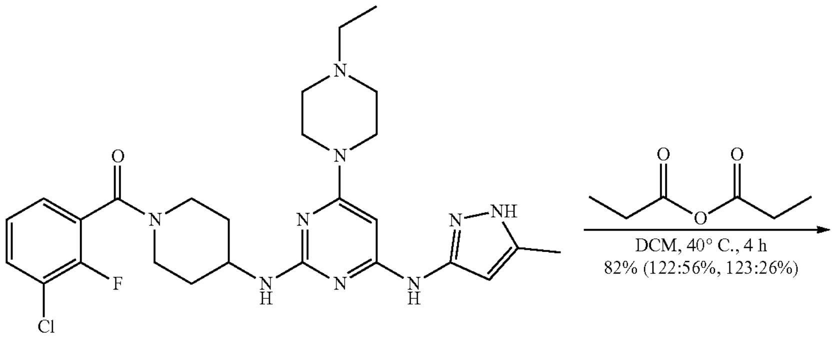

86

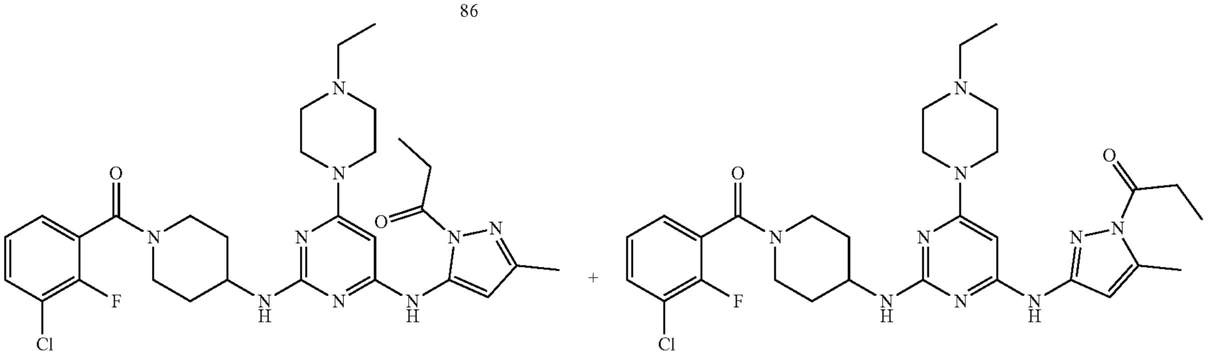

122 123

Step 1: Preparation of Compound F

Tert-butyl 4-aminopiperidine-1-carboxylate (20 g, 100 mmol) was added dropwise at −70° C. over 1 h to a solution of the starting material 4,6-dichloro-2-(methylsulfonyl)pyrimidine (20 g, 88.1 mmol), triethylamine (25.5 mL, 176.2 mmol) in THF (200 mL). The reaction mixture was warmed up to room temperature, stirred for 6 h and then quenched with brine (100 mL). The aqueous phase was extracted with ethyl acetate (3×200 mL). The combined organic extracts were washed with water and brine, dried over magnesium sulfate, and filtered. The filtrate was concentrated to afford crude residue. The residue was purified by flash column chromatography over silica gel with n-hexane/ethyl acetate (4:1) to afford compound F (16.4 g, 49.3 mmol, 56% yield) as a white solid.

$^1$H NMR (400 MHz, $CDCl_3$) δ 6.64 (s, 1H), 5.27 (brs, 1H), 4.25-3.80 (m, 4H), 2.97 (t, J=11.9 Hz, 2H), 2.03 (d, J=9.6 Hz, 2H), 1.49 (s, 9H), 1.46-1.34 (m, 1H). ESMS m/z: 369.1 (M+23).

Step 2: Preparation Compound G

A solution of compound F (40 g, 115 mmol), 3-amino-5-methylpyrazole (44.7 g, 461 mmol), triethylamine (32 mL, 230 mmol) and NaI (19 g, 115 mmol) in DMSO (60 mL) was stirred at 90° C. for 24 h. The solution was cooled down to room temperature and poured into water. A precipitate was formed, collected, and purified by flash column chromatography over silica gel with n-hexane/ethyl acetate (1:1) to give compound G (35 g, 86 mmol, 75% yield) as a yellow solid.

$^1$H NMR (400 MHz, $CDCl_3$) δ 6.35 (s, 1H), 6.08 (s, 1H), 4.20-3.87 (m, 4H), 2.97 (t, J=11.6 Hz, 2H), 2.34 (s, 3H), 2.05 (d, J=13.3 Hz, 2H), 1.49 (s, 9H), 1.46-1.34 (m, 1H). ESMS m/z: 408.2 (M+1).

Step 3: Preparation of Compound H

A solution of compound G (20 g, 49.1 mmol), 1-ethylpiperazine (11.2 g, 98.3 mmol) in 1-pentanol (20 mL) was heated at 140° C. for 3 h, then quenched with brine (100 mL). The aqueous phase was extracted with ethyl acetate (3×200 mL). The combined organic extracts were washed with water and brine, dried over magnesium sulfate, and filtered. The filtrate was concentrated to give crude residue, which was purified by flash column chromatography over silica gel with ethyl acetate/methanol (90:10) to afford compound H (17.7 g, 36.3 mmol, 74% yield) as a yellow solid.

$^1$H NMR (400 MHz, $CDCl_3$) δ 5.86 (s, 1H), 5.80 (s, 1H), 4.04 (brs, 1H), 3.94 (brs, 1H), 3.68-3.52 (m, 4H), 2.97 (t, J=11.7 Hz, 2H), 2.54-2.49 (m, 6H), 2.50-2.43 (m, 4H), 2.30 (s, 3H), 2.04 (d, J=8.0 Hz, 2H), 1.49 (s, 9H), 1.47-1.37 (m, 1H), 1.14 (t, J=7.2 Hz, 3H). ESMS m/z: 486.3 (M+1).

Step 4: Preparation of Compound 86

A solution of 2 N hydrochloric acid in ether (129 mL, 257 mmol) was added to a solution of compound H (25 g, 51.5 mmol) in dichloromethane/methanol (2:1, 129 mL) at room temperature. The resulting mixture was stirred at room temperature for 3 h and then concentrated in vacuo to give a HCl salt of compound H without further purification.

Then a solution of triethylamine (10.8 mL, 77.3 mmol) and 3-chloro-2-fluorobenzoic acid (9.9 g, 56.7 mmol) and propanephosphonic acid anhydride (T3P) (≥50 wt % in ethyl acetate; 39 g, 61.9 mmol) in dichloromethane (100 mL) was stirred for 2 h. The mixture were added to a solution of the HCl salt of compound H and triethylamine (28.7 mL, 206 mmol) in dichloromethane (250 mL) at room temperature. The resulting mixture was stirred at room temperature for 16 h and then quenched with brine (100 mL). The aqueous phase was extracted with ethyl acetate (3×500 mL). The combined organic extracts were washed with water and brine, dried over magnesium sulfate, and filtered. The filtrate was concentrated to afford a crude residue. The residue was purified by flash column chromatography over silica gel with ethyl acetate/methanol (85:15) to give compound 86 (23 g, 42.5 mmol, 81% yield) as a white solid.

Compound 86: $^1$H NMR (400 MHz, $CDCl_3$) δ 7.44 (t, J=7.8 Hz, 1H), 7.29-7.22 (m, 1H), 7.14 (t, J=7.8 Hz, 1H), 5.86 (s, 1H), 5.66 (s, 1H), 4.58 (d, J=13.0 Hz, 1H), 4.09-3.98 (m, 1H), 3.57-3.47 (m, 5H), 3.29-3.02 (m, 2H), 2.50-2.38 (m, 6H), 2.28 (s, 3H), 2.16 (d, J=13.0 Hz, 1H), 2.06 (d, J=13.0 Hz, 1H), 1.62-1.46 (m, 2H), 1.11 (t, J=7.2 Hz, 3H). ESMS m/z: 542.2 (M+1).

Step 5: Preparation of Compounds 122 and 123

A solution of propionic anhydride (1.4 g, 10.8 mmol) in dichloromethane (200 mL) was added to a solution of compound 86 (5 g, 9.2 mmol) in dichloromethane (800 mL) at 40° C. The resulting mixture was stirred at 40° C. for 4 h, cooled to room temperature, and then concentrated in vacuo. The residue was purified by flash column chromatography over silica gel with n-hexane/ethyl acetate/triethylamine (60:35:5) to afford compound 122 (3.1 g, 5.2 mmol, 56% yield) and 123 (1.4 g, 2.4 mmol, 26% yield) as pale yellow solids.

Compound 122: $^1$H NMR (300 MHz, $CDCl_3$) δ 9.88 (brs, 1H), 7.45 (td, J=7.8, 1.8 Hz, 1H), 7.31-7.26 (m, 1H), 7.16 (t, J=7.8 Hz, 1H), 6.55 (s, 1H), 5.33 (s, 1H), 4.71 (brs, 1H), 4.64 (d, J=14.0 Hz, 1H), 4.14-3.97 (m, 1H), 3.57 (d, J=14.0 Hz, 1H), 3.54 (t, J=5.0 Hz, 4H), 3.47 (q, J=7.0 Hz, 1H), 3.23-3.00 (m, 3H), 2.53-2.39 (m, 6H), 2.25 (s, 3H), 2.22 (d, J=14.0 Hz, 1H), 2.10 (d, J=14.0 Hz, 1H), 1.58-1.47 (m, 2H), 1.24 and 1.21 (t, J=7.0 Hz, 3H), 1.12 (t, J=7.0 Hz, 3H). ESMS 598.3 (M+1).

Compound 123: $^1$H NMR (300 MHz, $CDCl_3$) δ 7.45 (t, J=7.8 Hz, 1H), 7.31-7.26 (m, 1H), 7.15 (t, J=7.8 Hz, 1H), 6.69 (brs, 1H), 6.22 (s, 1H), 6.09 (s, 1H), 4.66-4.54 (m, 2H), 4.11-3.95 (m, 1H), 3.59 (t, J=4.8 Hz, 4H), 3.57-3.48 (m, 1H), 3.21-2.99 (m, 4H), 2.57 (s, 3H), 2.53-2.39 (m, 6H), 2.18 (d, J=14.0 Hz, 1H), 2.06 (d, J=14.0 Hz, 1H), 1.59-1.49 (m, 2H), 1.25 (t, J=7.2 Hz, 3H), 1.14 and 1.12 (t, J=7.2 Hz, 3H). ESMS 598.3 (M+1).

Procedures similar to those described above were used to prepare compounds 1-40, 42-70, 73-85, 87-121, and 124-127.

Compound 1: $^1$H NMR (400 MHz, $CDCl_3$) δ 9.49 (brs, 1H), 7.87 and 7.86 (s, 1H), 7.43 (t, J=7.8 Hz, 1H), 7.22 and 7.20 (dd, J=8.4, 2.0 Hz, 1H), 7.17 and 7.12 (dd, J=9.2, 2.0 Hz, 1H), 5.38 and 5.34 (s, 1H), 5.04 and 4.98 (brs, 1H), 4.75-4.50 (m, 1H), 4.08-3.69 (m, 2H), 3.62-3.25 (m, 6H), 2.53-2.26 (m, 7H), 2.13-2.00 (m, 1H), 1.12 and 1.12 (t, J=7.2 Hz, 3H). ESMS m/z: 556.2 (M+1).

Compound 2: $^1$H NMR (400 MHz, $CDCl_3$) δ 9.30 (brs, 1H), 8.03 (s, 1H), 7.45-7.37 (m, 1H), 7.29-7.08 (m, 2H), 5.39 and 5.35 (s, 1H), 5.01 and 4.95 (brs, 1H), 4.84-4.54 (m, 1H), 4.34 (quin, J=6.8 Hz, 2H), 4.09-3.64 (m, 2H), 3.63-3.23 (m, 6H), 2.52-2.38 (m, 5H), 2.35 and 2.34 (s, 3H), 2.13-2.00 (m, 1H), 1.38 and 1.36 (t, J=7.2 Hz, 3H). ESMS m/z: 589.2 (M+1).

Compound 3: $^1$H NMR (400 MHz, DMSO-d6) δ 7.95 and 7.93 (s, 1H), 7.59-7.46 (m, 2H), 7.42-7.37 (m, 1H), 5.67 and 5.61 (s, 1H), 4.74-4.50 (m, 1H), 3.85-3.04 (m, 8H), 2.70-2.54 (m, 4H), 2.49-2.41 (m, 3H), 2.34-2.12 (m, 1H), 2.09-1.92 (m, 1H). ESMS m/z: 561.2 (M+1).

Compound 4: $^1$H NMR (300 MHz, $CDCl_3$) δ 7.48-7.41 (m, 1H), 7.29-7.22 (m, 1H), 7.09 and 7.07 (t, J=7.8 Hz, 1H), 6.46 and 6.43 (s, 1H), 5.92 and 5.88 (s, 1H), 5.72 (brs, 1H), 5.30 and 5.10 (brs, 1H), 4.58-4.40 (m, 1H), 3.87-3.22 (m, 8H), 2.45 and 2.37 (t, J=4.9 Hz, 4H), 2.34-2.26 (m, 6H), 2.25-2.12 (m, 1H), 2.02-1.84 (m, 1H). ESMS m/z: 531.2 (M+1).

Compound 5: $^1$H NMR (300 MHz, $CDCl_3$) δ 7.41 and 7.41 (t, J=8.9 Hz, 1H), 7.22 and 7.22 (dd, J=8.9, 6.2 Hz, 1H), 7.16 and 7.15 (t, J=8.9 Hz, 1H), 6.04 and 5.99 (brs, 1H), 5.98 and 5.94 (s, 1H), 4.76-4.55 (m, 1H), 4.15-3.32 (m, 9H), 2.75-2.50 (m, 6H), 2.29 and 2.28 (s, 3H), 2.24-2.01 (m, 2H), 1.21 and 1.19 (t, J=7.1 Hz, 3H). ESMS m/z: 529.2 (M+1).

Compound 6: $^1$H NMR (300 MHz, $CDCl_3$) δ 7.41-7.31 (m, 2H), 7.23-7.08 (m, 2H), 6.93 (d, J=3.6 Hz, 1H), 6.48 and 6.43 (s, 1H), 4.62-4.40 (m, 1H), 4.06-3.71 (m, 2H), 3.71-

3.17 (m, 6H), 2.57-2.39 (m, 6H), 2.37-1.95 (m, 2H), 1.13 (t, J=7.4 Hz, 3H). ESMS m/z: 515.2 (M+1).

Compound 7: $^1$H NMR (400 MHz, $CDCl_3$) δ 7.38 and 7.37 (t, J=8.6 Hz, 1H), 7.19 and 7.18 (t, J=8.6 Hz, 1H), 7.14 and 7.11 (dd, J=9.6, 2.0 Hz, 1H), 4.90 and 4.86 (s, 1H), 4.69 (brs, 1H), 4.58-4.37 (m, 1H), 4.07-3.94 (m, 1H), 3.84-3.43 (m, 6H), 3.43-3.14 (m, 1H), 2.52-2.14 (m, 9H), 1.99-1.65 (m, 6H), 1.12 and 1.11 (t, J=7.2 Hz, 3H). ESMS m/z: 502.2 (M+1).

Compound 8: $^1$H NMR (400 MHz, $CDCl_3$) δ 7.32-7.26 (m, 1H), 7.12-7.09 (m, 2H), 5.90 and 5.85 (s, 1H), 5.30 and 5.27 (s, 1H), 4.70-4.53 (m, 1H), 4.08-3.89 (m, 3H), 3.82-3.66 (m, 4H), 3.51-3.10 (m, 2H), 2.29 and 2.28 (s, 3H), 2.20 and 2.18 (s, 6H), 2.15-2.00 (m, 2H). ESMS m/z: 514.2 (M+1).

Compound 9: $^1$H NMR (300 MHz, $CDCl_3$) δ 7.31-7.24 (m, 1H), 7.19-7.09 (m, 2H), 5.89 and 5.86 (s, 1H), 5.55 and 5.52 (s, 1H), 4.72-4.47 (m, 1H), 4.37-4.00 (m, 2H), 3.90-3.57 (m, 2H), 3.54-3.13 (m, 4H), 2.69-2.55 (m, 1H), 2.34-2.03 (m, 7H), 1.27-1.02 (m, 6H). ESMS m/z: 528.2 (M+1).

Compound 10: $^1$H NMR (400 MHz, $CDCl_3$) δ 7.31 and 7.30 (t, J=7.7 Hz, 1H), 7.18-7.09 (m, 2H), 5.90 and 5.85 (s, 1H), 5.64 and 5.62 (s, 1H), 4.68-4.51 (m, 1H), 4.21-3.97 (m, 3H), 3.80-3.66 (m, 2H), 3.54-3.23 (m, 2H), 2.94-2.75 (m, 2H), 2.48-2.33 (m, 2H), 2.30 and 2.29 (s, 3H), 2.26-2.04 (m, 2H), 1.36 (d, J=6.4 Hz, 3H), 1.14 (d, J=6.4 Hz, 3H). ESMS m/z: 528.2 (M+1).

Compound 11: $^1$H NMR (300 MHz, $CD_3OD$) δ 7.49 (t, J=8.4 Hz, 1H), 7.40-7.31 (m, 2H), 5.80 (m, 1H), 4.71-4.51 (m, 2H), 4.06-3.34 (m, 7H), 2.44-2.30 (m, 5H), 2.23-2.02 (m, 2H). ESMS m/z: 512.1 (M+1).

Compound 12: $^1$H NMR (300 MHz, $CDCl_3$) δ 7.32-7.24 (m, 1H), 7.18-7.09 (m, 2H), 5.91 and 5.86 (s, 1H), 5.64 and 5.62 (s, 1H), 4.74-4.50 (m, 1H), 4.17-4.02 (m, 1H), 3.83-3.22 (m, 11H), 2.31 and 2.30 (s, 3H), 2.26-2.14 (m, 2H), 2.13 and 2.12 (s, 3H). ESMS m/z: 542.2 (M+1).

Compound 13: $^1$H NMR (400 MHz, $CDCl_3$) δ 7.30-7.25 (m, 1H), 7.17-7.09 (m, 2H), 5.91 and 5.86 (s, 1H), 5.61 and 5.59 (s, 1H), 4.72-4.52 (m, 1H), 4.16-3.98 (m, 1H), 3.80-3.64 (m, 2H), 3.62-3.41 (m, 7H), 3.40-3.22 (m, 5H), 2.60 (q, J=5.5 Hz, 2H), 2.54 (t, J=4.8 Hz, 2H), 2.50 (t, J=4.8 Hz, 2H), 2.30 and 2.29 (s, 3H), 2.26-2.17 (m, 1H), 2.15-2.04 (m, 1H). ESMS m/z: 558.2 (M+1).

Compound 14: $^1$H NMR (400 MHz, $CDCl_3$) δ 8.01 (s, 1H), 7.29-7.24 (m, 1H), 7.17-7.09 (m, 2H), 5.92 and 5.86 (s, 1H), 5.61 and 5.58 (s, 1H), 4.74-4.51 (m, 1H), 4.19-4.05 (m, 1H), 3.81-3.23 (m, 7H), 3.04-2.96 (m, 2H), 2.70 (t, J=4.8 Hz, 2H), 2.66 (t, J=4.8 Hz, 2H), 2.30 and 2.29 (s, 3H), 2.27-2.03 (m, 2H). ESMS m/z: 582.2 (M+1).

Compound 15: $^1$H NMR (400 MHz, $CDCl_3$) δ 7.30-7.27 (m, 1H), 7.17-7.09 (m, 2H), 5.92 and 5.86 (s, 1H), 5.60 and 5.58 (s, 1H), 4.70-4.51 (m, 1H), 4.16-3.90 (m, 3H), 3.80-3.64 (m, 2H), 3.52-3.24 (m, 2H), 2.69-2.55 (m, 2H), 2.30 and 2.29 (s, 3H), 2.28 and 2.27 (s, 3H), 2.25-2.03 (m, 5H), 1.16-1.07 (m, 6H). ESMS m/z: 542.2 (M+1).

Compound 16: $^1$H NMR (400 MHz, $CDCl_3$) δ 7.29-7.22 (m, 1H), 7.17-7.08 (m, 2H), 5.91 and 5.86 (s, 1H), 5.61 and 5.58 (s, 1H), 4.73-4.51 (m, 5H), 4.18-4.05 (m, 1H), 3.80-3.22 (m, 8H), 2.36 (t, J=5.0 Hz, 2H), 2.32 (t, J=5.0 Hz, 2H), 2.29 and 2.28 (s, 3H), 2.27-2.03 (m, 2H). ESMS m/z: 556.1 (M+1).

Compound 17: $^1$H NMR (400 MHz, $CDCl_3$) δ 7.34-7.26 (m, 1H), 7.18-7.09 (m, 2H), 5.92 and 5.87 (s, 1H), 5.55 and 5.52 (s, 1H), 4.65-4.50 (m, 1H), 4.10-3.99 (m, 1H), 3.80-3.46 (m, 5H), 3.46-3.21 (m, 5H), 3.01 and 2.97 (s, 3H), 2.29 and 2.28 (s, 3H), 2.25-2.16 (m, 2H). ESMS m/z: 503.2 (M+1).

Compound 18: $^1$H NMR (400 MHz, $CDCl_3$) δ 7.33-7.27 (m, 1H), 7.19-7.09 (m, 2H), 5.92 and 5.86 (s, 1H), 5.40 and 5.37 (s, 1H), 4.71-4.52 (m, 1H), 4.08-3.98 (m, 1H), 3.82-3.06 (m, 7H), 2.83-2.68 (m, 1H), 2.35-2.00 (m, 12H), 1.91-1.74 (m, 1H). ESMS m/z: 528.2 (M+1).

Compound 19: $^1$H NMR (300 MHz, $CDCl_3$) δ 7.33 (t, J=7.2 Hz, 1H), 7.20-7.08 (m, 2H), 5.87 and 5.83 (s, 1H), 5.36 and 5.33 (s, 1H), 4.64-4.50 (m, 1H), 4.34-4.02 (m, 2H), 3.91-3.61 (m, 5H), 3.57-3.35 (m, 1H), 3.32 and 3.31 (s, 3H), 3.28-3.16 (m, 1H), 2.28 and 2.27 (s, 3H), 2.26-2.10 (m, 2H). ESMS m/z: 501.1 (M+1).

Compound 20: $^1$H NMR (300 MHz, $CDCl_3$) δ 7.42 (t, J=7.6 Hz, 1H), 7.25-7.19 (m, 1H), 7.10 and 7.09 (t, J=7.6 Hz, 1H), 5.93 and 5.87 (s, 1H), 5.39 and 5.36 (s, 1H), 4.75-4.52 (m, 1H), 4.11-3.98 (m, 1H), 3.82-3.06 (m, 7H), 2.83-2.67 (m, 1H), 2.34-2.00 (m, 12H), 1.92-1.74 (m, 1H). ESMS m/z: 528.2 (M+1).

Compound 21: $^1$H NMR (300 MHz, $CDCl_3$) δ 7.43 (t, J=7.2 Hz, 1H), 7.26-7.18 (m, 1H), 7.09 (t, J=7.8 Hz, 1H), 5.92 and 5.86 (s, 1H), 5.66 and 5.63 (s, 1H), 4.75-4.52 (m, 1H), 4.41-4.20 (m, 2H), 4.15-4.00 (m, 1H), 3.84-3.21 (m, 3H), 2.83-2.64 (m, 2H), 2.53-2.36 (m, 1H), 2.35-2.26 (m, 9H), 2.25-2.02 (m, 2H), 1.92-1.75 (m, 2H), 1.54-1.32 (m, 2H). ESMS m/z: 542.2 (M+1).

Compound 22: $^1$H NMR (300 MHz, $CDCl_3$) δ 7.47-7.40 (m, 1H), 7.33-7.27 (m, 1H), 7.16-7.08 (m, 1H), 5.90 and 5.85 (s, 1H), 5.46-5.36 (m, 2H), 4.59 (brs, 1H), 4.10-3.60 (m, 3H), 3.60-3.10 (m, 5H), 2.88-2.75 (m, 1H), 2.35-2.24 (m, 11H), 1.96-1.80 (m, 2H). ESMS m/z: 528.2 (M+1).

Compound 23: $^1$H NMR (300 MHz, $CDCl_3$) δ 7.43 (t, J=7.5 Hz, 1H), 7.25-7.17 (m, 1H), 7.10 (t, J=7.8 Hz, 1H), 5.94 and 5.88 (s, 1H), 5.43 and 5.41 (s, 1H), 4.75-4.56 (m, 1H), 4.39-4.00 (m, 2H), 3.84-3.54 (m, 3H), 3.53-3.15 (m, 7H), 2.29 and 2.28 (s, 3H), 2.24-2.08 (m, 2H), 2.07-1.81 (m, 4H). ESMS m/z: 529.2 (M+1).

Compound 24: $^1$H NMR (400 MHz, $CDCl_3$) δ 7.42 (t, J=7.4 Hz, 1H), 7.21 (t, J=6.6 Hz, 1H), 7.09 (t, J=8.0 Hz, 1H), 5.95 and 5.89 (s, 1H), 5.43 and 5.40 (s, 1H), 4.72-4.52 (m, 1H), 4.33-4.07 (m, 2H), 3.83-3.64 (m, 2H), 3.52-3.10 (m, 8H), 2.29 and 2.28 (s, 3H), 2.27-2.06 (m, 2H), 2.06-1.85 (m, 4H). ESMS m/z: 529.2 (M+1).

Compound 25: $^1$H NMR (300 MHz, $CDCl_3$) δ 7.42 and 7.42 (t, J=7.2 Hz, 1H), 7.24-7.17 (m, 1H), 7.09 (t, J=7.8 Hz, 1H), 5.91 and 5.85 (s, 1H), 5.29 and 5.26 (s, 1H), 4.71 and 4.58 (brs, 1H), 4.09-3.90 (m, 3H), 3.81-3.65 (m, 4H), 3.51-3.10 (m, 3H), 2.29 and 2.28 (s, 3H), 2.23-2.03 (m, 8H). ESMS m/z: 514.2 (M+1).

Compound 26: $^1$H NMR (300 MHz, $CD_3OD$) δ 7.59 (q, J=8.2 Hz, 1H), 7.43-7.32 (m, 1H), 7.32-7.21 (m, 1H), 5.97-5.73 (m, 2H), 4.55 and 4.40 (quin, J=5.6 Hz, 1H), 4.00-3.77 (m, 1H), 3.76-3.37 (m, 7H), 3.07 and 2.97 (t, J=5.3 Hz, 4H), 2.40-2.24 (m, 1H), 2.24 and 2.22 (s, 3H), 2.14-1.97 (m, 1H). ESMS m/z: 500.1 (M+1).

Compound 27: $^1$H NMR (400 MHz, $CDCl_3$) δ 7.43 (t, J=7.6 Hz, 1H), 7.25-7.20 (m, 1H), 7.10 (t, J=7.8 Hz, 1H), 5.93 and 5.88 (s, 1H), 5.51 and 5.49 (s, 1H), 4.69 and 4.60 (brs, 1H), 4.15-4.04 (m, 1H), 3.83-3.44 (m, 5H), 3.42-3.25 (m, 1H), 2.98 and 2.94 (s, 3H), 2.41-2.35 (m, 2H), 2.32-2.25 (m, 7H), 2.23 (s, 3H), 2.20-2.05 (m, 1H). ESMS m/z: 516.2 (M+1).

Compound 28: $^1$H NMR (400 MHz, $CDCl_3$) δ 7.43 (t, J=7.4 Hz, 1H), 7.24-7.18 (m, 1H), 7.09 (t, J=7.8 Hz, 1H), 5.92 and 5.87 (s, 1H), 5.65 and 5.62 (s, 1H), 4.74-4.54 (m, 1H), 4.17-4.03 (m, 1H), 3.99-3.66 (m, 3H), 3.52-3.07 (m, 8H), 2.30 and 2.29 (s, 3H), 2.27-2.04 (m, 2H), 1.95-1.80 (m, 2H), 1.63-1.42 (m, 2H). ESMS m/z: 529.2 (M+1).

Compound 29: $^1$H NMR (400 MHz, $CDCl_3$) δ 7.42 and 7.42 (d, J=8.4 Hz, 2H), 7.36 and 7.34 (d, J=8.4 Hz, 2H), 5.91 and 5.85 (s, 1H), 5.62 and 5.57 (s, 1H), 4.69 and 4.56 (brs, 1H), 4.20-4.14 (m, 1H), 3.77-3.66 (m, 2H), 3.64-3.40 (m, 8H), 2.50-2.40 (m, 6H), 2.29 and 2.28 (s, 3H), 2.26-2.17 (m, 1H), 2.14-2.05 (m, 1H), 1.12 and 1.11 (t, J=7.2 Hz, 3H). ESMS m/z: 510.2 (M+1).

Compound 30: $^1$H NMR (300 MHz, $CDCl_3$) δ 7.34-7.26 (m, 2H), 7.04 (t, J=8.0 Hz, 1H), 5.82 (s, 1H), 5.58 (s, 1H), 4.60-4.46 (m, 1H), 3.71 (s, 2H), 3.54 (t, J=5.0 Hz, 4H), 2.88-2.77 (m, 2H), 2.70-2.62 (m, 1H), 2.51-2.39 (m, 5H), 2.38-2.27 (m, 4H), 2.26 (s, 3H), 1.75-1.61 (m, 1H). ESMS m/z: 500.2 (M+1).

Compound 31: $^1$H NMR (400 MHz, $CDCl_3$) δ 7.32-7.26 (m, 2H), 7.04 (td, J=7.8, 1.2 Hz, 1H), 5.83 (s, 1H), 5.57 (s, 1H), 4.60-4.48 (m, 1H), 3.70 (s, 2H), 3.54 (t, J=5.0 Hz, 4H), 2.88-2.76 (m, 2H), 2.74-2.66 (m, 1H), 2.49-2.38 (m, 7H), 2.36-2.26 (m, 1H), 2.24 (s, 3H), 1.72-1.61 (m, 1H), 1.10 (t, J=7.2 Hz, 3H). ESMS m/z: 514.2 (M+1).

Compound 32: $^1$H NMR (400 MHz, $CDCl_3$) δ 7.42 and 7.41 (d, J=11.8 Hz, 1H), 7.25-7.23 (m, 1H), 7.22 and 7.20 (t, J=7.6 Hz, 1H), 5.91 and 5.86 (s, 1H), 5.65 and 5.64 (s, 1H), 4.57 (brs, 1H), 4.11-4.00 (m, 1H), 3.80-3.68 (m, 1H), 3.63-3.47 (m, 5H), 3.45-3.14 (m, 2H), 2.51-2.40 (m, 6H), 2.29 and 2.28 (s, 3H), 2.27-2.02 (m, 2H), 1.12 (t, J=7.6 Hz, 3H). ESMS m/z: 544.2 (M+1).

Compound 33: $^1$H NMR (400 MHz, $CDCl_3$) δ 7.36-7.30 (m, 2H), 7.23 and 7.23 (d, J=8.0 Hz, 1H), 5.91 and 5.84 (s, 1H), 5.64 and 5.61 (s, 1H), 4.65 and 4.56 (brs, 1H), 4.12-4.00 (m, 1H), 3.80-3.70 (m, 2H), 3.65-3.40 (m, 6H), 2.53-2.40 (m, 6H), 2.36 (s, 3H), 2.29 and 2.28 (s, 3H), 2.25-2.16 (m, 1H), 2.15-2.03 (m, 1H), 1.12 and 1.11 (t, J=7.2 Hz, 3H). ESMS m/z: 524.3 (M+1).

Compound 34: $^1$H NMR (400 MHz, $CDCl_3$) δ 7.22-7.07 (m, 3H), 5.91 and 5.86 (s, 1H), 5.66 (s, 1H), 4.55 (brs, 1H), 4.15-4.05 (m, 1H), 3.79-3.32 (m, 7H), 3.20-3.13 (m, 1H), 2.54-2.40 (m, 6H), 2.30-2.25 (m, 6H), 2.15-2.05 (m, 2H), 1.13 and 1.12 (t, J=7.0 Hz, 3H). ESMS m/z: 524.3 (M+1).

Compound 35: $^1$H NMR (300 MHz, $CDCl_3$) δ 7.43 (t, J=6.6 Hz, 1H), 7.24-7.18 (m, 1H), 7.09 (t, J=7.8 Hz, 1H), 5.93 and 5.87 (s, 1H), 5.63 and 5.60 (s, 1H), 4.72 and 4.78 (brs, 1H), 4.17-4.07 (m, 1H), 3.82-3.24 (m, 8H), 2.46-2.37 (m, 4H), 2.35-2.28 (m, 6H), 2.57-2.04 (m, 2H). ESMS m/z: 514.2 (M+1).

Compound 36: $^1$H NMR (300 MHz, $CDCl_3$) δ 7.31-7.26 (m, 1H), 7.18-7.08 (m, 2H), 5.92 and 5.86 (s, 1H), 5.63 and 5.61 (s, 1H), 4.73-4.51 (m, 1H), 4.16-4.01 (m, 1H), 3.82-3.54 (m, 3H), 3.54-3.23 (m, 4H), 2.49-2.37 (m, 4H), 2.33 and 2.31 (s, 3H), 2.30 and 2.29 (s, 3H), 2.27-2.19 (m, 1H), 2.16-2.03 (m, 1H). ESMS m/z: 514.2 (M+1).

Compound 37: $^1$H NMR (400 MHz, $CDCl_3$) δ 7.39-7.30 (m, 2H), 7.06 and 7.03 (t, J=8.8 Hz, 1H), 5.89 and 5.85 (s, 1H), 5.73 and 5.71 (s, 1H), 4.56 (brs, 1H), 3.99-3.80 (m, 1H), 3.80-3.50 (m, 6H), 3.46-3.24 (m, 2H), 2.62-2.45 (m, 6H), 2.31 and 2.29 (s, 3H), 2.23-2.15 (m, 2H), 1.17 and 1.15 (t, J=7.2 Hz, 3H). ESMS m/z: 528.2 (M+1).

Compound 38: $^1$H NMR (400 MHz, $CDCl_3$) δ 7.43 and 7.43 (t, J=7.5 Hz, 1H), 7.21 and 7.20 (q, J=7.5 Hz, 1H), 7.09 (t, J=7.5 Hz, 1H), 5.93 and 5.87 (s, 1H), 5.62 and 5.59 (s, 1H), 4.72 and 4.58 (brs, 1H), 4.13 (m, 1H), 3.82-3.66 (m, 2H), 3.62-3.42 (m, 5H), 3.41-3.25 (m, 1H), 2.51-2.40 (m, 6H), 2.31 and 2.29 (s, 3H), 2.28-2.21 (m, 1H), 2.16-2.05 (m, 1H), 1.12 and 1.12 (t, J=7.2 Hz, 3H). ESMS m/z: 528.3 (M+1).

Compound 39: $^1$H NMR (700 MHz, DMSO-d6) δ 8.70 (brs, 1H), 7.68 and 7.64 (t, J=8.1 Hz, 1H), 7.60 and 7.57 (dd, J=9.8, 1.4 Hz, 1H), 6.51 (brs, 1H), 6.06 (brs, 1H), 5.80 (brs, 1H), 4.41 and 4.20 (brs, 1H), 3.85-3.73 (m, 1H), 3.67-3.62 (m, 1H), 3.61-3.50 (m, 1H), 3.50-3.40 (m, 3H), 2.49-2.22 (m, 6H), 2.16 and 2.13 (s, 3H), 2.11-2.09 (m, 1H), 2.03-1.86 (m, 1H), 1.07-0.99 (m, 3H). ESMS m/z: 528.2 (M+1).

Compound 40: $^1$H NMR (700 MHz, $CDCl_3$) δ 7.18 (t, J=7.0 Hz, 1H), 7.04 (s, 1H), 5.93 and 5.87 (s, 1H), 5.63 and 5.60 (s, 1H), 4.70 and 4.58 (brs, 1H), 4.11 (m, 1H), 3.79-3.68 (m, 2H), 3.60-3.57 (m, 1H), 3.56-3.46 (m, 4H), 3.41-3.27 (m, 1H), 2.50-2.41 (m, 6H), 2.30 and 2.29 (s, 3H), 2.27-2.22 (m, 1H), 2.16-2.08 (m, 1H), 1.12 and 1.11 (t, J=7.0 Hz, 3H). ESMS m/z: 546.2 (M+1).

Compound 42: $^1$H NMR (400 MHz, $CDCl_3$) δ 7.33-7.23 (m, 1H), 7.01-6.92 (m, 1H), 5.87 and 5.84 (s, 1H), 5.74 and 5.72 (s, 1H), 4.54 (brs, 1H), 3.96-3.80 (m, 2H), 3.78-3.50 (m, 5H), 3.49-3.26 (m, 2H), 2.60-2.50 (m, 6H), 2.31 and 2.30 (s, 3H), 2.22-2.03 (m, 2H), 1.17 and 1.16 (t, J=7.0 Hz, 3H). ESMS m/z: 530.3 (M+1).

Compound 43: $^1$H NMR (400 MHz, $CDCl_3$) δ 7.23-7.10 (m, 2H), 5.91 and 5.86 (s, 1H), 5.70 and 5.68 (s, 1H), 4.63 and 4.58 (brs, 1H), 4.02-3.95 (m, 1H), 3.80-3.70 (m, 2H), 3.65-3.47 (m, 5H), 3.44-3.25 (m, 1H), 2.55-2.42 (m, 6H), 2.30 and 2.29 (s, 3H), 2.22-2.03 (m, 2H), 1.14 and 1.13 (t, J=7.2 Hz, 3H). ESMS m/z: 546.2 (M+1).

Compound 44: $^1$H NMR (400 MHz, $CDCl_3$) δ 7.34 and 7.32 (t, J=8.0 Hz, 1H), 6.92-6.78 (m, 2H), 5.92 and 5.86 (s, 1H), 5.63 and 5.60 (s, 1H), 4.73-4.53 (m, 1H), 4.15-4.04 (m, 1H), 3.80-3.52 (m, 3H), 3.52-3.25 (m, 4H), 2.52-2.39 (m, 6H), 2.31 and 2.29 (s, 3H), 2.28-2.18 (m, 1H), 2.17-2.05 (m, 1H), 1.11 and 1.11 (t, J=7.2 Hz, 3H). ESMS m/z: 512.3 (M+1).

Compound 45: $^1$H NMR (400 MHz, $CDCl_3$) δ 7.18 and 7.15 (d, J=7.0 Hz, 2H), 5.88 and 5.84 (s, 1H), 5.76 and 5.73 (s, 1H), 4.57 (brs, 1H), 4.01-3.85 (m, 1H), 3.82-3.53 (m, 6H), 3.52-3.40 (m, 2H), 2.58-2.45 (m, 6H), 2.30 and 2.29 (s, 3H), 2.20-2.15 (m, 2H), 1.20-1.10 (m, 3H). ESMS m/z: 546.2 (M+1).

Compound 46: $^1$H NMR (300 MHz, $CD_3OD$) δ 7.74-7.55 (m, 3H), 5.87 and 5.82 (s, 1H), 4.56 and 4.42 (brs, 1H), 4.01-3.77 (m, 1H), 3.77-3.62 (m, 4H), 3.62-3.57 (m, 3H), 3.57-3.40 (m, 1H), 2.83-2.57 (m, 6H), 2.40-2.30 (m, 1H), 2.24 and 2.22 (s, 3H), 2.15-2.02 (m, 1H), 1.27-1.14 (m, 3H). ESMS m/z: 562.3 (M+1).

Compound 47: $^1$H NMR (400 MHz, $CDCl_3$) δ 7.10-6.95 (m, 2H), 5.88 and 5.85 (s, 1H), 5.76 and 5.74 (s, 1H), 4.58 (brs, 1H), 4.21-3.87 (m, 2H), 3.80-3.68 (m, 1H), 3.67-3.47 (m, 5H), 3.43-3.17 (m, 1H), 2.57-2.43 (m, 6H), 2.38-2.30 (m, 1H), 2.29 and 2.28 (s, 3H), 2.24-2.25 (m, 1H), 1.14 and 1.14 (t, J=7.2 Hz, 3H). ESMS m/z: 546.2 (M+1).

Compound 48: $^1$H NMR (300 MHz, $CDCl_3$) δ 7.65 (t, J=7.2 Hz, 1H), 7.60-7.52 (m, 1H), 7.31-7.21 (m, 1H), 5.91 and 5.86 (s, 1H), 5.71 and 5.68 (s, 1H), 4.72-4.53 (m, 1H), 4.12-3.98 (m, 1H), 3.85-3.44 (m, 6H), 3.44-3.24 (m, 1H), 2.57-2.38 (m, 6H), 2.28 and 2.27 (s, 3H), 2.25-2.06 (m, 2H), 1.12 and 1.11 (t, J=7.2 Hz, 3H). ESMS m/z: 562.2 (M+1).

Compound 49: $^1$H NMR (300 MHz, $CDCl_3$) δ 7.82 and 7.78 (s, 1H), 7.59 (d, J=8.4 Hz, 1H), 7.51 (d, J=8.4 Hz, 1H), 5.91 and 5.85 (s, 1H), 5.66 and 5.62 (s, 1H), 4.74-4.53 (m, 1H), 4.20-4.02 (m, 1H), 3.82-3.47 (m, 6H), 3.47-3.37 (m, 1H), 2.55-2.39 (m, 6H), 2.28 (s, 3H), 2.26-2.18 (m, 1H), 2.18-2.00 (m, 1H), 1.12 and 1.11 (t, J=7.2 Hz, 3H). ESMS m/z: 578.2 (M+1).

Compound 50: $^1$H NMR (300 MHz, $CDCl_3$) δ 7.50 (q, J=8.2 Hz, 1H), 7.43-7.35 (m, 1H), 5.88 and 5.85 (s, 1H), 5.76 and 5.74 (s, 1H), 4.73-4.54 (m, 1H), 3.96-3.74 (m, 2H), 3.74-3.34 (m, 6H), 2.57-2.43 (m, 6H), 2.30 and 2.29 (s, 3H), 2.25-2.05 (m, 2H), 1.14 and 1.13 (t, J=7.2 Hz, 3H). ESMS m/z: 529.3 (M+1).

Compound 51: $^1$H NMR (300 MHz, $CDCl_3$) δ 8.41 and 8.39 (d, J=1.2 Hz, 1H), 7.59 and 7.56 (dd, J=8.4, 1.2 Hz, 1H), 5.89 and 5.86 (s, 1H), 5.65 and 5.63 (s, 1H), 4.76-4.58 (m, 1H), 4.01-3.60 (m, 4H), 3.60-3.39 (m, 4H), 2.59-2.43 (m, 6H), 2.29 (s, 3H), 2.25-2.06 (m, 2H), 1.14 and 1.13 (t, J=7.2 Hz, 3H). ESMS m/z: 529.2 (M+1).

Compound 52: $^1$H NMR (400 MHz, $CDCl_3$) δ 8.53 and 8.52 (d, J=2.8 Hz, 1H), 7.80-7.76 (m, 1H), 7.36 and 7.35 (d, J=8.4 Hz, 1H), 5.90 and 5.84 (s, 1H), 5.65 and 5.63 (s, 1H), 4.71-4.55 (m, 1H), 4.16-4.01 (m, 1H), 3.84-3.58 (m, 3H), 3.58-3.40 (m, 4H), 2.53-2.42 (m, 6H), 2.29 and 2.28 (s, 3H), 2.26-2.05 (m, 2H), 1.12 and 1.11 (t, J=7.2 Hz, 3H). ESMS m/z: 511.2 (M+1).

Compound 53: $^1$H NMR (400 MHz, $CDCl_3$) δ 7.82 and 7.82 (t, J=8.2 Hz, 1H), 7.29-7.24 (m, 1H), 5.90 and 5.85 (s, 1H), 5.68 and 5.66 (s, 1H), 4.63 and 4.59 (brs, 1H), 4.04-3.93 (m, 1H), 3.83-3.72 (m, 2H), 3.63-3.26 (m, 6H), 2.53-2.42 (m, 6H), 2.31 and 2.30 (s, 3H), 2.22-2.04 (m, 2H), 1.13 and 1.13 (t, J=7.2 Hz, 3H). ESMS m/z: 529.2 (M+1).

Compound 54: $^1$H NMR (400 MHz, $CDCl_3$) δ 7.60 and 7.55 (d, J=8.0 Hz, 1H), 7.28 (d, J=8.0 Hz, 1H), 5.93 and 5.87 (s, 1H), 5.63 and 5.62 (s, 1H), 4.68-4.54 (m, 1H), 4.17-4.01 (m, 1H), 3.81-3.45 (m, 5H), 3.45-3.16 (m, 2H), 2.52-2.40 (m, 6H), 2.37-2.22 (m, 4H), 2.18-2.04 (m, 1H), 1.12 (t, J=7.2 Hz, 3H). ESMS m/z: 545.2 (M+1).

Compound 55: $^1$H NMR (300 MHz, $CDCl_3$) δ 8.29 and 8.29 (s, 1H), 7.43 and 7.40 (s, 1H), 5.90 and 5.86 (s, 1H), 5.67 and 5.66 (s, 1H), 4.59 (m, 1H), 4.14-3.97 (m, 1H), 3.84-3.61 (m, 3H), 3.61-3.14 (m, 4H), 2.62-2.42 (m, 6H), 2.36-2.20 (m, 4H), 2.20-2.02 (m, 1H), 1.16 and 1.15 (t, J=7.2 Hz, 3H). ESMS m/z: 545.2 (M+1).

Compound 56: $^1$H NMR (300 MHz, $CD_3OD$) δ 7.95 and 7.91 (d, J=7.5 Hz, 1H), 5.87 (s, 1H), 5.82 (s, 1H), 4.63-4.38 (m, 1H), 3.99-3.59 (m, 6H), 3.59-3.36 (m, 2H), 3.04-2.95 (m, 2H), 2.95-2.79 (m, 4H), 2.42-2.28 (m, 1H), 2.25 and 2.24 (s, 3H), 2.17-2.01 (m, 1H), 1.28 and 1.28 (t, J=7.2 Hz, 3H). ESMS m/z: 563.2 (M+1).

Compound 57: $^1$H NMR (400 MHz, $CDCl_3$) δ 8.42 and 8.41 (d, J=2.0 Hz, 1H), 7.90 and 7.88 (d, J=2.0 Hz, 1H), 5.91 and 5.85 (s, 1H), 5.65 and 5.64 (s, 1H), 4.70-4.56 (m, 1H), 4.15-3.99 (m, 1H), 3.84-3.54 (m, 4H), 3.54-3.43 (m, 3H), 2.52-2.39 (m, 6H), 2.30 and 2.29 (s, 3H), 2.28-2.20 (m, 1H), 2.18-2.04 (m, 1H), 1.12 and 1.11 (t, J=7.2 Hz, 3H). ESMS m/z: 545.2 (M+1).

Compound 58: $^1$H NMR (300 MHz, $CDCl_3$) δ 7.43 (t, J=7.6 Hz, 1H), 7.24-7.16 (m, 1H), 7.09 (t, J=7.6 Hz, 1H), 5.93 and 5.87 (s, 1H), 5.62 and 5.59 (s, 1H), 4.77-4.52 (m, 1H), 4.20-4.03 (m, 1H), 3.84-3.53 (m, 3H), 3.53-3.22 (m, 4H), 2.53-2.38 (m, 6H), 2.30 and 2.29 (s, 3H), 2.27-2.19 (m, 1H), 2.16-2.03 (m, 1H), 1.11 and 1.11 (t, J=7.2 Hz, 3H). ESMS m/z: 528.2 (M+1).

Compound 59: $^1$H NMR (300 MHz, $CDCl_3$) δ 7.43 (t, J=7.8 Hz, 1H), 7.24-7.17 (m, 1H), 7.09 (t, J=7.8 Hz, 1H), 5.92 and 5.87 (s, 1H), 5.63 and 5.61 (s, 1H), 4.75-4.53 (m, 1H), 4.18-4.02 (m, 1H), 3.84-3.53 (m, 3H), 3.53-3.22 (m, 4H), 2.50-2.37 (m, 4H), 2.33 and 2.31 (s, 3H), 2.31 and 2.29 (s, 3H), 2.27-2.19 (m, 1H), 2.17-2.03 (m, 1H). ESMS m/z: 514.2 (M+1).

Compound 60: $^1$H NMR (400 MHz, $CDCl_3$) δ 7.42-7.33 (m, 1H), 7.23-7.08 (m, 2H), 6.84 and 6.78 (brs, 1H), 5.85 and 5.83 (s, 1H), 5.63 and 5.60 (s, 1H), 5.32-5.03 (m, 1H), 3.97-3.86 (m, 1H), 3.67-3.25 (m, 9H), 2.57-2.38 (m, 6H), 2.28-2.18 (m, 4H), 2.15-2.07 (m, 1H), 1.21-1.05 (m, 6H). ESMS m/z: 556.3 (M+1).

Compound 61: $^1$H NMR (400 MHz, $CDCl_3$) δ 7.91 (d, J=2.0 Hz, 1H), 7.64 (dd, J=8.4, 2.0 Hz, 1H), 7.57 (d, J=8.4 Hz, 1H), 5.86 (s, 1H), 5.72 (s, 1H), 4.44-4.38 (m, 1H), 3.57-3.42 (m, 7H), 3.40-3.30 (m, 1H), 2.51-2.41 (m, 6H), 2.30 (s, 3H), 2.13-1.88 (m, 2H), 1.12 (t, J=7.2 Hz, 3H). ESMS m/z: 580.2 (M+1).

Compound 62: $^1$H NMR (300 MHz, $CDCl_3$) δ 7.86 (d, J=8.2 Hz, 1H), 7.32 (s, 1H), 7.29 (d, J=8.2 Hz, 1H), 5.90 (s, 1H), 5.65 (s, 1H), 4.67-4.56 (m, 1H), 3.64-3.41 (m, 7H), 3.39-3.27 (m, 1H), 2.63 (s, 3H), 2.52-2.39 (m, 6H), 2.31 (s, 3H), 2.16-2.02 (m, 1H), 1.99-1.88 (m, 1H), 1.12 (t, J=7.2 Hz, 3H). ESMS m/z: 560.2 (M+1).

Compound 63: $^1$H NMR (400 MHz, $CDCl_3$) δ 8.02 (d, J=8.4 Hz, 1H), 7.53 (d, J=2.0 Hz, 1H), 7.36 (dd, J=8.4, 2.0 Hz, 1H), 5.88 (s, 1H), 5.68 (s, 1H), 4.61-4.53 (m, 1H), 3.69-3.59 (m, 2H), 3.57-3.42 (m, 6H), 2.50-2.40 (m, 6H), 2.30 (s, 3H), 2.21-2.10 (m, 1H), 2.08-1.99 (m, 1H), 1.11 (t, J=7.2 Hz, 3H). ESMS m/z: 580.2 (M+1).

Compound 64: $^1$H NMR (300 MHz, $CD_3OD$) δ 7.81 and 7.80 (t, J=7.5 Hz, 1H), 7.34-7.28 (m, 2H), 5.82 (s, 1H), 5.57 (s, 1H), 4.27 (brs, 1H), 3.80-3.66 (m, 4H), 3.63-3.45 (m, 5H), 3.02-2.80 (m, 6H), 2.26 (s, 3H), 2.23-2.15 (m, 1H), 2.04-1.93 (m, 1H), 1.28 and 1.27 (t, J=7.1 Hz, 3H). ESMS m/z: 564.2 (M+1).

Compound 65: $^1$H NMR (300 MHz, $CDCl_3$) δ 7.81 (ddd, J=7.8, 6.0, 1.8 Hz, 1H), 7.61 (ddd, J=7.8, 6.0, 1.8 Hz, 1H), 7.21 (td, J=7.8, 1.2 Hz, 1H), 5.89 (s, 1H), 5.66 (s, 1H), 4.61-4.49 (m, 1H), 3.71-3.59 (m, 1H), 3.59-3.42 (m, 7H), 2.51-2.39 (m, 6H), 2.31 (s, 3H), 2.15-2.00 (m, 2H), 1.11 (t, J=7.2 Hz, 3H). ESMS m/z: 564.2 (M+1).

Compound 66: $^1$H NMR (400 MHz, $CDCl_3$) δ 7.61 (d, J=8.6 Hz, 1H), 7.58-7.51 (m, 2H), 5.87 (s, 1H), 5.71 (s, 1H), 4.46-4.38 (m, 1H), 3.57-3.41 (m, 7H), 3.38-3.30 (m, 1H), 2.51-2.40 (m, 6H), 2.30 (s, 3H), 2.12-2.01 (m, 1H), 2.00-1.90 (m, 1H), 1.12 (t, J=7.2 Hz, 3H). ESMS m/z: 564.2 (M+1).

Compound 67: $^1$H NMR (300 MHz, $CDCl_3$) δ 7.85 (d, J=7.2 Hz, 2H), 7.65-7.50 (m, 3H), 5.91 (s, 1H), 5.63 (s, 1H), 4.56-4.45 (m, 1H), 3.62-3.41 (m, 6H), 3.33-3.18 (m, 2H), 2.41 (t, J=4.8 Hz, 4H), 2.32 (s, 3H), 2.31 (s, 3H), 2.06-1.84 (m, 2H). ESMS m/z: 498.2 (M+1).

Compound 68: $^1$H NMR (400 MHz, $CDCl_3$) δ 7.77 (d, J=8.6 Hz, 2H), 7.49 (d, J=8.6 Hz, 2H), 5.88 (s, 1H), 5.68 (s, 1H), 4.49-4.42 (m, 1H), 3.56-3.43 (m, 6H), 3.41-3.32 (m, 1H), 3.30-3.24 (m, 1H), 2.50-2.40 (m, 6H), 2.31 (s, 3H), 2.03-1.93 (m, 2H), 1.11 (t, J=7.2 Hz, 3H). ESMS m/z: 546.2 (M+1).

Compound 69: $^1$H NMR (400 MHz, $CDCl_3$) δ 8.13 (d, J=2.0 Hz, 1H), 7.92 (dd, J=8.6, 2.0 Hz, 1H), 7.64 (d, J=8.6 Hz, 1H), 5.86 (s, 1H), 5.71 (s, 1H), 4.46-4.38 (m, 1H), 3.58-3.42 (m, 7H), 3.41-3.32 (m, 1H), 2.51-2.41 (m, 6H), 2.30 (s, 3H), 2.15-2.03 (m, 1H), 2.01-1.92 (m, 1H), 1.12 (t, J=7.2 Hz, 3H). ESMS m/z: 614.2 (M+1).

Compound 70: $^1$H NMR (300 MHz, $CDCl_3$) δ 9.80 (brs, 1H), 7.43-7.35 (m, 1H), 7.24-7.08 (m, 2H), 6.57 and 6.50 (s, 1H), 5.36 and 5.32 (s, 1H), 4.84 and 4.78 (brs, 1H), 4.65-4.44 (m, 1H), 4.11-3.71 (m, 2H), 3.68-3.32 (m, 6H), 2.66 and 2.65 (s, 3H), 2.57-2.41 (m, 6H), 2.30-2.13 (m, 4H), 2.09-1.97 (m, 1H), 1.13 (t, J=7.2 Hz, 3H). ESMS m/z: 570.2 (M+1).

Compound 73: $^1$H NMR (400 MHz, $CDCl_3$) δ 7.42-7.35 (m, 1H), 7.23-7.09 (m, 2H), 6.55 and 6.50 (s, 1H), 5.87 and 5.84 (s, 1H), 4.92 and 4.79 (brs, 1H), 4.56 and 4.47 (q, J=5.7 Hz, 1H), 4.06-3.79 (m, 1H), 3.77-3.55 (m, 5H), 3.54-3.19 (m, 2H), 2.56-2.40 (m, 9H), 2.36-2.22 (m, 1H), 2.03-1.94 (m, 1H), 1.53 and 1.51 (s, 9H), 1.16-1.12 (m, 3H). ESMS m/z: 612.3 (M+1).

Compound 74: $^1$H NMR (400 MHz, $CDCl_3$) δ 7.39 and 7.37 (dd, J=8.0, 4.8 Hz, 1H), 7.21 and 7.18 (dd, J=8.4, 2.0 Hz, 1H), 7.15 and 7.11 (dd, J=9.4, 2.0 Hz, 1H), 6.83 and 6.76

(brs, 1H), 6.53 and 6.49 (s, 1H), 5.86 and 5.83 (s, 1H), 4.74 and 4.68 (brs, 1H), 4.60-4.42 (m, 1H), 4.08-3.70 (m, 2H), 3.68-3.45 (m, 5H), 3.45-3.18 (m, 1H), 2.58-2.48 (m, 5H), 2.48-2.40 (m, 4H), 2.37-2.18 (m, 1H), 2.03-1.91 (m, 1H), 1.53 and 1.51 (s, 9H), 1.13 and 1.13 (t, J=7.2 Hz, 3H). ESMS m/z: 612.3 (M+1).

Compound 75: $^1$H NMR (400 MHz, $CDCl_3$) δ 7.39 and 7.37 (dd, J=8.2, 7.0 Hz, 1H), 7.20 and 7.17 (dd, J=8.2, 2.0 Hz, 1H), 7.14 and 7.11 (dd, J=9.4, 2.0 Hz, 1H), 6.95 (brs, 1H), 6.02 and 5.98 (s, 1H), 5.90 and 5.89 (s, 1H), 5.87 (s, 2H), 5.07 and 4.90 (brs, 1H), 4.61-4.41 (m, 1H), 4.04-3.69 (m, 2H), 3.66-3.45 (m, 5H), 3.45-3.18 (m, 1H), 2.55-2.41 (m, 6H), 2.32 and 2.31 (s, 3H), 2.27-2.17 (m, 1H), 2.03-1.92 (m, 1H), 1.18 and 1.17 (s, 9H), 1.13 and 1.12 (t, J=7.2 Hz, 3H). ESMS m/z: 642.3 (M+1).

Compound 76: $^1$H NMR (400 MHz, $CDCl_3$) δ 9.35 and 9.31 (brs, 1H), 7.38 (q, J=7.3 Hz, 1H), 7.22-7.07 (m, 2H), 6.56 and 6.48 (s, 1H), 5.37 and 5.33 (s, 1H), 4.90 and 4.84 (brs, 1H), 4.62-4.44 (m, 3H), 4.04-3.68 (m, 2H), 3.66-3.45 (m, 4H), 3.43-3.21 (m, 2H), 2.57-2.40 (m, 6H), 2.38-2.29 (m, 1H), 2.27 and 2.26 (s, 3H), 2.06-1.95 (m, 1H), 1.47 and 1.46 (t, J=7.2 Hz, 3H), 1.13 and 1.12 (t, J=7.2 Hz, 3H). ESMS m/z: 600.3 (M+1).

Compound 77: $^1$H NMR (400 MHz, $CDCl_3$) δ 7.37 (q, J=7.5 Hz, 1H), 7.17 (q, J=10.3 Hz, 1H), 7.10 (d, J=9.6 Hz, 1H), 6.31 and 6.26 (s, 1H), 5.97 and 5.89 (s, 1H), 4.98 and 4.88 (brs, 1H), 4.58-4.39 (m, 3H), 4.04-3.67 (m, 2H), 3.65-3.51 (m, 4H), 3.50-3.19 (m, 2H), 2.53 and 2.52 (s, 3H), 2.50-2.42 (m, 6H), 2.35-2.17 (m, 2H), 1.43 and 1.42 (t, J=7.0 Hz, 3H), 1.13 and 1.12 (t, J=7.2 Hz, 3H). ESMS m/z: 600.3 (M+1).

Compound 78: $^1$H NMR (400 MHz, $CDCl_3$) δ 9.33 (brs, 1H), 7.43-7.32 (m, 1H), 7.24-7.06 (m, 2H), 6.55 and 6.48 (s, 1H), 5.38 and 5.33 (s, 1H), 4.85 and 4.79 (brs, 1H), 4.65-4.44 (m, 1H), 4.23 and 4.22 (d, J=6.8 Hz, 1H), 4.07-3.70 (m, 2H), 3.67-3.20 (m, 6H), 2.53-2.39 (m, 6H), 2.38-2.31 (m, 1H), 2.28 and 2.27 (s, 3H), 2.24-2.13 (m, 1H), 2.08-1.96 (m, 1H), 1.12 (t, J=6.8 Hz, 3H), 1.02 and 1.01 (d, J=6.6 Hz, 6H). ESMS m/z: 628.3 (M+1).

Compound 79: $^1$H NMR (300 MHz, $CDCl_3$) δ 7.43-7.33 (m, 1H), 7.24-7.07 (m, 2H), 6.91 and 6.81 (brs, 1H), 6.22 and 6.17 (s, 1H), 6.13 and 6.06 (s, 1H), 4.84 and 4.75 (brs, 1H), 4.62-4.39 (m, 1H), 4.17 and 4.17 (d, J=6.4 Hz, 1H), 4.08-3.68 (m, 2H), 3.68-3.17 (m, 6H), 2.59-2.38 (m, 9H), 2.36-2.19 (m, 1H), 2.18-2.05 (m, 1H), 2.05-1.92 (m, 1H), 1.12 (t, J=7.2 Hz, 3H), 1.03 and 1.02 (d, J=7.0 Hz, 6H). ESMS m/z: 628.3 (M+1).

Compound 80: $^1$H NMR (400 MHz, $CDCl_3$) δ 9.44 and 9.42 (brs, 1H), 7.39 (q, J=7.7 Hz, 1H), 7.24-7.09 (m, 2H), 6.55 and 6.47 (s, 1H), 5.39 and 5.35 (s, 1H), 4.83 and 4.78 (brs, 1H), 4.63-4.45 (m, 2H), 4.23-4.00 (m, 2H), 3.92-3.72 (m, 2H), 3.65-3.48 (m, 2H), 3.47-3.23 (m, 1H), 2.55-2.39 (m, 4H), 2.39-2.32 (m, 2H), 2.28 and 2.27 (s, 3H), 2.07-1.99 (m, 2H), 1.56 (s, 9H), 1.14 and 1.12 (t, J=7.2 Hz, 3H). ESMS m/z: 628.3 (M+1).

Compound 81: $^1$H NMR (400 MHz, $CDCl_3$) δ 7.38 and 7.37 (dd, J=8.2, 6.6 Hz, 1H), 7.20 and 7.18 (dd, J=8.2, 2.0 Hz, 1H), 7.15 and 7.11 (dd, J=9.4, 2.0 Hz, 1H), 7.00 (brs, 1H), 6.27 and 6.18 (s, 1H), 6.12 and 6.09 (s, 1H), 4.87 and 4.78 (brs, 1H), 4.60-4.41 (m, 1H), 4.05-3.69 (m, 2H), 3.68-3.52 (m, 5H), 3.52-3.19 (m, 1H), 2.54-2.40 (m, 9H), 2.36-2.17 (m, 1H), 2.04-1.92 (m, 1H), 1.63 and 1.62 (s, 9H), 1.12 and 1.12 (t, J=7.2 Hz, 3H). ESMS m/z: 628.3 (M+1).

Compound 82: $^1$H NMR (400 MHz, $CDCl_3$) δ 8.13 (d, J=2.0 Hz, 1H), 7.92 (dd, J=8.6, 2.0 Hz, 1H), 7.64 (d, J=8.6 Hz, 1H), 5.86 (s, 1H), 5.71 (s, 1H), 4.46-4.38 (m, 1H), 3.58-3.42 (m, 7H), 3.41-3.32 (m, 1H), 2.51-2.41 (m, 6H), 2.30 (s, 3H), 2.15-1.92 (m, 2H), 1.12 (t, J=7.2 Hz, 3H). ESMS m/z: 630.2 (M+1).

Compound 83: $^1$H NMR (400 MHz, $CDCl_3$) δ 7.45 and 7.42 (t, J=7.8 Hz, 1H), 7.22-7.16 (m, 1H), 7.16-7.10 (m, 1H), 6.65-6.35 (m, 1H), 6.24 and 6.21 (s, 1H), 4.56-4.42 (m, 3H), 4.24-3.53 (m, 9H), 3.47-3.24 (m, 4H), 3.22-2.86 (m, 6H), 2.50 (s, 3H), 2.31-2.18 (m, 1H), 2.13-2.01 (m, 1H), 1.44-1.36 (m, 3H). ESMS m/z: 630.3 (M+1).

Compound 84: $^1$H NMR (300 MHz, $CDCl_3$) δ 7.44 (t, J=7.8 Hz, 1H), 7.34 (s, 1H), 7.29-7.22 (m, 1H), 7.14 (t, J=7.8 Hz, 1H), 6.93 (s, 1H), 6.48 (s, 1H), 4.57 (d, J=13.0 Hz, 1H), 4.12-3.97 (m, 1H), 3.67-3.46 (m, 5H), 3.28-3.00 (m, 2H), 2.54-2.38 (m, 6H), 2.14 (d, J=13.0 Hz, 1H), 2.04 (d, J=13.0 Hz, 1H), 1.67-1.46 (m, 2H), 1.12 and 1.10 (t, J=7.2 Hz, 3H). ESMS m/z: 529.2 (M+1).

Compound 85: $^1$H NMR (300 MHz, $CDCl_3$) δ 7.45 (t, J=7.8 Hz, 1H), 7.30-7.23 (m, 1H), 7.15 (t, J=7.8 Hz, 1H), 6.08 (s, 1H), 5.99 (s, 1H), 4.80 (brs, 1H), 4.57 (d, J=14.0 Hz, 1H), 4.10-3.94 (m, 1H), 3.60 (t, J=5.2 Hz, 4H), 3.58-3.48 (m, 1H), 3.27-3.02 (m, 2H), 2.52-2.39 (m, 6H), 2.37 (s, 3H), 2.16 (d, J=14.0 Hz, 1H), 2.05 (d, J=14.0 Hz, 1H), 1.63-1.46 (m, 2H), 1.10 (t, J=7.2 Hz, 3H). ESMS m/z: 543.2 (M+1).

Compound 87: $^1$H NMR (400 MHz, $CDCl_3$) δ 7.45 (t, J=8.0 Hz, 1H), 7.31-7.24 (m, 1H), 7.16 (t, J=8.0 Hz, 1H), 6.57 (brs, 1H), 5.82 (s, 1H), 5.49 (s, 1H), 4.91 (d, J=13.0 Hz, 1H), 4.82-4.64 (m, 1H), 3.61 (d, J=13.0 Hz, 1H), 3.56 (t, J=4.9 Hz, 4H), 3.48 (q, J=7.2 Hz, 2H), 3.31-3.03 (m, 1H), 2.92-2.79 (m, 1H), 2.52-2.40 (m, 6H), 2.27 (s, 3H), 1.94 (d, J=13.0 Hz, 1H), 1.89-1.73 (m, 3H), 1.22 (t, J=7.2 Hz, 3H), 1.12 (t, J=7.2 Hz, 3H). ESMS m/z: 570.3 (M+1).

Compound 88: $^1$H NMR (300 MHz, $CDCl_3$) δ 7.34-7.26 (m, 2H), 7.05 (t, J=8.0 Hz, 1H), 6.65 (brs, 1H), 5.83 (s, 1H), 5.58 (s, 1H), 4.66 (brs, 1H), 3.85-3.70 (m, 1H), 3.61 (s, 2H), 3.55 (t, J=4.8 Hz, 4H), 2.85 (d, J=13.0 Hz, 2H), 2.51-2.38 (m, 6H), 2.27 (s, 3H), 2.23 (d, J=13.0 Hz, 2H), 2.05 (d, J=13.0 Hz, 2H), 1.63-1.43 (m, 2H), 1.11 (t, J=7.2 Hz, 3H). ESMS m/z: 528.3 (M+1).

Compound 89: $^1$H NMR (400 MHz, $CDCl_3$) δ 7.44 (t, J=8.0 Hz, 1H), 7.29-7.24 (m, 1H), 7.15 (t, J=8.0 Hz, 1H), 5.84 (s, 1H), 5.31 (s, 1H), 4.57 (d, J=13.0 Hz, 1H), 4.10-4.01 (m, 1H), 4.00 (t, J=8.0 Hz, 2H), 3.81 (t, J=8.0 Hz, 2H), 3.53 (d, J=13.0 Hz, 1H), 3.28-3.02 (m, 3H), 2.27 (s, 3H), 2.22-2.12 (m, 7H), 2.09-1.96 (m, 1H), 1.68-1.48 (m, 2H). ESMS m/z: 528.2 (M+1).

Compound 90: $^1$H NMR (400 MHz, $CDCl_3$) δ 7.45 (t, J=7.5 Hz, 1H), 7.26-7.26 (m, 1H), 7.15 (t, J=7.5 Hz, 1H), 5.85 (s, 1H), 5.68 (s, 1H), 4.65-4.38 (m, 1H), 4.16-4.01 (m, 1H), 3.69 (m, 5H), 3.48-3.05 (m, 2H), 2.47-2.44 (m. 4H), 2.33 (s, 3H), 2.30 (s, 3H), 2.18-2.03 (m, 2H), 1.30-1.26 (m, 2H). ESMS m/z: 528.2 (M+1).

Compound 91: $^1$H NMR (400 MHz, $CDCl_3$) δ 7.45 (t, J=7.4 Hz, 1H), 7.32-7.26 (m, 1H), 7.15 (t, J=7.4 Hz, 1H), 5.84-5.68 (m, 2H), 4.65-4.40 (m, 2H), 4.08-3.98 (m, 2H), 3.61-3.39 (m, 8H), 3.34-2.98 (m, 2H), 2.27 (s, 3H), 2.16-2.02 (m, 1H), 1.41-1.38 (m, 2H). ESMS m/z: 514.2 (M+1).

Compound 92: $^1$H NMR (400 MHz, $CDCl_3$) δ 7.44 (t, J=7.6 Hz, 1H), 7.26-7.25 (m, 1H), 7.15 (t, J=7.6 Hz, 1H), 5.84 (s, 1H), 5.68 (s, 1H), 4.57 (brs, 1H), 4.33-7.30 (m, 2H), 4.04 (brs, 1H), 3.56-3.52 (m, 2H), 3.27-3.17 (m, 4H), 2.77 (t, J=12 Hz, 2H), 2.53-2.38 (m, 2H), 2.32 (s, 6H), 2.28 (s, 3H), 2.18-2.05 (m, 2H), 1.58-1.25 (m, 4H). ESMS m/z: 556.3 (M+1).

Compound 93: $^1$H NMR (400 MHz, $CDCl_3$) δ 7.46 (t, J=7.7 Hz, 1H), 7.33-7.26 (m, 1H), 7.16 (t, J=7.7 Hz, 1H), 5.86 (s, 1H), 5.67 (s, 1H), 4.64-4.10 (m, 2H), 3.80-3.62 (m, 6H), 3.38-3.05 (m, 2H), 2.34 (s, 3H), 2.22-2.12 (m, 4H), 2.10 (s, 3H), 2.05-1.98 (m, 1H), 1.44-1.21 (m, 2H). ESMS m/z: 556.3 (M+1).

Compound 94: $^1$H NMR (400 MHz, $CDCl_3$) δ 7.44 (t, J=7.6 Hz, 1H), 7.29-7.26 (m, 1H), 7.15 (t, J=7.6 Hz, 1H), 5.86 (s, 1H), 5.37 (s, 1H), 4.19-4.11 (m, 2H), 3.66-3.58 (m, 2H), 3.48-3.10 (m, 4H), 2.86-2.77 (m, 2H), 2.69-2.39 (m, 2H), 2.33 (s, 3H), 2.30 (s, 6H), 2.24-1.90 (m, 2H), 1.35-1.20 (m, 2H). ESMS m/z: 542.2 (M+1).

Compound 95: $^1$H NMR (400 MHz, $CDCl_3$) δ 7.44 (t, J=7.4 Hz, 1H), 7.30-7.26 (m, 1H), 7.15 (t, J=7.4 Hz, 1H), 5.86 (s, 1H), 5.51 (s, 1H), 4.63-4.51 (m, 2H), 4.08-3.98 (m, 2H), 3.70-3.49 (m, 4H), 3.31-3.01 (m, 2H), 3.00 (s, 3H), 2.50-2.46 (m, 2H), 2.30 (s, 6H), 2.28 (s, 3H), 2.19-2.04 (m, 1H). ESMS m/z: 530.3 (M+1).

Compound 96: $^1$H NMR (400 MHz, $CDCl_3$) δ 7.45 (t, J=8.0 Hz, 1H), 7.30-7.24 (m, 1H), 7.15 (t, J=8.0 Hz, 1H), 5.85 (s, 1H), 5.44 (s, 1H), 4.13-4.00 (m, 2H), 3.70-3.50 (m, 3H), 3.49-3.36 (m, 6H), 3.34-3.05 (m, 8H), 2.28 (s, 3H), 2.17-1.91 (m, 1H), 1.72-1.52 (m, 2H). ESMS m/z: 542.2 (M+1).

Compound 97: $^1$H NMR (400 MHz, $CD_3OD$) δ 7.60 (t, J=7.8 Hz, 1H), 7.38-7.32 (m, 1H), 7.29 (t, J=7.8 Hz, 1H), 4.10-4.00 (m, 2H), 4.53-4.50 (m, 2H), 4.20-4.03 (m, 2H), 3.85-3.60 (m, 4H), 3.59-3.44 (m, 3H), 3.25-3.11 (m, 3H), 2.33 (s, 3H), 2.23 (s, 3H), 1.68-1.48 (m, 4H). ESMS m/z: 543.2 (M+1).

Compound 98: $^1$H NMR (400 MHz, $CD_3OD$) δ 7.59 (t, J=7.8 Hz, 1H), 7.36-7.32 (m, 1H), 7.28 (t, J=7.8 Hz, 1H), 5.78 (s, 1H), 5.39 (s, 1H), 4.53-4.50 (m, 2H), 4.11-3.98 (m, 2H), 3.68 (t, J=8.0 Hz, 2H), 3.57-3.54 (m, 2H), 3.34 (s, 3H), 3.00 (s, 3H), 2.98-2.95 (m, 1H), 2.23 (s, 3H), 2.19-1.98 (m, 2H), 1.68-1.49 (m, 2H). ESMS m/z: 517.3 (M+1).

Compound 99: $^1$H NMR (400 MHz, $CD_3OD$) δ 7.61 (t, J=8.0 Hz, 1H), 7.40-7.26 (m, 1H), 7.29 (t, J=8.0 Hz, 1H), 5.76 (s, 1H), 5.12 (s, 1H), 4.59-4.55 (m, 1H), 4.39-4.28 (m, 3H), 3.96-3.93 (m, 2H), 3.59-3.55 (m, 2H), 3.34 (s, 3H), 3.24-3.16 (m, 2H), 2.29 (s, 3H), 2.19-2.04 (m, 2H), 1.67-1.57 (m, 2H). ESMS m/z: 515.2 (M+1).

Compound 100: $^1$H NMR (400 MHz, $CDCl_3$) δ 7.45 (t, J=8.0 Hz, 1H), 7.31-7.22 (m, 1H), 7.15 (t, J=8.0 Hz, 1H), 5.84 (s, 1H), 5.67 (s, 1H), 4.88-4.80 (m, 1H), 4.62-4.54 (m, 1H), 4.13-3.96 (m, 3H), 3.57-3.53 (m, 1H), 3.37-3.00 (m, 3H), 2.75-2.55 (m, 2H), 2.28 (s, 6H), 220-2.07 (m, 2H), 1.58-1.55 (m, 2H), 1.17 (d, J=6.2 Hz, 6H). ESMS m/z: 556.2 (M+1).

Compound 101: $^1$H NMR (400 MHz, $CDCl_3$) δ 7.44 (t, J=8.0 Hz, 1H), 7.30-7.24 (m, 1H), 7.15 (t, J=8.0 Hz, 1H), 5.84 (s, 1H), 5.66 (s, 1H), 4.76 (brs, 1H), 4.58 (brs, 1H), 4.08-4.01 (m, 1H), 3.57-3.52 (m, 8H), 3.36 (s, 3H), 3.29-3.02 (m, 2H), 2.60 (t, J=8.0 Hz, 2H), 2.54-2.52 (m, 4H), 2.28 (s, 3H), 2.20-2.04 (m, 2H), 1.50-1.36 (m, 2H). ESMS m/z: 572.3 (M+1).

Compound 102: $^1$H NMR (400 MHz, $CDCl_3$) δ 7.45 (t, J=8.0, 1H), 7.31-7.24 (m, 1H), 7.15 (t, J=8.0 Hz, 1H), 5.84 (s, 1H), 5.71 (s, 1H), 4.57 (brs, 1H), 4.13-4.04 (m, 3H), 3.57-3.49 (m, 1H), 3.32-3.07 (m, 2H), 2.92-2.80 (m, 2H), 2.38 (t, J=8.0 Hz, 2H), 2.28 (s, 3H), 2.20-2.05 (m, 2H), 2.62-2.46 (m, 2H), 1.14 (d, J=6.3 Hz, 6H). ESMS m/z: 542.2 (M+1).

Compound 103: $^1$H NMR (400 MHz, $CDCl_3$) δ 7.45 (t, J=8.0 Hz, 1H), 7.31-7.23 (m, 1H), 7.15 (t, J=8.0 Hz, 1H), 5.85 (s, 1H), 5.70 (s, 1H), 4.70-4.60 (m, 5H), 4.08-4.01 (m, 1H), 3.59-3.53 (m, 4H), 3.51-3.47 (m, 2H), 3.35-3.03 (m, 2H), 2.38-2.35 (m, 4H), 2.28 (s, 3H), 2.19-2.05 (m, 2H), 1.54-1.42 (m, 2H). ESMS m/z: 570.3 (M+1).

Compound 104: $^1$H NMR (400 MHz, $CDCl_3$) δ 7.45 (t, J=8.0 Hz, 1H), 7.32-7.23 (m, 1H), 7.15 (t, J=8.0 Hz, 1H), 5.98-5.74 (m, 1H), 5.58-5.25 (m, 1H), 4.89-4.72 (m, 1H), 4.62-4.59 (m, 1H), 4.32-4.11 (m, 1H), 4.14-3.99 (m, 1H), 3.47-3.49 (m, 2H), 3.46-3.38 (m, 2H), 3.49-3.34 (m, 4H), 3.23 (t, J=8.0 Hz, 2H), 3.18-3.06 (m, 2H), 2.27 (s, 3H), 2.22-1.94 (m, 5H). ESMS m/z: 543.2 (M+1).

Compound 105: $^1$H NMR (400 MHz, $CD_3OD$) δ 7.60 (t, J=7.2 Hz, 1H), 7.33-7.26 (m, 2H), 5.76 (s, 1H), 5.51 (s, 1H), 4.54-4.51 (m, 1H), 4.00-3.95 (m, 1H), 3.55-3.41 (m, 5H), 3.35-3.31 (m, 4H), 3.19-2.98 (m, 2H), 2.33 (s, 3H), 2.14-1.92 (m, 4H), 1.64-1.38 (m, 4H). ESMS m/z: 543.2 (M+1).

Compound 106: $^1$H NMR (400 MHz, $CD_3OD$) δ 7.60 (t, J=7.8 Hz, 1H), 7.38-7.31 (m, 1H), 7.29 (t, J=7.8 Hz, 1H), 6.20-5.80 (m, 1H), 5.69-5.20 (m, 1H), 4.53-4.50 (m, 1H), 4.10-4.02 (m, 1H), 3.62-3.49 (m, 5H), 3.40-3.22 (m, 2H), 3.10 (q, J=9.6 Hz, 2H), 2.71-2.69 (m, 4H), 2.23 (s, 3H), 2.17-2.01 (m, 2H), 1.60-1.58 (m, 2H). ESMS m/z: 596.3 (M+1).

Compound 107: $^1$H NMR (600 MHz, $CD_3OD$) δ 7.59 (t, J=8.0 Hz, 1H), 7.38-7.32 (m, 1H), 7.28 (t, J=8.0 Hz, 1H), 6.25-5.88 (m, 1H) 5.70-5.43 (m, 1H), 4.54-4.48 (m, 1H), 4.08-4.01 (m, 1H), 3.57-3.52 (m, 1H), 3.25-3.19 (m, 4H), 2.91 (d, J=8.0 Hz, 1H), 2.74-7.68 (m, 1H), 2.59 (d, J=8.0 Hz, 1H), 2.39 (t, J=8.0 Hz, 1H), 2.23 (s, 3H), 2.16-2.03 (m, 2H), 1.65-1.47 (m, 2H), 1.29-1.14 (m, 6H). ESMS m/z: 542.2 (M+1).

Compound 108: $^1$H NMR (300 MHz, $CD_3OD$) δ 7.78 (d, J=5.4 Hz, 1H), 6.43-5.97 (m, 2H), 3.78-3.65 (m, 1H), 3.65-3.52 (m, 1H), 2.26 (s, 3H), 2.08 (d, J=11.4 Hz, 2H), 1.99 (d, J=11.4 Hz, 2H), 1.51-1.24 (m, 4H). ESMS m/z: 289.2 (M+1).

Compound 109: $^1$H NMR (400 MHz, $CD_3OD$) δ 7.62 (td, J=7.2, 1.8 Hz, 1H), 7.50-7.35 (m, 1H), 7.31 (t, J=7.8 Hz, 1H), 5.83 (s, 1H), 5.68 (s, 1H), 4.74-4.50 (m, 2H), 3.75-3.60 (m, 5H), 3.48 (t, J=12.8 Hz, 2H), 3.44-3.34 (m, 1H), 3.34-3.23 (m, 4H), 3.15 (t, J=12.8 Hz, 2H), 3.10-3.01 (m, 1H), 2.31 (s, 3H), 2.08-1.78 (m, 4H), 1.42 (t, J=7.2 Hz, 3H), 1.41-1.33 (m, 3H). ESMS m/z: 570.2 (M+1).

Compound 110: $^1$H NMR (300 MHz, $CD_3OD$) δ 8.09-7.75 (m, 1H), 7.72-7.61 (m, 2H), 7.34 (t, J=8.0 Hz, 1H), 6.61-6.30 (m, 2H), 4.53 (s, 2H), 4.32-4.00 (m, 1H), 3.68 (d, J=12.0 Hz, 2H), 3.58-3.47 (m, 1H), 3.36 (d, J=12.0 Hz, 1H), 2.42 (s, 3H), 2.38-2.15 (m, 2H), 2.12-1.89 (m, 2H). ESMS m/z: 416.2 (M+1).

Compound 111: $^1$H NMR (300 MHz, $CDCl_3$) δ 7.39-7.27 (m, 2H), 7.06 (t, J=7.8 Hz, 1H), 6.70 (brs, 1H), 6.04 (s, 1H), 5.94 (s, 1H), 4.70-4.55 (m, 1H), 3.65 (s, 2H), 3.05 (s, 3H), 3.01 (d, J=11.0 Hz, 2H), 2.28 (s, 3H), 2.27-2.17 (m, 5H), 1.95-1.77 (m, 2H), 1.76-1.64 (m, 2H). ESMS m/z: 444.2 (M+1).

Compound 112: $^1$H NMR (300 MHz, $CD_3OD$) δ 7.84-7.64 (m, 5H), 6.22-6.04 (m, 2H), 4.65-4.47 (m, 1H), 4.12-3.99 (m, 1H), 3.76-3.59 (m, 1H), 3.37-3.05 (m, 2H), 2.27 (s, 3H), 2.23-1.94 (m, 2H), 1.70-1.42 (m, 2H). ESMS m/z: 446.2 (M+1).

Compound 113: $^1$H NMR (300 MHz, $CD_3OD$) δ 7.81 (d, J=6.0 Hz, 1H), 7.44-7.33 (m, 1H), 7.32-7.24 (m, 1H), 7.23-7.13 (m, 1H), 6.32-5.90 (m, 2H), 4.59 (d, J=13.5 Hz, 1H), 4.14-3.97 (m, 1H), 3.59 (d, J=13.5 Hz, 1H), 3.30-3.09 (m, 2H), 2.26 (s, 3H), 2.17 (d, J=13.5 Hz, 1H), 2.03 (d, J=13.5 Hz, 1H), 1.72-1.42 (m, 2H). ESMS m/z: 414.2 (M+1).

Compound 114: $^1$H NMR (400 MHz, $CDCl_3$) δ 7.25-7.09 (m, 3H), 6.12 (s, 1H), 6.05 (s, 1H), 4.57 (d, J=14.0 Hz, 1H), 4.16-4.03 (m, 1H), 3.57 (d, J=14.0 Hz, 1H), 3.29-3.07 (m, 2H), 2.31 (s, 3H), 2.23 (s, 3H), 2.19 (d, J=11.6 Hz, 1H), 2.06 (d, J=11.6 Hz, 1H), 1.66-1.38 (m, 2H). ESMS m/z: 428.2 (M+1).

Compound 115: $^1$H NMR (400 MHz, $CDCl_3$) δ 9.97 (brs, 1H), 7.45 (d, J=3.8 Hz, 1H), 7.36-7.30 (m, 2H), 7.08 (t, J=7.8 Hz, 1H), 6.88 (d, J=3.8 Hz, 1H), 5.88 (s, 1H), 4.88-4.77 (m, 1H), 3.67 (s, 2H), 3.14 (s, 3H), 3.02 (d, J=11.0 Hz, 2H), 2.35-2.24 (m, 5H), 1.96-1.83 (m, 2H), 1.80-1.70 (m, 2H). ESMS m/z: 447.2 (M+1).

Compound 116: $^1$H NMR (400 MHz, DMSO-d6) δ 7.49 (t, J=7.8 Hz, 1H), 7.43-7.36 (m, 2H), 7.22 (t, J=7.8 Hz, 1H), 7.11 (d, J=3.6 Hz, 1H), 6.97 (brs, 1H), 6.01 (s, 1H), 3.97-3.83 (m, 1H), 3.57 (s, 2H), 2.83 (d, J=11.6 Hz, 2H), 2.20-2.13 (m, 2H), 2.12 (s, 3H), 1.96-1.83 (m, 2H), 1.56-1.42 (m, 2H). ESMS m/z: 433.2 (M+1).

Compound 117: $^1$H NMR (300 MHz, $CD_3OD$) δ 7.79 (s, 1H), 7.61 (d, J=8.1 Hz, 1H), 7.44 (t, J=8.1 Hz, 1H), 7.27 (d, J=8.1 Hz, 1H), 6.41-5.88 (m, 2H), 4.16 (d, J=13.5 Hz, 2H), 4.12-3.99 (m, 1H), 3.12 (t, J=11.7 Hz, 2H), 2.27 (s, 3H), 2.19 (s, 3H), 2.11 (d, J=13.0 Hz, 1H), 1.61-1.45 (m, 2H). ESMS m/z: 475.2 (M+1).

Compound 118: $^1$H NMR (300 MHz, $CD_3OD$) δ 7.81 (d, J=6.0 Hz, 1H), 7.63 and 7.62 (dd, J=7.8, 1.8 Hz, 1H), 7.42 and 7.41 (t, J=7.8 Hz, 1H), 7.34 and 7.29 (dd, J=7.8, 1.8 Hz, 1H), 6.39-5.83 (m, 2H), 4.66-4.52 (m, 1H), 4.11-3.95 (m, 1H), 3.52-3.37 (m, 1H), 3.29-3.06 (m, 2H), 2.26 (s, 3H), 2.17 (d, J=14.0 Hz, 1H), 2.00 (d, J=14.0 Hz, 1H), 1.72-1.36 (m, 2H). ESMS m/z: 446.1 (M+1).

Compound 119: $^1$H NMR (300 MHz, $CD_3OD$) δ 7.47-7.31 (m, 2H), 7.15 (td, J=7.8, 1.2 Hz, 1H), 6.39-6.15 (s, 1H), 6.13-5.85 (s, 1H), 3.86-3.71 (m, 1H), 3.68 (s, 2H), 2.92 (d, J=11.7 Hz, 2H), 2.38-2.25 (m, 2H), 2.24 (s, 3H), 2.16 (s, 3H), 2.04 (d, J=11.7 Hz, 2H), 1.70-1.50 (m, 2H). ESMS m/z: 430.2 (M+1).

Compound 120: $^1$H NMR (400 MHz, $CDCl_3$) δ 7.45 (t, J=7.8 Hz, 1H), 7.30-7.24 (m, 1H), 7.15 (t, J=7.8 Hz, 1H), 6.12 (s, 1H), 6.04 (s, 1H), 5.15 (brs, 1H), 4.59 (d, J=14.0 Hz, 1H), 4.15-4.04 (m, 1H), 3.54 (d, J=14.0 Hz, 1H), 3.30-3.04 (m, 2H), 2.31 (s, 3H), 2.22 (s, 3H), 2.19 (d, J=14.0 Hz, 1H), 2.07 (d, J=14.0 Hz, 1H), 1.63-1.49 (m, 2H). ESMS m/z: 444.1 (M+1).

Compound 121: $^1$H NMR (400 MHz, $CDCl_3$) δ 7.48 and 7.47 (dd, J=7.8, 1.2 Hz, 1H), 7.29-7.15 (m, 2H), 6.11 and 6.10 (s, 1H), 6.04 and 6.02 (s, 1H), 5.44 and 5.29 (brs, 1H), 4.65-4.51 (m, 1H), 4.15-4.01 (m, 1H), 3.50-3.37 (m, 1H), 3.27-3.06 (m, 2H), 2.30 and 2.29 (s, 3H), 2.26-2.15 (m, 4H), 2.09-1.97 (m, 1H), 1.67-1.29 (m, 2H). ESMS m/z: 460.1 (M+1).

Compound 124: $^1$H NMR (400 MHz, $CDCl_3$) δ 9.95 (brs, 1H), 7.45 (t, J=7.8 Hz, 1H), 7.31-7.25 (m, 1H), 7.15 (t, J=7.8 Hz, 1H), 6.56 (s, 1H), 5.32 (s, 1H), 4.72 (brs, 1H), 4.58 (d, J=12.8 Hz, 1H), 4.11-4.00 (m, 1H), 3.86 (sep, J=6.8 Hz, 1H), 3.62-3.47 (m, 5H), 3.32-3.00 (m, 2H), 2.47 (t, J=4.8 Hz, 4H), 2.44 (q, J=7.2 Hz, 2H), 2.25 (s, 3H), 2.24-2.17 (m, 1H), 2.06 (d, J=12.8 Hz, 1H), 1.64-1.48 (m, 2H), 1.26 (d, J=6.8 Hz, 6H), 1.11 (t, J=7.2 Hz, 3H). ESMS m/z: 612.3 (M+1).

Compound 125: $^1$H NMR (400 MHz, $CDCl_3$) δ 9.89 (brs, 1H), 7.45 (t, J=7.8 Hz, 1H), 7.31-7.25 (m, 1H), 7.15 (t, J=7.8 Hz, 1H), 6.56 (s, 1H), 5.33 (s, 1H), 4.73 (brs, 1H), 4.63 (d, J=12.4 Hz, 1H), 4.12-4.00 (m, 1H), 3.64-3.48 (m, 5H), 3.33-3.02 (m, 4H), 2.48 (t, J=4.8 Hz, 4H), 2.44 (q, J=7.2 Hz, 2H), 2.29-2.17 (m, 4H), 2.09 (d, J=12.4 Hz, 1H), 1.83-1.71 (m, 2H), 1.65-1.47 (m, 2H), 1.11 (t, J=7.2 Hz, 3H), 1.02 (t, J=7.4 Hz, 3H). ESMS m/z: 612.3 (M+1).

Compound 126: $^1$H NMR (400 MHz, $CDCl_3$) δ 9.93 (brs, 1H), 7.45 (t, J=8.0 Hz, 1H), 7.31-7.26 (m, 1H), 7.16 (t, J=8.0 Hz, 1H), 6.59 (s, 1H), 5.30 (s, 1H), 4.72 (brs, 1H), 4.63 (d, J=12.0 Hz, 1H), 4.12-4.00 (m, 1H), 3.62-3.47 (m, 5H), 3.19-3.03 (m, 2H), 2.51-2.40 (m, 6H), 2.28 (s, 3H), 2.22 (d, J=13.0 Hz, 1H), 2.10 (d, J=13.0 Hz, 1H), 1.66-1.51 (m, 3H), 1.25-1.20 (m, 2H), 1.16-1.07 (m, 5H). ESMS m/z: 610.3 (M+1).

Compound 127: $^1$H NMR (300 MHz, $CDCl_3$) δ 9.32 (brs, 1H), 7.43 (t, J=7.8 Hz, 1H), 7.30-7.22 (m, 1H), 7.14 (t, J=7.8 Hz, 1H), 6.55 (s, 1H), 5.34 (s, 1H), 4.77 (brs, 1H), 4.61 (d, J=12.3 Hz, 1H), 4.50 (q, J=7.3 Hz, 2H), 4.12-3.97 (m, 1H), 3.62-3.41 (m, 5H), 3.32-2.99 (m, 2H), 2.47 (t, J=4.7 Hz, 4H), 2.43 (q, J=7.1 Hz, 2H), 2.26 (s, 3H), 2.20 (d, J=15.0 Hz, 1H), 2.08 (d, J=12.3 Hz, 1H), 1.64-1.47 (m, 2H), 1.46 (t, J=7.1 Hz, 3H), 1.11 (t, J=7.1 Hz, 3H). ESMS m/z: 614.3 (M+1).

Example 2: In Vitro Inhibition of Aurora a Kinase Activity

The efficacies of 75 compounds of Formula (I) in inhibiting Aurora A kinase activity in vitro were assessed using the Kinase-Glo® Luminescent Kinase assay (Promega, USA) as described below. These 75 compounds are compounds 1, 2, 8, 12-17, 19-41, 43-44, 47-50, 54, 58, 62-63, 65, 86-90, 92-97, 99-104, 106-107, 109-111, 113-116, and 118-123.

Recombinant glutathione S-transferase (GST)-tagged N-terminal truncated human Aurora A (amino acids 123-401) was expressed in Sf9 insect cells and then purified by glutathione affinity chromatography to afford recombinant Aurora A. Recombinant Aurora A (150 ng) was reacted with each test compound (100 nM) in 50 μL of 50 mM Tris-HCl pH 7.4, 10 mM NaCl, 10 mM $MgCl_2$, 0.01% bovine serum albumin, 5.0 μM ATP, 1 mM dithiothreitol, 15 μM tetra(-LRRASLG) peptide at 37° C. for 120 minutes. Then, to the reaction was added 50 μL of Kinase-Glo Plus Reagent. The resulting mixture was incubated at 25° C. for 20 minutes. A 70 μL aliquot of the mixture was transferred to a black microliter plate. Luminescence was measured using a Wallac Vector 1420 multilabel counter (PerkinElmer, USA).

As shown in Table 1, each test compound exhibited an $IC_{50}$ value of lower than 100 nM.

These results indicate that compounds of Formula (I) have high in vitro efficacy in inhibiting Aurora A kinase activity.

TABLE 1

Inhibition of Aurora A Kinase Activity

| Compound No. | Chemical Structure | Aurora A $IC_{50}$ (nM) |
|---|---|---|
| 1 | 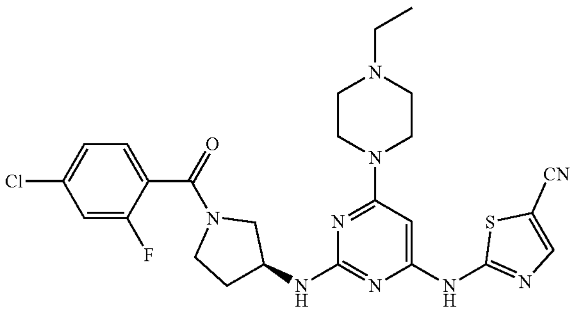 [SMILES: CCN1CCN(c2cc(Nc3ncc(C#N)s3)nc(N[C@H]3CCN(C(=O)c4ccc(Cl)cc4F)C3)n2)CC1] | <100 |

TABLE 1-continued
| Inhibition of Aurora A Kinase Activity | | |
|---|---|---|
| Compound No. | Chemical Structure | Aurora A $IC_{50}$ (nM) |
| 2 | 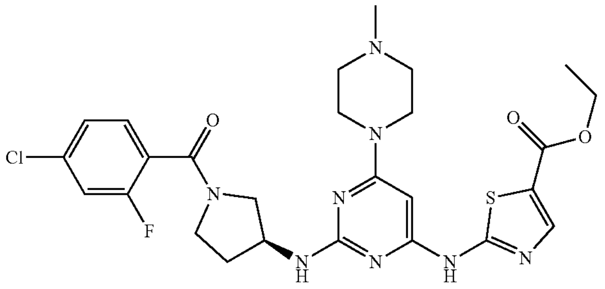 [SMILES: CCOC(=O)c1cnc(Nc2cc(N3CCN(C)CC3)nc(N[C@H]3CCN(C(=O)c4ccc(Cl)cc4F)C3)n2)s1] | <100 |
| 8 | 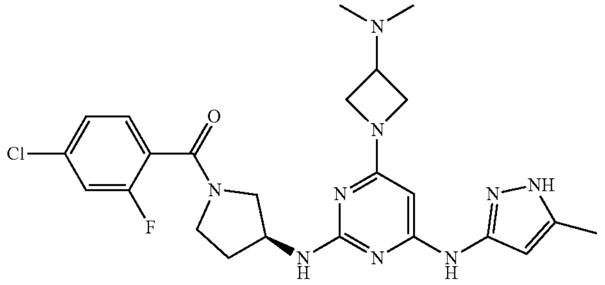 [SMILES: Cc1cc(Nc2cc(N3CC(N(C)C)C3)nc(N[C@H]3CCN(C(=O)c4ccc(Cl)cc4F)C3)n2)n[nH]1] | <100 |
| 12 | 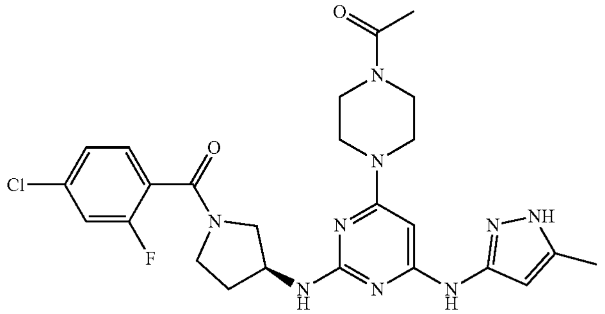 [SMILES: CC(=O)N1CCN(c2cc(Nc3cc(C)[nH]n3)nc(N[C@H]3CCN(C(=O)c4ccc(Cl)cc4F)C3)n2)CC1] | <100 |
| 13 | 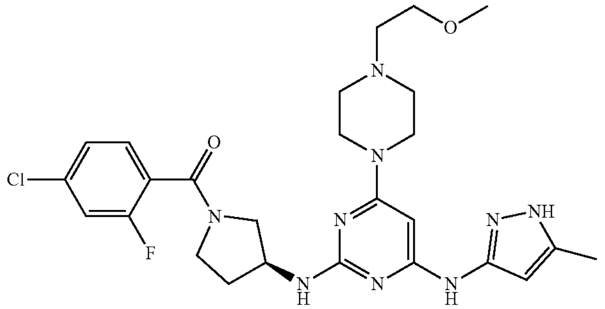 [SMILES: COCCN1CCN(c2cc(Nc3cc(C)[nH]n3)nc(N[C@H]3CCN(C(=O)c4ccc(Cl)cc4F)C3)n2)CC1] | <100 |
| 14 | 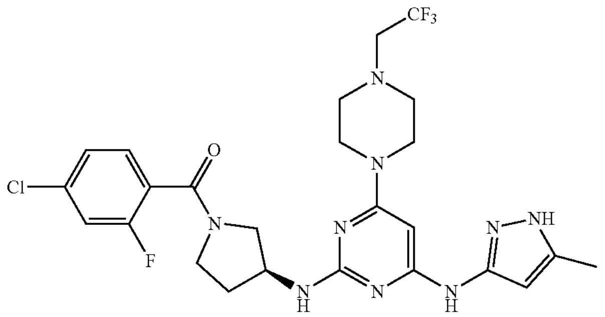 [SMILES: Cc1cc(Nc2cc(N3CCN(CC(F)(F)F)CC3)nc(N[C@H]3CCN(C(=O)c4ccc(Cl)cc4F)C3)n2)n[nH]1] | <100 |

TABLE 1-continued
| Inhibition of Aurora A Kinase Activity | | |
|---|---|---|
| Compound No. | Chemical Structure | Aurora A $IC_{50}$ (nM) |
| 15 | 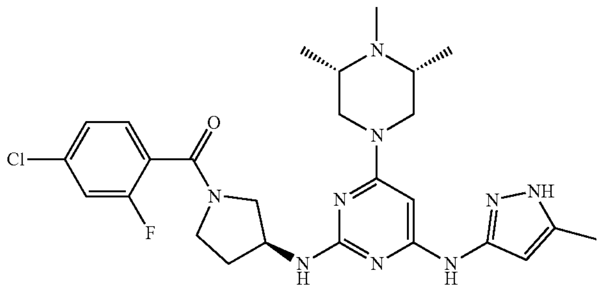 [SMILES: Cc1cc(Nc2cc(N3C[C@@H](C)N(C)[C@@H](C)C3)nc(N[C@H]3CCN(C(=O)c4ccc(Cl)cc4F)C3)n2)n[nH]1] | <100 |
| 16 | 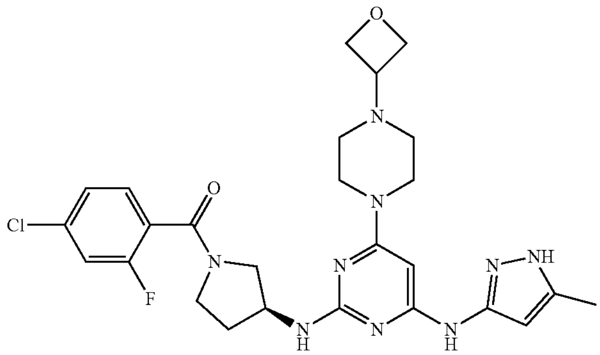 [SMILES: Cc1cc(Nc2cc(N3CCN(C4COC4)CC3)nc(N[C@H]3CCN(C(=O)c4ccc(Cl)cc4F)C3)n2)n[nH]1] | <100 |
| 17 | 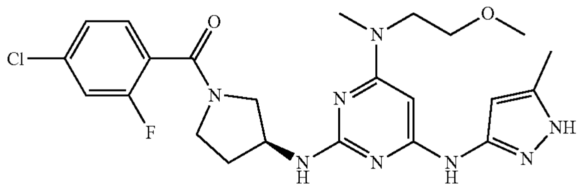 [SMILES: COCCN(C)c1cc(Nc2cc(C)[nH]n2)nc(N[C@H]2CCN(C(=O)c3ccc(Cl)cc3F)C2)n1] | <100 |
| 19 | 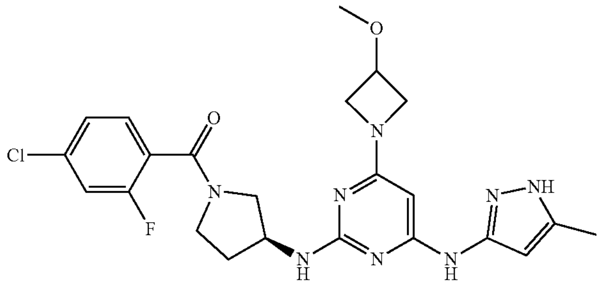 [SMILES: COC1CN(c2cc(Nc3cc(C)[nH]n3)nc(N[C@H]3CCN(C(=O)c4ccc(Cl)cc4F)C3)n2)C1] | <100 |
| 20 | 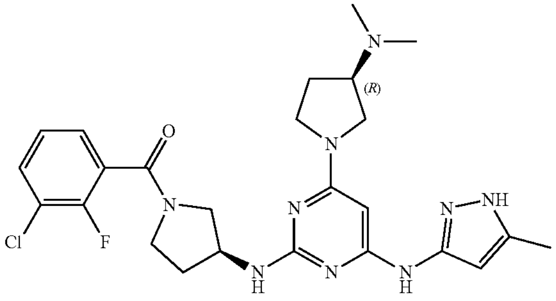 | <100 |

TABLE 1-continued
| Inhibition of Aurora A Kinase Activity | | |
|---|---|---|
| Compound No. | Chemical Structure | Aurora A $IC_{50}$ (nM) |
| 21 | 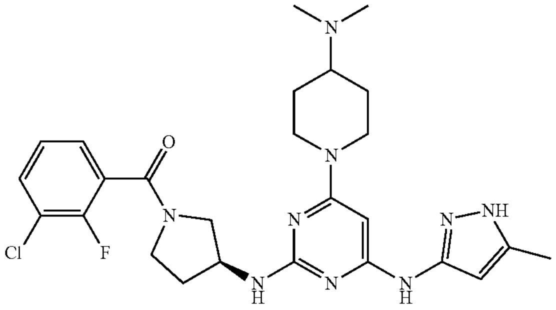 [SMILES: Cc1cc(Nc2cc(N3CCC(N(C)C)CC3)nc(N[C@H]3CCN(C(=O)c4cccc(Cl)c4F)C3)n2)n[nH]1] | <100 |
| 22 | 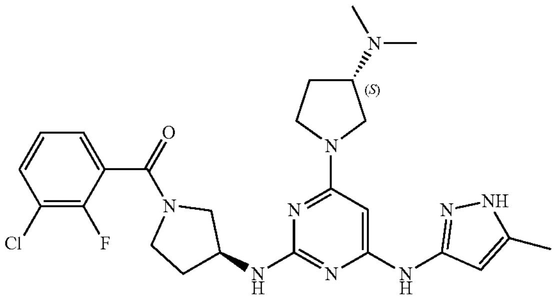 | <100 |
| 23 | 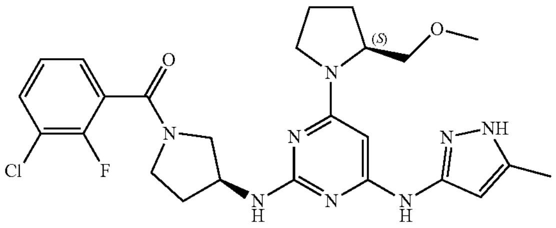 | <100 |
| 24 | 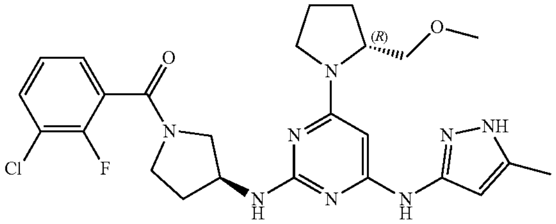 | <100 |
| 25 | 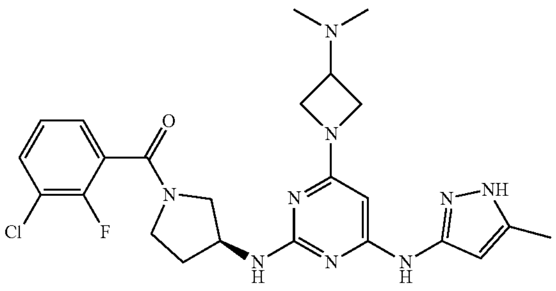 [SMILES: Cc1cc(Nc2cc(N3CC(N(C)C)C3)nc(N[C@H]3CCN(C(=O)c4cccc(Cl)c4F)C3)n2)n[nH]1] | <100 |

TABLE 1-continued
| Inhibition of Aurora A Kinase Activity | | |
|---|---|---|
| Compound No. | Chemical Structure | Aurora A $IC_{50}$ (nM) |
| 26 | 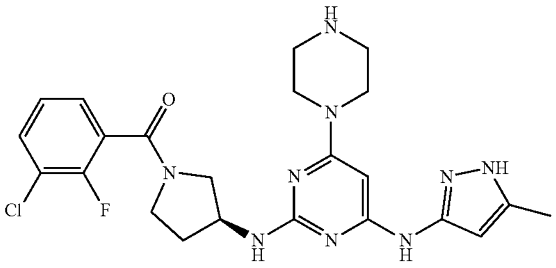 [SMILES: Cc1cc(Nc2cc(N3CCNCC3)nc(N[C@H]3CCN(C(=O)c4cccc(Cl)c4F)C3)n2)n[nH]1] | <100 |
| 27 | 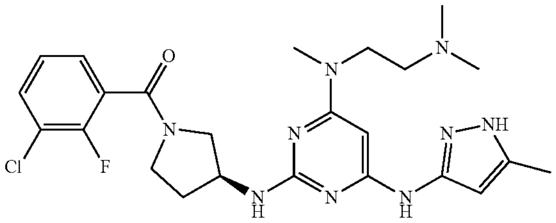 [SMILES: Cc1cc(Nc2cc(N(C)CCN(C)C)nc(N[C@H]3CCN(C(=O)c4cccc(Cl)c4F)C3)n2)n[nH]1] | <100 |
| 28 | 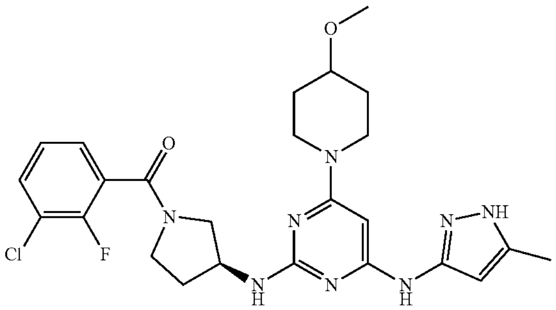 | <100 |
| 29 | 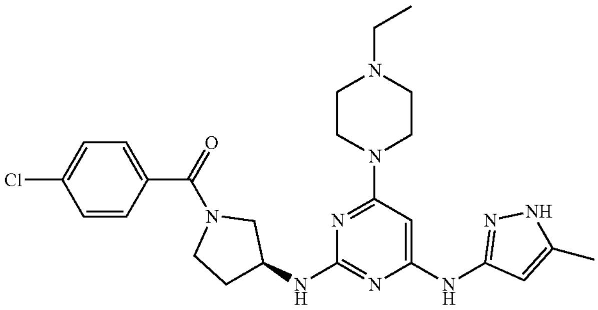 [SMILES: CCN1CCN(c2cc(Nc3cc(C)[nH]n3)nc(N[C@H]3CCN(C(=O)c4ccc(Cl)cc4)C3)n2)CC1] | <100 |
| 30 | 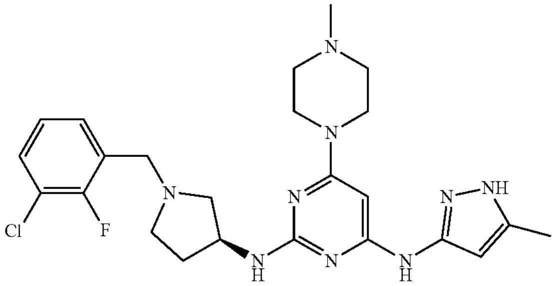 [SMILES: Cc1cc(Nc2cc(N3CCN(C)CC3)nc(N[C@H]3CCN(Cc4cccc(Cl)c4F)C3)n2)n[nH]1] | <100 |

TABLE 1-continued
Inhibition of Aurora A Kinase Activity
| Compound No. | Chemical Structure | Aurora A $IC_{50}$ (nM) |
|---|---|---|
| 31 | 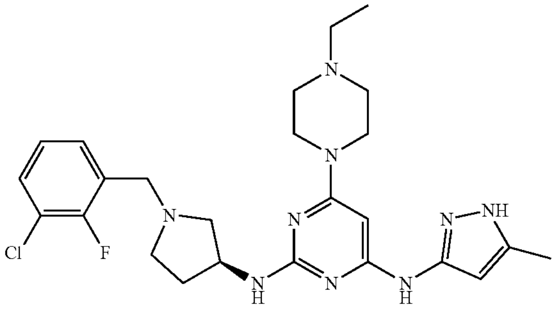 [SMILES: CCN1CCN(c2cc(Nc3cc(C)[nH]n3)nc(N[C@H]3CCN(Cc4cccc(Cl)c4F)C3)n2)CC1] | <100 |
| 32 | 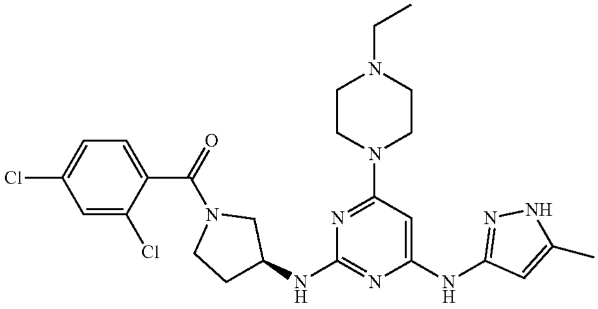 | <100 |
| 33 | 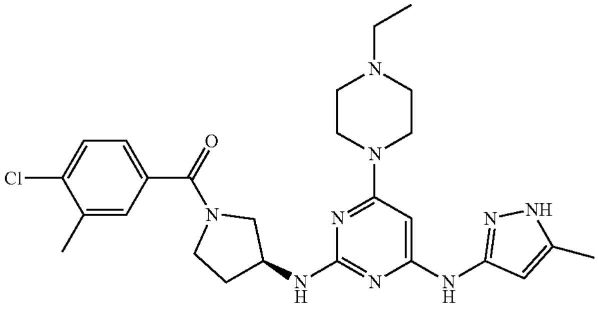 [SMILES: CCN1CCN(c2cc(Nc3cc(C)[nH]n3)nc(N[C@H]3CCN(C(=O)c4ccc(Cl)c(C)c4)C3)n2)CC1] | <100 |
| 34 | 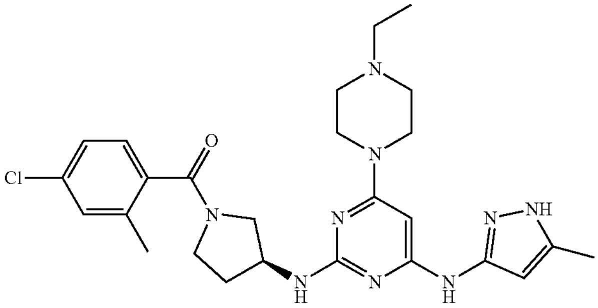 | <100 |
| 35 | 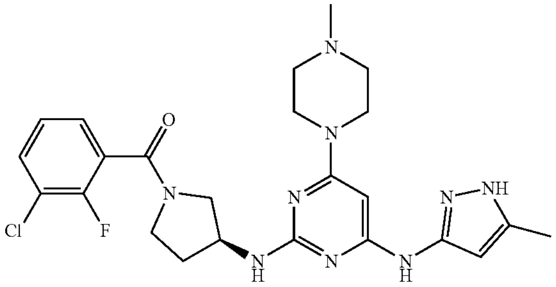 [SMILES: Cc1cc(Nc2cc(N3CCN(C)CC3)nc(N[C@H]3CCN(C(=O)c4cccc(Cl)c4F)C3)n2)n[nH]1] | <100 |

TABLE 1-continued
| Inhibition of Aurora A Kinase Activity | | |
|---|---|---|
| Compound No. | Chemical Structure | Aurora A $IC_{50}$ (nM) |
| 36 | 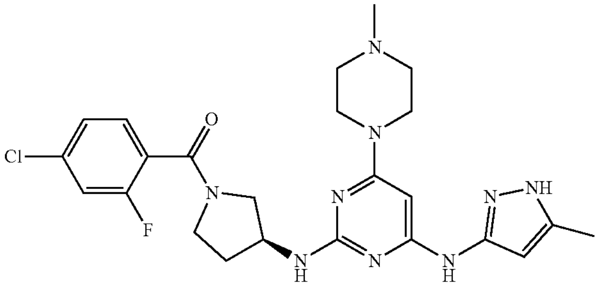 [SMILES: Cc1cc(Nc2cc(N3CCN(C)CC3)nc(N[C@H]3CCN(C(=O)c4ccc(Cl)cc4F)C3)n2)n[nH]1] | <100 |
| 37 | 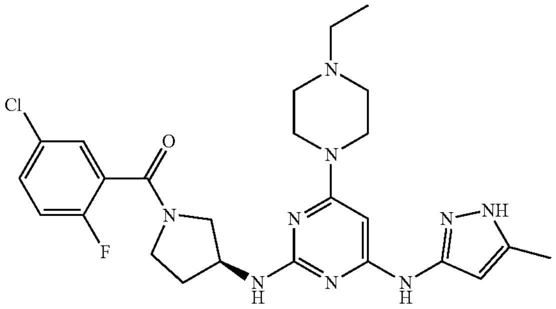 [SMILES: CCN1CCN(c2cc(Nc3cc(C)[nH]n3)nc(N[C@H]3CCN(C(=O)c4cc(Cl)ccc4F)C3)n2)CC1] | <100 |
| 38 | 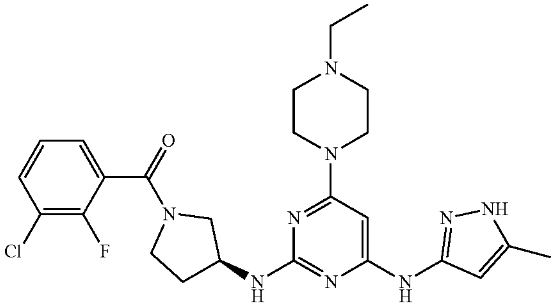 [SMILES: CCN1CCN(c2cc(Nc3cc(C)[nH]n3)nc(N[C@H]3CCN(C(=O)c4cccc(Cl)c4F)C3)n2)CC1] | <100 |
| 39 | 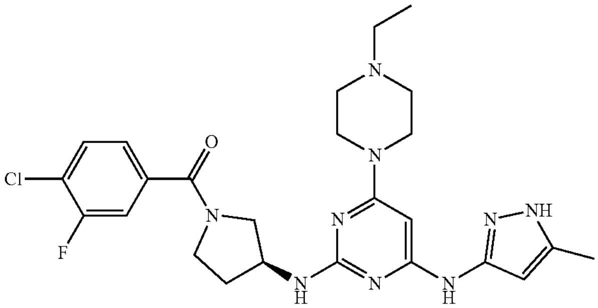 [SMILES: CCN1CCN(c2cc(Nc3cc(C)[nH]n3)nc(N[C@H]3CCN(C(=O)c4ccc(Cl)c(F)c4)C3)n2)CC1] | <100 |

TABLE 1-continued
Inhibition of Aurora A Kinase Activity
| Compound No. | Chemical Structure | Aurora A $IC_{50}$ (nM) |
|---|---|---|
| 40 | 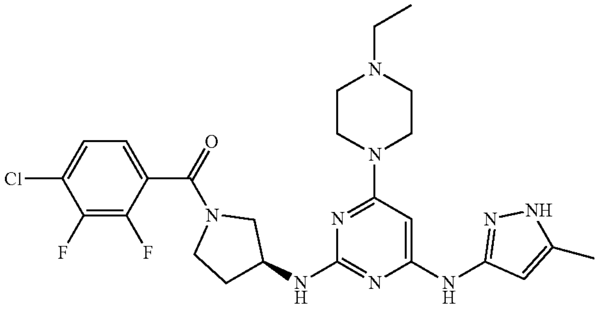 [SMILES: CCN1CCN(c2cc(Nc3cc(C)[nH]n3)nc(N[C@H]3CCN(C(=O)c4ccc(Cl)c(F)c4F)C3)n2)CC1] | <100 |
| 41 | 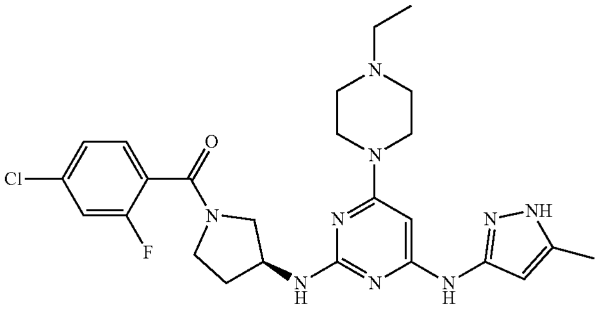 [SMILES: CCN1CCN(c2cc(Nc3cc(C)[nH]n3)nc(N[C@H]3CCN(C(=O)c4ccc(Cl)cc4F)C3)n2)CC1] | <100 |
| 43 | 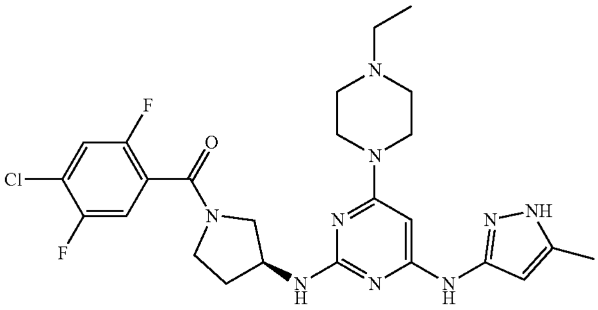 [SMILES: CCN1CCN(c2cc(Nc3cc(C)[nH]n3)nc(N[C@H]3CCN(C(=O)c4cc(F)c(Cl)cc4F)C3)n2)CC1] | <100 |
| 44 | 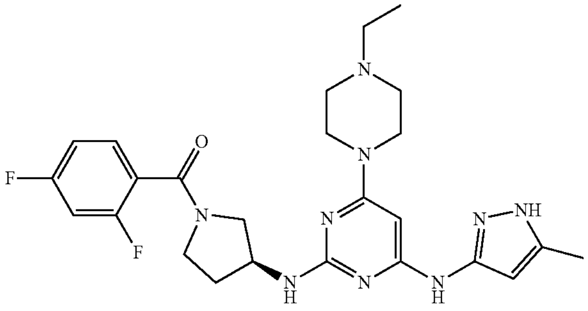 [SMILES: CCN1CCN(c2cc(Nc3cc(C)[nH]n3)nc(N[C@H]3CCN(C(=O)c4ccc(F)cc4F)C3)n2)CC1] | <100 |

TABLE 1-continued
| Inhibition of Aurora A Kinase Activity | | |
|---|---|---|
| Compound No. | Chemical Structure | Aurora A $IC_{50}$ (nM) |
| 47 | 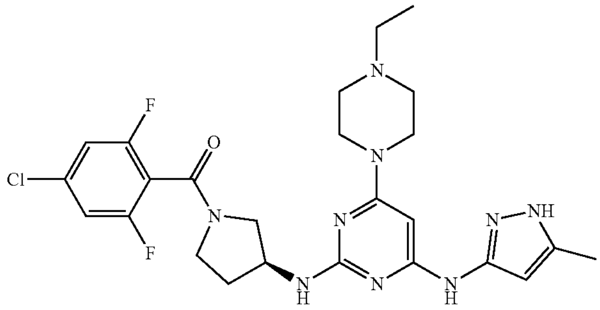 [SMILES: CCN1CCN(c2cc(Nc3cc(C)[nH]n3)nc(N[C@H]3CCN(C(=O)c4c(F)cc(Cl)cc4F)C3)n2)CC1] | <100 |
| 48 | 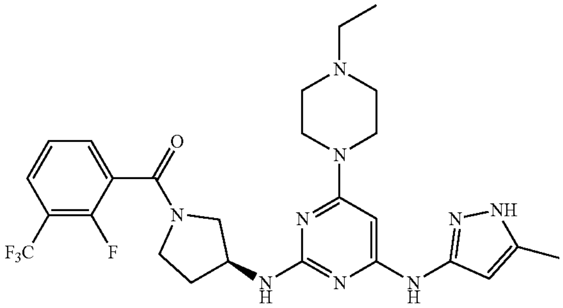 [SMILES: CCN1CCN(c2cc(Nc3cc(C)[nH]n3)nc(N[C@H]3CCN(C(=O)c4cccc(C(F)(F)F)c4F)C3)n2)CC1] | <100 |
| 49 | 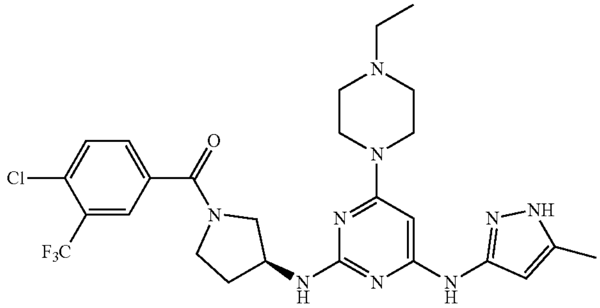 [SMILES: CCN1CCN(c2cc(Nc3cc(C)[nH]n3)nc(N[C@H]3CCN(C(=O)c4ccc(Cl)c(C(F)(F)F)c4)C3)n2)CC1] | <100 |
| 50 | 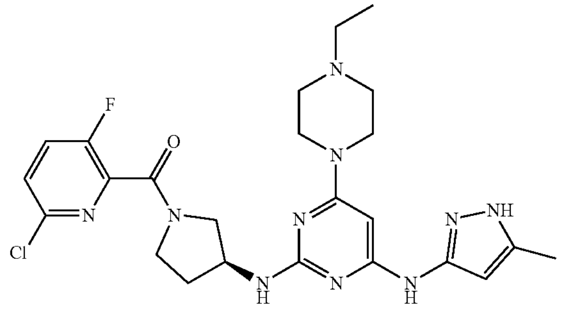 [SMILES: CCN1CCN(c2cc(Nc3cc(C)[nH]n3)nc(N[C@H]3CCN(C(=O)c4nc(Cl)ccc4F)C3)n2)CC1] | <100 |

TABLE 1-continued
| Inhibition of Aurora A Kinase Activity | | |
|---|---|---|
| Compound No. | Chemical Structure | Aurora A $IC_{50}$ (nM) |
| 54 | 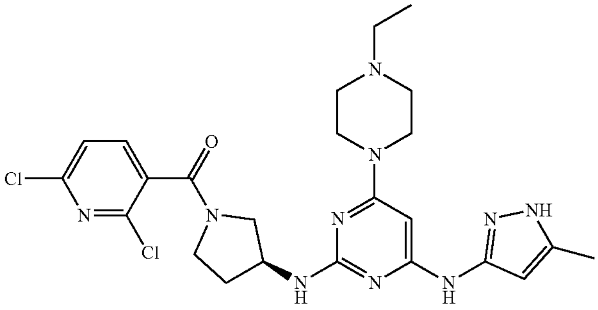 | <100 |
| 58 | 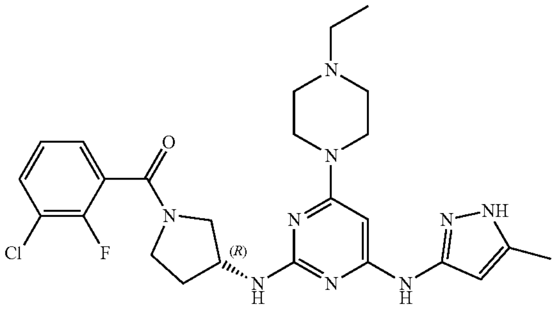 | <100 |
| 62 | 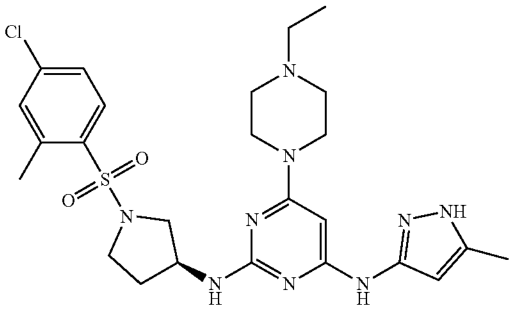 | <100 |
| 63 | 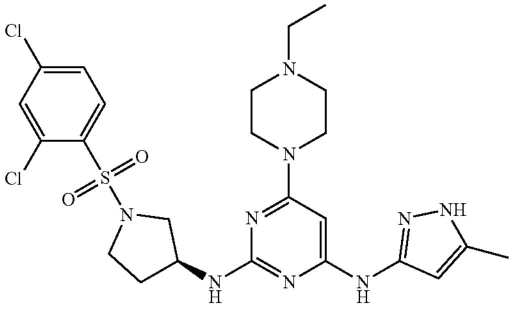 [SMILES: CCN1CCN(c2cc(Nc3cc(C)[nH]n3)nc(N[C@H]3CCN(S(=O)(=O)c4ccc(Cl)cc4Cl)C3)n2)CC1] | <100 |

TABLE 1-continued
| Inhibition of Aurora A Kinase Activity | | |
|---|---|---|
| Compound No. | Chemical Structure | Aurora A $IC_{50}$ (nM) |
| 65 | 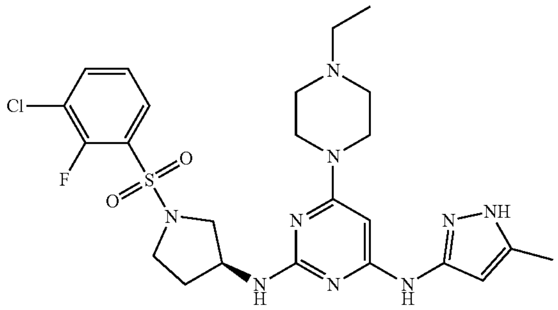 [SMILES: CCN1CCN(c2cc(Nc3cc(C)[nH]n3)nc(N[C@H]3CCN(S(=O)(=O)c4cccc(Cl)c4F)C3)n2)CC1] | <100 |
| 86 | 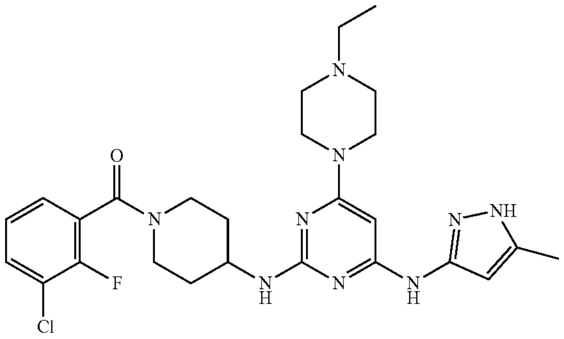 [SMILES: CCN1CCN(c2cc(Nc3cc(C)[nH]n3)nc(NC3CCN(C(=O)c4cccc(Cl)c4F)CC3)n2)CC1] | <100 |
| 87 | 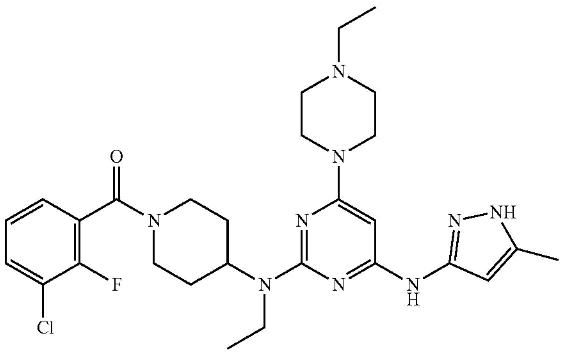 [SMILES: CCN1CCN(c2cc(Nc3cc(C)[nH]n3)nc(N(CC)C3CCN(C(=O)c4cccc(Cl)c4F)CC3)n2)CC1] | <100 |
| 88 | 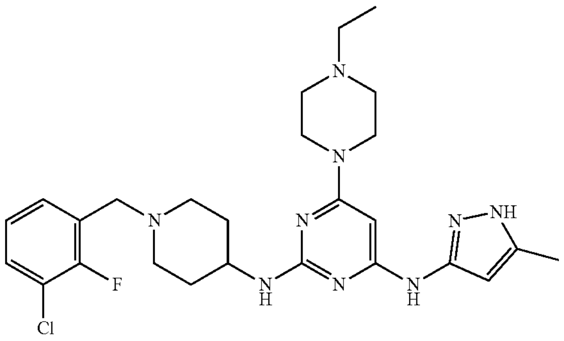 [SMILES: CCN1CCN(c2cc(Nc3cc(C)[nH]n3)nc(NC3CCN(Cc4cccc(Cl)c4F)CC3)n2)CC1] | <100 |

TABLE 1-continued
| Inhibition of Aurora A Kinase Activity | | |
|---|---|---|
| Compound No. | Chemical Structure | Aurora A $IC_{50}$ (nM) |
| 89 | 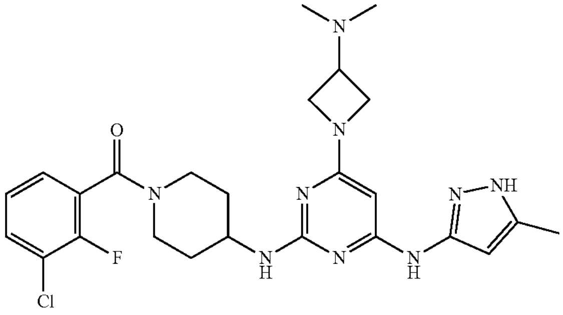 [SMILES: Cc1cc(Nc2cc(N3CC(N(C)C)C3)nc(NC3CCN(C(=O)c4cccc(Cl)c4F)CC3)n2)n[nH]1] | <100 |
| 90 | 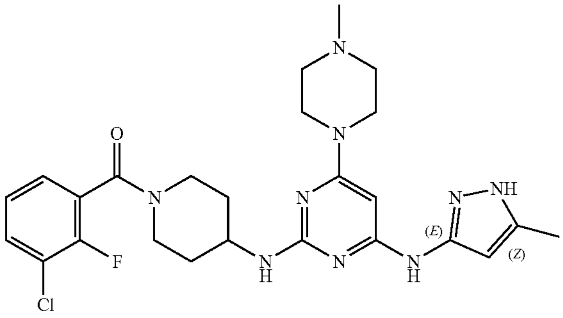 | <100 |
| 92 | 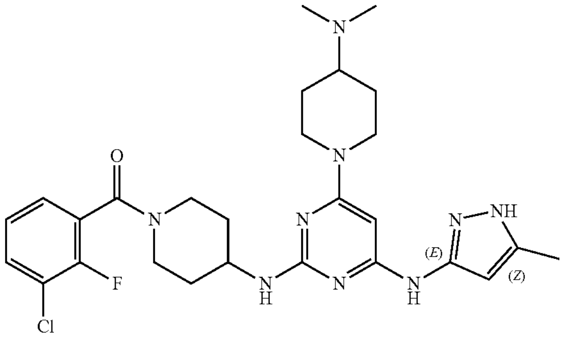 | <100 |
| 93 | 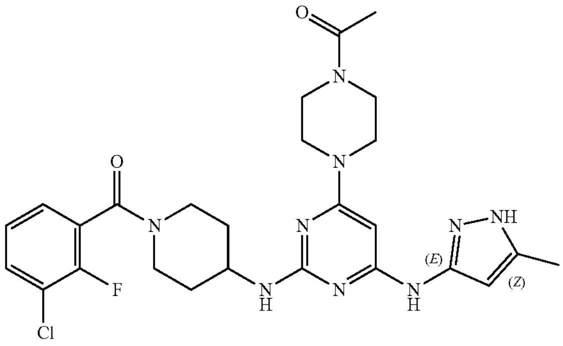 | <100 |

TABLE 1-continued
| Inhibition of Aurora A Kinase Activity | | |
|---|---|---|
| Compound No. | Chemical Structure | Aurora A $IC_{50}$ (nM) |
| 94 | 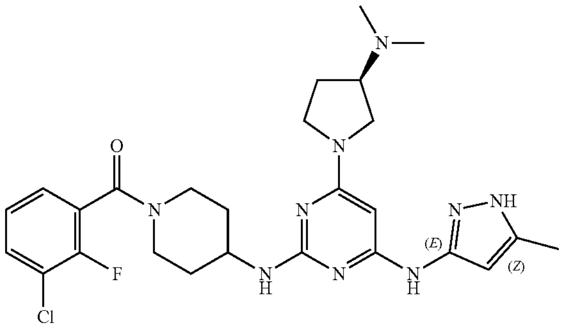 | <100 |
| 95 | 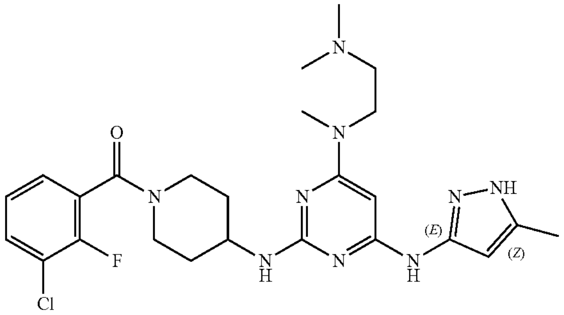 | <100 |
| 96 | 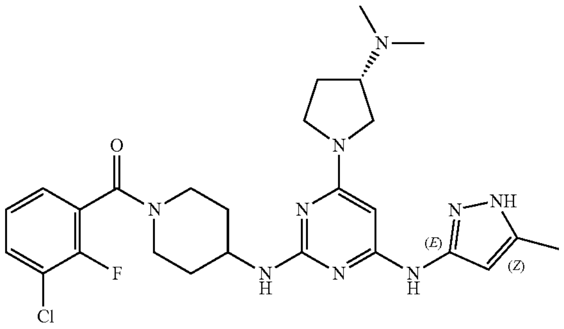 | <100 |
| 97 | 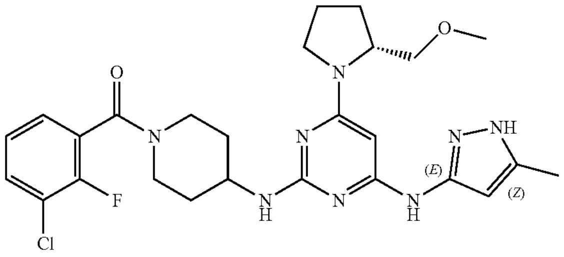 | <100 |

TABLE 1-continued
| Inhibition of Aurora A Kinase Activity | | |
|---|---|---|
| Compound No. | Chemical Structure | Aurora A $IC_{50}$ (nM) |
| 99 | 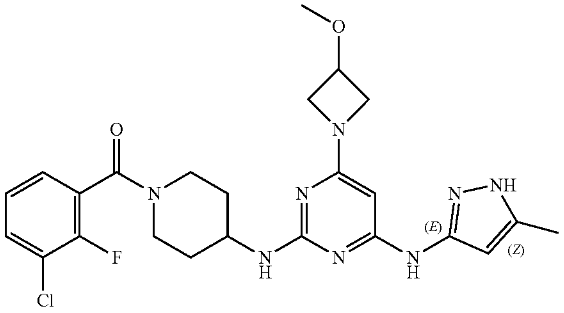 | <100 |
| 100 | 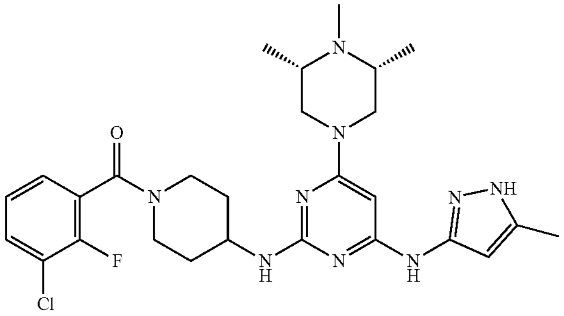 [SMILES: Cc1cc(Nc2cc(N3C[C@@H](C)N(C)[C@@H](C)C3)nc(NC3CCN(C(=O)c4cccc(Cl)c4F)CC3)n2)n[nH]1] | <100 |
| 101 | 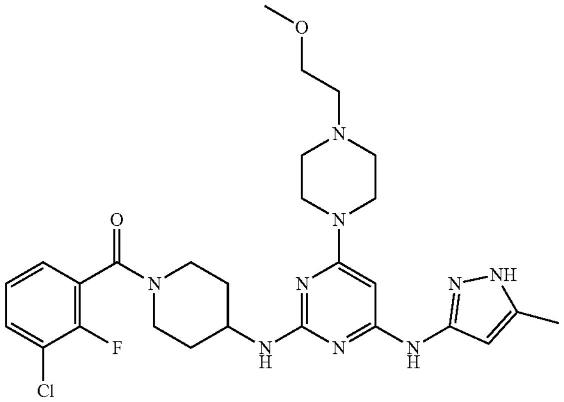 [SMILES: COCCN1CCN(c2cc(Nc3cc(C)[nH]n3)nc(NC3CCN(C(=O)c4cccc(Cl)c4F)CC3)n2)CC1] | <100 |
| 102 | 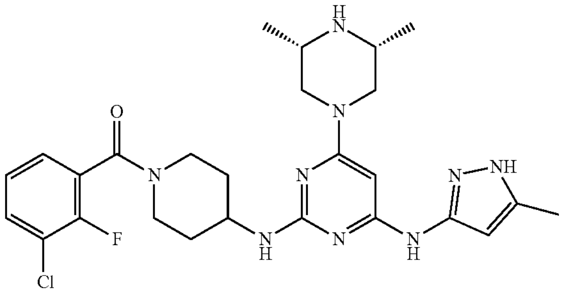 [SMILES: Cc1cc(Nc2cc(N3C[C@@H](C)N[C@@H](C)C3)nc(NC3CCN(C(=O)c4cccc(Cl)c4F)CC3)n2)n[nH]1] | <100 |

TABLE 1-continued
| Inhibition of Aurora A Kinase Activity | | |
|---|---|---|
| Compound No. | Chemical Structure | Aurora A $IC_{50}$ (nM) |
| 103 | 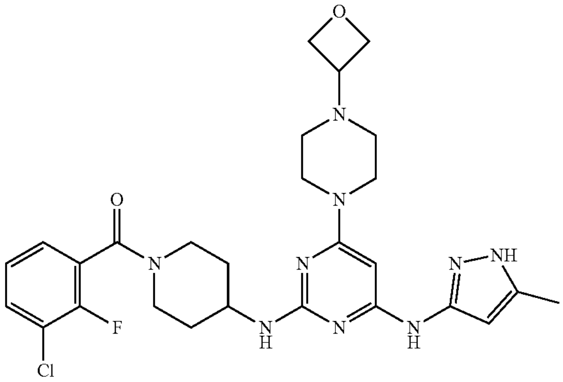 [SMILES: Cc1cc(Nc2cc(N3CCN(C4COC4)CC3)nc(NC3CCN(C(=O)c4cccc(Cl)c4F)CC3)n2)n[nH]1] | <100 |
| 104 | 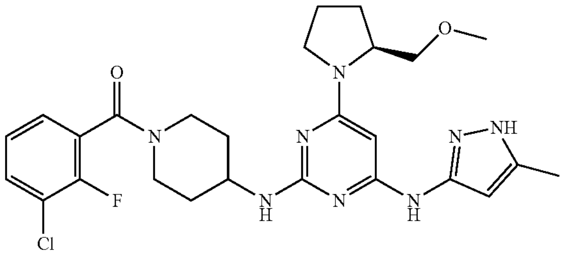 [SMILES: COC[C@@H]1CCCN1c1cc(Nc2cc(C)[nH]n2)nc(NC2CCN(C(=O)c3cccc(Cl)c3F)CC2)n1] | <100 |
| 106 | 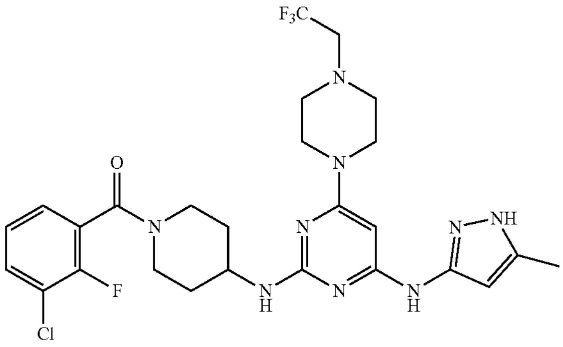 [SMILES: Cc1cc(Nc2cc(N3CCN(CC(F)(F)F)CC3)nc(NC3CCN(C(=O)c4cccc(Cl)c4F)CC3)n2)n[nH]1] | <100 |
| 107 | 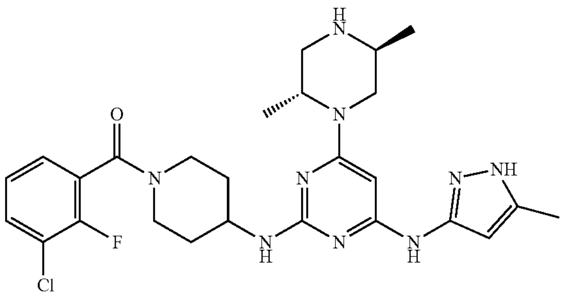 [SMILES: Cc1cc(Nc2cc(N3C[C@H](C)NC[C@H]3C)nc(NC3CCN(C(=O)c4cccc(Cl)c4F)CC3)n2)n[nH]1] | <100 |

TABLE 1-continued
Inhibition of Aurora A Kinase Activity
| Compound No. | Chemical Structure | Aurora A $IC_{50}$ (nM) |
|---|---|---|
| 109 | 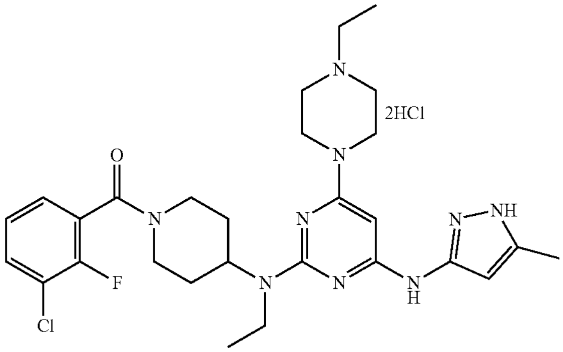 [SMILES: CCN1CCN(c2cc(Nc3cc(C)[nH]n3)nc(N(CC)C3CCN(C(=O)c4cccc(Cl)c4F)CC3)n2)CC1] | <100 |
| 110 | 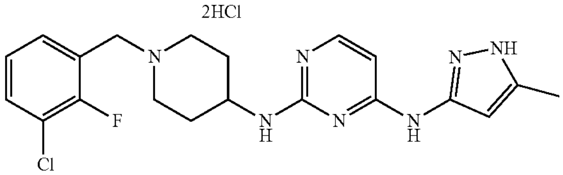 [SMILES: Cc1cc(Nc2ccnc(NC3CCN(Cc4cccc(Cl)c4F)CC3)n2)n[nH]1] | <100 |
| 111 | 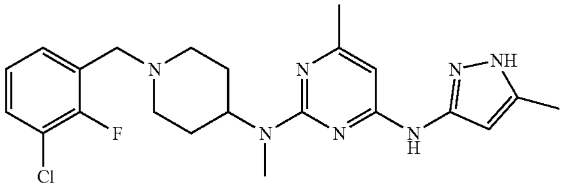 [SMILES: Cc1cc(Nc2cc(C)[nH]n2)nc(N(C)C2CCN(Cc3cccc(Cl)c3F)CC2)n1] | <100 |
| 113 | 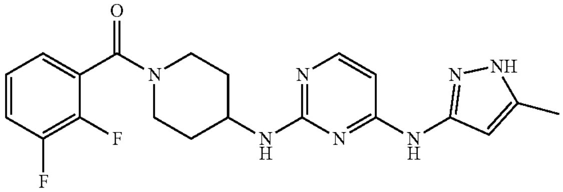 [SMILES: Cc1cc(Nc2ccnc(NC3CCN(C(=O)c4cccc(F)c4F)CC3)n2)n[nH]1] | <100 |
| 114 | 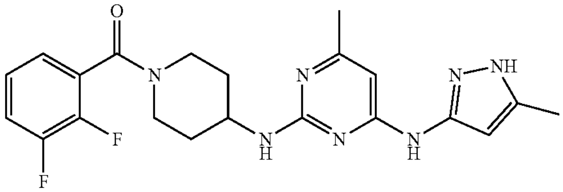 [SMILES: Cc1cc(Nc2cc(C)[nH]n2)nc(NC2CCN(C(=O)c3cccc(F)c3F)CC2)n1] | <100 |
| 115 | 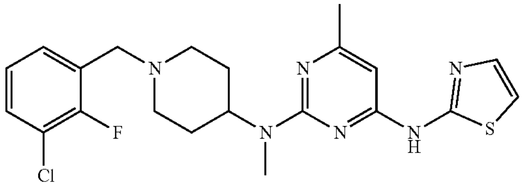 [SMILES: Cc1cc(Nc2nccs2)nc(N(C)C2CCN(Cc3cccc(Cl)c3F)CC2)n1] | <100 |
| 116 | 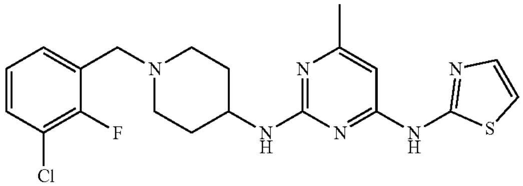 [SMILES: Cc1cc(Nc2nccs2)nc(NC2CCN(Cc3cccc(Cl)c3F)CC2)n1] | <100 |

TABLE 1-continued
| Inhibition of Aurora A Kinase Activity | | |
|---|---|---|
| Compound No. | Chemical Structure | Aurora A $IC_{50}$ (nM) |
| 118 | 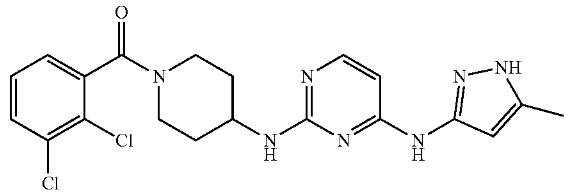 [SMILES: Cc1cc(Nc2ccnc(NC3CCN(C(=O)c4cccc(Cl)c4Cl)CC3)n2)n[nH]1] | <100 |
| 119 | 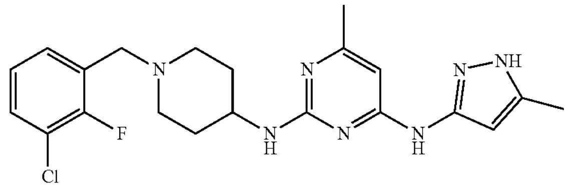 | <100 |
| 120 | 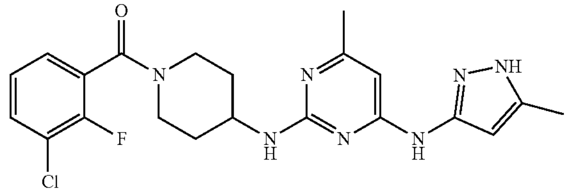 [SMILES: Cc1cc(Nc2cc(C)[nH]n2)nc(NC2CCN(C(=O)c3cccc(Cl)c3F)CC2)n1] | <100 |
| 121 | 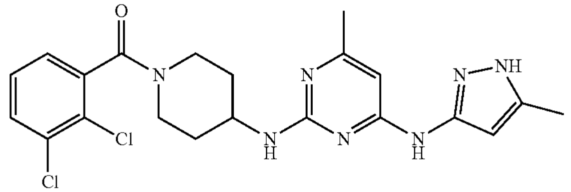 [SMILES: Cc1cc(Nc2cc(C)[nH]n2)nc(NC2CCN(C(=O)c3cccc(Cl)c3Cl)CC2)n1] | <100 |
| 122 | 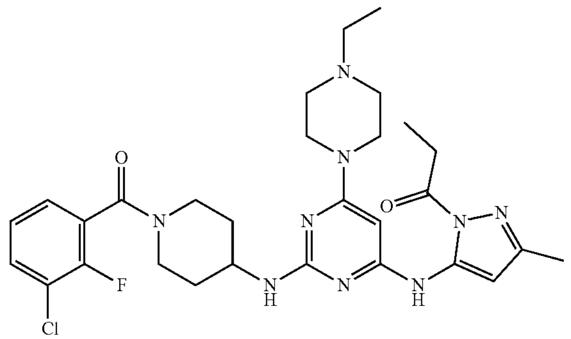 [SMILES: CCC(=O)n1nc(C)cc1Nc1cc(N2CCN(CC)CC2)nc(NC2CCN(C(=O)c3cccc(Cl)c3F)CC2)n1] | <100 |
| 123 | 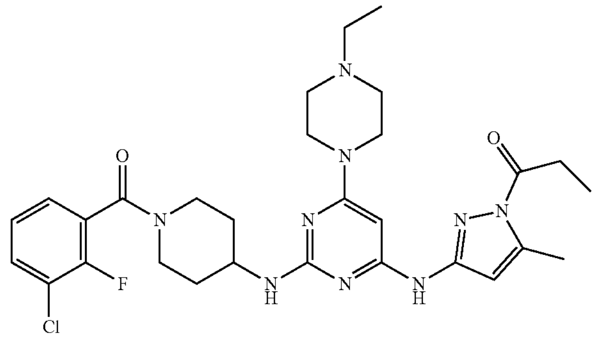 [SMILES: CCC(=O)n1nc(Nc2cc(N3CCN(CC)CC3)nc(NC3CCN(C(=O)c4cccc(Cl)c4F)CC3)n2)cc1C] | <100 |

Example 3: Reducing cMYC and MYCN Protein Levels in cMYC/MYCN Amplified Cancer Cells Compounds 41 and 86, both covered by Formula (I), were tested to assess their efficacies in reducing the level of cMYC oncoprotein in a human small-cell-lung-cancer ("SCLC") cell line NCI-H82 (ATCC® HTB-175, USA) and the level of MYCN oncoprotein in a human neuroblastoma cell line SK-N-BE(2) (ATCC® CRL-2271, USA) as follows.

NCI-H82 was maintained in RPMI1640 medium (ThermoFisher Scientific, USA) supplemented with 10% fetal bovine serum (FBS, HyClone, USA) and antibiotics. SK-N-BE(2) was maintained in Minimum Essential Medium (MEM, ThermoFisher Scientific, USA) supplemented with 10% FBS (HyClone, USA) and antibiotics. The cancer cells from each cell line were treated with each of compounds 41 and 86 at 4 different compound concentrations, i.e., 50 nM, 200 nM, 500 nM, and 1000 nM. After 24 hours, each cancer cell solution was washed with 1× phosphate buffered saline (PBS), lysed in 1× Laemmli protein sample buffer, and boiled at 100° C. for 10 minutes. Each lysate was separated by SDS-PAGE, transferred to polyvinylidene fluoride (PVDF, Millipore, USA) membrane, and blotted with antibodies. Primary antibodies used for Western blotting were cMYC (Cell Signaling, Cat No. 5605S), MYCN (Cell Signaling, 9405S), PARP-1 (Abcam, ab32378), and GAPDH (Genetex, GTX100118). After blotting with the primary antibodies, the membranes were washed with 1× blotting buffer (0.2% Casein in 1×PBS), corresponding alkaline phosphatase-conjugated secondary antibodies (Sigma-Aldrich) were added. The blots were developed by chemiluminescence (PerkinElmer, USA). Cleaved PARP1 (cPARP-1) served as an indicator of cell apoptosis and GAPDH was used as a control.

As shown in FIG. 1, compounds 41 and 86 greatly reduced the protein levels of cMYC and MYCN in two types of human cancer cells, i.e., SCLC and neuroblastoma.

These results indicate that the compounds of Formula (I) have high in vitro efficacy in reducing the cMYC and MYCN protein levels in cancer cells.

Example 4: Small-Cell-Lung Cancer Cell Proliferation Inhibition Assay

The efficacies of 74 compounds of Formula (I) in inhibiting cancer cell proliferation were determined using PrestoBlue™ Cell Viability Reagent (ThermoFisher Scientific, USA). These 74 compounds are compounds 1-2, 8-10, 12-19, 21-22, 25-27, 31-32, 35-41, 43-44, 47-50, 54, 62-63, 65, 70-75, 78-83, 86, 88-90, 92-107, 122-125, and 127.

Small cell lung cancer cells NCI-H82 (ATCC HTB-175, cMYC amplified), NCI-H446 (ATCC® HTB-171, cMYC amplified), and NCI-H69 (ATCC® HTB-119, MYCN amplified) were seeded at the density of 5000-10000 cells per well in 96-well plates. After 24 hours, the cancer cells were treated with each compound at various concentrations (0-10 μM) and then incubated for another 72 hours. $IC_{50}$ values were computed based on duplicated 8-point titration.

As shown in Table 2, each test compound exhibited an $IC_{50}$ value of lower than 1.0 μM in one or more of the three types of small-cell-lung-cancer cells.

These results indicate that the compounds of Formula (I) have high in vitro efficacy in inhibiting proliferation of small-cell-lung-cancer cells.

TABLE 2

Inhibition of Small-Cell-Lung-Cancer Cells Proliferation

| Compd. No. | Chemical Structure | NCI-H69 IC50 (nM) | NCI-H446 $IC_{50}$ (nM) | NCI-H82 IC50 (nM) |
|---|---|---|---|---|
| 1 | 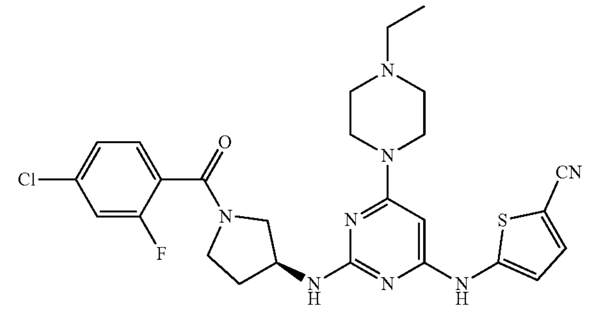 [SMILES: CCN1CCN(c2cc(Nc3ccc(C#N)s3)nc(N[C@H]3CCN(C(=O)c4ccc(Cl)cc4F)C3)n2)CC1] | | <1000 | <1000 |
| 2 | 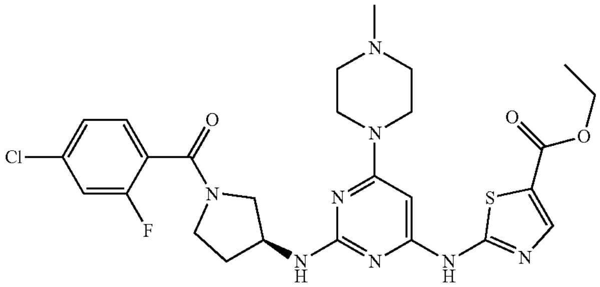 [SMILES: CCOC(=O)c1cnc(Nc2cc(N3CCN(C)CC3)nc(N[C@H]3CCN(C(=O)c4ccc(Cl)cc4F)C3)n2)s1] | | | <1000 |

TABLE 2-continued
Inhibition of Small-Cell-Lung-Cancer Cells Proliferation
| Compd. No. | Chemical Structure | NCI-H69 IC50 (nM) | NCI-H446 $IC_{50}$ (nM) | NCI-H82 IC50 (nM) |
|---|---|---|---|---|
| 8 | 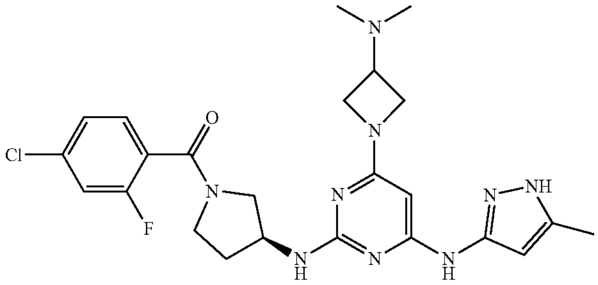 [SMILES: Cc1cc(Nc2cc(N3CC(N(C)C)C3)nc(N[C@H]3CCN(C(=O)c4ccc(Cl)cc4F)C3)n2)n[nH]1] | | <1000 | <1000 |
| 9 | 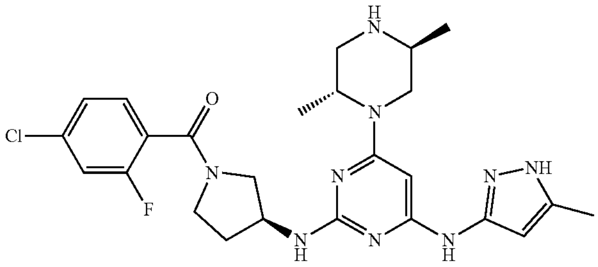 [SMILES: Cc1cc(Nc2cc(N3C[C@H](C)NC[C@H]3C)nc(N[C@H]3CCN(C(=O)c4ccc(Cl)cc4F)C3)n2)n[nH]1] | <1000 | <1000 | <1000 |
| 10 | 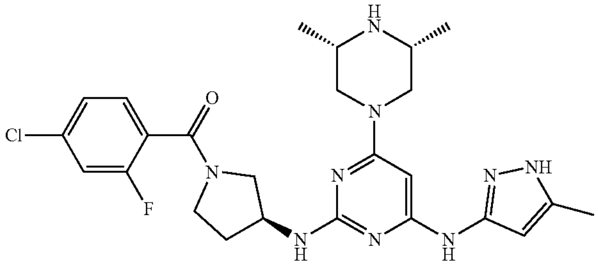 [SMILES: Cc1cc(Nc2cc(N3C[C@@H](C)N[C@@H](C)C3)nc(N[C@H]3CCN(C(=O)c4ccc(Cl)cc4F)C3)n2)n[nH]1] | <1000 | <1000 | <1000 |
| 12 | 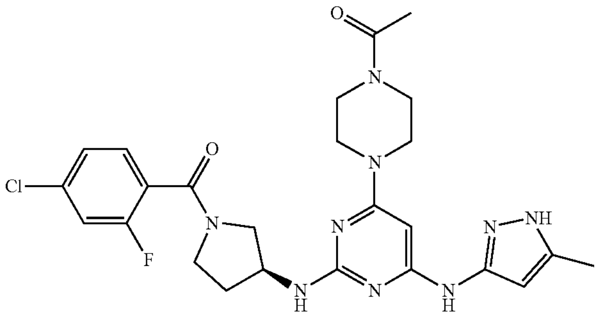 [SMILES: CC(=O)N1CCN(c2cc(Nc3cc(C)[nH]n3)nc(N[C@H]3CCN(C(=O)c4ccc(Cl)cc4F)C3)n2)CC1] | | <1000 | <1000 |
| 13 | 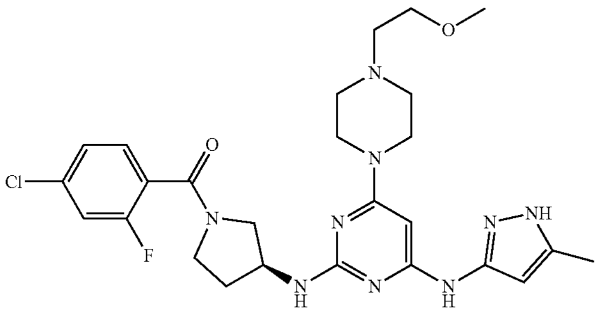 [SMILES: COCCN1CCN(c2cc(Nc3cc(C)[nH]n3)nc(N[C@H]3CCN(C(=O)c4ccc(Cl)cc4F)C3)n2)CC1] | <1000 | | <1000 |

TABLE 2-continued
Inhibition of Small-Cell-Lung-Cancer Cells Proliferation
| Compd. No. | Chemical Structure | NCI-H69 IC50 (nM) | NCI-H446 $IC_{50}$ (nM) | NCI-H82 IC50 (nM) |
|---|---|---|---|---|
| 14 | 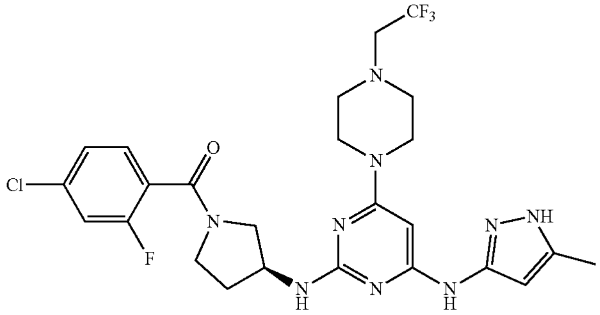 [SMILES: Cc1cc(Nc2cc(N3CCN(CC(F)(F)F)CC3)nc(N[C@H]3CCN(C(=O)c4ccc(Cl)cc4F)C3)n2)n[nH]1] | <1000 | <1000 | <1000 |
| 15 | 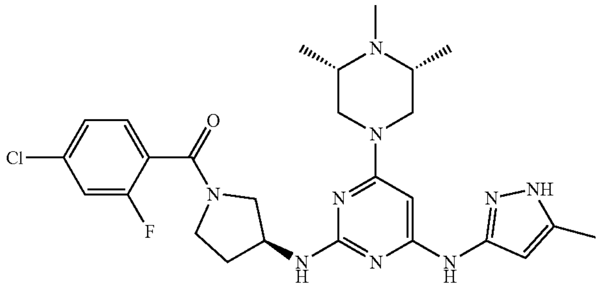 [SMILES: Cc1cc(Nc2cc(N3C[C@@H](C)N(C)[C@@H](C)C3)nc(N[C@H]3CCN(C(=O)c4ccc(Cl)cc4F)C3)n2)n[nH]1] | <1000 | <1000 | <1000 |
| 16 | 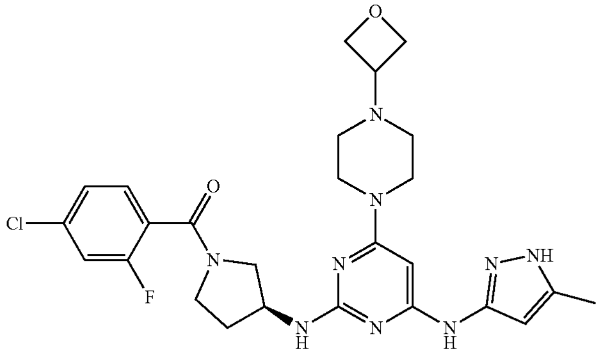 [SMILES: Cc1cc(Nc2cc(N3CCN(C4COC4)CC3)nc(N[C@H]3CCN(C(=O)c4ccc(Cl)cc4F)C3)n2)n[nH]1] | <1000 | <1000 | <1000 |
| 17 | 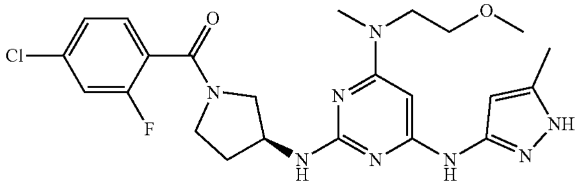 [SMILES: COCCN(C)c1cc(Nc2cc(C)[nH]n2)nc(N[C@H]2CCN(C(=O)c3ccc(Cl)cc3F)C2)n1] | | <1000 | <1000 |
| 18 | 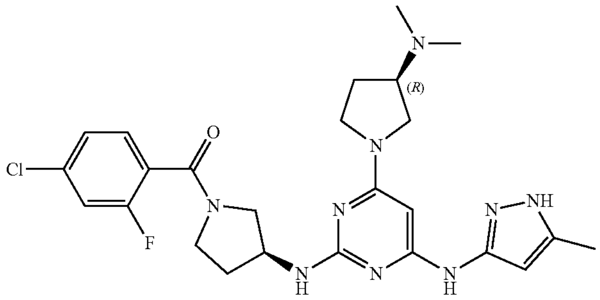 | | <1000 | <1000 |

TABLE 2-continued
Inhibition of Small-Cell-Lung-Cancer Cells Proliferation
| Compd. No. | Chemical Structure | NCI-H69 IC50 (nM) | NCI-H446 $IC_{50}$ (nM) | NCI-H82 IC50 (nM) |
|---|---|---|---|---|
| 19 | 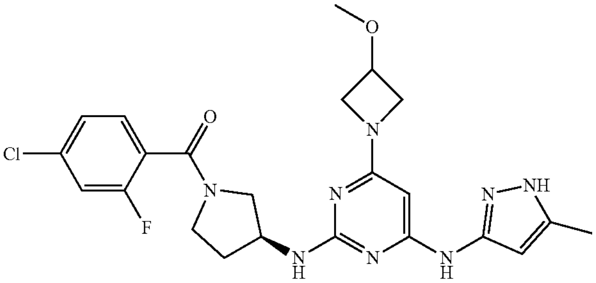 [SMILES: COC1CN(c2cc(Nc3cc(C)[nH]n3)nc(N[C@H]3CCN(C(=O)c4ccc(Cl)cc4F)C3)n2)C1] | | <1000 | <1000 |
| 21 | 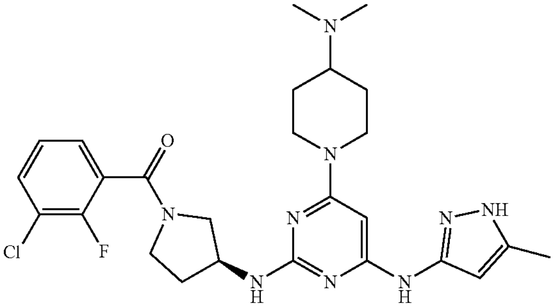 [SMILES: Cc1cc(Nc2cc(N3CCC(N(C)C)CC3)nc(N[C@H]3CCN(C(=O)c4cccc(Cl)c4F)C3)n2)n[nH]1] | <1000 | <1000 | <1000 |
| 22 | 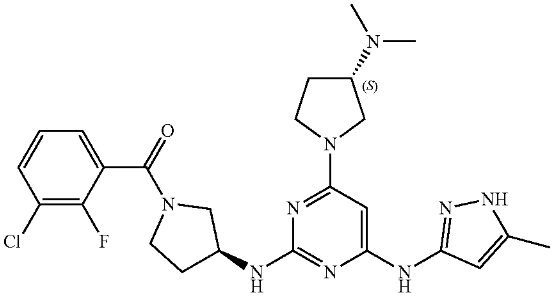 | | <1000 | <1000 |
| 25 | 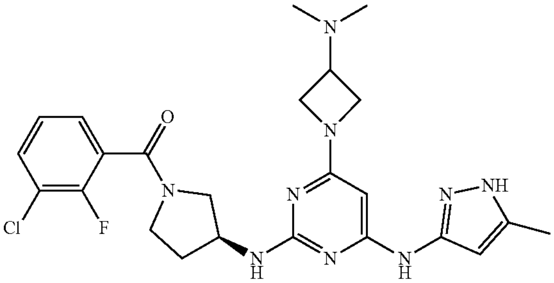 [SMILES: Cc1cc(Nc2cc(N3CC(N(C)C)C3)nc(N[C@H]3CCN(C(=O)c4cccc(Cl)c4F)C3)n2)n[nH]1] | | <1000 | <1000 |
| 26 | 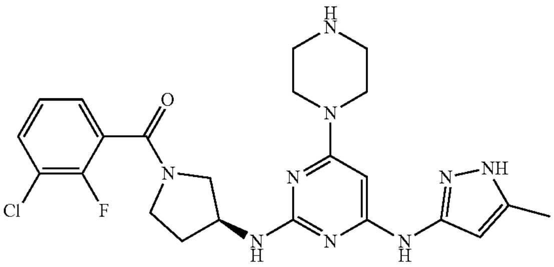 [SMILES: Cc1cc(Nc2cc(N3CCNCC3)nc(N[C@H]3CCN(C(=O)c4cccc(Cl)c4F)C3)n2)n[nH]1] | | <1000 | <1000 |

TABLE 2-continued
Inhibition of Small-Cell-Lung-Cancer Cells Proliferation
| Compd. No. | Chemical Structure | NCI-H69 IC50 (nM) | NCI-H446 $IC_{50}$ (nM) | NCI-H82 IC50 (nM) |
| --- | --- | --- | --- | --- |
| 27 | 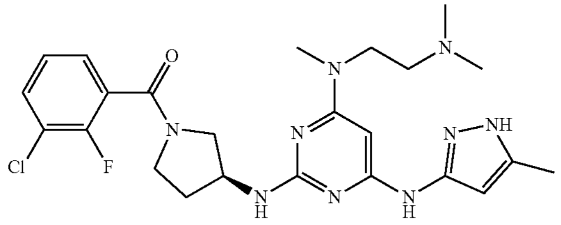 [SMILES: Cc1cc(Nc2cc(N(C)CCN(C)C)nc(N[C@H]3CCN(C(=O)c4cccc(Cl)c4F)C3)n2)n[nH]1] | | <1000 | <1000 |
| 31 | 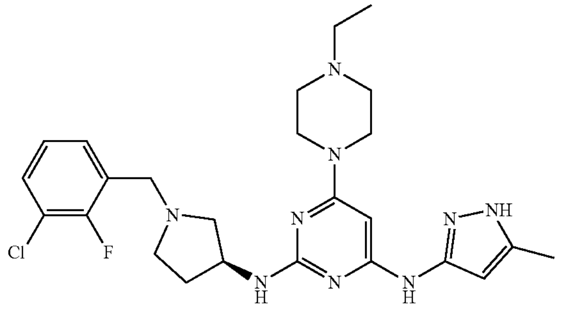 [SMILES: CCN1CCN(c2cc(Nc3cc(C)[nH]n3)nc(N[C@H]3CCN(Cc4cccc(Cl)c4F)C3)n2)CC1] | | <1000 | <1000 |
| 32 | 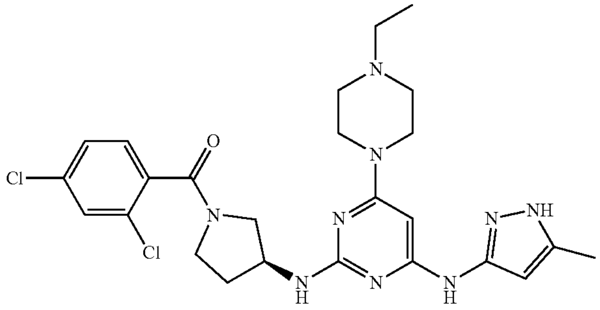 | | <1000 | <1000 |
| 35 | 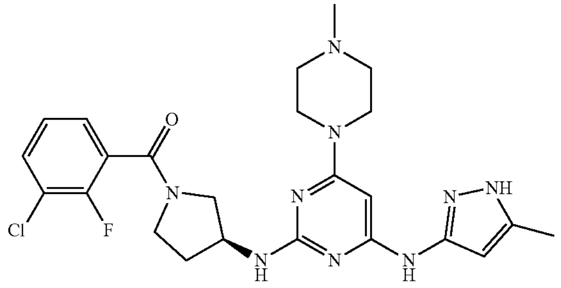 [SMILES: Cc1cc(Nc2cc(N3CCN(C)CC3)nc(N[C@H]3CCN(C(=O)c4cccc(Cl)c4F)C3)n2)n[nH]1] | | <1000 | <1000 |
| 36 | 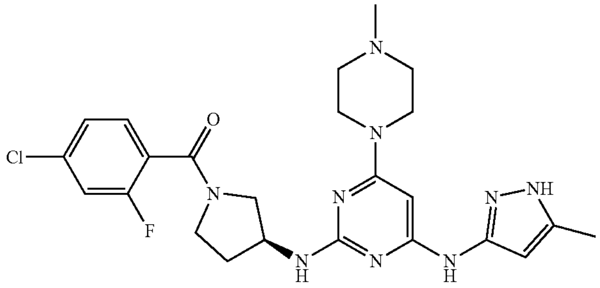 [SMILES: Cc1cc(Nc2cc(N3CCN(C)CC3)nc(N[C@H]3CCN(C(=O)c4ccc(Cl)cc4F)C3)n2)n[nH]1] | | <1000 | <1000 |

TABLE 2-continued
Inhibition of Small-Cell-Lung-Cancer Cells Proliferation
| Compd. No. | Chemical Structure | NCI-H69 IC50 (nM) | NCI-H446 $IC_{50}$ (nM) | NCI-H82 IC50 (nM) |
|---|---|---|---|---|
| 37 | 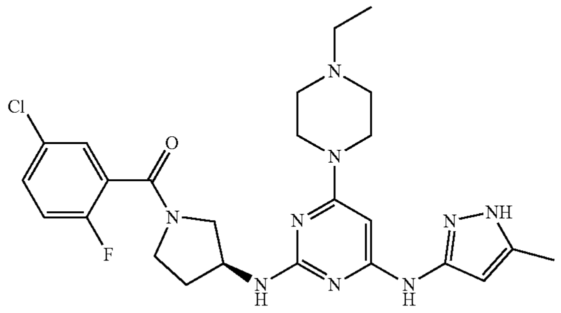 [SMILES: CCN1CCN(c2cc(Nc3cc(C)[nH]n3)nc(N[C@H]3CCN(C(=O)c4cc(Cl)ccc4F)C3)n2)CC1] | | <1000 | <1000 |
| 38 | 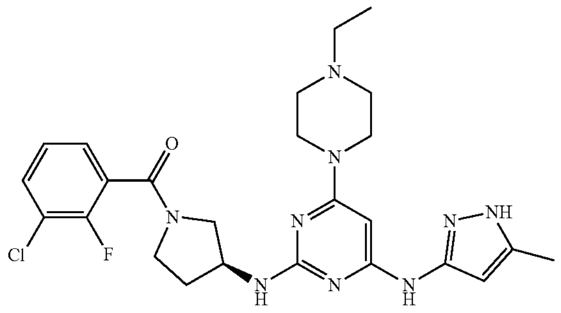 [SMILES: CCN1CCN(c2cc(Nc3cc(C)[nH]n3)nc(N[C@H]3CCN(C(=O)c4cccc(Cl)c4F)C3)n2)CC1] | | <1000 | <1000 |
| 39 | 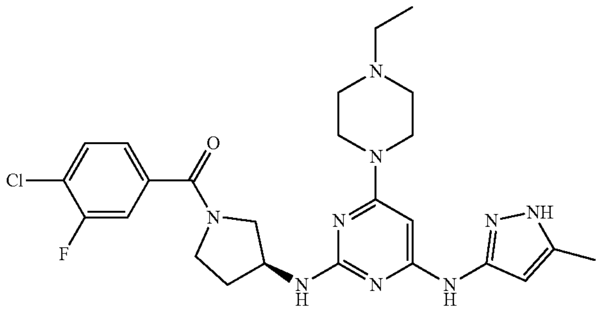 [SMILES: CCN1CCN(c2cc(Nc3cc(C)[nH]n3)nc(N[C@H]3CCN(C(=O)c4ccc(Cl)c(F)c4)C3)n2)CC1] | | <1000 | <1000 |
| 40 | 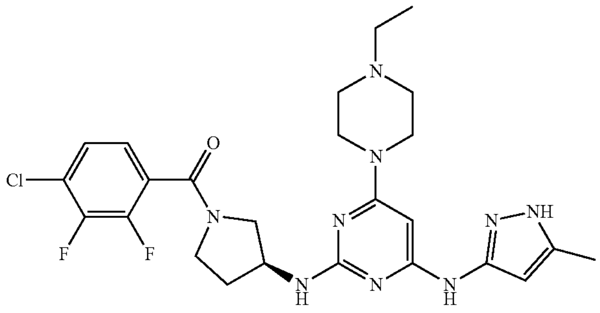 [SMILES: CCN1CCN(c2cc(Nc3cc(C)[nH]n3)nc(N[C@H]3CCN(C(=O)c4ccc(Cl)c(F)c4F)C3)n2)CC1] | | <1000 | <1000 |

TABLE 2-continued
| Inhibition of Small-Cell-Lung-Cancer Cells Proliferation | | | | |
|---|---|---|---|---|
| Compd. No. | Chemical Structure | NCI-H69 IC50 (nM) | NCI-H446 $IC_{50}$ (nM) | NCI-H82 IC50 (nM) |
| 41 | 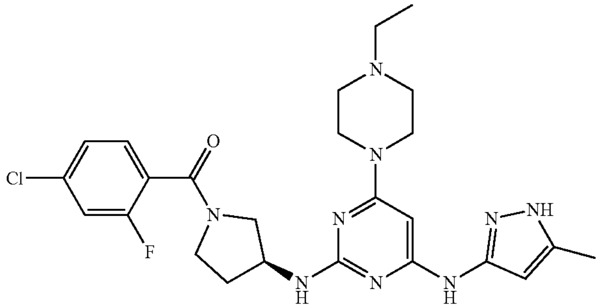 [SMILES: CCN1CCN(c2cc(Nc3cc(C)[nH]n3)nc(N[C@H]3CCN(C(=O)c4ccc(Cl)cc4F)C3)n2)CC1] | | <1000 | <1000 |
| 43 | 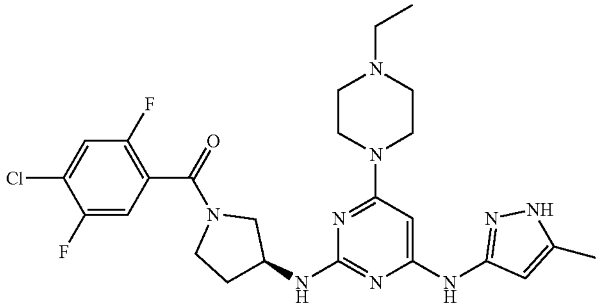 [SMILES: CCN1CCN(c2cc(Nc3cc(C)[nH]n3)nc(N[C@H]3CCN(C(=O)c4cc(F)c(Cl)cc4F)C3)n2)CC1] | | <1000 | <1000 |
| 44 | 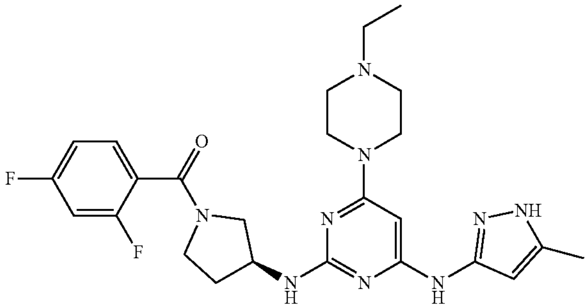 [SMILES: CCN1CCN(c2cc(Nc3cc(C)[nH]n3)nc(N[C@H]3CCN(C(=O)c4ccc(F)cc4F)C3)n2)CC1] | | <1000 | <1000 |
| 47 | 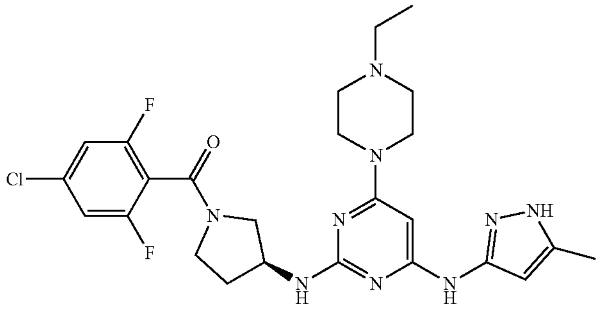 [SMILES: CCN1CCN(c2cc(Nc3cc(C)[nH]n3)nc(N[C@H]3CCN(C(=O)c4c(F)cc(Cl)cc4F)C3)n2)CC1] | | <1000 | <1000 |

TABLE 2-continued
| Inhibition of Small-Cell-Lung-Cancer Cells Proliferation | | | | |
|---|---|---|---|---|
| Compd. No. | Chemical Structure | NCI-H69 IC50 (nM) | NCI-H446 $IC_{50}$ (nM) | NCI-H82 IC50 (nM) |
| 48 | 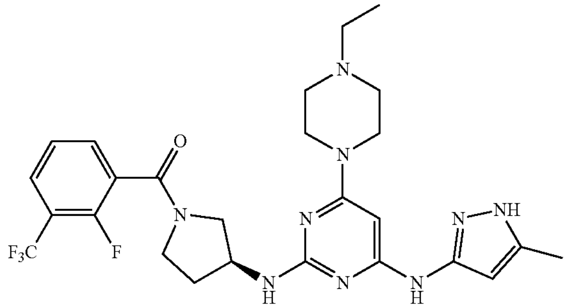 [SMILES: CCN1CCN(c2cc(Nc3cc(C)[nH]n3)nc(N[C@H]3CCN(C(=O)c4cccc(C(F)(F)F)c4F)C3)n2)CC1] | | <1000 | <1000 |
| 49 | 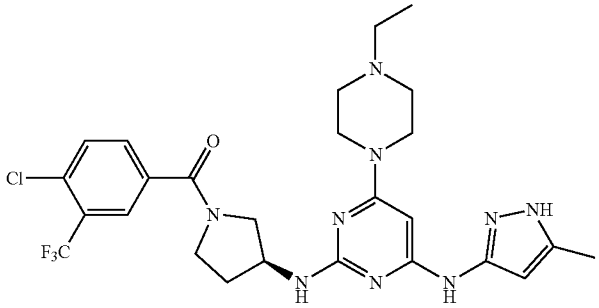 [SMILES: CCN1CCN(c2cc(Nc3cc(C)[nH]n3)nc(N[C@H]3CCN(C(=O)c4ccc(Cl)c(C(F)(F)F)c4)C3)n2)CC1] | | <1000 | <1000 |
| 50 | 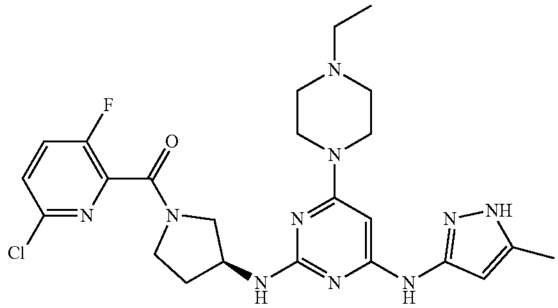 [SMILES: CCN1CCN(c2cc(Nc3cc(C)[nH]n3)nc(N[C@H]3CCN(C(=O)c4nc(Cl)ccc4F)C3)n2)CC1] | | <1000 | <1000 |
| 54 | 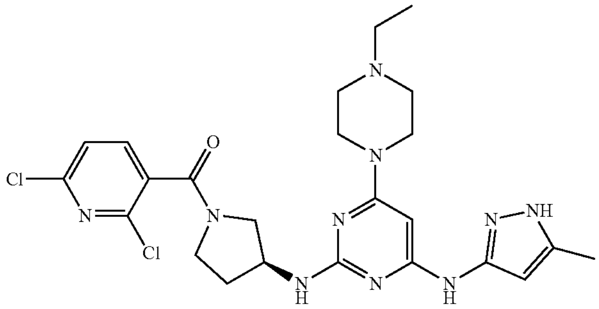 | | <1000 | <1000 |

TABLE 2-continued
| Inhibition of Small-Cell-Lung-Cancer Cells Proliferation | | | | |
|---|---|---|---|---|
| Compd. No. | Chemical Structure | NCI-H69 IC50 (nM) | NCI-H446 $IC_{50}$ (nM) | NCI-H82 IC50 (nM) |
| 62 | 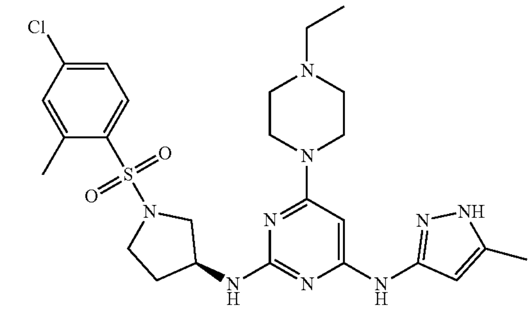 [SMILES: CCN1CCN(c2cc(Nc3cc(C)[nH]n3)nc(N[C@H]3CCN(S(=O)(=O)c4ccc(Cl)cc4C)C3)n2)CC1] | | <1000 | <1000 |
| 63 | 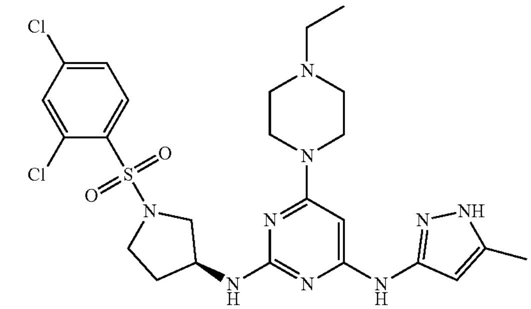 [SMILES: CCN1CCN(c2cc(Nc3cc(C)[nH]n3)nc(N[C@H]3CCN(S(=O)(=O)c4ccc(Cl)cc4Cl)C3)n2)CC1] | | <1000 | <1000 |
| 65 | 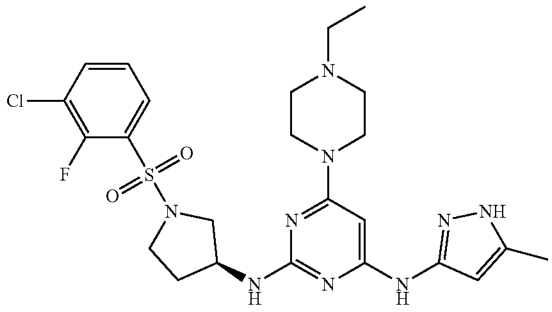 [SMILES: CCN1CCN(c2cc(Nc3cc(C)[nH]n3)nc(N[C@H]3CCN(S(=O)(=O)c4cccc(Cl)c4F)C3)n2)CC1] | | <1000 | <1000 |
| 70 | 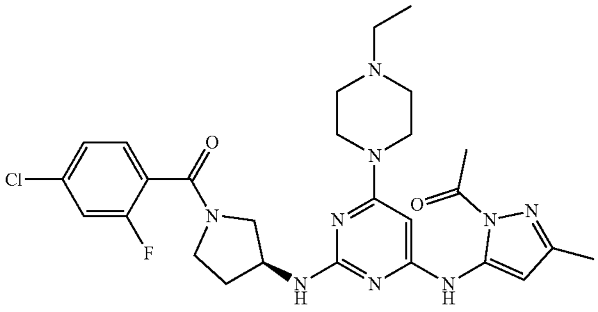 [SMILES: CCN1CCN(c2cc(Nc3cc(C)nn3C(C)=O)nc(N[C@H]3CCN(C(=O)c4ccc(Cl)cc4F)C3)n2)CC1] | | <1000 | <1000 |

TABLE 2-continued
Inhibition of Small-Cell-Lung-Cancer Cells Proliferation
| Compd. No. | Chemical Structure | NCI-H69 IC50 (nM) | NCI-H446 $IC_{50}$ (nM) | NCI-H82 IC50 (nM) |
|---|---|---|---|---|
| 71 | 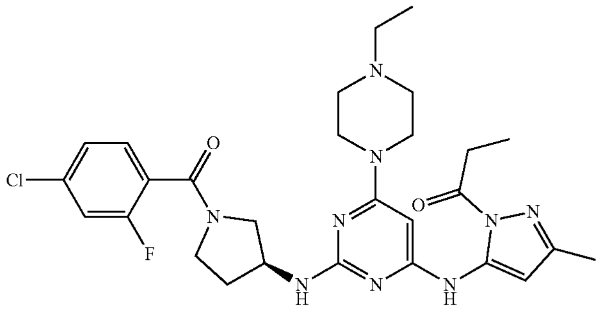 [SMILES: CCC(=O)n1nc(C)cc1Nc1cc(N2CCN(CC)CC2)nc(N[C@H]2CCN(C(=O)c3ccc(Cl)cc3F)C2)n1] | <1000 | <1000 | <1000 |
| 72 | 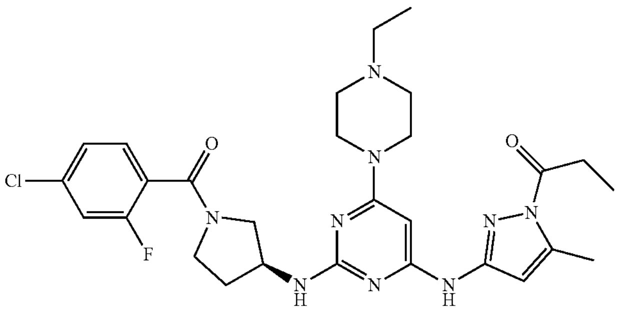 [SMILES: CCC(=O)n1nc(Nc2cc(N3CCN(CC)CC3)nc(N[C@H]3CCN(C(=O)c4ccc(Cl)cc4F)C3)n2)cc1C] | <1000 | <1000 | <1000 |
| 73 | 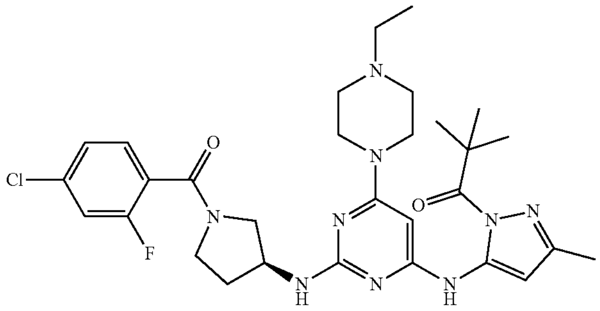 [SMILES: CCN1CCN(c2cc(Nc3cc(C)nn3C(=O)C(C)(C)C)nc(N[C@H]3CCN(C(=O)c4ccc(Cl)cc4F)C3)n2)CC1] | <1000 | <1000 | <1000 |
| 74 | 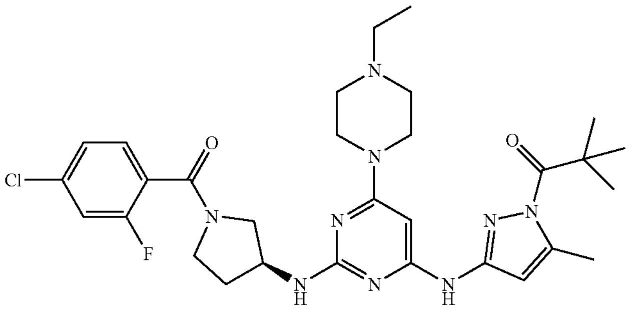 [SMILES: CCN1CCN(c2cc(Nc3cc(C)n(C(=O)C(C)(C)C)n3)nc(N[C@H]3CCN(C(=O)c4ccc(Cl)cc4F)C3)n2)CC1] | <1000 | <1000 | <1000 |

TABLE 2-continued
| Inhibition of Small-Cell-Lung-Cancer Cells Proliferation | | | | |
|---|---|---|---|---|
| Compd. No. | Chemical Structure | NCI-H69 IC50 (nM) | NCI-H446 $IC_{50}$ (nM) | NCI-H82 IC50 (nM) |
| 75 | 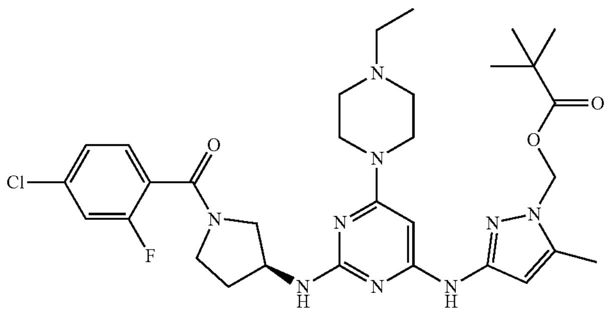 [SMILES: CCN1CCN(c2cc(Nc3cc(C)n(COC(=O)C(C)(C)C)n3)nc(N[C@H]3CCN(C(=O)c4ccc(Cl)cc4F)C3)n2)CC1] | <1000 | <1000 | <1000 |
| 78 | 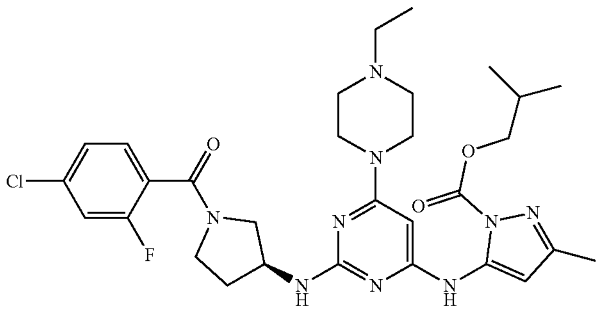 [SMILES: CCN1CCN(c2cc(Nc3cc(C)nn3C(=O)OCC(C)C)nc(N[C@H]3CCN(C(=O)c4ccc(Cl)cc4F)C3)n2)CC1] | <1000 | <1000 | <1000 |
| 79 | 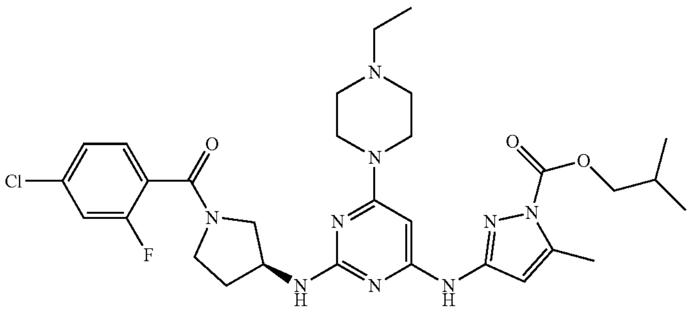 [SMILES: CCN1CCN(c2cc(Nc3cc(C)n(C(=O)OCC(C)C)n3)nc(N[C@H]3CCN(C(=O)c4ccc(Cl)cc4F)C3)n2)CC1] | <1000 | <1000 | <1000 |
| 80 | 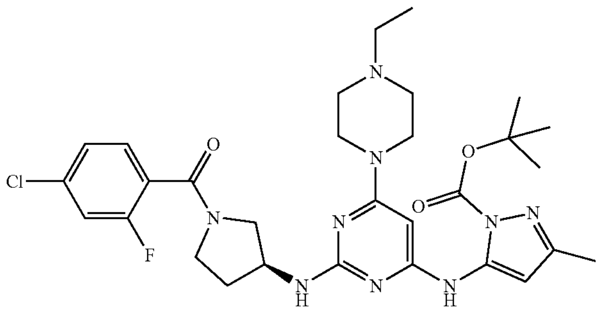 [SMILES: CCN1CCN(c2cc(Nc3cc(C)nn3C(=O)OC(C)(C)C)nc(N[C@H]3CCN(C(=O)c4ccc(Cl)cc4F)C3)n2)CC1] | <1000 | <1000 | <1000 |

TABLE 2-continued
Inhibition of Small-Cell-Lung-Cancer Cells Proliferation
| Compd. No. | Chemical Structure | NCI-H69 IC50 (nM) | NCI-H446 $IC_{50}$ (nM) | NCI-H82 IC50 (nM) |
|---|---|---|---|---|
| 81 | 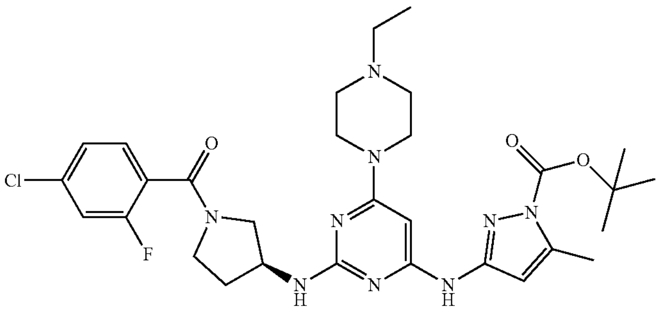 [SMILES: CCN1CCN(c2cc(Nc3cc(C)n(C(=O)OC(C)(C)C)n3)nc(N[C@H]3CCN(C(=O)c4ccc(Cl)cc4F)C3)n2)CC1] | <1000 | <1000 | <1000 |
| 82 | 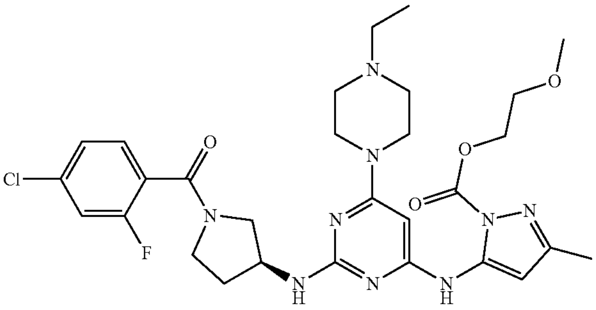 [SMILES: CCN1CCN(c2cc(Nc3cc(C)nn3C(=O)OCCOC)nc(N[C@H]3CCN(C(=O)c4ccc(Cl)cc4F)C3)n2)CC1] | <1000 | <1000 | <1000 |
| 83 | 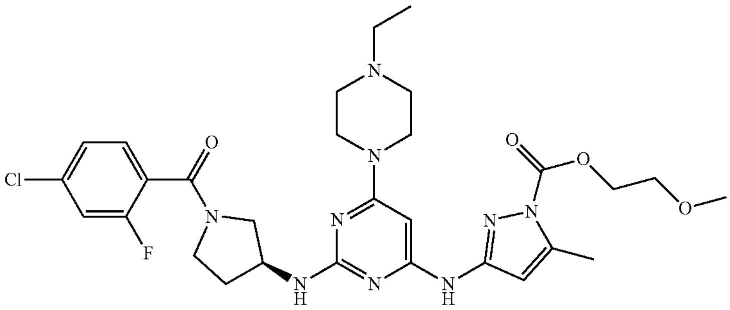 [SMILES: CCN1CCN(c2cc(Nc3cc(C)n(C(=O)OCCOC)n3)nc(N[C@H]3CCN(C(=O)c4ccc(Cl)cc4F)C3)n2)CC1] | <1000 | <1000 | <1000 |
| 86 | 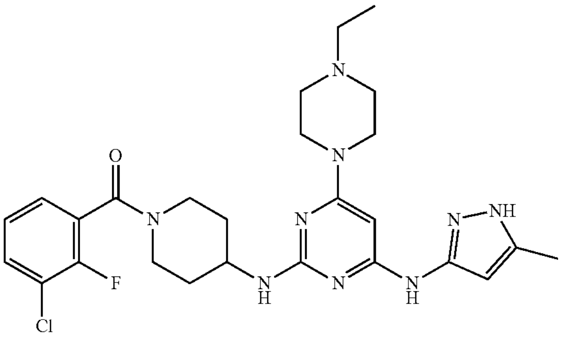 [SMILES: CCN1CCN(c2cc(Nc3cc(C)[nH]n3)nc(NC3CCN(C(=O)c4cccc(Cl)c4F)CC3)n2)CC1] | <1000 | <1000 | <1000 |

TABLE 2-continued
| Inhibition of Small-Cell-Lung-Cancer Cells Proliferation | | | | |
|---|---|---|---|---|
| Compd. No. | Chemical Structure | NCI-H69 IC50 (nM) | NCI-H446 $IC_{50}$ (nM) | NCI-H82 IC50 (nM) |
| 88 | 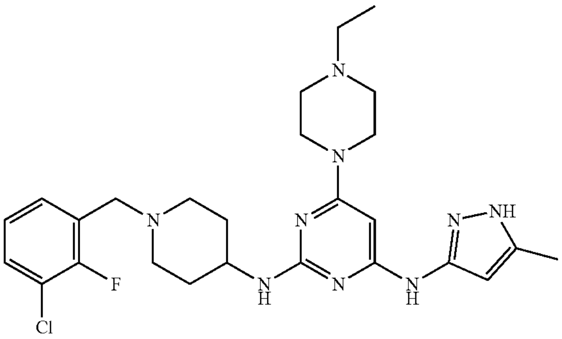 [SMILES: CCN1CCN(c2cc(Nc3cc(C)[nH]n3)nc(NC3CCN(Cc4cccc(Cl)c4F)CC3)n2)CC1] | | <1000 | <1000 |
| 89 | 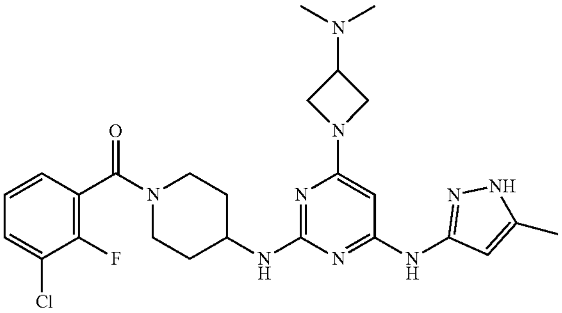 [SMILES: Cc1cc(Nc2cc(N3CC(N(C)C)C3)nc(NC3CCN(C(=O)c4cccc(Cl)c4F)CC3)n2)n[nH]1] | | <1000 | <1000 |
| 90 | 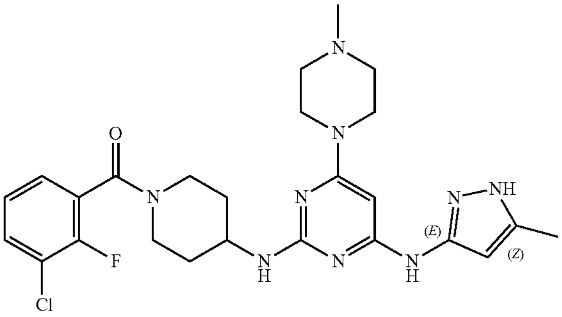 | <1000 | <1000 | <1000 |
| 92 | 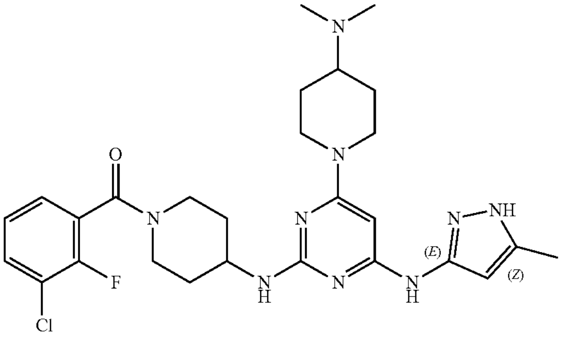 | <1000 | <1000 | <1000 |

TABLE 2-continued
| Compd. No. | Chemical Structure | NCI-H69 IC50 (nM) | NCI-H446 $IC_{50}$ (nM) | NCI-H82 IC50 (nM) |
|---|---|---|---|---|
| Inhibition of Small-Cell-Lung-Cancer Cells Proliferation | | | | |
| 93 | 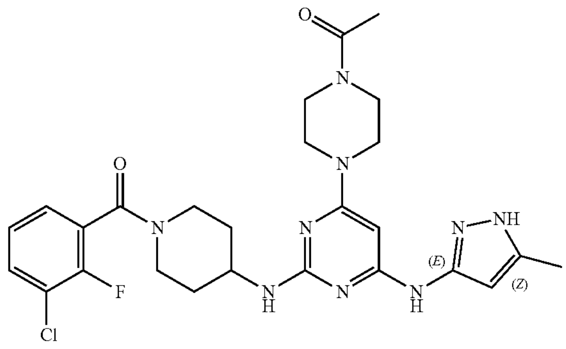 | <1000 | <1000 | <1000 |
| 94 | 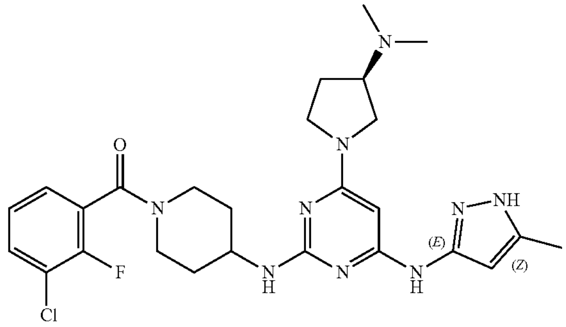 | <1000 | <1000 | <1000 |
| 95 | 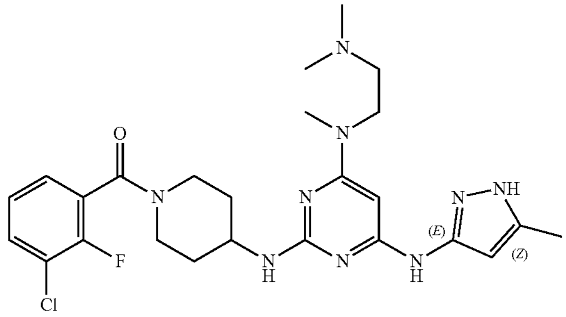 | | <1000 | <1000 |
| 96 | 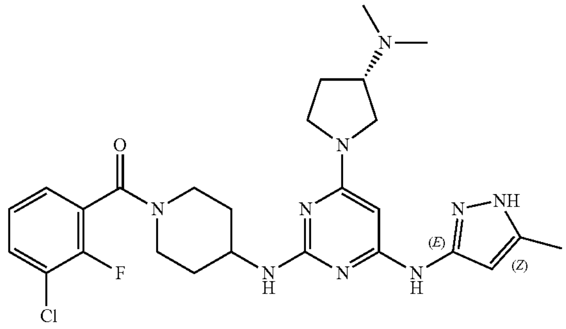 | <1000 | <1000 | <1000 |

TABLE 2-continued
Inhibition of Small-Cell-Lung-Cancer Cells Proliferation
| Compd. No. | Chemical Structure | NCI-H69 IC50 (nM) | NCI-H446 IC$_{50}$ (nM) | NCI-H82 IC50 (nM) |
|---|---|---|---|---|
| 97 | 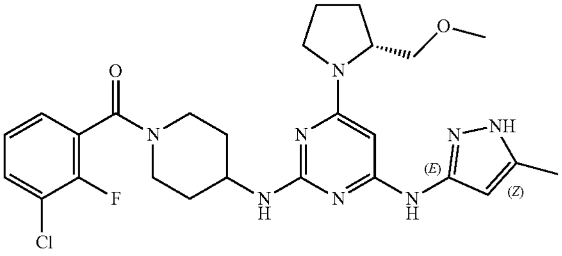 | <1000 | <1000 | <1000 |
| 98 | 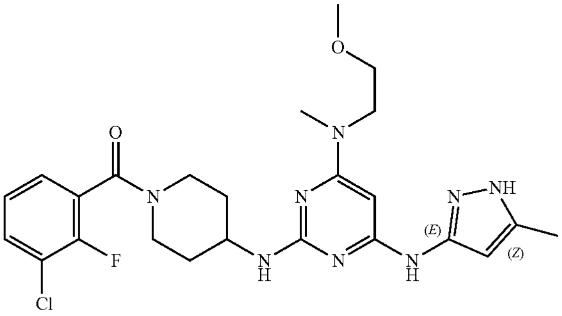 | | <1000 | <1000 |
| 99 | 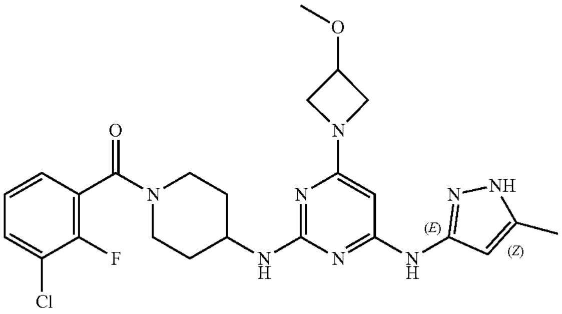 | <1000 | <1000 | |
| 100 | 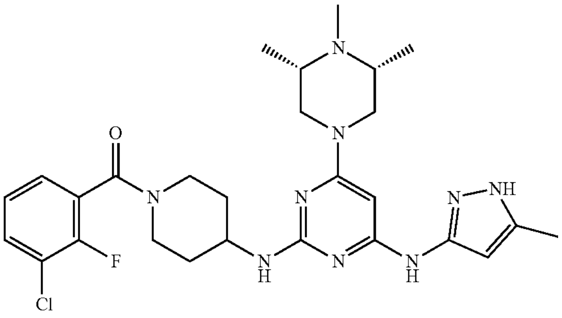 [SMILES: Cc1cc(Nc2cc(N3C[C@@H](C)N(C)[C@@H](C)C3)nc(NC3CCN(C(=O)c4cccc(Cl)c4F)CC3)n2)n[nH]1] | <1000 | <1000 | <1000 |

TABLE 2-continued
Inhibition of Small-Cell-Lung-Cancer Cells Proliferation
| Compd. No. | Chemical Structure | NCI-H69 IC50 (nM) | NCI-H446 $IC_{50}$ (nM) | NCI-H82 IC50 (nM) |
|---|---|---|---|---|
| 101 | 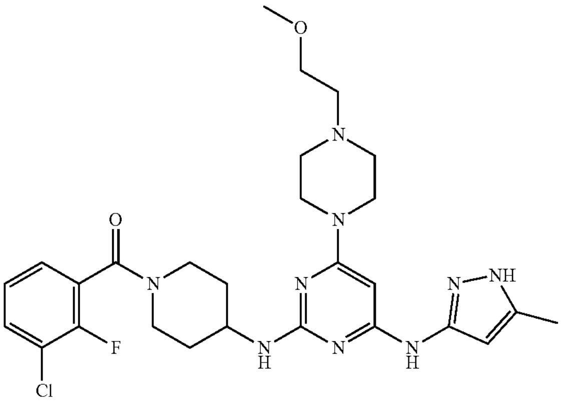 [SMILES: COCCN1CCN(c2cc(Nc3cc(C)[nH]n3)nc(NC3CCN(C(=O)c4cccc(Cl)c4F)CC3)n2)CC1] | <1000 | <1000 | |
| 102 | 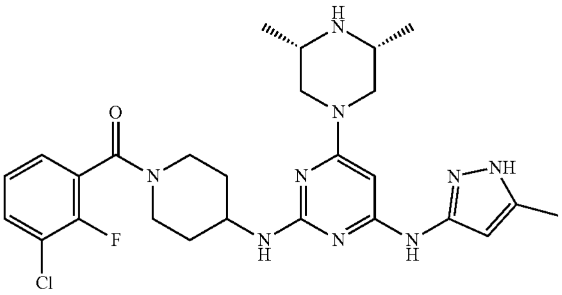 [SMILES: Cc1cc(Nc2cc(N3C[C@@H](C)N[C@@H](C)C3)nc(NC3CCN(C(=O)c4cccc(Cl)c4F)CC3)n2)n[nH]1] | <1000 | <1000 | <1000 |
| 103 | 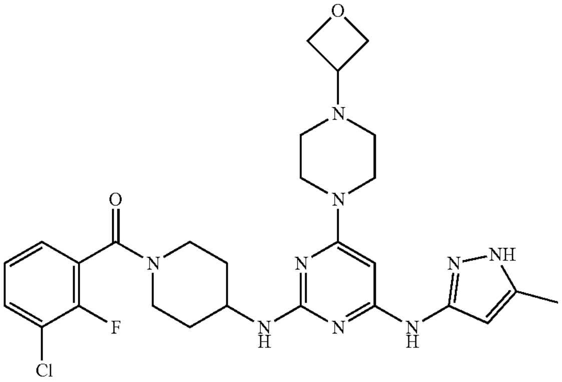 [SMILES: Cc1cc(Nc2cc(N3CCN(C4COC4)CC3)nc(NC3CCN(C(=O)c4cccc(Cl)c4F)CC3)n2)n[nH]1] | <1000 | <1000 | <1000 |
| 104 | 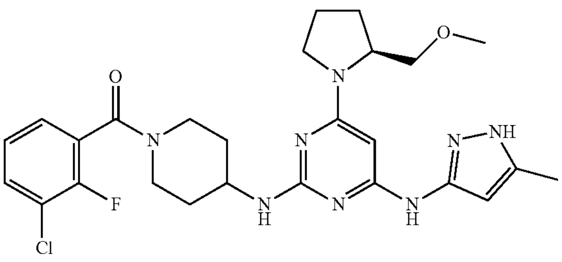 [SMILES: COC[C@@H]1CCCN1c1cc(Nc2cc(C)[nH]n2)nc(NC2CCN(C(=O)c3cccc(Cl)c3F)CC2)n1] | <1000 | | <1000 |

TABLE 2-continued
| Inhibition of Small-Cell-Lung-Cancer Cells Proliferation | | | | |
|---|---|---|---|---|
| Compd. No. | Chemical Structure | NCI-H69 IC50 (nM) | NCI-H446 $IC_{50}$ (nM) | NCI-H82 IC50 (nM) |
| 105 | 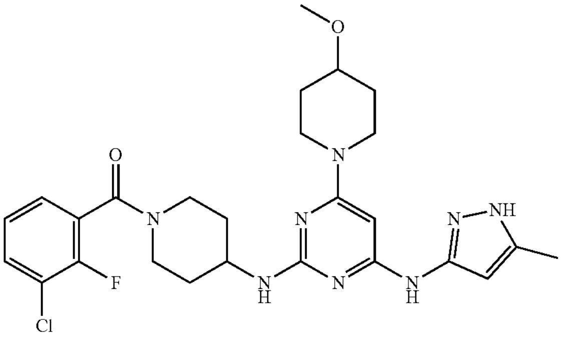 [SMILES: COC1CCN(c2cc(Nc3cc(C)[nH]n3)nc(NC3CCN(C(=O)c4cccc(Cl)c4F)CC3)n2)CC1] | <1000 | <1000 | <1000 |
| 106 | 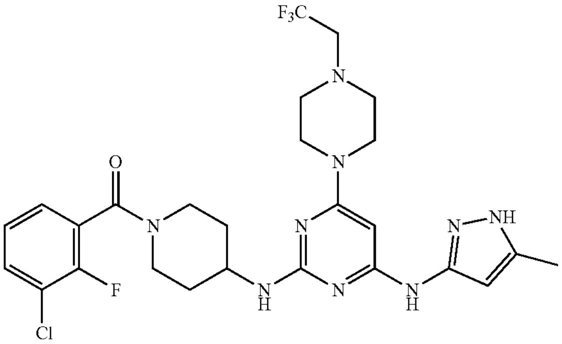 [SMILES: Cc1cc(Nc2cc(N3CCN(CC(F)(F)F)CC3)nc(NC3CCN(C(=O)c4cccc(Cl)c4F)CC3)n2)n[nH]1] | <1000 | <1000 | <1000 |
| 107 | 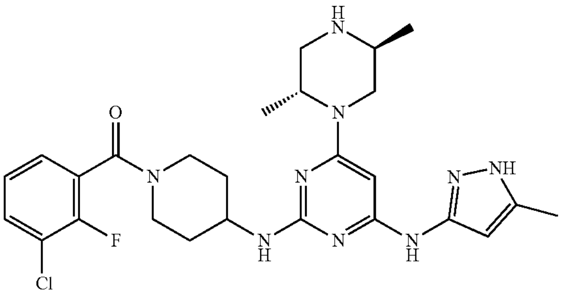 [SMILES: Cc1cc(Nc2cc(N3C[C@H](C)NC[C@H]3C)nc(NC3CCN(C(=O)c4cccc(Cl)c4F)CC3)n2)n[nH]1] | <1000 | <1000 | <1000 |
| 122 | 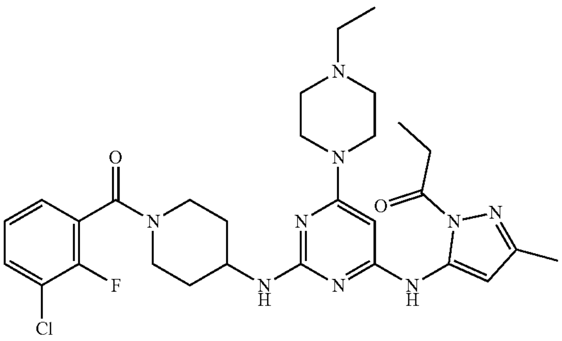 [SMILES: CCC(=O)n1nc(C)cc1Nc1cc(N2CCN(CC)CC2)nc(NC2CCN(C(=O)c3cccc(Cl)c3F)CC2)n1] | <1000 | <1000 | <1000 |

TABLE 2-continued
Inhibition of Small-Cell-Lung-Cancer Cells Proliferation
| Compd. No. | Chemical Structure | NCI-H69 IC50 (nM) | NCI-H446 $IC_{50}$ (nM) | NCI-H82 IC50 (nM) |
|---|---|---|---|---|
| 123 | 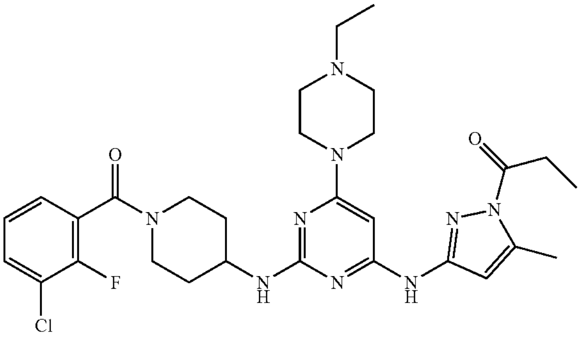 [SMILES: CCC(=O)n1nc(Nc2cc(N3CCN(CC)CC3)nc(NC3CCN(C(=O)c4cccc(Cl)c4F)CC3)n2)cc1C] | <1000 | <1000 | <1000 |
| 124 | 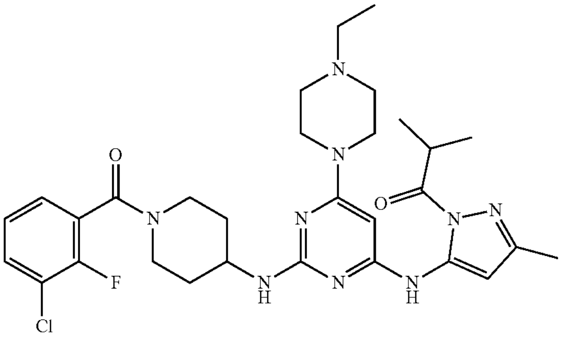 [SMILES: CCN1CCN(c2cc(Nc3cc(C)nn3C(=O)C(C)C)nc(NC3CCN(C(=O)c4cccc(Cl)c4F)CC3)n2)CC1] | | <1000 | <1000 |
| 125 | 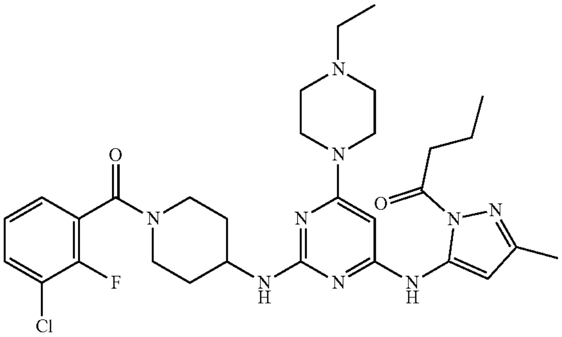 [SMILES: CCCC(=O)n1nc(C)cc1Nc1cc(N2CCN(CC)CC2)nc(NC2CCN(C(=O)c3cccc(Cl)c3F)CC2)n1] | | <1000 | <1000 |
| 127 | 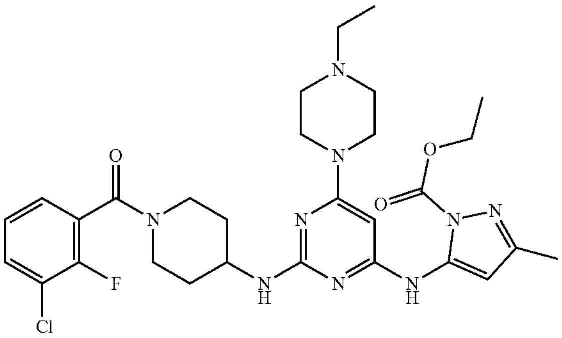 [SMILES: CCOC(=O)n1nc(C)cc1Nc1cc(N2CCN(CC)CC2)nc(NC2CCN(C(=O)c3cccc(Cl)c3F)CC2)n1] | <1000 | <1000 | <1000 |

Example 5: Assay on Proliferation Inhibition of Various Cancer Cells

The efficacies of compounds 41 and 86 of Formula (I) in inhibiting proliferation of eleven types of cancer cells were determined using PrestoBlue™ Cell Viability Reagent (ThermoFisher Scientific, USA). The eleven types of cancer cells are small cell lung cancer, non-small cell lung cancer, liver cancer, pancreatic cancer, breast cancer, colon cancer, prostate cancer, neuroblastoma, brain cancer, leukemia, and cholangiocarcinoma.

More specifically, eleven cancer cell lines, i.e., NCI-H82 (ATCC® HTB-175), NCI-H446 (ATCC® HTB-171), NCI-H69 (ATCC® HTB-119), NCI-H146 (ATCC® HTB-173), NCI-H1792 (ATCC® CRL-5895), NCI-H1299 (ATCC® CRL-5803), SNU-398 (ATCC® CRL-2233), PSN-1 (ATCC® CRL-3211), MIA PaCa-2 (ATCC® CRL-1420), MDA-MB-231 (ATCC® HTB-26), LOVO (ATCC® CCL-229), COLO 205 (ATCC® CCL-222), PC-3 (ATCC® CRL-1435), SK-N-BE(2) (ATCC® CRL-2271), D341 Med (ATCC® HTB-187), K562 (ATCC® CCL-243), MOLM-13 (DSMZ-German Collection of Microorganisms and Cell Cultures GmbH, ACC No. 554), and SNU-478 (KCLB 00478), were seeded at a density of 4000-10000 cells per well in 96-well plates for 24 hours. The cancer cells were then treated with each compound at various concentrations (0-10 μM), followed by incubation for another 72 hours. $IC_{50}$ values were computed based on duplicated 8-point titration.

As shown in Table 3, compound 41 and compound 86 both unexpectedly exhibited $IC_{50}$ values of lower than 10.0 μM in inhibiting proliferation of all the eleven types of cancer cells. More specifically, these two compounds unexpectedly showed $IC_{50}$ values of (i) lower than 0.2 μM in inhibiting proliferation of cells of small-cell-lung cancer, liver cancer, neuroblastoma, brain cancer, and leukemia; (ii) lower than 0.3 μM in inhibiting proliferation of cells of breast cancer; (iii) lower than 1.0 μM in inhibiting proliferation of cells of non-small cell lung cancer, pancreatic cancer, and colon cancer; (iv) lower than 2.0 μM in inhibiting proliferation of cells of cholangiocarcinoma; and (v) lower than 10.0 μM in inhibiting proliferation of cells of prostate cancer.

These results indicate that compounds 41 and 86 have high in vitro anticancer efficacy.

TABLE 3

Inhibition of Cancer Cells Proliferation

| Cancer | Cell Line | Compound 41 $IC_{50}$ (nM) | Compound 86 $IC_{50}$ (nM) |
|---|---|---|---|
| Small cell lung cancer | NCI-H82 | <200 | <300 |
| | NCI-H446 | <200 | <200 |
| | NCI-H69 | <200 | <200 |
| | NCI-H146 | <2000 | <10000 |
| Non-small cell lung cancer | NCI-H1792 | <2000 | <2000 |
| | NCI-H1299 | <1000 | <1000 |
| Liver cancer | SNU-398 | <200 | <200 |
| Pancreatic cancer | PSN-1 | <2000 | <2000 |
| | MIA PaCa-2 | <1000 | <1000 |
| Breast cancer | MDA-MB-231 | <300 | <300 |
| Colon cancer | LOVO | <10000 | <10000 |
| | Colo205 | <1000 | <1000 |
| Prostate cancer | PC-3 | <10000 | <10000 |
| Neuroblastoma | SK-N-BE(2) | <200 | <200 |
| Brain cancer | D341 Med | <200 | <300 |
| Leukemia | K562 | <1000 | <1000 |
| | MOLM-13 | <200 | <200 |
| Cholangiocarcinoma | SNU-478 | <2000 | <2000 |

Example 6: Inhibition of Xenografted Tumor Growth in Mice

The efficacies of two compounds of Formula (I), i.e., compound 71 and compound 122, in inhibiting tumor growth were determined using a NCI-H446-xenografted tumorigenicity mouse model as below.

Male athymic nu/nu nude mice (BioLASCO, Taiwan) at age 6 wk were housed in sterile cages maintained under 12-h light/dark cycles with controlled temperature and humidity. The mice were inoculated s.c. with $1\times10^6$ NCI-H446 cells (ATCC® HTB-171) resuspended in saline mixed with 50% Metrigel Matrix (Corning, USA). The sizes of the xenografted tumors were measured by a digital caliper (GMC-190; Goldsun Electronics Co.) and calculated using the algorithm: tumor volume ($mm^3$)=length×(width)$^2$/2. Body weight and tumor size were measured at least twice a week. When the xenografted tumor reached a size of ≥200 $mm^3$, compound 71, compound 122, reference compound MLN8237 (the structure shown below), and reference compound LY3295668 (the structure also shown below), were each administered orally to the mice at a dosage of 100 mg/kg and a 5-on-2-off dosing regimen for two to four weeks, with mice treated with vehicles as controls.

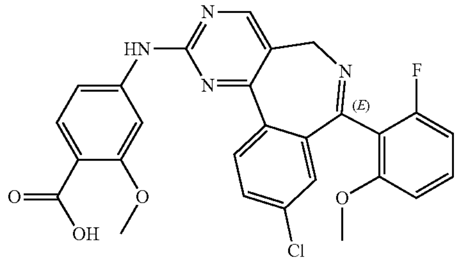

MLN8237

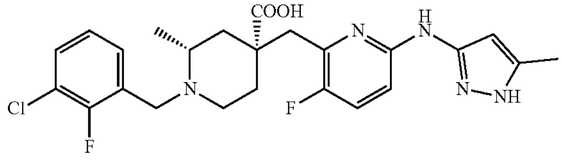

LY3295668

As shown in FIGS. 2A and 2C, compound 71 at 100 mg/kg unexpectedly reduced a tumor size in mice substantially from about 250 $mm^3$ to smaller than 50 $mm^3$ in 10 days and from larger than 750 $mm^3$ to smaller than 50 $mm^3$ in 14 days. These results indicate that compound 71 unexpectedly induced more than 80% tumor regression.

As also shown in FIG. 2A, compound 71 unexpectedly exhibited a much higher efficacy than reference compound MCLN8237. While both compounds at 100 mg/kg reduced tumor sizes from about 250 $mm^3$ to smaller than 50 $mm^3$ in 10 days, the tumor size in mice treated with compound 71 remained smaller than 50 $mm^3$, as compared to the tumor size in mice treated with compound MCLN8237 increased to larger than 700 $mm^3$ 6 weeks after the treatment stopped.

FIG. 2B shows that compound 122 unexpectedly induced more than 80% tumor regression and much higher efficacy than reference compound LY3295668. Specifically, while compound 122 at 100 mg/kg reduced a tumor size substantially from about 250 $mm^3$ to smaller than 50 $mm^3$, compound LY3295668 at 100 mg/kg increased a tumor size from about 250 $mm^3$ to larger than 350 $mm^3$.

The results set forth above demonstrate that compounds of Formula (I) have unexpected high in vivo efficacies in inhibiting tumor growth.

Example 7: In Vivo cMYC Protein Level Reduction and Cell Apoptosis Induction The efficacy of a compound of Formula (I), i.e., compound 71, in reducing the cMYC protein level and in inducing cell apoptosis was assessed using an NCI-H446 xenograft tumorigenicity mouse model as follows.

Male athymic nu/nu nude mice (BioLASCO. Taiwan) at 6-week age were housed in sterile cages maintained under 12-h light/dark cycles with controlled temperature and humidity. Mice were inoculated s.c. with $1\times10^6$ NCI-H446 cells resuspended in saline mixed with 50% Metrigel Matrix (Corning, USA). The sizes of the xenografted tumors were measured by a digital caliper (GMC-190; Goldsun Electronics Co.) and calculated using the algorithm: tumor volume $(mm^3)=\text{length}\times(\text{width})^2/2$. Body weight and tumor size were measured at least twice a week. When the xenografted NCI-H446 tumor reached a size ≥500 $mm^3$, the xenografted tumor-bearing nude mice were oral (PO) administered with compound 71 at one dosage of 100 mg/kg. Tumors were harvested at 2 hours, 4 hours, 8 hours, and 24 hours after the administration. Tissue lysates of the tumors were subjected for Western blot analysis. The primary antibodies used were cMYC (Cell Signaling, Cat No. 5605S), PARP-1 (Abcam, ab32378), and β-ACTIN (Sigma-Aldrich, A1978).

As shown in FIG. 3 below, compound 71 significantly induced cell apoptosis, as indicated by increased amounts of cleaved PARP-1 (cPARP-1) in more than 80% of the xenografted tumors at 24 hours after the administration of compound 71. Further, compound 71 reduced the cMYC protein level in more than 50% of the xenografted tumors.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. For example, compounds structurally analogous to the compounds of this invention also can be made, screened for their efficacy in treating a condition that relates to cells containing inside-out phosphatidylserine. Thus, other embodiments are also within the claims.

REFERENCES

1. Carmena, M., and Earnshaw, W. C. (2003) The cellular geography of aurora kinases. *Nat Rev Mol Cell Biol* 4, 842-854
2. Lens, S. M., Voest, E. E., and Medema, R. H. (2010) Shared and separate functions of polo-like kinases and aurora kinases in cancer. *Nat Rev Cancer* 10, 825-841
3. Fu, J., Bian, M., Jiang, Q., and Zhang, C. (2007) Roles of Aurora kinases in mitosis and tumorigenesis. *Mol Cancer Res* 5, 1-10
4. Agnese, V., Bazan, V., Fiorentino, F. P., Fanale, D., Badalamenti, G., Colucci, G., Adamo, V., Santini, D., and Russo, A. (2007) The role of Aurora-A inhibitors in cancer therapy. *Ann Oncol* 18 Suppl 6, vi47-52
5. Tatsuka, M., Katayama, H., Ota, T., Tanaka, T., Odashima, S., Suzuki, F., and Terada, Y. (1998) Multinuclearity and increased ploidy caused by overexpression of the aurora- and Ip11-like midbody-associated protein mitotic kinase in human cancer cells. *Cancer Res* 58, 4811-4816
6. Kollareddy, M., Zheleva, D., Dzubak, P., Brahmkshatriya, P. S., Lepsik, M., and Hajduch, M. (2012) Aurora kinase inhibitors: progress towards the clinic. *Invest New Drugs* 30, 2411-2432
7. Anand, S., Penrhyn-Lowe, S., and Venkitaraman, A. R. (2003) Aurora-A amplification overrides the mitotic spindle assembly checkpoint, inducing resistance to Taxol. *Cancer Cell* 3, 51-62
8. Glover, D. M., Leibowitz, M. H., McLean, D. A., and Parry, H. (1995) Mutations in aurora prevent centrosome separation leading to the formation of monopolar spindles. *Cell* 81, 95-105
9. Terada, Y., Uetake, Y., and Kuriyama, R. (2003) Interaction of Aurora-A and centrosomin at the microtubule-nucleating site in *Drosophila* and mammalian cells. *J Cell Biol* 162, 757-763
10. Zeitlin, S. G., Shelby, R. D., and Sullivan, K. F. (2001) CENP-A is phosphorylated by Aurora B kinase and plays an unexpected role in completion of cytokinesis. *J Cell Biol* 155, 1147-1157
11. Uren, A. G., Wong, L., Pakusch, M., Fowler, K. J., Burrows, F. J., Vaux, D. L., and Choo, K. H. (2000) Survivin and the inner centromere protein INCENP show similar cell-cycle localization and gene knockout phenotype. *Curr Biol* 10, 1319-1328
12. Hanson, K. K., Kelley, A. C., and Bienz, M. (2005) Loss of *Drosophila* borealin causes polyploidy, delayed apoptosis and abnormal tissue development. *Development* 132, 4777-4787
13. Wilkinson, R. W., Odedra, R., Heaton, S. P., Wedge, S. R., Keen, N. J., Crafter, C., Foster, J. R., Brady, M. C., Bigley, A., Brown, E., Byth, K. F., Barrass, N. C., Mundt, K. E., Foote, K. M., Heron, N. M., Jung, F. H., Mortlock, A. A., Boyle, F. T., and Green, S. (2007) AZD1152, a selective inhibitor of Aurora B kinase, inhibits human tumor xenograft growth by inducing apoptosis. *Clin Cancer Res* 13, 3682-3688
14. Koh, C. M., Sabo, A., and Guccione, E. (2016) Targeting MYC in cancer therapy: RNA processing offers new opportunities. *Bioessays* 38, 266-275
15. Dang, C. V. (2013) MYC, metabolism, cell growth, and tumorigenesis. *Cold Spring Harb Perspect Med* 3
16. Brockmann, M., Poon, E., Berry, T., Carstensen, A., Deubzer, H. E., Rycak, L., Jamin, Y., Thway, K., Robinson, S. P., Roels, F., Witt, O., Fischer, M., Chesler, L., and Eilers, M. (2013) Small molecule inhibitors of aurora-a induce proteasomal degradation of N-myc in childhood neuroblastoma. *Cancer Cell* 24, 75-89

17. Dauch, D., Rudalska, R., Cossa, G., Nault, J. C., Kang, T. W., Wuestefeld, T., Hohmeyer, A., Imbeaud, S., Yevsa, T., Hoenicke, L., Pantsar, T., Bozko, P., Malek, N. P., Longerich, T., Laufer, S., Poso, A., Zucman-Rossi, J., Eilers, M., and Zender, L. (2016) A MYC-aurora kinase A protein complex represents an actionable drug target in p53-altered liver cancer. *Nat Med* 22, 744-753
18. Lee, J. K., Phillips, J. W., Smith, B. A., Park, J. W., Stoyanova, T., McCaffrey, E. F., Baertsch, R., Sokolov, A., Meyerowitz, J. G., Mathis, C., Cheng, D., Stuart, J. M., Shokat, K. M., Gustafson, W. C., Huang, J., and Witte, O. N. (2016) N-Myc Drives Neuroendocrine Prostate Cancer Initiated from Human Prostate Epithelial Cells. *Cancer Cell* 29, 536-547

What is claimed is:

1. A compound of formula (I):

(I)

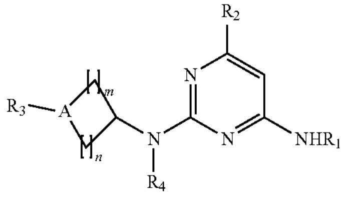

in which,

A is N;

$R_1$ is $C_{3-10}$ cycloalkyl or 5-membered heteroaryl;

$R_2$ is

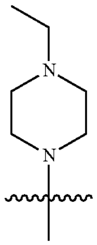, 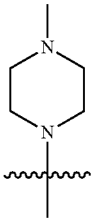, 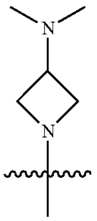, 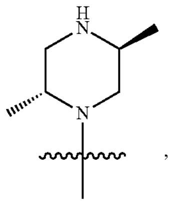,

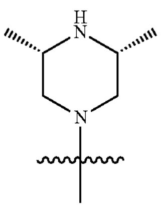, 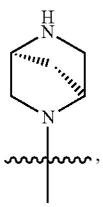, 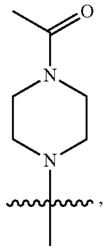, 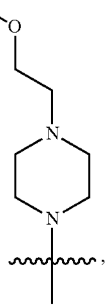,

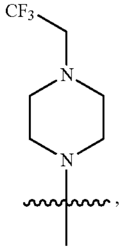, 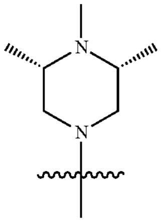, 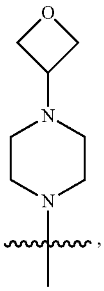,

-continued

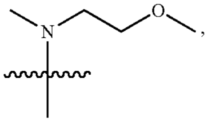, 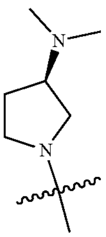, 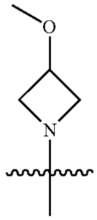,

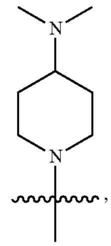, 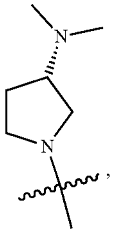, 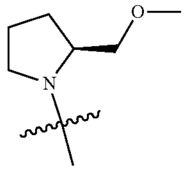,

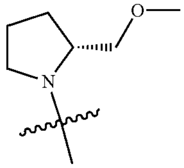, 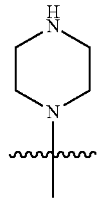, 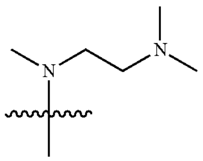, or

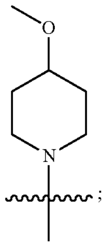;

$R_3$ is $C_{1-6}$ alkyl, $C_{1-6}$ alkoxyl, $C_{3-10}$ cycloalkyl, $C_{7-12}$ aralkyl, $C_{1-12}$ heteroaralkyl, —C(O) $R_8$, or —$S(O)_2R_8$, in which $R_8$ is aryl or heteroaryl;

$R_4$ is H or $C_{1-6}$ alkyl; and each of m and n, independently, is 1 or 2 and the sum of m and n is 3;

wherein each of $C_{1-6}$ alkyl, $C_{1-6}$ alkoxyl, $C_{3-10}$ cycloalkyl, $C_{1-10}$ heterocycloalkyl, $C_{7-12}$ aralkyl, $C_{1-12}$ heteroaralkyl, aryl, and heteroaryl, independently, is unsubstituted or mono-, di-, or tri-substituted with halo, OH, CN, $NH_2$, $NO_2$, $SO_2$, $C_{1-6}$ alkyl, $C_{1-6}$ haloalkyl, $C_{3-13}$ cycloalkyl, $C_{2-8}$ heterocycloalkyl, $C_{1-6}$ alkoxyl, $C_{1-6}$ haloalkoxyl, $C_{1-6}$ alkylamino, $C_{2-6}$ dialkylamino, $C_{7-12}$ aralkyl, $C_{1-12}$ heteroaralkyl, aryl, heteroaryl, —C(O) $R_9$, —C(O)$OR_9$, or —C(O)$NR_9R_{10}$, each of $R_9$ and $R_{10}$, independently, being H, halo, OH, CN, COOH, acetyl, acetamide, dialkylamino, alkylamino, $C_{1-6}$ alkyl, $C_{1-6}$ multihaloalkyl, $C_{1-6}$ alkoxyl, $C_{1-6}$ multihaloalkoxyl, $C_{3-8}$ cycloalkyl, $C_{1-10}$ heterocycloalkyl, aryl, or heteroaryl.

2. The compound of claim 1, wherein $R_3$ is $C_{7-12}$ aralkyl, —C(O)$R_8$, or —$S(O)_2R_8$.

3. The compound of claim 2, wherein the compound is one of the following compounds:

41
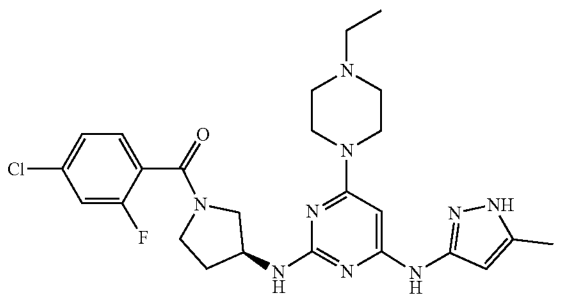
71
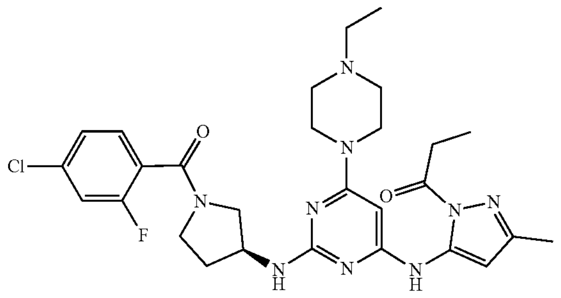
76
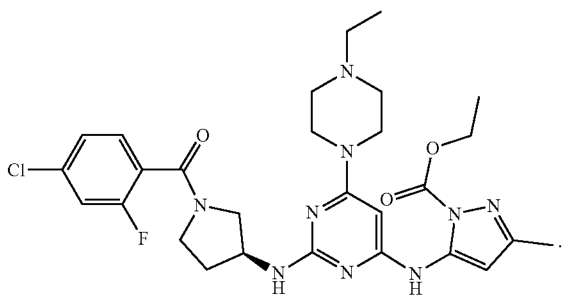
4. The compound of claim 1, wherein $R_4$ is H.
5. A compound that is one of the following compounds:
1
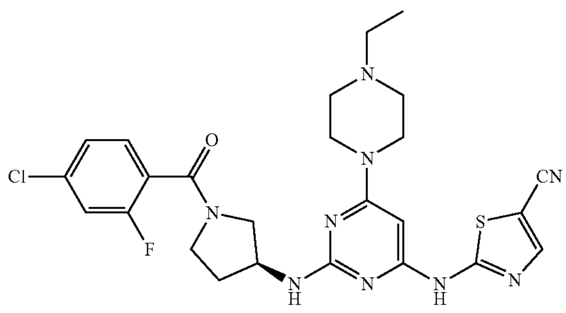
-continued
2
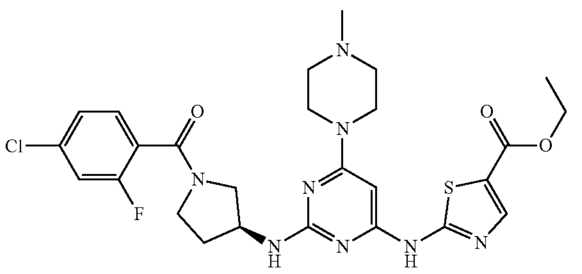
3
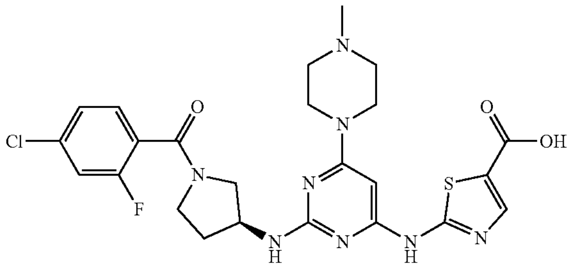
4
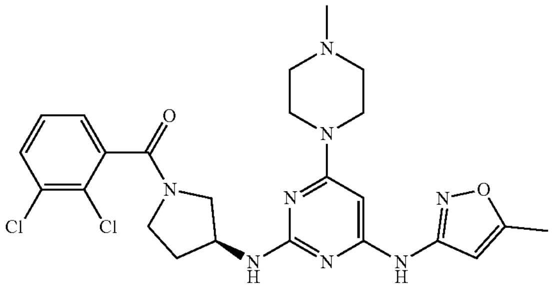
5
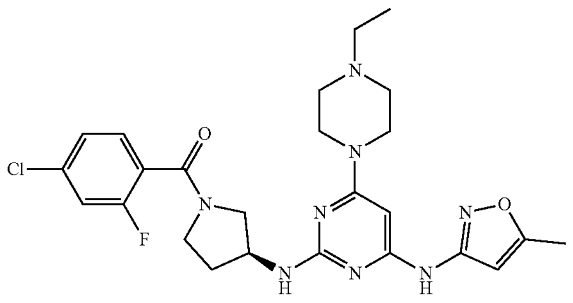
6
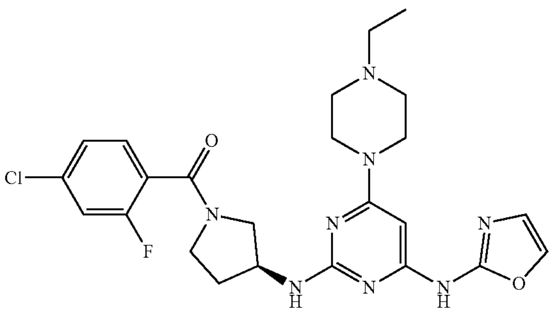

-continued
7
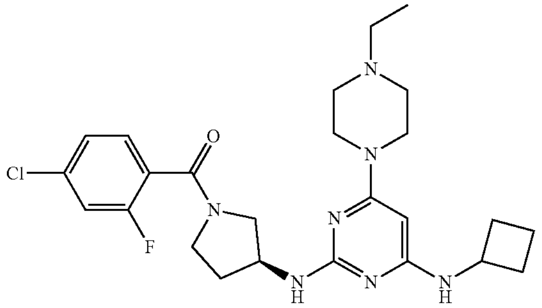
8
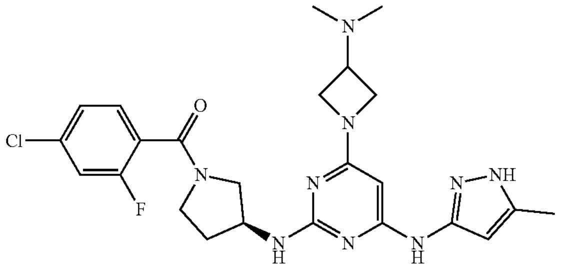
9
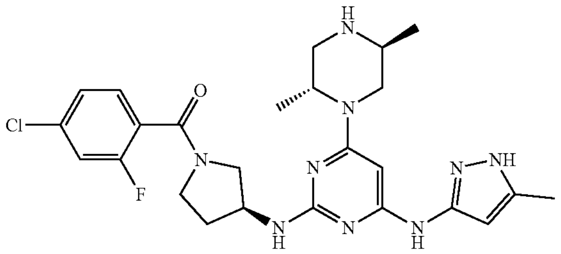
10
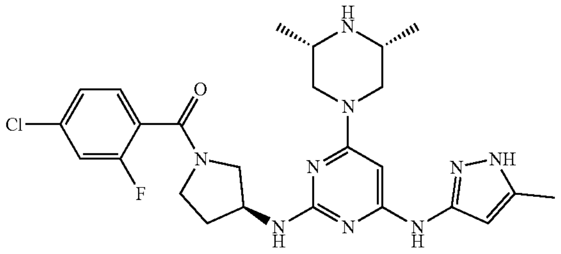
11
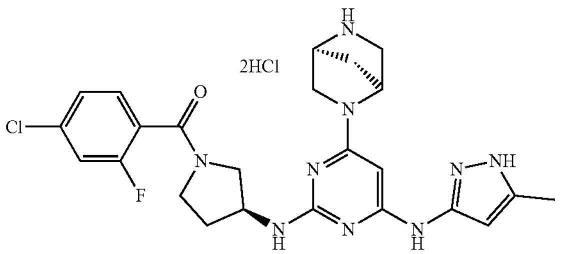
2HCl
-continued
12
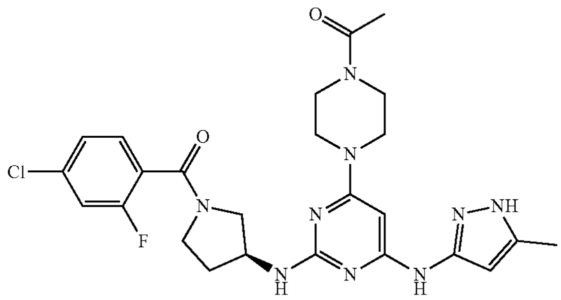
13
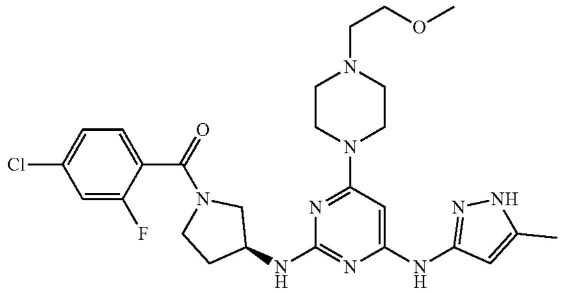
14
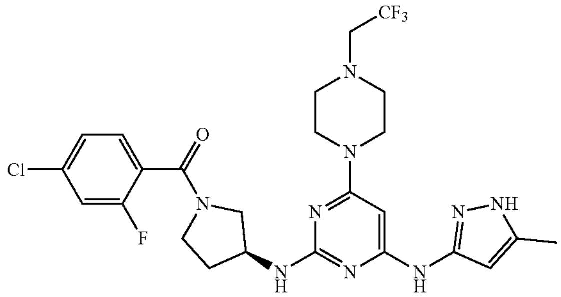
15
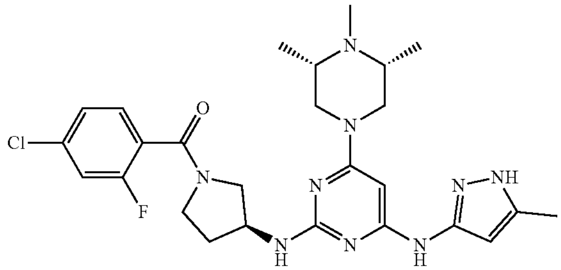
16
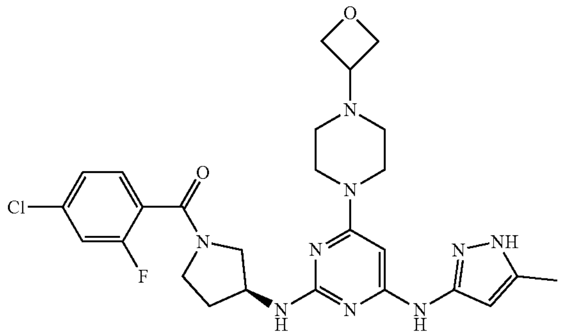

-continued
17
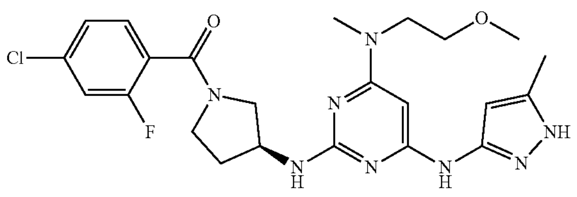
18
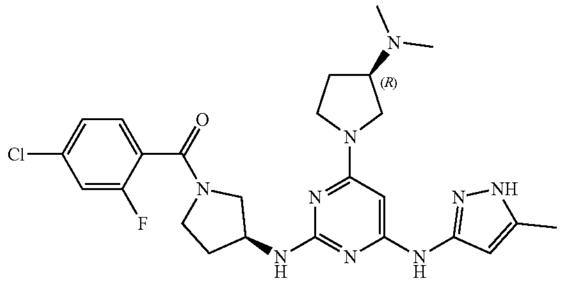
19
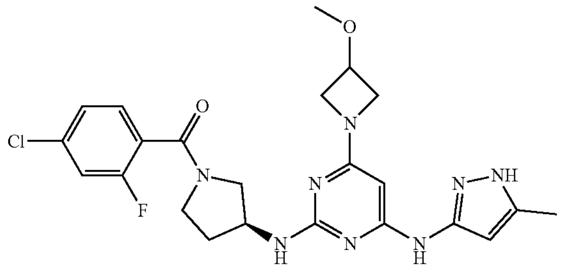
20
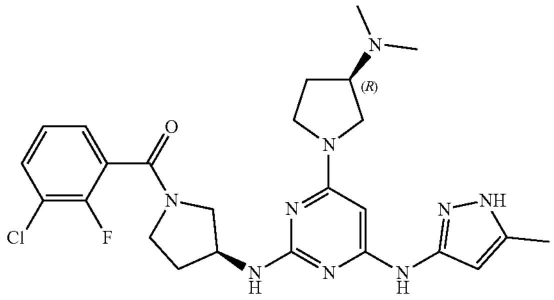
21
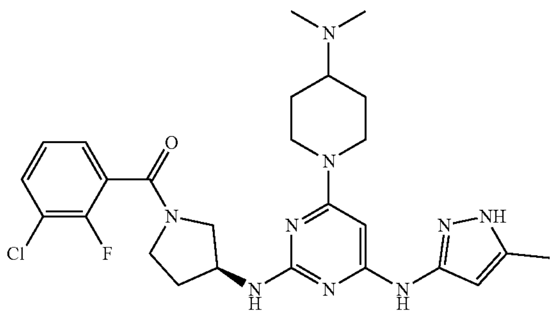
-continued
22
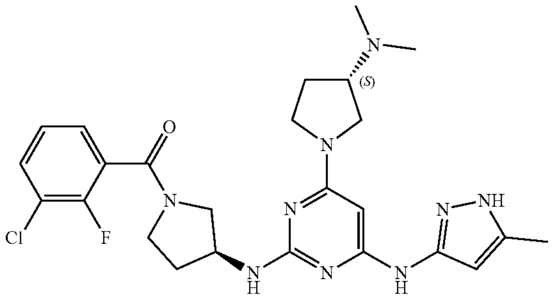
23
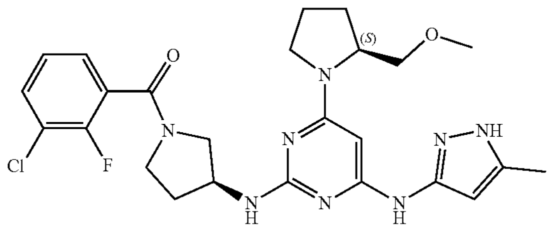
24
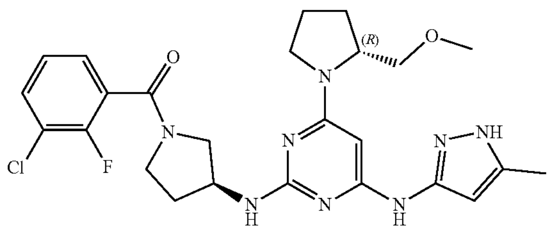
25
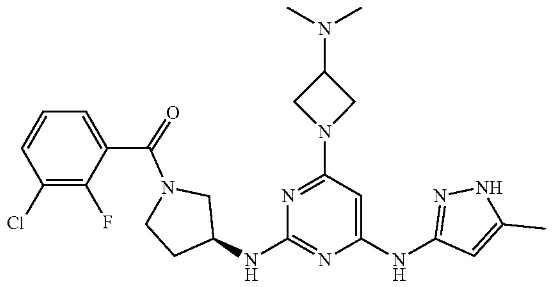
26
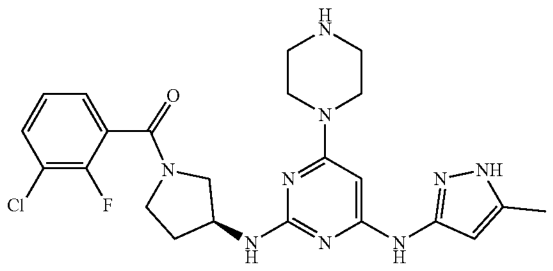

27
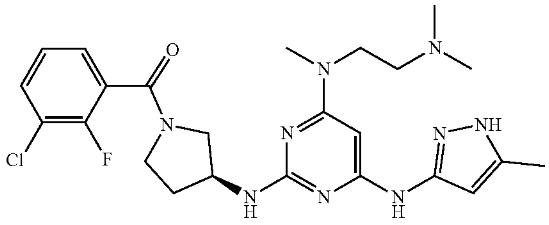
28
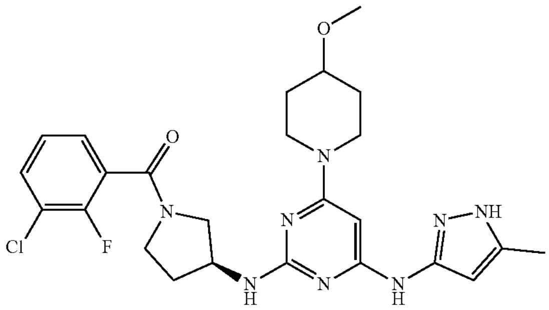
29
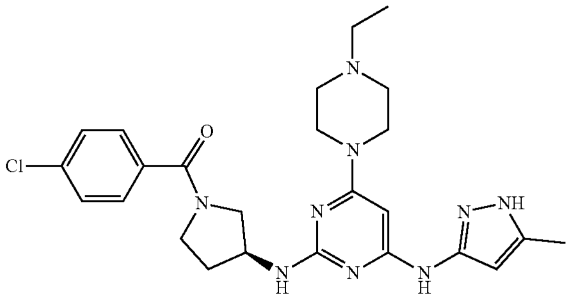
30
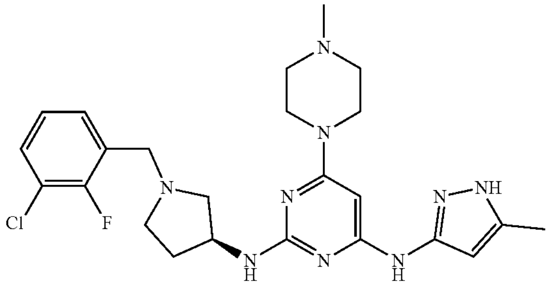
31
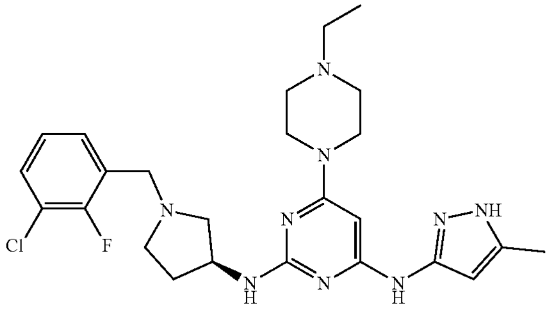
32
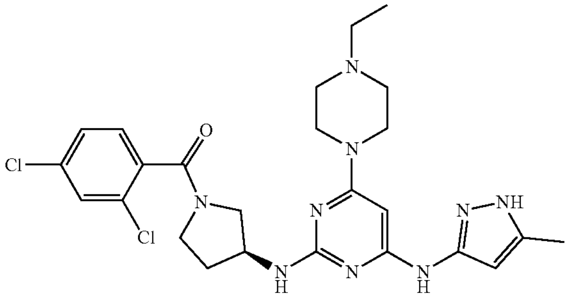
33
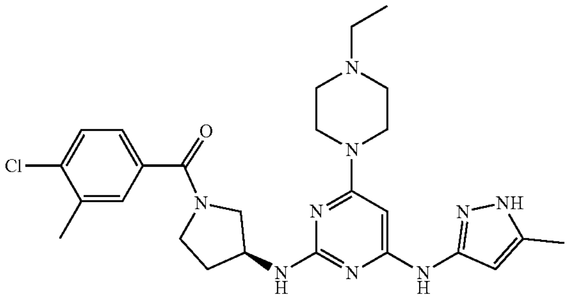
34
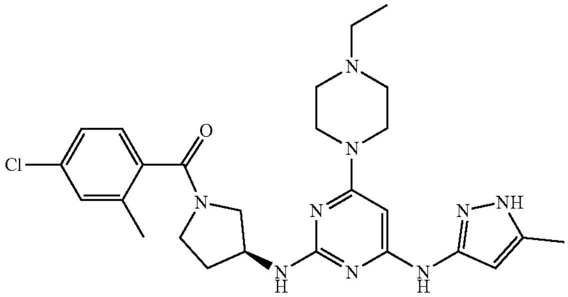
35
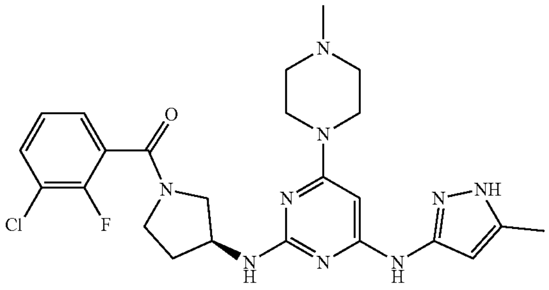
36
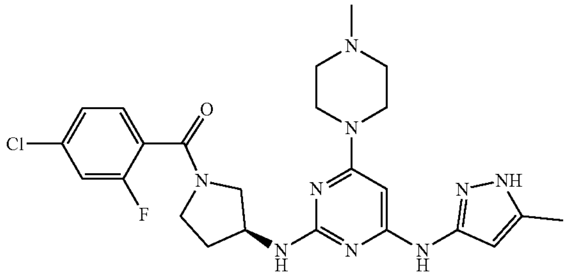

-continued
37
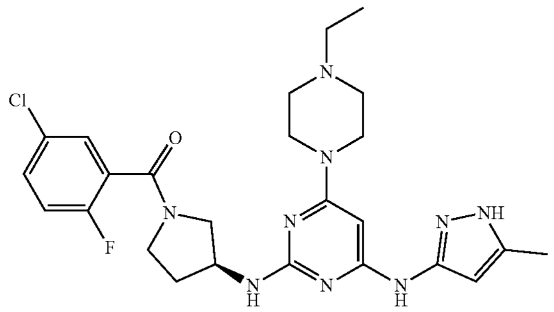
38
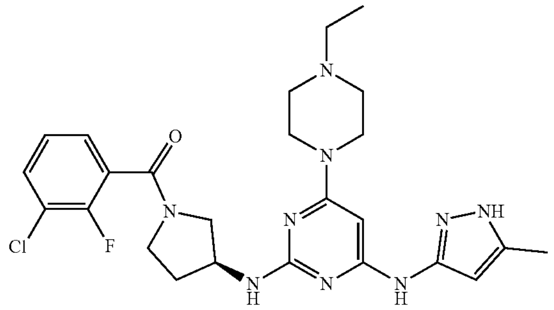
39
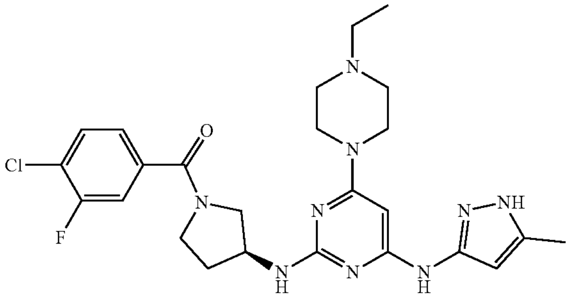
40
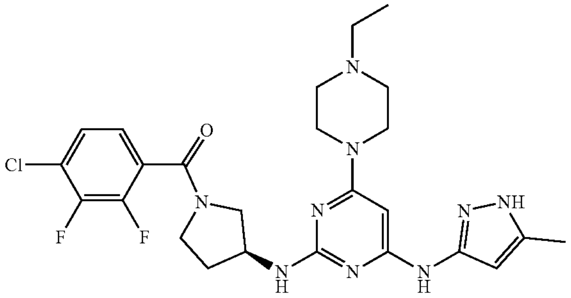
41
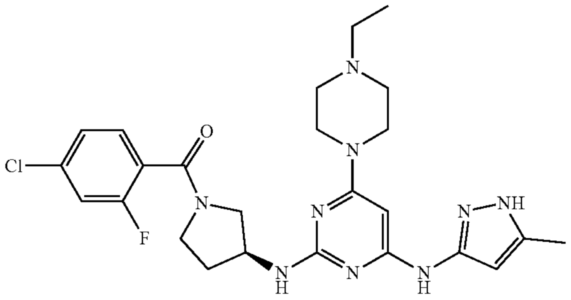
-continued
42
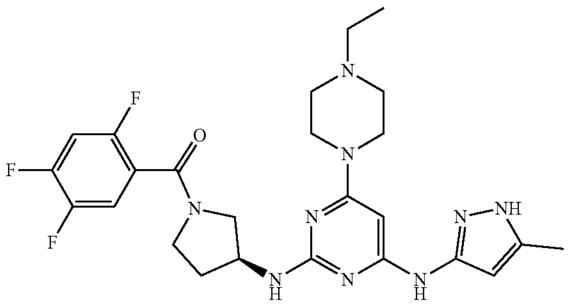
43
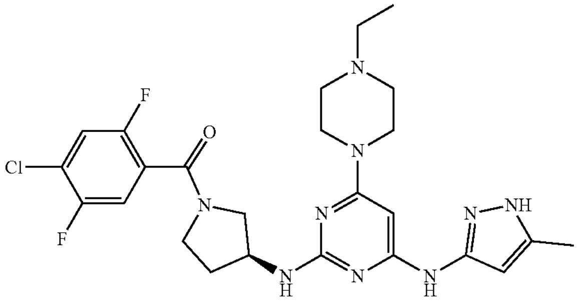
44
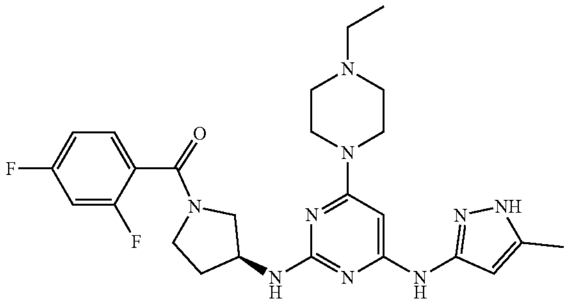
45
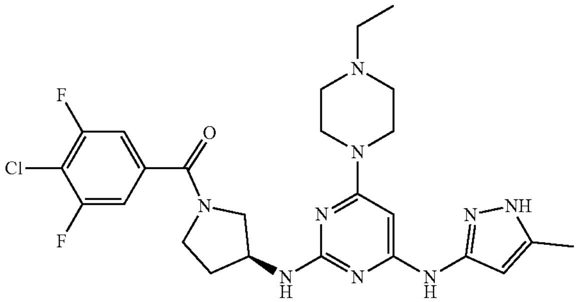
46
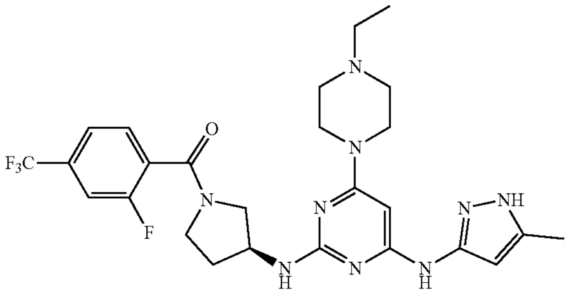

-continued
47
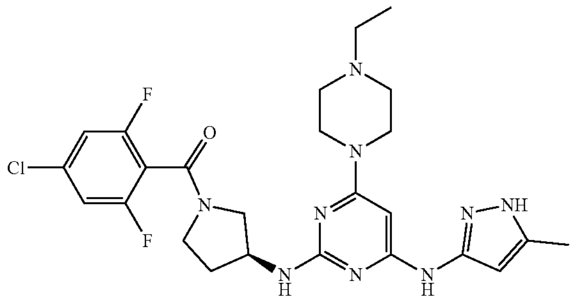
48
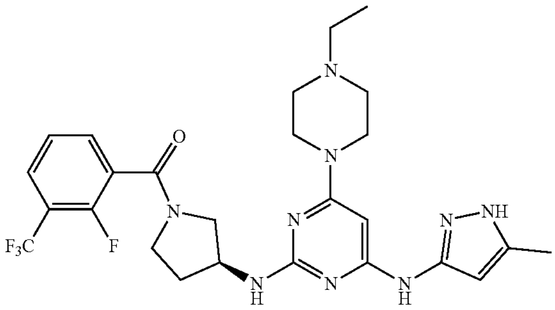
49
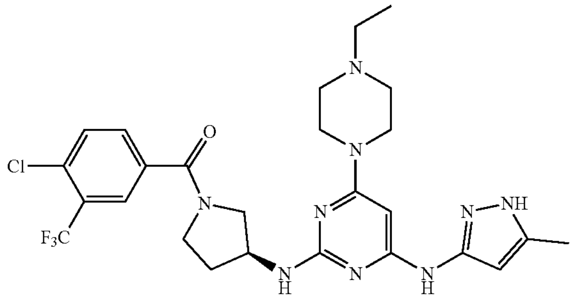
50
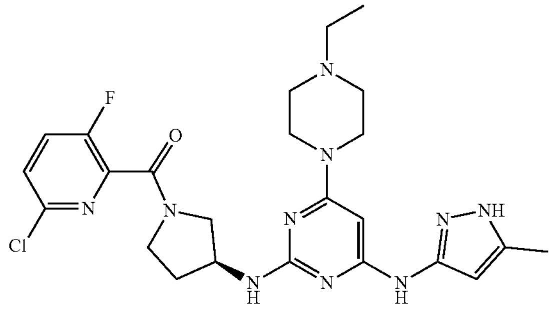
51
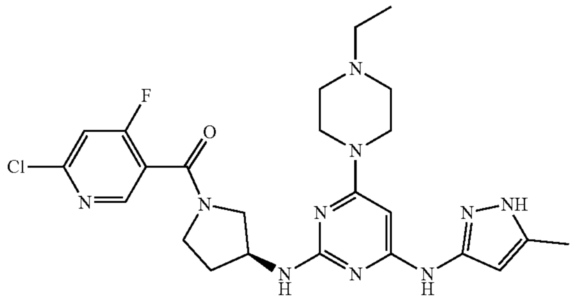
-continued
52
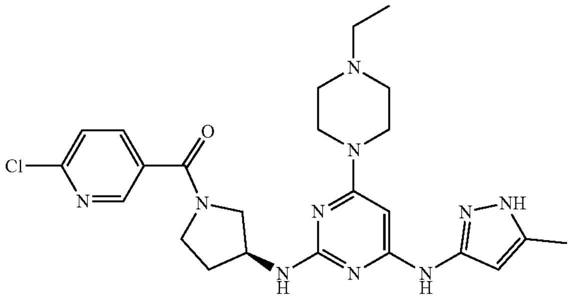
53
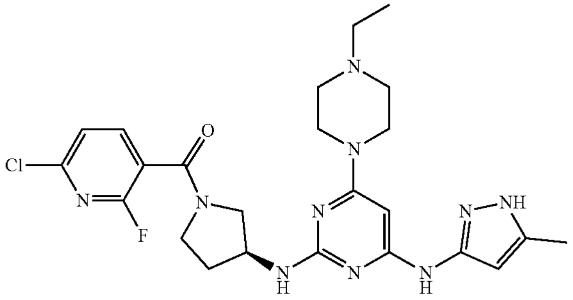
54
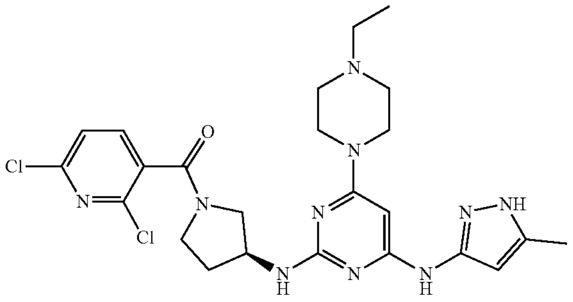
55
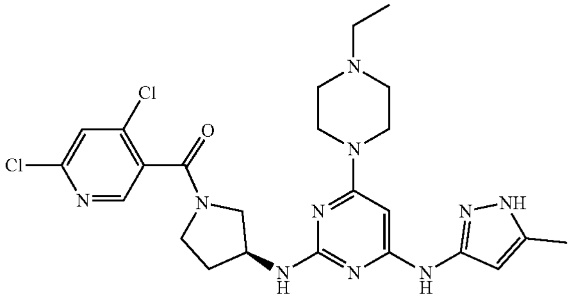
56
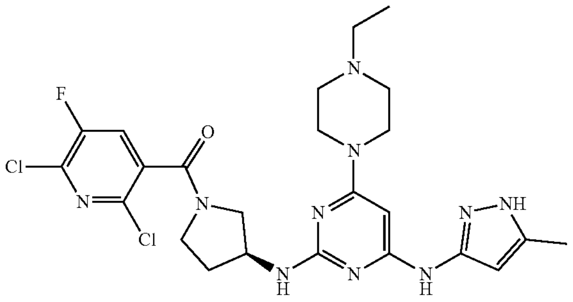

-continued
57
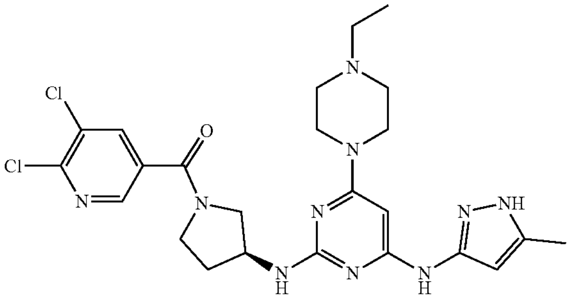
58
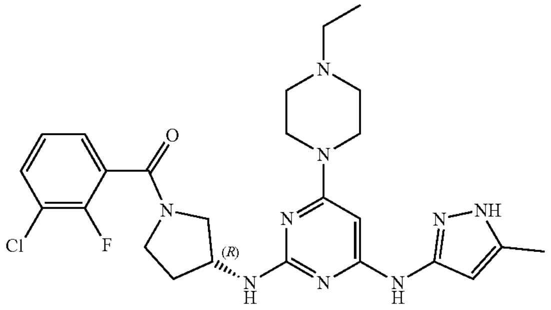
59
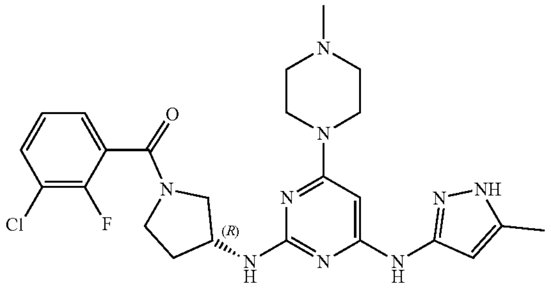
60
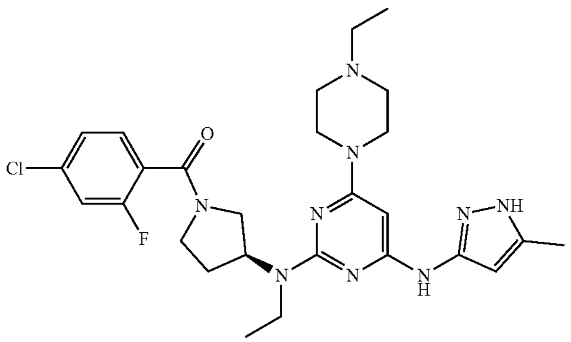
-continued
61
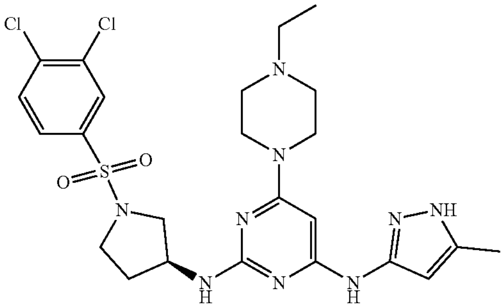
62
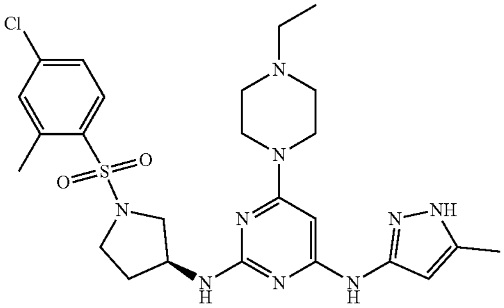
63
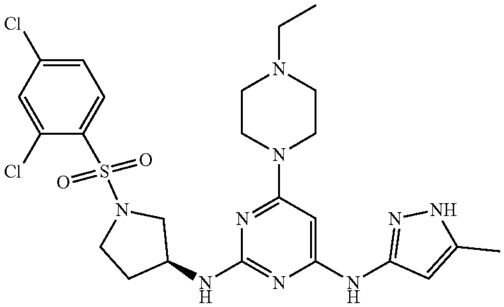
64
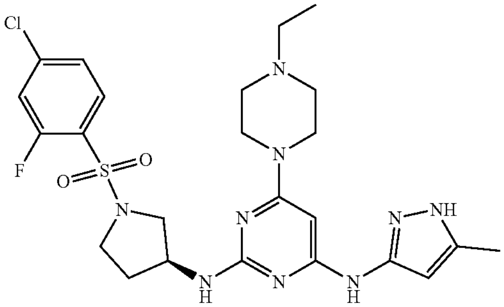

-continued
65
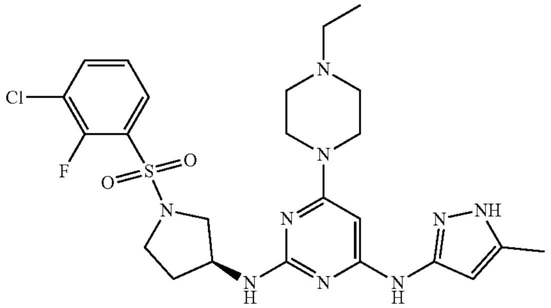
66
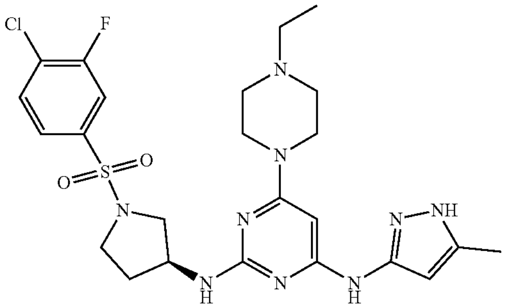
67
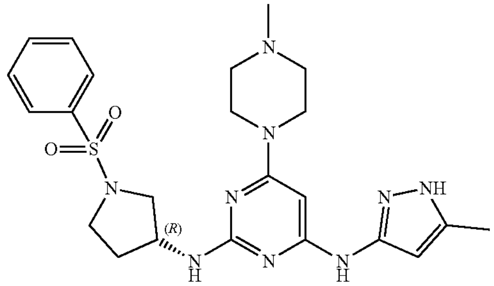
68
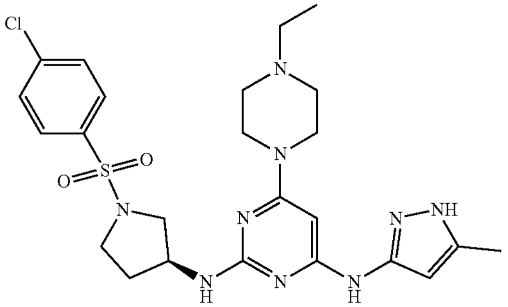
69
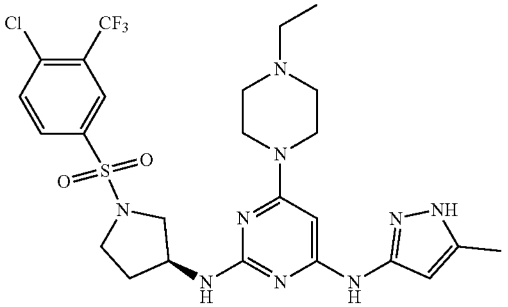
-continued
70
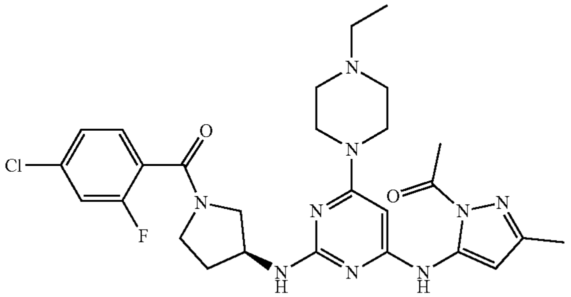
71
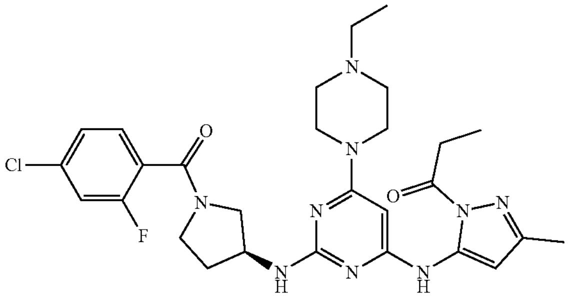
72
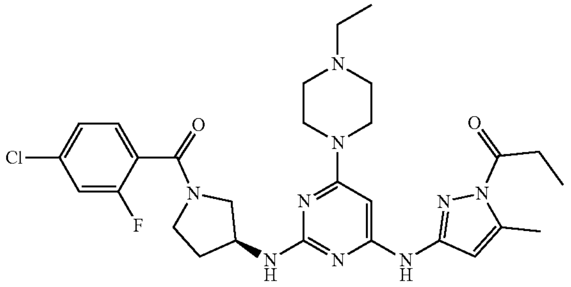
73
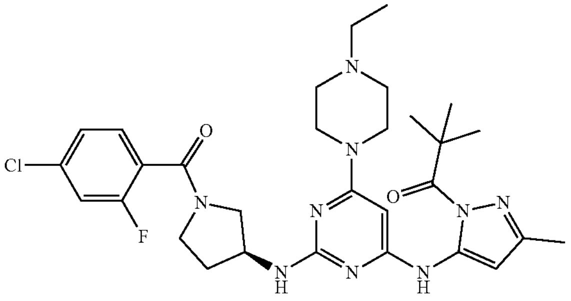
74
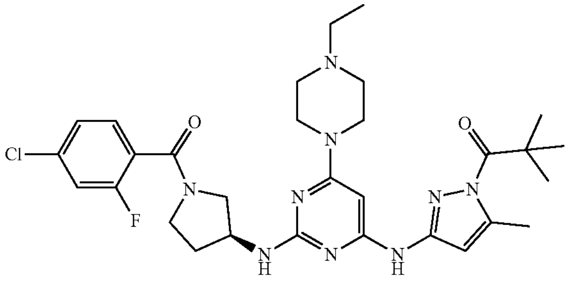

-continued
75
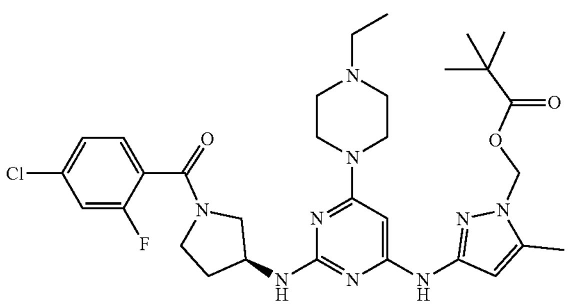
76
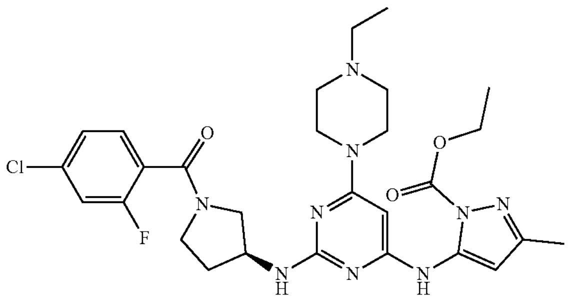
77
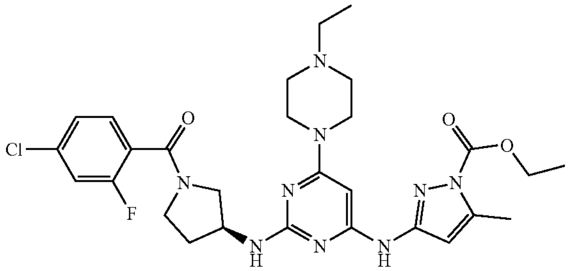
78
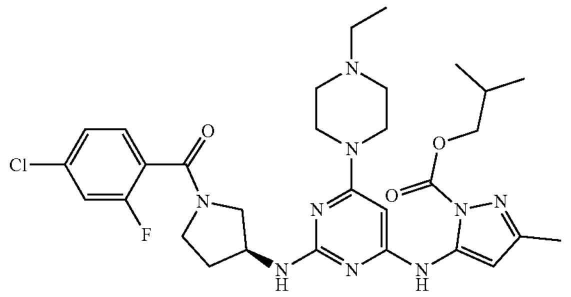
79
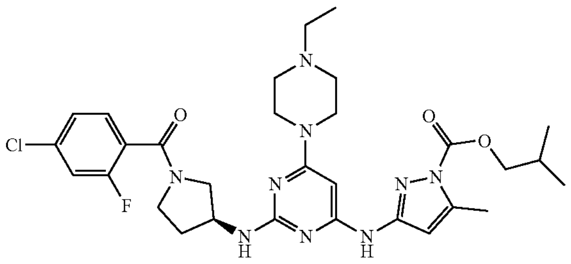
-continued
80
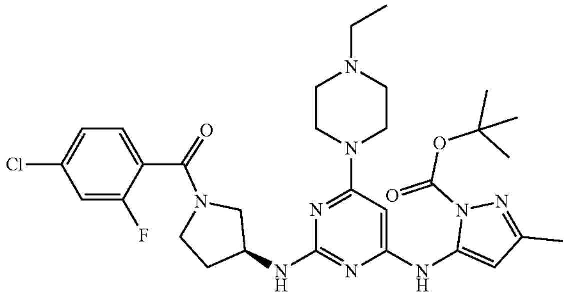
81
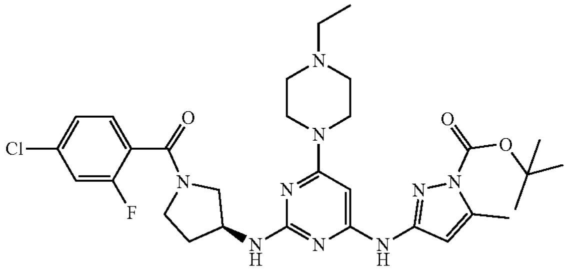
82
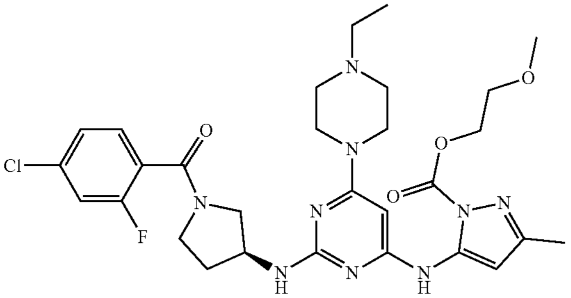
83
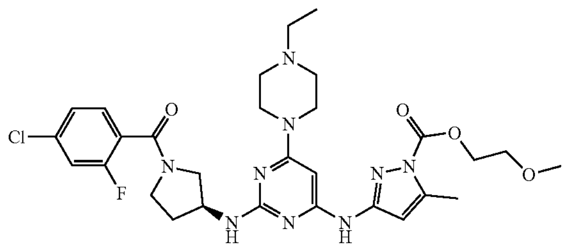
84
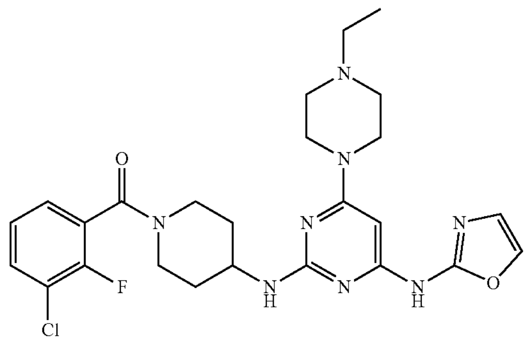

-continued
85
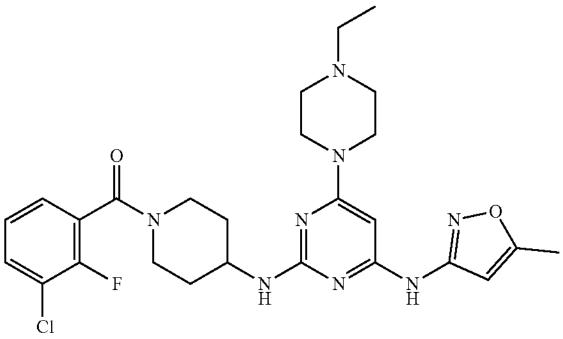
86
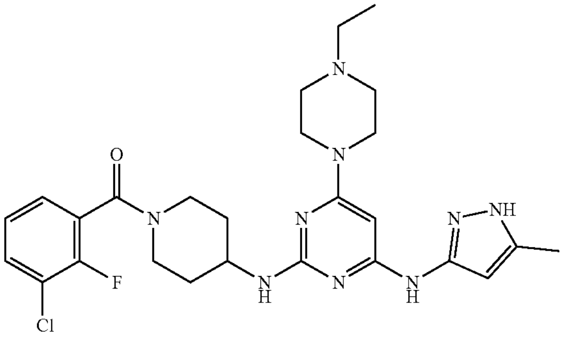
87
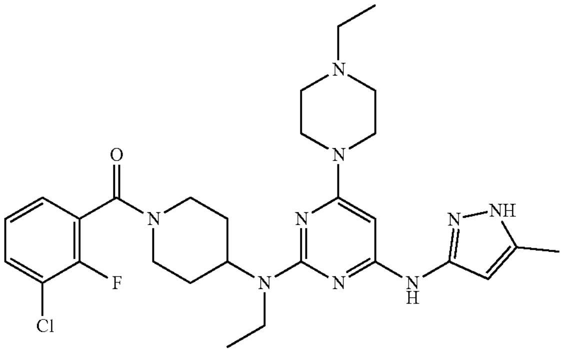
88
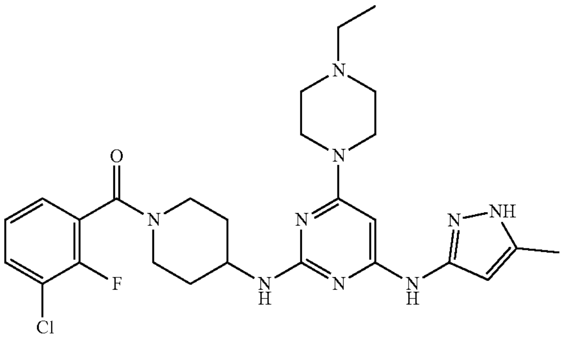
-continued
89
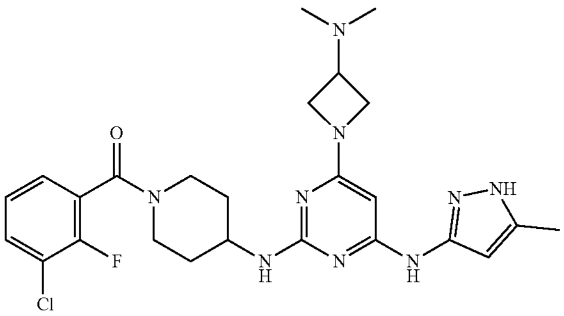
90
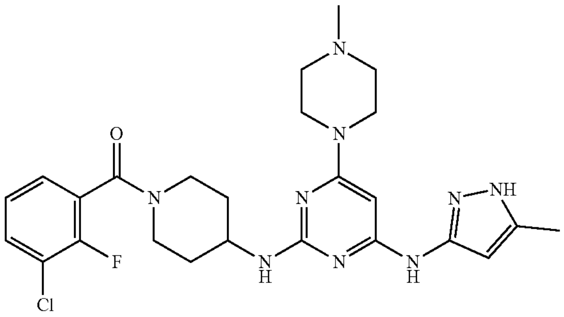
91
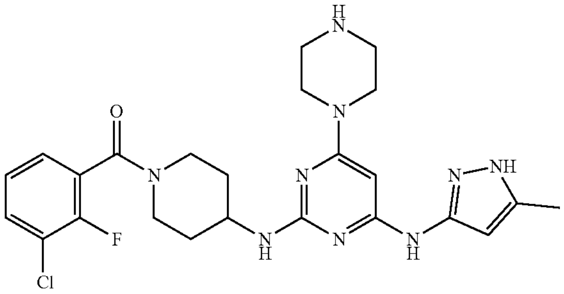
92
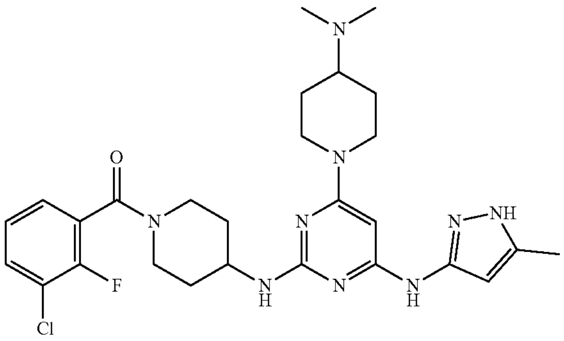

-continued
93
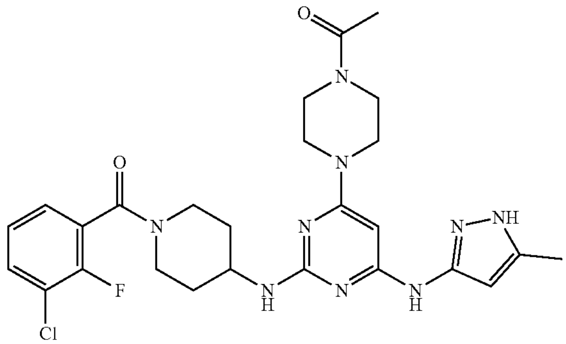
94
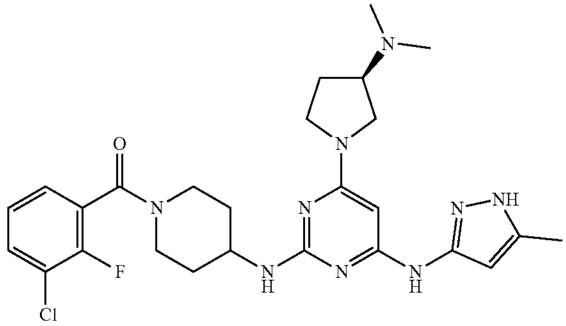
95
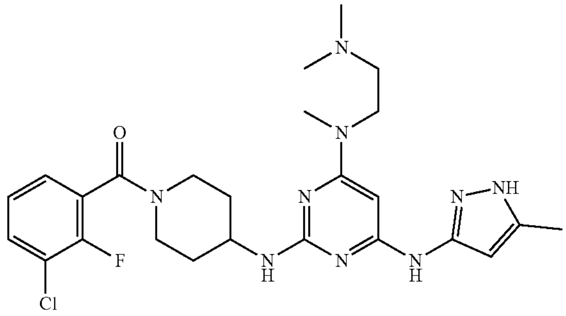
96
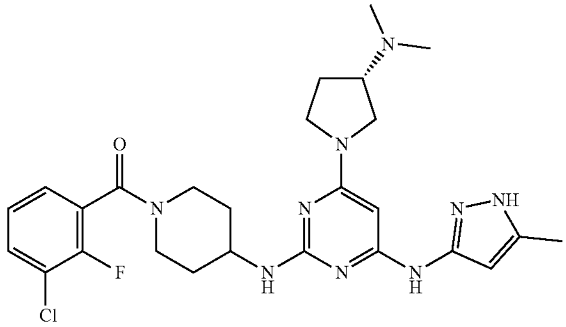
-continued
97
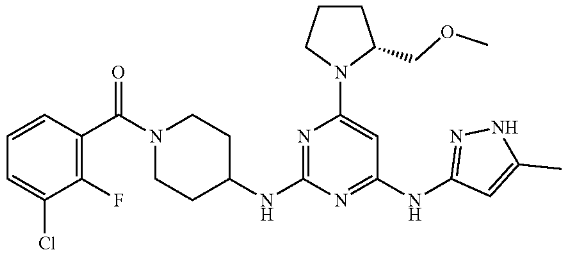
98
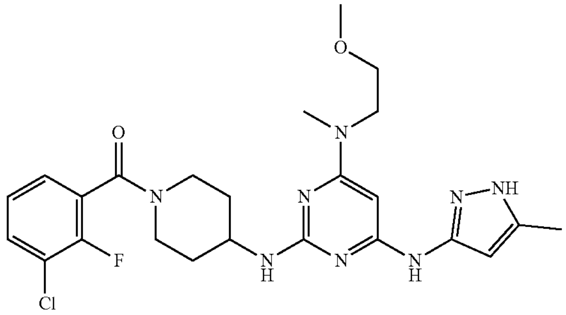
99
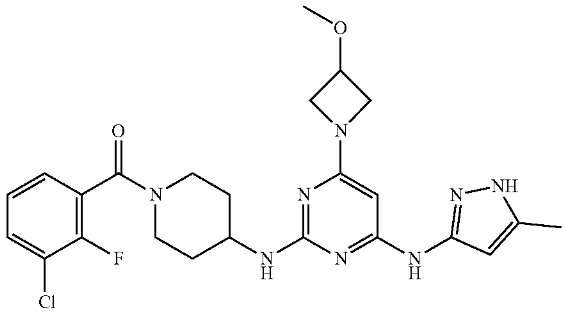
100
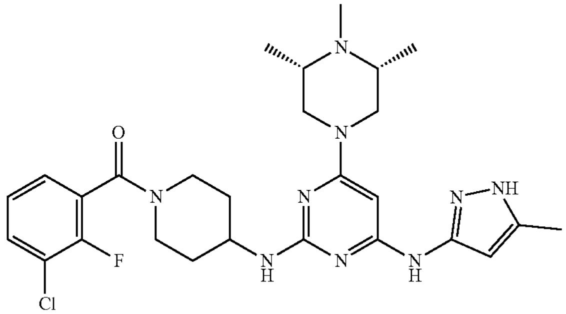

-continued
101
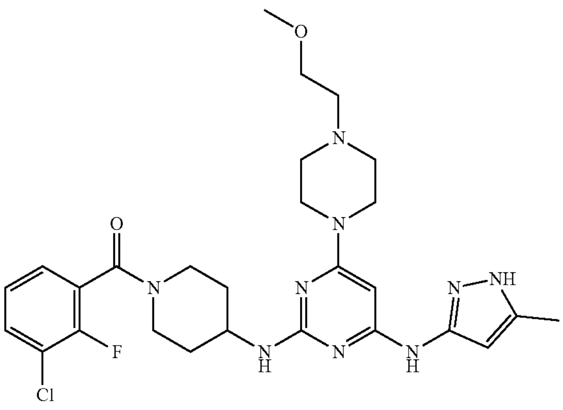
102
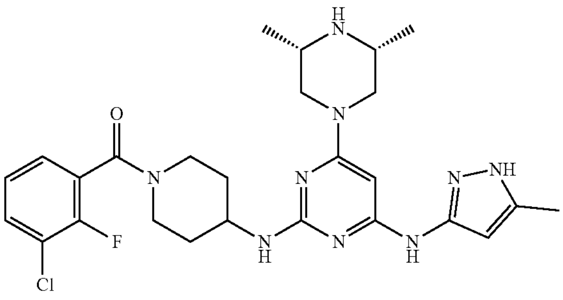
103
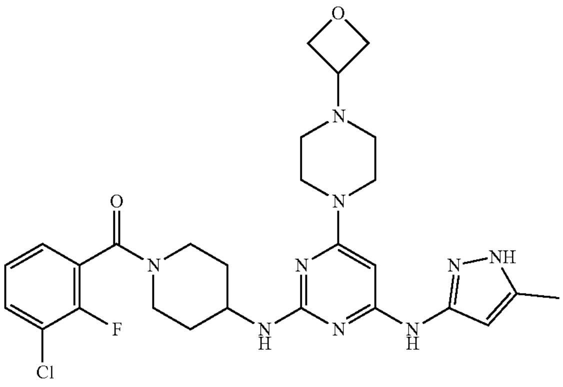
104
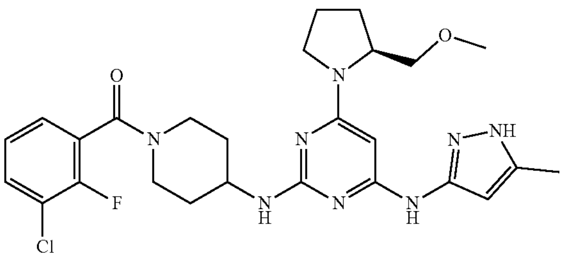
-continued
105
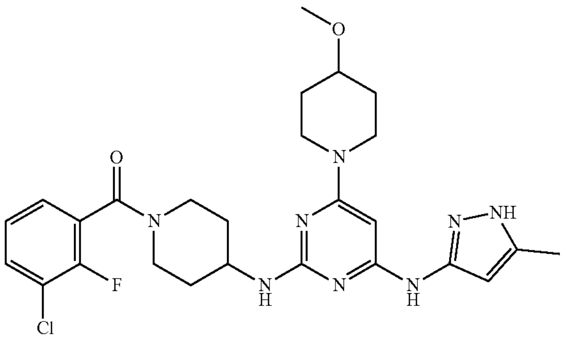
106
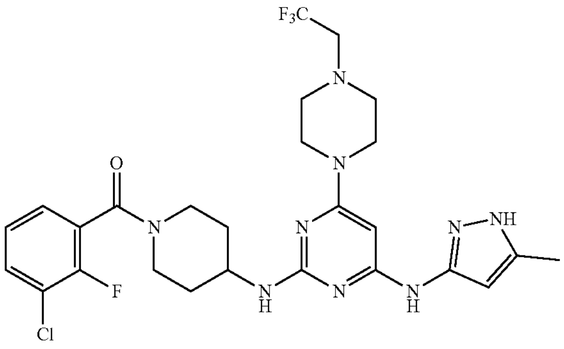
107
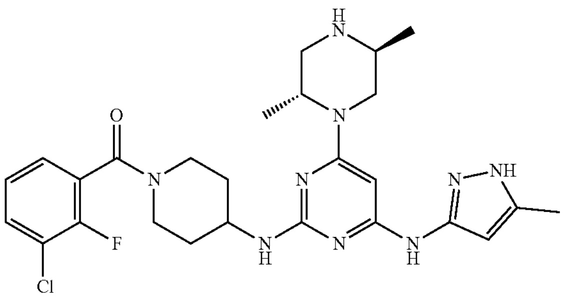
108
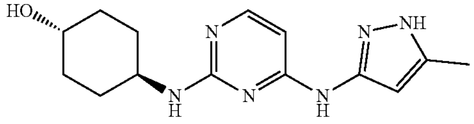
109
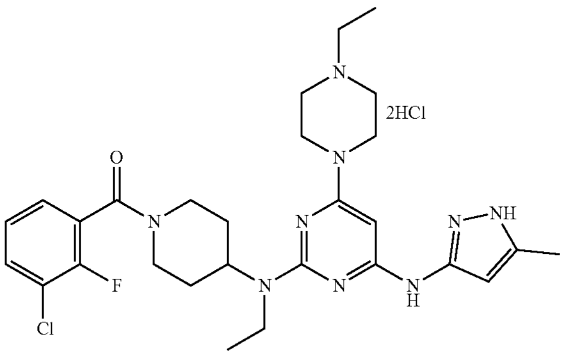

-continued
110
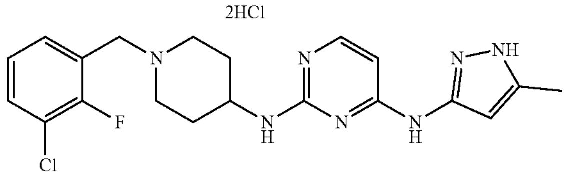
111
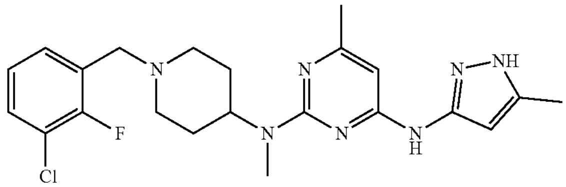
112
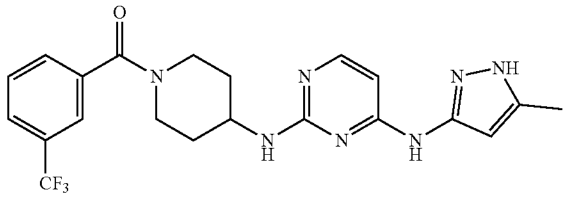
113
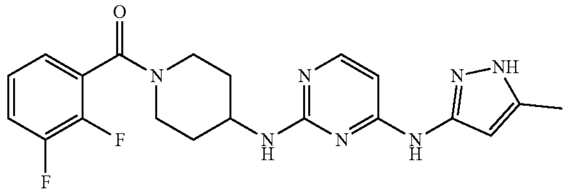
114
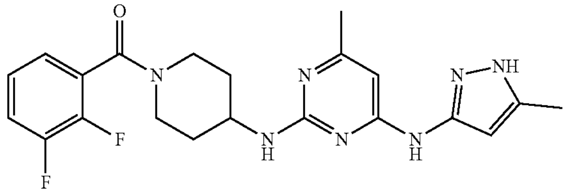
115
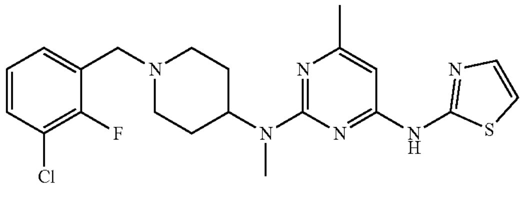
116
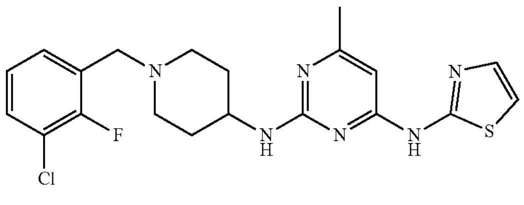
-continued
117
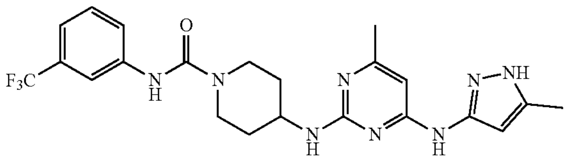
118
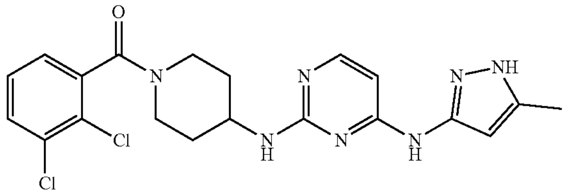
119
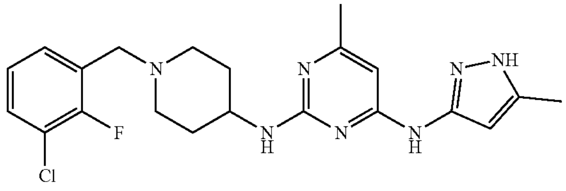
120
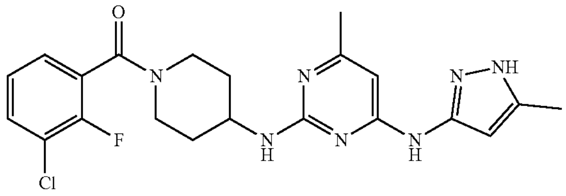
121
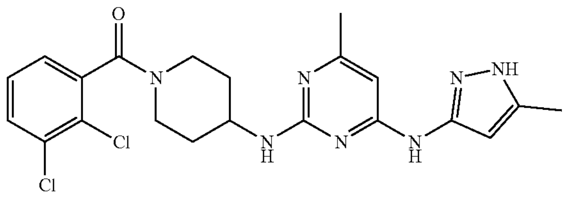
122
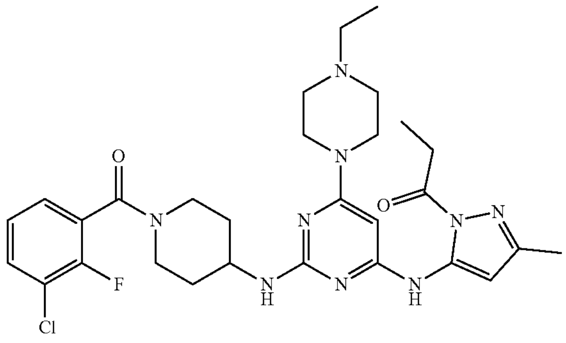

-continued

123

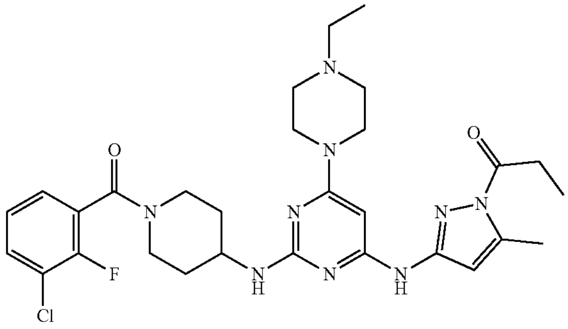

124

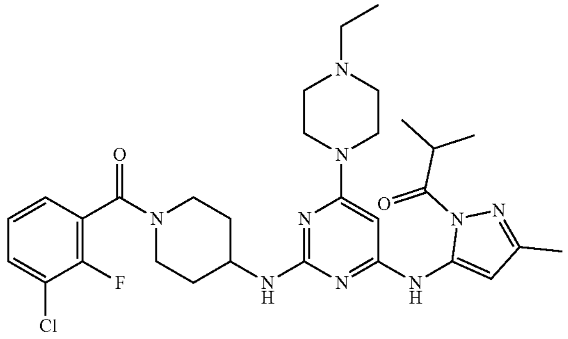

125

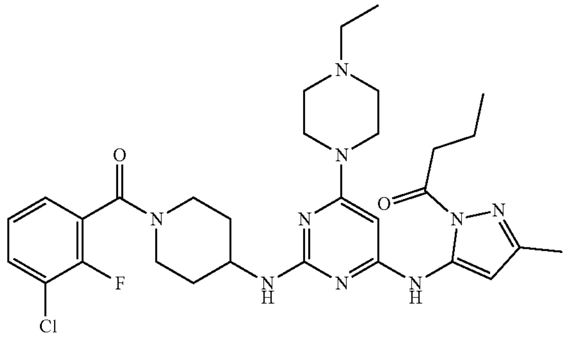

-continued

126

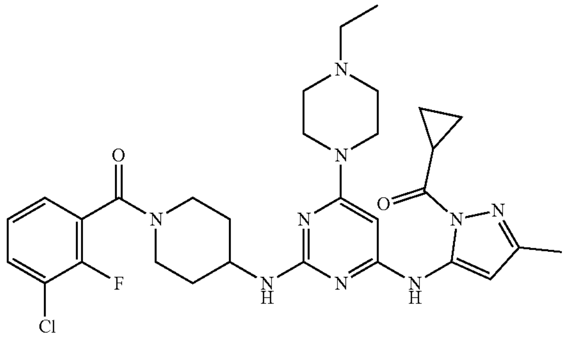

127

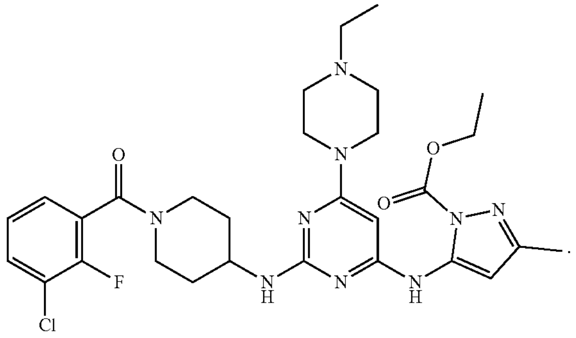

6. A method of treating cancer, the method comprising administering to a subject in need thereof an effective amount of a compound of claim 1.

7. The method of claim 6, wherein the cancer is leukemia, lung cancer, colon cancer, breast cancer, pancreatic cancer, prostate cancer, or neuroblastoma.

8. The method of claim 6, wherein the cancer is liver cancer, brain cancer, or cholangiocarcinoma.

9. A pharmaceutical composition comprising a compound of claim 1 and a pharmaceutically acceptable carrier.

10. A pharmaceutical composition comprising a compound of claim 5 and a pharmaceutically acceptable carrier.

* * * * *